(12) United States Patent
Meldrum et al.

(10) Patent No.: US 11,603,368 B2
(45) Date of Patent: Mar. 14, 2023

(54) FUSED THIOPHENE DERIVATIVES AND THEIR USES

(71) Applicant: ENYO PHARMA, Lyons (FR)

(72) Inventors: Eric Meldrum, Riehen (CH); Benoît De Chassey, Lyons (FR); Peter Machin, London (GB); Roberta Lanaro, Saffron Walden (GB); Calum Macleod, Bishop's Stortford (GB); Karine Fabienne Malagu, Saffron Walden (GB); Nicolas Proisy, Royston (GB); David Robert Vesey, Harlow (GB); Paul Colin Michael Winship, Saffron Walden (GB); Mark Chambers, Saffron Walden (GB); Jean-Laurent Paparin, Vendemian (FR)

(73) Assignee: ENYO PHARMA, Lyons (FR)

(*) Notice: Subject to any disclaimer, the term of this patent is extended or adjusted under 35 U.S.C. 154(b) by 7 days.

(21) Appl. No.: 16/967,751

(22) PCT Filed: Feb. 8, 2019

(86) PCT No.: PCT/EP2019/053072
§ 371 (c)(1),
(2) Date: Aug. 6, 2020

(87) PCT Pub. No.: WO2019/154949
PCT Pub. Date: Aug. 15, 2019

(65) Prior Publication Data
US 2020/0369682 A1    Nov. 26, 2020

(30) Foreign Application Priority Data
Feb. 8, 2018  (EP) .................................... 18305133

(51) Int. Cl.
| | | |
|---|---|---|
| *C07D 495/04* | (2006.01) |
| *C07D 413/14* | (2006.01) |
| *A61P 31/14* | (2006.01) |
| *A61P 31/16* | (2006.01) |
| *A61P 35/00* | (2006.01) |
| *C07D 333/68* | (2006.01) |
| *C07D 401/12* | (2006.01) |
| *C07D 403/12* | (2006.01) |
| *C07D 409/12* | (2006.01) |
| *C07D 413/12* | (2006.01) |
| *C07D 491/107* | (2006.01) |
| *C07D 333/66* | (2006.01) |
| *C07D 409/14* | (2006.01) |
| *A61P 29/00* | (2006.01) |
| *A61P 25/28* | (2006.01) |

(52) U.S. Cl.
CPC ............ *C07D 413/14* (2013.01); *A61P 25/28* (2018.01); *A61P 29/00* (2018.01); *A61P 31/14* (2018.01); *A61P 31/16* (2018.01); *A61P 35/00* (2018.01); *C07D 333/66* (2013.01); *C07D 333/68* (2013.01); *C07D 401/12* (2013.01); *C07D 403/12* (2013.01); *C07D 409/12* (2013.01); *C07D 409/14* (2013.01); *C07D 413/12* (2013.01); *C07D 491/107* (2013.01); *C07D 495/04* (2013.01)

(58) Field of Classification Search
CPC .................................................... C07D 495/04
See application file for complete search history.

(56) References Cited

U.S. PATENT DOCUMENTS

| | | | | |
|---|---|---|---|---|
| 6,083,706 A | * | 7/2000 | Florkiewicz | ........... A61K 31/19 435/7.1 |
| 8,765,803 B1 | | 7/2014 | Wandinger-Ness et al. | |
| 2013/0143765 A1 | * | 6/2013 | Verkman | ............... C07D 277/42 506/10 |
| 2019/0352275 A1 | | 11/2019 | Meldrum et al. | |
| 2020/0361924 A1 | | 11/2020 | Meldrum et al. | |
| 2020/0369655 A1 | | 11/2020 | Meldrum et al. | |
| 2021/0038566 A1 | | 2/2021 | Meldrum et al. | |
| 2021/0040059 A1 | | 2/2021 | Meldrum et al. | |

FOREIGN PATENT DOCUMENTS

| | | |
|---|---|---|
| WO | WO 2006/044826 | 4/2006 |
| WO | WO 2006/093518 | 9/2006 |
| WO | WO 2009/026172 | 2/2009 |
| WO | WO 2009/079373 | 6/2009 |
| WO | WO 2010/088414 | 8/2010 |
| WO | WO 2011/097607 | 8/2011 |
| WO | WO 2012/148889 | 11/2012 |
| WO | WO 2017/184947 | 10/2017 |
| WO | WO 2019/154950 | 8/2019 |
| WO | WO 2019/154953 | 8/2019 |
| WO | WO 2019/154956 | 8/2019 |

OTHER PUBLICATIONS

Agola et al. ACS Chem. Biol. 2012, 7, 1095-1108 (Year: 2012).*
National Center for Biotechnology Information (2022). PubChem Compound Summary for CID 817029. Created Jul. 8, 2005; Retrieved Feb. 9, 2022 from https://pubchem.ncbi.nlm.nih.gov/compound/817029 (Year: 2005).*
National Center for Biotechnology Information (2022). PubChem Bioassay Record for AID 1030, Source: National Center for Advancing Translational Sciences (NCATS). Deposited Jan. 11, 2008; Retrieved Feb. 9, 2022 from https://pubchem.ncbi.nlm.nih.gov/bioassay/1030 (Year: 2008).*
Pinkerton et al. Bioorg. Med. Chem. Lett. 2007, 17, 3562-3569 (Year: 2007).*

(Continued)

*Primary Examiner* — Matthew P Coughlin
(74) *Attorney, Agent, or Firm* — Saliwanchik, Lloyd & Eisenschenk

(57) ABSTRACT

The present invention relates to a new class of fused thiophene derivatives and their uses for treating diseases such as infection, cancer, metabolic diseases, cardiovascular diseases, iron storage disorders and inflammatory disorders.

2 Claims, No Drawings
Specification includes a Sequence Listing.

(56) References Cited

OTHER PUBLICATIONS

National Center for Biotechnology Information (2022). PubChem Compound Summary for CID 28860807. Created May 28, 2009; Retrieved Jun. 27, 2022 from https://pubchem.ncbi.nlm.nih.gov/compound/28860807 (Year: 2009).*

Bai, F. et al. "The Fe—S cluster-containing NEET proteins mitoNEET and NAF-1 as chemotherapeutic targets in breast cancer" *PNAS*, Mar. 24, 2015, pp. 3698-3703, vol. 112, No. 12.

Bill, A et al. "Small Molecule-facilitated Degradation of ANO1 Protein; A New Targeting Approach for Anticancer Therapeutics" *The Journal of Biological Chemistry*, Apr. 18, 2014, pp. 11029-11041, vol. 289, No. 16.

Fujita, M. et al. "Synthesis and Bioactivities of Novel Bicyclic Thiophenes and 4,5,6,7-Tetrahydrothieno[2,3-c]pyridines as Inhibitors of Tumor Necrosis Factor-α (TNF-α) Production" *Bioorganic & Medicinal Chemistry Letters*, 2002, pp. 1897-1900, vol. 12.

Katzman, B. M. et al. "A novel class of negative allosteric modulators of NMDA receptor function" *Bioorganic & Medicinal Chemistry Letters*, 2015, pp. 5583-5588, vol. 25, No. 23.

Massari, S. et al. "Structural Investigation of Cycloheptathiophene-3-carboxamide Derivatives Targeting Influenza Virus Polymerase Assembly" *J. Med. Chem.*, 2013, pp. 10118-10131, vol. 56, No. 24.

Pinkerton, A. B. et al. "Synthesis and SAR of thiophene containing kinesin spindle protein (KSP) inhibitors" *Bioorganic & Medicinal Chemistry Letters*, 2007, pp. 3562-3569, vol. 17, No. 13.

Redondo, M. et al. "Identification in Silico and Experimental Validation of Novel Phosphodiesterase 7 Inhibitors with Efficacy in Experimental Autoimmune Encephalomyelitis Mice" *ACS Chem. Neurosci.*, 2012, pp. 793-803, vol. 3, No. 10.

Takasawa, R. et al. "Discovery of a new type inhibitor of human glyoxalase I by myricetin-based 4-point pharmacophore" *Bioorganic & Medicinal Chemistry Letters*, 2011, pp. 4337-4342, vol. 21, No. 14.

Database Registry [Online] Chemical Abstracts Service, Accession No. 2128688-81-1, Sep. 19, 2017, XP-002780167, p. 1.

Database Registry [Online] Chemical Abstracts Service, Accession No. 1082139-93-2, Dec. 9, 2008, XP-002780168, p. 1.

Written Opinion in International Application No. PCT/EP2019/053072, dated May 6, 2019, pp. 1-11.

* cited by examiner

SEQUENCE LISTING

```
<160> NUMBER OF SEQ ID NOS: 4

<210> SEQ ID NO 1
<211> LENGTH: 35
<212> TYPE: DNA
<213> ORGANISM: artificial
<220> FEATURE:
<223> OTHER INFORMATION: NFKB-NLUC-F

<400> SEQUENCE: 1
ggctctatgg gtcgacggcc taactggccg gtacc                               35

<210> SEQ ID NO 2
<211> LENGTH: 37
<212> TYPE: DNA
<213> ORGANISM: artificial
<220> FEATURE:
<223> OTHER INFORMATION: NFKB-NLUC-R

<400> SEQUENCE: 2
agcttagtac tgtcgacgat cagcggaaga gcgccca                             37

<210> SEQ ID NO 3
<211> LENGTH: 25
<212> TYPE: DNA
<213> ORGANISM: artificial
<220> FEATURE:
<223> OTHER INFORMATION: AAVS1-T2A-1

<400> SEQUENCE: 3
caccgggggc cactagggac aggat                                          25

<210> SEQ ID NO 4
<211> LENGTH: 25
<212> TYPE: DNA
<213> ORGANISM: artificial
<220> FEATURE:
<223> OTHER INFORMATION: AAVS1-T2A-2

<400> SEQUENCE: 4
aaacatcctg tccctagtgg ccccc                                          25
```

FUSED THIOPHENE DERIVATIVES AND THEIR USES

CROSS-REFERENCE TO RELATED APPLICATION

This application is the U.S. national stage application of International Patent Application No. PCT/EP2019/053072, filed Feb. 8, 2019.

The Sequence Listing for this application is labeled "Seq-List.txt" which was created on Jul. 5, 2020 and is 1 KB. The entire content of the sequence listing is incorporated herein by reference in its entirety.

FIELD OF THE INVENTION

The present invention relates to the field of medicine, in particular fused thiophene derivatives and their uses for treating diseases such as infection, cancer, metabolic diseases, cardiovascular diseases, iron storage disorders and inflammatory disorders.

BACKGROUND OF THE INVENTION

Viruses are small infectious agents that replicates only inside living cells of other organisms. They can infect all types of life forms, from animals and plants to microorganisms, including bacteria and archaea. Among them, more than 400 species of virus are known to be responsible of diseases in humans, many of them leading to serious pathologies and eventually death. In particular, HIV was classified at the sixth leading cause of death worldwide in 2012 with 1.5 million deaths per year (WHO, Fact sheet N° 310, 2014). Seasonal influenza viruses are responsible of flu that affects approximately 20% of the world population and causes 250,000 to 500,000 deaths per year (WHO, Fact sheet N° 211, 2014). Among other examples, Hepatitis B and C are responsible altogether for about 1.4 million of death each year and human Papillomaviruses are responsible of cervix cancer, the second most common women cancer worldwide, leading to 270,000 death in 2012 (WHO, Fact sheets, 2016).

Because viruses use vital metabolic pathways within host cells to replicate, they are difficult to eliminate without using drugs that cause toxic effects to host cells in general. The most effective medical approaches to viral diseases are vaccinations to provide immunity to infection, and antiviral drugs that selectively interfere with viral replication. Vaccines are very effective on stable viruses for a preventive use. However, vaccines are of limited use in treating a patient who has already been infected. They are also difficult to successfully deploy against rapidly mutating viruses, such as influenza (the vaccine for which is updated every year) and HIV. Antiviral drugs may be particularly useful in these cases.

Antiviral drugs are a class of medication used specifically for treating viral infections. Antiviral drugs do not destroy their target pathogens, instead they inhibit their development. Antiviral drugs may target any stage of the viral life cycle: attachment to a host cell, release of viral genes and possibly enzymes into the host cell, replication of viral components using host-cell machinery, assembly of viral components into complete viral particles, and release of viral particles to infect new host cells. The most common antiviral drugs are nucleoside analogues that block viruses' replication. Most antiviral drugs are used for specific viral infections, while broad-spectrum antiviral drugs are effective against a wide range of viruses.

Soon after the development of antiviral drugs, resistance appeared. Antiviral drug resistance can be defined as a decreased susceptibility to a drug through either a minimally effective, or completely ineffective, treatment response to prevent associated illnesses from a particular virus. Antiviral drug resistance remains a major obstacle to antiviral therapy as it has developed to almost all specific and effective antiviral drugs. For example, there are two main groups of antiviral drugs available for treatment and prophylaxis of influenza: M2 inhibitors (amantadine and rimantadine) and neuraminidase inhibitors (oseltamivir and zanamivir). Despite the effectiveness of these drugs in reducing influenza-related morbidity and mortality, the emergence of drug resistance poses a critical limitation on their application and have raised an urgent need for developing new anti-influenza drugs against resistant forms.

Thus, there is nowadays a strong need for the development of new antiviral drugs, and in particular broad-spectrum antiviral drugs. The present invention seeks to meet these and other needs.

SUMMARY OF THE INVENTION

The present invention relates to a compound for use for treating a disease selected from the group consisting of an infection, preferably a viral or a bacterial infection, a cancer, a metabolic disease, a cardiovascular disease, an inflammatory disorder, and iron storage disease/disorder, wherein the compound has the formula (I):

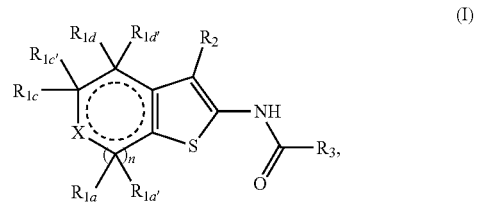

wherein:
X represents:
    a —$CR_{1b}R_{1b'}$ unit,
    a N—$R_{1b''}$ unit, or
    an oxygen atom;
n is 0, 1, or 2;
when X is a —$CR_{1b}R_{1b'}$ unit, then at most one of $R_{1a}$, $R_{1a'}$, $R_{1b}$, $R_{1b'}$, $R_{1c}$, $R_{1c'}$, $R_{1d}$, and $R_{1d'}$ represents:
    a halogen,
    a ($C_1$-$C_6$)alkyl, optionally substituted by at least one halogen, preferably a fluorine,
    a ($C_1$-$C_6$)alkyloxy optionally substituted by at least one halogen, preferably a fluorine,
    a cyano, or
    an aryl optionally substituted by at least one radical selected in the group consisting of:
        a halogen,
        a ($C_1$-$C_6$)alkyl optionally substituted by at least one halogen, preferably a fluorine,
        a hydroxy, and
        a ($C_1$-$C_6$)alkyloxy optionally substituted by at least one halogen, preferably a fluorine,
and the others represent a hydrogen;

when X is a —N—$R_{1b''}$ unit or an oxygen atom, then $R_{1a}$, $R_{1a'}$, $R_{1c}$, $R_{1c'}$, $R_{1d}$, and $R_{1d'}$ represent independently:
a hydrogen,
a halogen,
a $(C_1-C_6)$alkyl, optionally substituted by at least one halogen, preferably a fluorine,
a $(C_1-C_6)$alkyloxy optionally substituted by at least one halogen, preferably a fluorine,
a cyano,
an aryl optionally substituted by at least one radical selected in the group consisting of:
  a halogen,
  a $(C_1-C_6)$alkyl optionally substituted by at least one halogen, preferably a fluorine,
  a hydroxy, or
  a $(C_1-C_6)$alkyloxy optionally substituted by at least one halogen, preferably a fluorine;
and $R_{1b''}$ represents
an aryl optionally substituted by at least one radical selected in the group consisting of:
  a halogen,
  a $(C_1-C_6)$alkyl optionally substituted by at least one halogen, preferably a fluorine,
  a hydroxy, and
  a $(C_1-C_6)$alkyloxy optionally substituted by at least one halogen, preferably a fluorine,
a $(C_1-C_6)$alkyl optionally substituted by at least one halogen, preferably a fluorine, or
a —$CO_2$—$R_8$ with $R_8$ being a $(C_1-C_6)$alkyl;
$R_2$ represents —COOH;
$R_3$ represents:
a 5-10 membered ring, saturated or unsaturated selected in the group consisting of:
  an aryl optionally fused to a dioxole,
  a heteroaryl,
  a cycloalkyl,
  a heterocycloalkyl, and
  a 5-10 membered bridged carbocyclyl or heterocyclyl, said 5-10 membered ring is optionally substituted by at least one radical selected in the group consisting of:
    a halogen,
    a $(C_1-C_6)$alkyl optionally substituted by at least one halogen, preferably a fluorine, or a $(C_1-C_6)$alkyloxy,
    a —NH—$(C_1-C_6)$alkyl or a —N—$((C_1-C_6)$alkyl$)_2$, optionally substituted by a heterocycloalkyl or a $(C_1-C_6)$alkyloxy,
    a —NH-heterocycloalkyl, a —NH-cycloalkyl, a —N$((C_1-C_6)$alkyl)-heterocycloalkyl or a —N$((C_1-C_6)$alkyl)-cycloalkyl, optionally substituted by
    a $(C_1-C_6)$alkyloxy or a —CO—$R_4$ with $R_4$ being a hydrogen or a $(C_1-C_6)$alkyl,
    a hydroxy, a —CO—$R_4$ or a —$CO_2R_4$ with $R_4$ being a hydrogen or a $(C_1-C_6)$alkyl,
    a $(C_1-C_6)$alkyloxy optionally substituted by at least one radical selected in the group consisting of a halogen, preferably a fluorine, a hydroxy, a $(C_1-C_6)$alkyloxy, a —$NR_5R_6$ with $R_5$ and $R_6$ are independently a hydrogen or a $(C_1-C_6)$alkyl, a —$NHCOR_7$, a —$NHCO_2R_7$, with $R_7$ being a $(C_1-C_6)$alkyl, a —$CO_2R_4$ with $R_4$ being a hydrogen or a $(C_1-C_6)$alkyl, and a heterocycle,
    a —$NHCOR_7$ or —$NHCO_2R_7$ with $R_7$ being a $(C_1-C_6)$alkyl, and
    a heterocycloalkyl, a heterocycloalkyloxy or a spiroheterocycloalkyl, optionally substituted by a $(C_1-C_6)$alkyloxy, a hydroxy, a halogen or a $(C_1-C_6)$alkyl optionally substituted by a $(C_1-C_6)$alkyloxy, or
    a $(C_1-C_6)$alkyl or a $(C_2-C_6)$alkenyl, optionally substituted by a 5-10 membered ring as defined above or a —$CO_2R_4$ with $R_4$ being a hydrogen or a $(C_1-C_6)$alkyl;
and with the proviso that $R_3$ is not a 5-membered heteroaryl; and the stereoisomers, and the pharmaceutical salts thereof.

In a particular embodiment, X represents a —$CR_{1b}R_{1b'}$ unit and one of $R_{1a}$, $R_{1a'}$, $R_{1b}$, $R_{1b'}$, $R_{1c}$, $R_{1c'}$, $R_{1d}$, and $R_{1d'}$ represents a $(C_1-C_6)$alkyl, a $(C_1-C_6)$alkyloxy, or a phenyl optionally substituted by at least one radical selected in the group consisting of a hydroxy, a halogen, preferably a fluorine, and a $(C_1-C_3)$alkyl, optionally substituted by at least one halogen, preferably a fluorine, and the others represent a hydrogen.

In a further particular embodiment, X represents a N—$R_{1b}''$ unit with $R_{1b}$-represents an aryl, preferably a phenyl, optionally substituted by at least one radical selected in the group consisting of:
a halogen, preferably a fluorine, and
a $(C_1-C_6)$alkyl optionally substituted by at least one halogen, preferably a fluorine, and $R_{1a}$, $R_{1a'}$, $R_{1c}$, $R_{1c'}$, $R_{1d}$, and $R_{1d'}$ are a hydrogen.

In a further particular embodiment, X represents an oxygen atom and $R_{1a}$, $R_{1a'}$, $R_{1c}$, $R_{1c'}$, $R_{1d}$, and $R_{1d'}$ represent independently a hydrogen or a $(C_1-C_6)$alkyl, preferably a methyl, optionally substituted by at least one halogen, preferably a fluorine.

In a particular embodiment, $R_3$ represents a phenyl, a cyclohexyl, a piperidinyl, or a pyridinyl, preferably a phenyl, optionally substituted by at least one radical selected in the group consisting of:
a halogen, preferably a fluorine or a chlorine,
a $(C_1-C_6)$alkyl, preferably a methyl, optionally substituted by at least one halogen, preferably a fluorine,
a —NH—$(C_1-C_6)$alkyl or a —N—$((C_1-C_6)$alkyl$)_2$, optionally substituted by a tetrahydropyranyl or a $(C_1-C_6)$alkyloxy,
a —NH-tetrahydropyranyl,
a hydroxy,
a $(C_1-C_6)$alkyloxy optionally substituted by at least one radical selected in the group consisting of a halogen, preferably a fluorine, a hydroxy, a $(C_1-C_6)$alkyloxy, a —$NR_5R_6$ with $R_5$ and $R_6$ are independently a hydrogen or a $(C_1-C_6)$alkyl, a —$NHCOR_7$, a —$NHCO_2R_7$, with $R_7$ being a $(C_1-C_6)$alkyl, and a —$CO_2R_4$ with $R_4$ being a hydrogen or a $(C_1-C_6)$alkyl,
a —$NHCOR_7$ or —$NHCO_2R_7$ with $R_7$ being a $(C_1-C_6)$alkyl, preferably a methyl, and
a morpholinyl or an azetidinyl, optionally substituted by a $(C_1-C_6)$alkyloxy.

In a further preferred embodiment,
X represents a unit;
n is 1;
$R_{1a}$, $R_{1a'}$, $R_{1c'}$, and $R_{1d'}$ represent a hydrogen, and $R_{1b''}$ represents a phenyl optionally substituted by at least one $(C_1-C_6)$alkyl, preferably a methyl, and/or a halogen, preferably a fluorine; and
$R_3$ represents a phenyl optionally substituted by at least one radical selected in the group consisting of a halogen, a difluoromethyloxy, a trifluoromethyloxy, a —O—$(CH_2)_2$—$OCH_3$, a —O—$(CH_2)_2$—OH, and a methoxy, preferably a methoxy.

In a further preferred embodiment,
X represents a —N—R$_{1b''}$ unit;
n is 1;
R$_{1a}$, R$_{1a'}$, R$_{1c}$, R$_{1c'}$, R$_{1d}$, and R$_{1d'}$ represent a hydrogen, and R$_{1b''}$ represents a a phenyl optionally substituted by at least one (C$_1$-C$_6$)alkyl, preferably a methyl, and/or a halogen, preferably a fluorine; and
R$_3$ represents a phenyl optionally substituted by at least one radical selected in the group consisting of a halogen, a difluoromethyloxy, a trifluoromethyloxy, a —O—(CH$_2$)$_2$—OCH$_3$, a —O—(CH$_2$)$_2$—OH, and a methoxy, preferably a methoxy.

In a more preferred embodiment, the compound for use of formula (I) is selected from the group consisting of compounds of the table A.

In a particular embodiment, the viral infection is an infection by a virus selected from the group consisting of Alphaviridae, Flaviviridae, Hepadnaviridae, Herpesviridae, Orthomyxoviridae, Papoviviridae, Paramyxoviridae, Picornaviridae, Polyomaviridae, Reoviridae, Retroviridae, Rhabdoviridae, and Tobamoviruses.

In a further particular embodiment, the bacterial infection is an infection by a bacterium selected from the group consisting of *Helicobacter pylori, Burkholderia cepacia, Pseudomonas aeruginosa, Pseudomonas fluorescens, Pseudomonas acidovorans, Pseudomonas alcaligenes, Pseudomonas putida, Stenotrophomonas maltophilia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella parapertussis, Bordetella bronchiseptica, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Campylobacter fetus, Campylobacter jejuni, Campylobacter coli, Borrelia burgdorferi, Vibrio cholerae, Vibrio parahaemolyticus, Listeria monocytogenes, Neisseria gonorrhoeae, Neisseria meningitidis, Kingella denitrificans, Kingella indologenes, Kingella kingae, Kingella oralis, Legionella pneumophila, Moraxella bovis, Moraxella catarrhalis, Moraxella lacunata, Gardnerella vaginalis, Bacteroides fragilis, Bacteroides distasonis, Bacteroides vulgatus, Bacteroides ovalus, Bacteroides thetaiotaomicron, Bacteroides uniformis, Bacteroides eggerthii, Bacteroides splanchnicus, Clostridium difficile, Clostridium tetani, Mycobacterium species, Corynebacterium ulcerans, Streptococcus agalactiae, Gardnerella vaginitis, Streptococcus pyogenes, Enterococcus faecalis, Enterococcus faecium, Fusobacterium nucleatum, Porphyromonas gingivalis, Vibrio vulnificus, Clostridium botulinum, Corynebacterium diptheriae, Staphylococcus aureus, Staphylococcus epidermidis, Staphylococcus saprophyticus, Staphylococcus intermedius, Staphylococcus hyicus, Staphylococcus haemolyticus, Staphylococcus hominis,* and *Staphylococcus saccharolyticus.*

In a further particular embodiment, the cancer is selected from the group consisting of a breast cancer, a lung cancer, in particular NSCLC, a melanoma, a colorectal cancer, an astrocytoma cancer, a liver cancer, leukemia, in particular acute myeloid leukemia, a gastric cancer, a head and neck cancer, a cervical cancer, a pancreatic cancer, and an ovarian cancer.

In a further particular embodiment, the metabolic disease is selected from the group consisting of Diabetes mellitus, in particular Diabetes mellitus from NEET proteins, insulin resistance, insulin deficiency, hepatic steatosis, nonalcoholic fatty liver disease, Nonalcoholic steatohepatitis (NASH), glucose intolerance, obesity, lipodystrophy, coronary heart disease, diabetic retinopathy, diabetic neuropathy, diabetic nephropathy, hypoglycemia, hyperglycemia, beta cell dysfunction or hyperinsulinaemia, Wolfram syndrome, in particular Wolfram syndrome from NEET proteins, Polycystic ovary syndrome, pyruvate dehydrogenase deficiency, Albright hereditary osteodystrophy, cystinosis, fructose intolerance, Walker-Warburg syndrome, hypobetalipoproteinemia, Alström syndrome, and cirrhosis.

In a further particular embodiment, the cardiovascular disease is selected in the group consisting of myocardial injury, Ischemia, Ischemia reperfusion injury and hypertension.

In an additional particular embodiment, the inflammatory disease or disorder is selected from the group consisting of Crohn disease, inflammatory bowel disease, asthma, chronic obtrusive pulmonary disease (COPD), systemic lupus erythematosus, cystic fibrosis, psoriasis, infectious arthritis, and multiple sclerosis.

In a further particular embodiment, the iron storage disorder or disease is selected from the group consisting of Ferroportin Deficiency, Hereditary Hemochromatosis, including Hereditary Hemochromatosis due to HFE mutations and Hereditary Hemochromatosis due to transferrin receptor 2 mutations, Juvenile Hemochromatosis, including Juvenile Hemochromatosis due to hepcidin mutations and Juvenile Hemochromatosis due to hemojuvelin mutations, Iron Overload, including African Iron Overload, Iron Overload secondary to atransferrinemia and Iron Overload secondary to aceruloplasminemia, Thalassemia, Myelodysplastic Syndromes, Congenital Dyserythropoietic Anemias, Sickle Cell Disease and other Hemoglobinopathies, Red Cell Enzyme Deficiencies and Multiple Blood Transfusions.

The present invention also provides a new compound of formula (I):

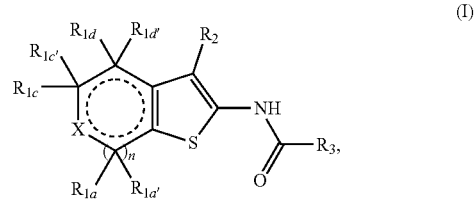

wherein:
X represents:
a —CR$_{1b}$R$_{1b'}$ unit,
a N—R$_{1b''}$ unit, or
an oxygen atom;
n is 0, 1, or 2;
when X is a —CR$_{1b}$R$_{1b'}$ unit, and n is 0 or 2, then one of R$_{1a}$, R$_{1a'}$, R$_{1b}$, R$_{1b'}$, R$_{1c}$, R$_{1c'}$, R$_{1d}$, and R$_{1d'}$ represents:
a halogen,
a (C$_1$-C$_6$)alkyl, optionally substituted by at least one halogen, preferably a fluorine, a ($C_1$-$C_6$)alkyloxy optionally substituted by at least one halogen, preferably a fluorine,
a cyano, or
an aryl optionally substituted by at least one radical selected in the group consisting of:
a halogen,
a ($C_1$-$C_6$)alkyl optionally substituted by at least one halogen, preferably a fluorine,
a hydroxy,
a ($C_1$-$C_6$)alkyloxy optionally substituted by at least one halogen, preferably a fluorine,
and the others represent a hydrogen;
when X is a N—$R_{1b''}$ unit, then $R_{1a}$, $R_{1a'}$, $R_{1c}$, $R_{1c'}$, $R_{1d}$, and $R_{1d'}$ represent independently:
a hydrogen,
a halogen,
a ($C_1$-$C_6$)alkyl, optionally substituted by at least one halogen, preferably a fluorine,
a ($C_1$-$C_6$)alkyloxy optionally substituted by at least one halogen, preferably a fluorine,
a cyano,
an aryl optionally substituted by at least one radical selected in the group consisting of:
a halogen,
a ($C_1$-$C_6$)alkyl optionally substituted by at least one halogen, preferably a fluorine,
a hydroxy, or
a ($C_1$-$C_6$)alkyloxy optionally substituted by at least one halogen, preferably a fluorine;
and $R_{1b''}$ represents:
an aryl optionally substituted by at least one radical selected in the group consisting of:
a halogen,
a ($C_1$-$C_6$)alkyl optionally substituted by at least one halogen, preferably a fluorine,
a hydroxy, and
a ($C_1$-$C_6$)alkyloxy optionally substituted by at least one halogen, preferably a fluorine, or
a ($C_1$-$C_6$)alkyl optionally substituted by at least one halogen, preferably a fluorine, or
a —$CO_2$—$R_8$ with $R_8$ being a ($C_1$-$C_6$)alkyl; and
when X is an oxygen atom, then at least one of $R_{1a}$, $R_{1a'}$, $R_{1c}$, $R_{1c'}$, $R_{1d}$, and $R_{1d'}$ represents:
a halogen,
a ($C_1$-$C_6$)alkyl, optionally substituted by at least one halogen, preferably a fluorine,
a ($C_1$-$C_6$)alkyloxy optionally substituted by at least one halogen, preferably a fluorine,
a cyano, or
an aryl optionally substituted by at least one radical selected in the group consisting of:
a halogen,
a ($C_1$-$C_6$)alkyl optionally substituted by at least one halogen, preferably a fluorine,
a hydroxy,
a ($C_1$-$C_6$)alkyloxy optionally substituted by at least one halogen, preferably a fluorine,
and the other represent a hydrogen;
$R_2$ represents —COOH; and
$R_3$ represents:
a 5-10 membered ring, saturated or unsaturated selected in the group consisting of:
an aryl optionally fused to a dioxole,
a heteroaryl,
a cycloalkyl,
a heterocycloalkyl, and
a 5-10 membered bridged carbocyclyl or heterocyclyl, said 5-10 membered ring is optionally substituted by at least one radical selected in the group consisting of:
a halogen,
a ($C_1$-$C_6$)alkyl optionally substituted by at least one halogen, preferably a fluorine, or a ($C_1$-$C_6$)alkyloxy,
a —NH—($C_1$-$C_6$)alkyl or a —N—(($C_1$-$C_6$)alkyl)$_2$, optionally substituted by a heterocycloalkyl or a ($C_1$-$C_6$)alkyloxy,
a —NH-heterocycloalkyl, a —NH-cycloalkyl, a —N(($C_1$-$C_6$)alkyl)-heterocycloalkyl or a —N(($C_1$-$C_6$)alkyl)-cycloalkyl, optionally substituted by a ($C_1$-$C_6$)alkyloxy or a —CO—$R_4$ with $R_4$ being a hydrogen or a ($C_1$-$C_6$)alkyl,
a hydroxy, a —CO—$R_4$ or a —$CO_2R_4$ with $R_4$ being a hydrogen or a ($C_1$-$C_6$)alkyl,
a ($C_1$-$C_6$)alkyloxy optionally substituted by at least one radical selected in the group consisting of a halogen, preferably a fluorine, a hydroxy, a ($C_1$-$C_6$)alkyloxy, a —$NR_5R_6$ with $R_5$ and $R_6$ are independently a hydrogen or a ($C_1$-$C_6$)alkyl, a —$NHCOR_7$, a —$NHCO_2R_7$, with $R_7$ being a ($C_1$-$C_6$)alkyl, a —$CO_2R_4$ with $R_4$ being a hydrogen or a ($C_1$-$C_6$)alkyl, and a heterocycle,
a —$NHCOR_7$ or —$NHCO_2R_7$ with $R_7$ being a ($C_1$-$C_6$)alkyl, and
a heterocycloalkyl, a heterocycloalkyloxy or a spiroheterocycloalkyl, optionally substituted by a ($C_1$-$C_6$)alkyloxy, a hydroxy, a halogen or a ($C_1$-$C_6$)alkyl optionally substituted by a ($C_1$-$C_6$)alkyloxy, or
a ($C_1$-$C_6$)alkyl or a ($C_2$-$C_6$)alkenyl, optionally substituted by a 5-10 membered ring as defined above or a —$CO_2R_4$ with $R_4$ being a hydrogen or a ($C_1$-$C_6$)alkyl;
and the stereoisomers, and the pharmaceutical salts thereof.

Preferably, a new compound of formula (I) is selected in the group consisting of:
2-Benzamido-6-phenyl-5,7-dihydro-4H-thieno[2,3-c]pyridine-3-carboxylic acid (Compound #52);
2-Benzamido-6-(4-fluoro-2-methylphenyl)-5,7-dihydro-4H-thieno[2,3-c]pyridine-3-carboxylic acid (Compound #53);
2-[(3,4-Dimethoxybenzoyl)amino]-6-(4-fluoro-2-methylphenyl)-5,7-dihydro-4H-thieno[2,3-c]pyridine-3-carboxylic acid (Compound #54);
2-[(2-Fluoro-4-methoxybenzoyl)amino]-6-(4-fluoro-2-methyl-phenyl)-5,7-dihydro-4H-thieno[2,3-c]pyridine-3-carboxylic acid (Compound #55);
2-Benzamido-6-(2,4-difluorophenyl)-5,7-dihydro-4H-thieno[2,3-c]pyridine-3-carboxylic acid (Compound #56);
2-Benzamido-6-(o-tolyl)-5,7-dihydro-4H-thieno[2,3-c]pyridine-3-carboxylic acid (Compound #57);
2-Benzamido-6-[4-(trifluoromethyl)phenyl]-5,7-dihydro-4H-thieno[2,3-c]pyridine-3-carboxylic acid (Compound #92);
2-[(3,4-Dimethoxybenzoyl)amino]-6-(4-fluorophenyl)-5,7-dihydro-4H-thieno[2,3-c]pyridine-3-carboxylic acid (Compound #113);
2-Benzamido-5,5-dimethyl-4,7-dihydrothieno[2,3-c]pyran-3-carboxylic acid (Compound #116);
2-[(3,4-Dimethoxybenzoyl)amino]-5,5-dimethyl-4,7-dihydrothieno[2,3-c]pyran-3-carboxylic acid (Compound #119);

6-tert-Butoxycarbonyl-2-[(2-methylbenzoyl)amino]-5,7-dihydro-4H-thieno[2,3-c]pyridine-3-carboxylic acid (Compound #126);
6-iso-Butyl-2-[(2-methylbenzoyl)amino]-5,7-dihydro-4H-thieno[2,3-c]pyridine-3-carboxylic acid formate salt (Compound #129);
2-Benzamido-5,5,7,7-tetramethyl-4H-thieno[2,3-c]pyran-3-carboxylic acid (Compound #175);
2-[[4-(3-Methoxyazetidin-1-yl)benzoyl]amino]-5,5,7,7-tetramethyl-4H-thieno[2,3-c]pyran-3-carboxylic acid (Compound #217);
5,5,7,7-Tetramethyl-2-(1H-pyrazole-3-carbonylamino)-4H-thieno[2,3-c]pyran-3-carboxylic acid (Compound #218);
5,5,7,7-Tetramethyl-2-[[4-(tetrahydropyran-4-ylamino)benzoyl]amino]-4H-thieno[2,3-c]pyran-3-carboxylic acid (Compound #232);
5,5,7,7-Tetramethyl-2-[[4-(tetrahydropyran-4-ylmethylamino) benzoyl]amino]-4H-thieno[2,3-c]pyran-3-carboxylic acid (Compound #233);
2-[[4-(2-Methoxyethylamino)benzoyl]amino]-5,5,7,7-tetramethyl-4H-thieno[2,3-c]pyran-3-carboxylic acid (Compound #234); and
2-[[4-[2-Methoxyethyl(methyl)amino]benzoyl]amino]-5,5,7,7-tetramethyl-4H-thieno[2,3-c]pyran-3-carboxylic acid (Compound #235).

A further object of the invention is a new compound selected in the group consisting of:
6-tert-Butyl-2-[(4-methoxybenzoyl)amino]-4,5,6,7-tetrahydrobenzothiophene-3-carboxylic acid (Compound #1);
6-tert-Butyl-2-[(3-methoxybenzoyl)amino]-4,5,6,7-tetrahydrobenzothiophene-3-carboxylic acid (Compound #2);
6-tert-Butyl-2-[(3,4-dimethoxybenzoyl)amino]-4,5,6,7-tetrahydrobenzothiophene-3-carboxylic acid (Compound #3);
6-tert-Butyl-2-[(3,4,5-trimethoxybenzoyl)amino]-4,5,6,7-tetrahydrobenzo thiophene-3-carboxylic acid (Compound #4);
6-tert-Butyl-2-[(2-fluoro-4-methoxybenzoyl)amino]-4,5,6,7-tetrahydrobenzothiophene-3-carboxylic acid (Compound #5);
6-tert-Butyl-2-[(2,3-difluoro-4-methoxy-benzoyl)amino]-4,5,6,7-tetrahydrobenzothiophene-3-carboxylic acid (Compound #6);
6-tert-Butyl-2-[[4-(difluoromethoxy)benzoyl]amino]-4,5,6,7-tetrahydrobenzothiophene-3-carboxylic acid (Compound #7);
6-tert-Butyl-2-[[4-(trifluoromethoxy)benzoyl]amino]-4,5,6,7-tetrahydrobenzothiophene-3-carboxylic acid (Compound #8);
6-tert-Butyl-2-[(4-morpholinobenzoyl)amino]-4,5,6,7-tetrahydrobenzothiophene-3-carboxylic acid (Compound #9);
6-tert-Butyl-2-[(4-chlorobenzoyl)amino]-4,5,6,7-tetrahydrobenzothiophene-3-carboxylic acid (Compound #10);
2-[[4-[3-(tert-Butoxycarbonylamino)propoxy]benzoyl]amino]-6-tert-butyl-4,5,6,7-tetrahydrobenzothiophene-3-carboxylic acid (Compound #11);
6-tert-Butyl-2-[[4-(2-hydroxyethoxy)benzoyl]amino]-4,5,6,7-tetrahydrobenzothiophene-3-carboxylic acid (Compound #12);
2-[(2-Methylbenzoyl)amino]-6-phenyl-4,5,6,7-tetrahydrobenzothiophene-3-carboxylic acid (Compound #45);
2-Benzamido-6-phenyl-4,5,6,7-tetrahydrobenzothiophene-3-carboxylic acid (Compound #46);
2-[(3,4-Dimethoxybenzoyl)amino]-6-phenyl-4,5,6,7-tetrahydrobenzothiophene-3-carboxylic acid (Compound #48);
2-[(4-Hydroxybenzoyl)amino]-6-phenyl-4,5,6,7-tetrahydrobenzothiophene-3-carboxylic acid (Compound #49);
2-[[4-(2-Hydroxyethoxy)benzoyl]amino]-6-phenyl-4,5,6,7-tetrahydrobenzothiophene-3-carboxylic acid (Compound #50);
2-[[4-(2-Methoxyethoxy)benzoyl]amino]-6-phenyl-4,5,6,7-tetrahydrobenzothiophene-3-carboxylic acid (Compound #51);
2-Benzamido-6-tert-butyl-4,5,6,7-tetrahydrobenzothiophene-3-carboxylic acid (Compound #71);
6-tert-Butyl-2-[(4-fluorobenzoyl)amino]-4,5,6,7-tetrahydrobenzothiophene-3-carboxylic acid (Compound #236);
6-tert-Butyl-2-[(2-fluorobenzoyl)amino]-4,5,6,7-tetrahydrobenzothiophene-3-carboxylic acid (Compound #73);
4-Methyl-2-[(4-morpholinobenzoyl)amino]-4,5,6,7-tetrahydrobenzothiophene-3-carboxylic acid (Compound #70);
6-tert-Butyl-2-(pyridine-2-carbonylamino)-4,5,6,7-tetrahydrobenzothiophene-3-carboxylic acid (Compound #72);
2-Benzamido-4-methyl-4,5,6,7-tetrahydrobenzothiophene-3-carboxylic acid (Compound #74);
2-[[4-(Difluoromethoxy)benzoyl]amino]-4-methyl-4,5,6,7-tetrahydrobenzothiophene-3-carboxylic acid (Compound #75);
2-[(2-Fluoro-4-methoxybenzoyl)amino]-4-methyl-4,5,6,7-tetrahydrobenzothiophene-3-carboxylic acid (Compound #76);
2-[(3,4-Dimethoxybenzoyl)amino]-4-methyl-4,5,6,7-tetrahydrobenzothiophene-3-carboxylic acid (Compound #81);
6-tert-Butyl-2-[(2-methylbenzoyl)amino]-4,5,6,7-tetrahydrobenzothiophene-3-carboxylic acid (Compound #82);
6-tert-Butyl-2-[(3-fluorobenzoyl)amino]-4,5,6,7-tetrahydrobenzothiophene-3-carboxylic acid (Compound #83);
6-Methyl-2-[(2-methylbenzoyl)amino]-4,5,6,7-tetrahydrobenzothiophene-3-carboxylic acid (Compound #86);
6-tert-Butyl-2-[(2-methylcyclohexanecarbonyl)amino]-4,5,6,7-tetrahydrobenzothiophene-3-carboxylic acid (Compound #89);
6-tert-Butyl-2-[(5-methoxypyridine-2-carbonyl)amino]-4,5,6,7-tetrahydrobenzothiophene-3-carboxylic acid (Compound #91);
2-[(4-Acetamidobenzoyl)amino]-6-tert-butyl-4,5,6,7-tetrahydrobenzothiophene-3-carboxylic acid (Compound #93);
6-tert-Butyl-2-[[2-(trifluoromethyl)benzoyl]amino]-4,5,6,7-tetrahydrobenzothiophene-3-carboxylic acid (Compound #100);
6-tert-Butyl-2-[(2,2-difluoro-1,3-benzodioxole-5-carbonyl)amino]-4,5,6,7-tetrahydrobenzothiophene-3-carboxylic acid (Compound #99);
6-tert-Butyl-2-[(1-methylpyrazole-4-carbonyl)amino]-4,5,6,7-tetrahydrobenzothiophene-3-carboxylic acid (Compound #101);
2-[[3-(Difluoromethoxy)benzoyl]amino]-4-methyl-4,5,6,7-tetrahydrobenzothiophene-3-carboxylic acid (Compound #102);
2-Benzamido-6-iso-propoxy-4,5,6,7-tetrahydrobenzothiophene-3-carboxylic acid (Compound #103);
6-tert-Butyl-2-[(2-methoxybenzoyl)amino]-4,5,6,7-tetrahydrobenzothiophene-3-carboxylic acid (Compound #104);
2-(2,2-Dimethylpropanoylamino)-6-phenyl-4,5,6,7-tetrahydrobenzothiophene-3-carboxylic acid (Compound #106);
6-tert-Butyl-2-[(2-chlorobenzoyl)amino]-4,5,6,7-tetrahydrobenzothiophene-3-carboxylic acid (Compound #107);
2-[[4-(Difluoromethoxy)benzoyl]amino]-4-phenyl-4,5,6,7-tetrahydrobenzothiophene-3-carboxylic acid (Compound #108);

6-tert-Butyl-2-[(3-methylfuran-2-carbonyl)amino]-4,5,6,7-tetrahydrobenzothiophene-3-carboxylic acid (Compound #110);

6-tert-Butyl-2-[(2-methylbenzoyl)amino]benzothiophene-3-carboxylic acid (Compound #111);

2-Benzamido-4-phenyl-4,5,6,7-tetrahydrobenzothiophene-3-carboxylic acid (Compound #112);

6-tert-Butyl-2-(cyclohexanecarbonylamino)-4,5,6,7-tetrahydrobenzothiophene-3-carboxylic acid (Compound #115);

6-tert-Butyl-2-[(2,6-dimethylbenzoyl)amino]-4,5,6,7-tetrahydrobenzothiophene-3-carboxylic acid (Compound #118);

6-tert-Butyl-2-(piperidine-1-carbonylamino)-4,5,6,7-tetrahydrobenzothiophene-3-carboxylic acid (Compound #120);

2-Benzamido-6-(4-hydroxyphenyl)-4,5,6,7-tetrahydrobenzothiophene-3-carboxylic acid (Compound #122);

6-tert-Butyl-2-(pyridine-4-carbonylamino)-4,5,6,7-tetrahydrobenzothiophene-3-carboxylic acid (Compound #123);

2-[[4-(3-Aminopropoxy)benzoyl]amino]-6-tert-butyl-4,5,6,7-tetrahydrobenzothiophene-3-carboxylic acid hydrochloride salt (Compound #124);

6-tert-Butyl-2-[(2-phenylacetyl)amino]-4,5,6,7-tetrahydrobenzothiophene-3-carboxylic acid (Compound #125);

6-tert-Butyl-2-[[4-(6-methoxy-6-oxo-hexoxy)benzoyl]amino]-4,5,6,7-tetrahydrobenzothiophene-3-carboxylic acid (Compound #172); and 2-Benzamido-5-phenyl-4,5,6,7-tetrahydrobenzothiophene-3-carboxylic acid (Compound #240).

Another object of the invention is a new compound as defined above for use as a medicine. A further object of the invention is a pharmaceutical composition comprising a new compound as defined above, and an acceptable pharmaceutical excipient. In another further particular embodiment, the present invention relates to a new compound of the present invention for use in the treatment of aging or a neurodegenerative disease or disorder.

DETAILED DESCRIPTION OF THE INVENTION

Definitions

According to the present invention, the terms below have the following meanings:

The terms mentioned herein with prefixes such as for example $C_1$-$C_3$, $C_1$-$C_6$ or $C_2$-$C_6$ can also be used with lower numbers of carbon atoms such as $C_1$-$C_2$, $C_1$-$C_5$, or $C_2$-$C_5$. If, for example, the term $C_1$-$C_3$ is used, it means that the corresponding hydrocarbon chain may comprise from 1 to 3 carbon atoms, especially 1, 2 or 3 carbon atoms. If, for example, the term $C_1$-$C_6$ is used, it means that the corresponding hydrocarbon chain may comprise from 1 to 6 carbon atoms, especially 1, 2, 3, 4, 5 or 6 carbon atoms. If, for example, the term $C_2$-$C_6$ is used, it means that the corresponding hydrocarbon chain may comprise from 2 to 6 carbon atoms, especially 2, 3, 4, 5 or 6 carbon atoms.

The term "alkyl" refers to a saturated, linear or branched aliphatic group. The term "($C_1$-$C_3$)alkyl" more specifically means methyl, ethyl, propyl, or isopropyl. The term "($C_1$-$C_6$)alkyl" more specifically means methyl, ethyl, propyl, isopropyl, butyl, isobutyl, tert-butyl, pentyl or hexyl. In a preferred embodiment, the "alkyl" is a methyl, an ethyl, a propyl, an isopropyl, or a tert-butyl, more preferably a methyl.

The term "alkenyl" refers to an unsaturated, linear or branched aliphatic group comprising at least one carbon-carbon double bound. The term "($C_2$-$C_6$)alkenyl" more specifically means ethenyl, propenyl, isopropenyl, butenyl, isobutenyl, pentenyl, or hexenyl.

The term "alkoxy" or "alkyloxy" corresponds to the alkyl group as above defined bonded to the molecule by an —O— (ether) bond. ($C_1$-$C_3$)alkoxy includes methoxy, ethoxy, propyloxy, and isopropyloxy. ($C_1$-$C_6$)alkoxy includes methoxy, ethoxy, propyloxy, isopropyloxy, butyloxy, isobutyloxy, tert-butyloxy, pentyloxy and hexyloxy. In a preferred embodiment, the "alkoxy" or "alkyloxy" is a methoxy.

The term "cycloalkyl" corresponds to a saturated or unsaturated mono-, bi- or tri-cyclic alkyl group comprising between 3 and 20 atoms of carbons. It also includes fused, bridged, or spiro-connected cycloalkyl groups. The term "cycloalkyl" includes for instance cyclopropyl, cyclobutyl, cyclopentyl, and cyclohexyl. The term "cycloalkyl" may also refer to a 5-10 membered bridged carbocyclyl such as bicyclo[2,2,1]heptanyl, bicyclo[2,2,2]octanyl, or adamantyl, preferably bicyclo[2,2,2]octanyl. In a preferred embodiment, the "cycloalkyl" is a cyclopropyl, cyclobutyl, cyclopentyl or a cyclohexyl.

The term "heterocycloalkyl" corresponds to a saturated or unsaturated cycloalkyl group as above defined further comprising at least one heteroatom such as nitrogen, oxygen, or sulphur atom. It also includes fused, bridged, or spiro-connected heterocycloalkyl groups. Representative heterocycloalkyl groups include, but are not limited to 3-dioxolane, benzo [1,3] dioxolyl, azetidinyl, oxetanyl, pyrazolinyl, pyranyl, thiomorpholinyl, pyrazolidinyl, piperidyl, piperazinyl, 1,4-dioxanyl, imidazolinyl, pyrrolinyl, pyrrolidinyl, piperidinyl, imidazolidinyl, morpholinyl, 1,4-dithianyl, pyrrolidinyl, oxozolinyl, oxazolidinyl, isoxazolinyl, isoxazolidinyl, thiazolinyl, thiazolidinyl, isothiazolinyl, isothiazolidinyl, dihydropyranyl, tetrahydro-2H-pyranyl, tetrahydrofuranyl, and tetrahydrothiophenyl. The term "heterocycloalkyl" may also refer to a 5-10 membered bridged heterocyclyl such as 7-oxabicyclo[2,2,1]heptanyl. In a particular embodiment, it may also refer to spiro-connected heterocycloalkyl groups or spiroheterocycloalkyl groups such as for instance oxetanyl spiro-connected with azetidinyl or piperidinyl. In a preferred embodiment, the heterocycloalkyl group is azetidinyl, oxetanyl, pyranyl, tetrahydrofuranyl, morpholinyl, piperidinyl, piperazinyl, and oxetanyl spiro-connected with azetidinyl or piperidinyl.

The term "aryl" corresponds to a mono- or bi-cyclic aromatic hydrocarbons having from 6 to 12 carbon atoms. For instance, the term "aryl" includes phenyl, biphenyl, or naphthyl. In a preferred embodiment, the aryl is a phenyl.

The term "heteroaryl" as used herein corresponds to an aromatic, mono- or poly-cyclic group comprising between 5 and 14 atoms and comprising at least one heteroatom such as nitrogen, oxygen or sulphur atom. Examples of such mono- and poly-cyclic heteroaryl group may be: pyridinyl, thiazolyl, thiophenyl, furanyl, pyrrolyl, pyrazolyl, imidazolyl, triazolyl, tetrazolyl, benzofuranyl, thianaphthalenyl, indolyl, indolinyl, quinolinyl, isoquinolinyl, benzimidazolyl, tetrahydroquinolinyl, tetrahydroisoquinolinyl, triazinyl, thianthrenyl, isobenzofuranyl, chromenyl, xanthenyl, phenoxanthinyl, isothiazolyl, isoxazolyl, pyrazinyl, pyridazinyl, indolizinyl, isoindolyl, indazolyl, purinyl, quinolizinyl, phtalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, indolinyl, isoindolinyl, oxazolidinyl, benzotriazolyl, benzoisoxazolyl, oxindolyl, benzoxazolinyl, benzothienyl, benzothiazolyl, isatinyl, dihydropyridyl, pyrimidinyl, s-triazinyl, oxazolyl, or thiofuranyl. In a preferred embodiment, the heteroaryl group is a pyridinyl, furanyl, pyrazolyl, pyrazinyl, pyrimidinyl, pyridazinyl, and isoxazolyl.

The terms "fused arylheterocycloalkyl" and "fused arylcycloalkyl" correspond to a bicyclic group in which an aryl as above defined is bounded to the heterocycloalkyl or the cycloalkyl as above defined by at least two carbons. In other terms, the aryl shares a carbon bond with the heterocycloalkyl or the cycloalkyl. A fused arylheterocycloalkyl is for instance a benzodioxole (phenyl fused to a dioxole) or an isobenzofurane. A fused arylcycloalkyl is for instance an indane.

The term "halogen" corresponds to a fluorine, chlorine, bromine, or iodine atom, preferably a fluorine, chlorine or bromine.

The expression "substituted by at least" means that the radical is substituted by one or several groups of the list.

The "stereoisomers" are isomeric compounds that have the same molecular formula and sequence of bonded atoms, but differ in the 3D-dimensional orientations of their atoms in space. The stereoisomers include enantiomers, diastereoisomers, Cis-trans and E-Z isomers, conformers, and anomers. In a preferred embodiment of the invention, the stereoisomers include diastereoisomers and enantiomers. The enantiomers compounds may be prepared from the racemate compound using any purification method known by a skilled person, such as LC/MS and chiral HPLC analysis methods and chiral SFC purification methods, such as those disclosed in the examples (Example A—Chemistry, Table 1 and Table 3).

The "pharmaceutically salts" include inorganic as well as organic acids salts. Representative examples of suitable inorganic acids include hydrochloric, hydrobromic, hydroiodic, phosphoric, and the like. Representative examples of suitable organic acids include formic, acetic, trichloroacetic, trifluoroacetic, propionic, benzoic, cinnamic, citric, fumaric, maleic, methanesulfonic and the like. Further examples of pharmaceutically inorganic or organic acid addition salts include the pharmaceutically salts listed in J. Pharm. Sci. 1977, 66, 2, and in Handbook of Pharmaceutical Salts: Properties, Selection, and Use edited by P. Heinrich Stahl and Camille G. Wermuth 2002. In a preferred embodiment, the salt is selected from the group consisting of maleate, chlorhydrate, bromhydrate, and methanesulfonate. The "pharmaceutically salts" also include inorganic as well as organic base salts. Representative examples of suitable inorganic bases include sodium or potassium salt, an alkaline earth metal salt, such as a calcium or magnesium salt, or an ammonium salt. Representative examples of suitable salts with an organic base includes for instance a salt with methylamine, dimethylamine, trimethylamine, piperidine, morpholine or tris-(2-hydroxyethyl)amine.

As used herein, the terms "treatment", "treat" or "treating" refer to any act intended to ameliorate the health status of patients such as therapy, prevention, prophylaxis and retardation of a disease, in particular an infection, preferably a viral infection. In certain embodiments, such terms refer to the amelioration or eradication of the disease, or symptoms associated with it. In other embodiments, this term refers to minimizing the spread or worsening of the disease, resulting from the administration of one or more therapeutic agents to a subject with such a disease.

As used herein, the terms "subject", "individual" or "patient" are interchangeable and refer to an animal, preferably to a mammal, even more preferably to a human, including adult, child, newborn and human at the prenatal stage. However, the term "subject" can also refer to non-human animals, in particular mammals such as dogs, cats, horses, cows, pigs, sheep and non-human primates, among others.

The terms "quantity," "amount," and "dose" are used interchangeably herein and may refer to an absolute quantification of a molecule.

As used herein, the terms "active principle", "active ingredient" and "active pharmaceutical ingredient" are equivalent and refers to a component of a pharmaceutical composition having a therapeutic effect.

As used herein, the term "therapeutic effect" refers to an effect induced by an active ingredient, or a pharmaceutical composition according to the invention, capable to prevent or to delay the appearance or development of a disease or disorder, or to cure or to attenuate the effects of a disease or disorder.

As used herein, the term "effective amount" refers to a quantity of an active ingredient or of a pharmaceutical composition which prevents, removes or reduces the deleterious effects of the disease, particularly infectious disease. It is obvious that the quantity to be administered can be adapted by the man skilled in the art according to the subject to be treated, to the nature of the disease, etc. In particular, doses and regimen of administration may be function of the nature, of the stage and of the severity of the disease to be treated, as well as of the weight, the age and the global health of the subject to be treated, as well as of the judgment of the doctor.

As used herein, the term "excipient or pharmaceutically acceptable carrier" refers to any ingredient except active ingredients that is present in a pharmaceutical composition. Its addition may be aimed to confer a particular consistency or other physical or gustative properties to the final product. An excipient or pharmaceutically acceptable carrier must be devoid of any interaction, in particular chemical, with the active ingredients.

The term "modulator", as used herein, refers to a molecule, a chemical or a substance targeting, added, applied or active to another, to modulate a reaction or to prevent an unwanted change. As used herein, the term "modulator" refers to any molecule or compound having an effect on Fe—S cluster binding by the NEET protein. The "modulator" as used herein may be either a stabiliser or a destabiliser. The term "stabiliser" as used herein refers to any compound, chemical, or substance able to stabilize the Fe—S cluster binding the NEET protein. Particularly, a stabiliser reduces the off-rate of iron (Fe) or slows the release of bound Fe—S. In a preferred embodiment, a compound of the invention as disclosed herein may be a "stabiliser" when it is able to increase the time needed to reach 50% Fe—S cluster bound loss by more than 25%. The term "destabiliser" as used herein refers to any compound, chemical, or substance able to destabilize the Fe—S cluster binding the NEET protein. Particularly, a destabiliser enhances the off-rate of iron (Fe). In a preferred embodiment, a compound of the invention as disclosed herein may be a "destabiliser" when it is able to decrease the time needed to reach 50% Fe—S cluster bound loss by more than 25%. The effect of the modulator can be determined by the protocol detailed in Example B2.

Compounds

Compounds for Therapeutic Applications According to the Invention

As illustrated by examples, the inventors have demonstrated an antiviral effect for the compounds of formula (I). Accordingly, the compounds can be useful as an antiviral drug, i.e., for treating a viral infection. The compounds can also be useful for treating a bacterial infection, cancer, a metabolic disease, a cardiovascular disease, iron storage disorder or an inflammatory disorder.

Accordingly, the present invention relates to a compound for use according to the present invention, said compound having the formula (I):

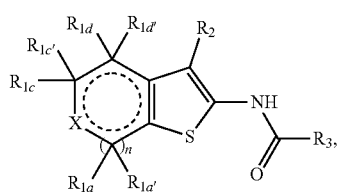

wherein:
X represents:
  a —$CR_{1b}R_{1b'}$ unit,
  a —N—$R_{1b''}$ unit, or
  an oxygen atom;
n is 0, 1, or 2;
when X is a —$CR_{1b}R_{1b'}$ unit, then at most one of $R_{1a}$, $R_{1a'}$, $R_{1b}$, $R_{1b'}$, $R_{1c}$, $R_{1c'}$, $R_{1d}$, and $R_{1d'}$ represents:
  a halogen,
  a ($C_1$-$C_6$)alkyl, optionally substituted by at least one halogen, preferably a fluorine,
  a ($C_1$-$C_6$)alkyloxy optionally substituted by at least one halogen, preferably a fluorine,
  a cyano, or
  an aryl optionally substituted by at least one radical selected in the group consisting of:
    a halogen,
    a ($C_1$-$C_6$)alkyl optionally substituted by at least one halogen, preferably a fluorine,
    a hydroxy, and
    a ($C_1$-$C_6$)alkyloxy optionally substituted by at least one halogen, preferably a fluorine,
  and the others represent a hydrogen;
when X is a —N—$R_{1b''}$ unit or an oxygen atom, then $R_{1a}$, $R_{1a'}$, $R_{1c}$, $R_{1c'}$, $R_{1d}$, and $R_{1d'}$ represent independently:
  a hydrogen,
  a halogen,
  a ($C_1$-$C_6$)alkyl, optionally substituted by at least one halogen, preferably a fluorine,
  a ($C_1$-$C_6$)alkyloxy optionally substituted by at least one halogen, preferably a fluorine,
  a cyano,
  an aryl optionally substituted by at least one radical selected in the group consisting of:
    a halogen,
    a ($C_1$-$C_6$)alkyl optionally substituted by at least one halogen, preferably a fluorine,
    a hydroxy, or
    a ($C_1$-$C_6$)alkyloxy optionally substituted by at least one halogen, preferably a fluorine;

and $R_{1b''}$ represents:
  an aryl optionally substituted by at least one radical selected in the group consisting of:
    a halogen,
    a ($C_1$-$C_6$)alkyl optionally substituted by at least one halogen, preferably a fluorine,
    a hydroxy, and
    a ($C_1$-$C_6$)alkyloxy optionally substituted by at least one halogen, preferably a fluorine,
  a ($C_1$-$C_6$)alkyl optionally substituted by at least one halogen, preferably optionally substituted by at least one fluorine, or
  a —$CO_2$—$R_8$ with $R_8$ being a ($C_1$-$C_6$)alkyl;
$R_2$ represents —COOH;
$R_3$ represents:
  a 5-10 membered ring, saturated or unsaturated selected in the group consisting of:
    an aryl optionally fused to a dioxole,
    a heteroaryl,
    a cycloalkyl,
    a heterocycloalkyl, and
    a 5-10 membered bridged carbocyclyl or heterocyclyl,
  said 5-10 membered ring is optionally substituted by at least one radical selected in the group consisting of:
    a halogen,
    a ($C_1$-$C_6$)alkyl optionally substituted by at least one halogen, preferably a fluorine, or a ($C_1$-$C_6$)alkyloxy,
    a —NH—($C_1$-$C_6$)alkyl or a —N—(($C_1$-$C_6$)alkyl)$_2$, optionally substituted by a heterocycloalkyl or a ($C_1$-$C_6$)alkyloxy,
    a —NH-heterocycloalkyl, a —NH-cycloalkyl, a —N(($C_1$-$C_6$)alkyl)-heterocycloalkyl or a —N(($C_1$-$C_6$)alkyl)-cycloalkyl, optionally substituted by a ($C_1$-$C_6$)alkyloxy or a —CO—$R_4$ with $R_4$ being a hydrogen or a ($C_1$-$C_6$)alkyl,
    a hydroxy, a —CO—$R_4$ or a —$CO_2R_4$ with $R_4$ being a hydrogen or a ($C_1$-$C_6$)alkyl,
    a ($C_1$-$C_6$)alkyloxy optionally substituted by at least one radical selected in the group consisting of a halogen, preferably a fluorine, a hydroxy, a ($C_1$-$C_6$)alkyloxy, a —$NR_5R_6$ with $R_5$ and $R_6$ are independently a hydrogen or a ($C_1$-$C_6$)alkyl, a —$NHCOR_7$, a —$NHCO_2R_7$, with $R_7$ being a ($C_1$-$C_6$)alkyl, a —$CO_2R_4$ with $R_4$ being a hydrogen or a ($C_1$-$C_6$)alkyl, and a heterocycle,
    a —$NHCOR_7$ or —$NHCO_2R_7$ with $R_7$ being a ($C_1$-$C_6$)alkyl, and
    a heterocycloalkyl, a heterocycloalkyloxy or a spiroheterocycloalkyl, optionally substituted by a ($C_1$-$C_6$)alkyloxy, a hydroxy, a halogen or a ($C_1$-$C_6$)alkyl optionally substituted by a ($C_1$-$C_6$)alkyloxy, or
  a ($C_1$-$C_6$)alkyl or a ($C_2$-$C_6$)alkenyl, optionally substituted by a 5-10 membered ring as defined above or a —$CO_2R_4$ with $R_4$ being a hydrogen or a ($C_1$-$C_6$)alkyl;
and with the proviso that $R_3$ is not a 5-membered heteroaryl;
and the stereoisomers, and the pharmaceutical salts thereof.

As used herein, the expression "at most one of $R_{1a}$, $R_{1a'}$, $R_{1b}$, $R_{1b'}$, $R_{1c}$, $R_{1c'}$, $R_{1d}$, and $R_{1d'}$ represents a radical as above defined and the others represent hydrogen" means that zero or one of $R_{1a}$, $R_{1a'}$, $R_{1b}$, $R_{1b'}$, $R_{1c}$, $R_{1c'}$, $R_{1d}$, and $R_{1d'}$ is substituted by a radical as above defined and the others are not substituted and represent a hydrogen. In the embodiment in which zero of $R_{1a}$, $R_{1a'}$, $R_{1b}$, $R_{1b'}$, $R_{1c}$, $R_{1c'}$, $R_{1d}$, and $R_{1d'}$ represents a radical as above defined, then all of $R_{1a}$, $R_{1a'}$, $R_{1b}$, $R_{1b'}$, $R_{1c}$, $R_{1c'}$, $R_{1d}$, and $R_{1d'}$ are unsubstituted and thus represent a hydrogen. In this particular aspect, $R_{1a}$, $R_{1a'}$, $R_{1b}$, $R_{1b'}$, $R_{1c}$, $R_{1c'}$, $R_{1d}$, and $R_{1d'}$ represent a hydrogen.

In a particular embodiment, X represents a —$CR_{1b}R_{1b'}$ and one of $R_{1a}$, $R_{1a'}$, $R_{1b}$, $R_{1b'}$, $R_{1c}$, $R_{1c'}$, $R_{1d}$, and $R_{1d'}$ represents a ($C_1$-$C_6$)alkyl, a ($C_1$-$C_6$)alkyloxy or a phenyl optionally substituted by at least one radical selected in the group consisting of a hydroxy, a halogen, preferably a fluorine, and a ($C_1$-$C_3$)alkyl, optionally substituted by at least one halogen, preferably a fluorine, and the others represent a hydrogen. In one particular aspect, one of $R_{1a}$, $R_{1a'}$, $R_{1b}$, $R_{1b'}$, $R_{1c}$, $R_{1c'}$, $R_{1d}$, and $R_{1d'}$ represents a ($C_1$-$C_6$)alkyl, preferably a methyl or a tert-butyl, more preferably a tert-butyl, and the others represent a hydrogen. Preferably, $R_{1a}$, $R_{1a'}$, $R_{1c}$, $R_{1c'}$, $R_{1d}$, and $R_{1d'}$ represent a hydrogen and one of $R_{1b}$ and $R_{1b'}$ represents a tert-buytyl and the other is a hydrogen. In one further particular aspect, one of $R_{1a}$, $R_{1a'}$, $R_{1b}$, $R_{1b'}$, $R_{1c}$, $R_{1c'}$, $R_{1d}$, and $R_{1d'}$ represents a phenyl, optionally substituted by at least one hydroxy, and the others represent a hydrogen. Preferably, $R_{1a}$, $R_{1a'}$, $R_{1c}$, $R_{1c'}$, $R_{1d}$, and $R_{1d'}$ represent a hydrogen and one of $R_{1b}$ and $R_{1b'}$ represents a phenyl optionally substituted by at least one radical selected in the group consisting of a halogen, a difluoromethyloxy, a trifluoromethyloxy, a methoxy, a methyl and a hydroxy, preferably a hydroxy, and the other is a hydrogen. According to this particular embodiment, n is preferably 1.

In a further particular embodiment, X represents a N—$R_{1b''}$ unit with $R_{1b''}$ represents an aryl optionally substituted by at least one radical selected in the group consisting of:
  a halogen, preferably a fluorine, and
  a ($C_1$-$C_6$)alkyl, preferably a methyl, optionally substituted by at least one halogen, preferably optionally substituted by at least one fluorine, and n, $R_{1a}$, $R_{1a'}$, $R_{1c}$, $R_{1c'}$, $R_{1d}$, $R_{1d'}$, $R_2$ and $R_3$ are such as defined herein. Preferably $R_{1a}$, $R_{1a'}$, $R_{1c}$, $R_{1c'}$, $R_{1d}$, and $R_{1d'}$ are a hydrogen.

According to this particular embodiment, n is preferably 1.

In a preferred embodiment, $R_{1b''}$ represents a phenyl, optionally substituted by at least one radical selected in the group consisting of a fluorine, a methyl and a trifluoromethyl. In a further preferred embodiment, $R_{1b''}$ represents a phenyl substituted by a methyl and a fluorine.

In a further particular embodiment, X represents a N—$R_{1b''}$ unit with $R_{1b''}$ represents a —$CO_2$—$R_8$ with $R_8$ being a ($C_1$-$C_6$)alkyl, preferably a tert-butyl.

In an additional embodiment, X represents a N—$R_{1b''}$ unit with $R_{1b''}$ represents a ($C_1$-$C_6$)alkyl, preferably an isobutyl.

In a further particular embodiment, X represents an oxygen atom, and n, $R_{1a}$, $R_{1a'}$, $R_{1c}$, $R_{1c'}$, $R_{1d}$, $R_{1d'}$, $R_2$ and $R_3$ are such as defined herein.

According to this particular embodiment, n is preferably 1.

In a preferred embodiment, $R_{1c}$ and $R_{1c'}$ represent a methyl, and $R_{1a}$, $R_{1a'}$, $R_{1d}$, and $R_{1d'}$ are a hydrogen. In a further preferred embodiment, $R_{1a}$, $R_{1a'}$, $R_{1c}$, and $R_{1c'}$ represent a methyl, and $R_{1d}$, and $R_{1d'}$ are a hydrogen.

According to the present invention, the compounds for use are of formula (I), in which $R_3$ represents:
  a 5-10 membered ring, saturated or unsaturated selected in the group consisting of:
    an aryl optionally fused to a dioxole,
    a heteroaryl,
    a cycloalkyl,
    a heterocycloalkyl, and
    a 5-10 membered bridged carbocyclyl or heterocyclyl,
  said 5-10 membered ring is optionally substituted by at least one radical selected in the group consisting of:
    a halogen,
    a ($C_1$-$C_6$)alkyl optionally substituted by at least one halogen, preferably a fluorine, or a ($C_1$-$C_6$)alkyloxy,
    a —NH—($C_1$-$C_6$)alkyl or a —N—(($C_1$-$C_6$)alkyl)$_2$, optionally substituted by a heterocycloalkyl or a ($C_1$-$C_6$)alkyloxy,
    a —NH-heterocycloalkyl, a —NH-cycloalkyl, a —N(($C_1$-$C_6$)alkyl)-heterocycloalkyl or a —N(($C_1$-$C_6$)alkyl)-cycloalkyl, optionally substituted by a ($C_1$-$C_6$)alkyloxy or a —CO—$R_4$ with $R_4$ being a hydrogen or a ($C_1$-$C_6$)alkyl,
    a hydroxy, a —CO—$R_4$ or a —$CO_2R_4$ with $R_4$ being a hydrogen or a ($C_1$-$C_6$)alkyl,
    a ($C_1$-$C_6$)alkyloxy optionally substituted by at least one radical selected in the group consisting of a halogen, preferably a fluorine, a hydroxy, a ($C_1$-$C_6$)alkyloxy, a —$NR_5R_6$ with $R_5$ and $R_6$ are independently a hydrogen or a ($C_1$-$C_6$)alkyl, a —NH-$COR_7$, a —$NHCO_2R_7$, with $R_7$ being a ($C_1$-$C_6$)alkyl, a —$CO_2R_4$ with $R_4$ being a hydrogen or a ($C_1$-$C_6$)alkyl, and a heterocycle,
    a —$NHCOR_7$ or —$NHCO_2R_7$ with $R_7$ being a ($C_1$-$C_6$)alkyl, and
    a heterocycloalkyl, a heterocycloalkyloxy or a spiroheterocycloalkyl, optionally substituted by a ($C_1$-$C_6$)alkyloxy, a hydroxy, a halogen or a ($C_1$-$C_6$)alkyl optionally substituted by a ($C_1$-$C_6$)alkyloxy, or
  a ($C_1$-$C_6$)alkyl or a ($C_2$-$C_6$)alkenyl, optionally substituted by a 5-10 membered ring as defined above or a —$CO_2R_4$ with $R_4$ being a hydrogen or a ($C_1$-$C_6$)alkyl,
and n, $R_{1a}$, $R_{1a'}$, $R_{1c}$, $R_{1c'}$, $R_{1d}$, $R_{1d'}$, and $R_2$ are such as defined herein.

In a particular embodiment, $R_3$ represents a phenyl, a cyclohexyl, a piperidinyl or a pyridinyl, preferably a phenyl, optionally substituted by at least one radical selected in the group consisting of:
  a halogen, preferably a fluorine or a chlorine,
  a ($C_1$-$C_6$)alkyl, preferably a methyl, optionally substituted by at least one halogen, preferably a fluorine,
  a —NH—($C_1$-$C_6$)alkyl or a —N—(($C_1$-$C_6$)alkyl)$_2$, optionally substituted by a ($C_1$-$C_6$)alkyloxy, a heterocycloalkyl selected in the group consisting of a tetrahydropyranyl, a tetrahydrofuranyl, an oxetanyl, a piperidinyl, and an azetidinyl, preferably a tetrahydropyranyl, or a cycloalkyl, preferably a cyclobutyl or a cyclohexyl, said cycloalkyl and heterocycloalkyl being optionally substituted by a ($C_1$-$C_6$)alkyloxy,
  a —NH-tetrahydropyranyl, a —N($CH_3$)-tetrahydropyranyl, a —NH-tetrahydrofuranyl, a NH-piperidinyl, a —NH-azetidinyl, a —NH-oxetanyl, a —NH-cyclohexyl, or a —N($CH_3$)-cyclobutyl, preferably a —NH-tetrahydropyranyl, optionally substituted by a ($C_1$-$C_6$)alkyloxy;
  a hydroxy,
  a ($C_1$-$C_6$)alkyloxy optionally substituted by at least one radical selected in the group consisting of a halogen, preferably a fluorine, a hydroxy, a ($C_1$-$C_6$)alkyloxy, a —$NR_5R_6$ with $R_5$ and $R_6$ are independently a hydrogen or a ($C_1$-$C_6$)alkyl, a —$NHCOR_7$, a —$NHCO_2R_7$, with R$_7$ being a (C$_1$-C$_6$)alkyl, and a —CO$_2$R$_4$ with R$_4$ being a hydrogen or a (C$_1$-C$_6$)alkyl, a —NHCOR$_7$ or —NHCO$_2$R$_7$ with R$_7$ being a (C$_1$-C$_6$) alkyl, preferably a methyl, and a heterocycloalkyl, preferably a morpholinyl, a piperidinyl, a piperazinyl, a tetrahydropyranyl, and an azetidinyl, preferably a morpholinyl or an azetidinyl, optionally substituted by a (C$_1$-C$_6$)alkyloxy.

In a preferred embodiment, R$_3$ is a phenyl, i.e. an unsubstituted phenyl.

In a further preferred embodiment, R$_3$ is a phenyl substituted by at least one radical selected in the group consisting of a halogen, preferably a chlorine, a fluorine, or a bromine, a methyl, a trifluoromethyl, a hydroxy, a methoxy, a difluoromethoxy, a trifluoromethoxy, an ethoxy substituted by a methoxy (—O—(CH$_2$)$_2$—OCH$_3$) or by a hydroxy (—O—(CH$_2$)$_2$—OH), and a —NHCOR$_7$ with R$_7$ being a methyl.

In a further preferred embodiment, R$_3$ is a phenyl substituted by a heterocycle, preferably an azetidinyl, an oxatenyl, a morpholinyl, a piperidinyl, a piperazinyl, a tetrahydropyranyl, or an azetidinyl, said heterocycle being optionally substituted by a methoxy, an ethoxy, a hydroxy, a methyl optionally substituted by a methoxy, a halogen, preferably a fluorine.

In a further preferred embodiment, R$_3$ is a phenyl substituted by a —NH—(C$_1$-C$_6$)alkyl or a —N—((C$_1$-C$_6$)alkyl)$_2$, optionally substituted by a heterocycloalkyl or a (C$_1$-C$_6$) alkyloxy, preferably a —NH—CH$_2$-azetidinyl, a —NH—CH$_2$-oxatenyl, a —NH—(CH$_2$)$_2$—OCH$_3$, a —NH—(CH$_2$)$_3$—OCH$_3$, a —NH—CH$_2$-tetrahydropyranyl, a —N(CH$_3$)—CH$_2$-tetrahydropyranyl, and a —N(CH$_3$)—(CH$_2$)$_2$—OCH$_3$.

In a further preferred embodiment, R$_3$ is a phenyl substituted by a —NH-heterocycloalkyl, a —NH-cycloalkyl, a —N((C$_1$-C$_6$)alkyl)-cycloalkyl, or a —N((C$_1$-C$_6$)alkyl)-heterocycloalkyl, optionally substituted by a (C$_1$-C$_6$)alkyloxy or a —CO—R$_4$ with R$_4$ being a hydrogen or a (C$_1$-C$_6$)alkyl, preferably a —NH-tetrahydropyranyl, a —NH-tetrahydrofuranyl, a —NH-oxetanyl, a —NH-piperidinyl optionally substituted by a —CO—CH$_3$, a —NH-azetidinyl optionally substituted by a —CO—CH$_3$, a —N(CH$_3$)-azetidinyl optionally substituted by a —CO—CH$_3$, a —N(CH$_3$)-tetrahydropyranyl, and a —NH-cyclohexyl.

In a further preferred embodiment, R$_3$ is a phenyl substituted by a (C$_1$-C$_6$)alkyloxy, preferably a methoxy, an ethoxy, a propoxy, a butoxy or a pentoxy substituted by a radical selected in the group consisting of a —NHCO$_2$R$_7$, with R$_7$ being a methyl, a —NR$_5$R$_6$ with R$_5$ and R$_6$ are a hydrogen, a —CO$_2$R$_4$ with R$_4$ being a methyl, and a heterocycle, preferably a tetrahydropyranyl or a oxetanyl.

In a further preferred embodiment, R$_3$ is a phenyl substituted by a heterocycloalkyloxy, preferably a tetrahydropyranyloxy.

In a more preferred embodiment, R$_3$ is a phenyl substituted by a radical selected in the group consisting of:

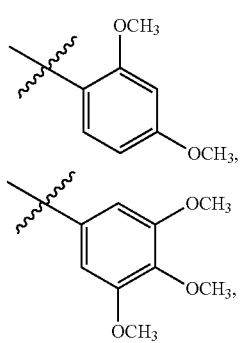

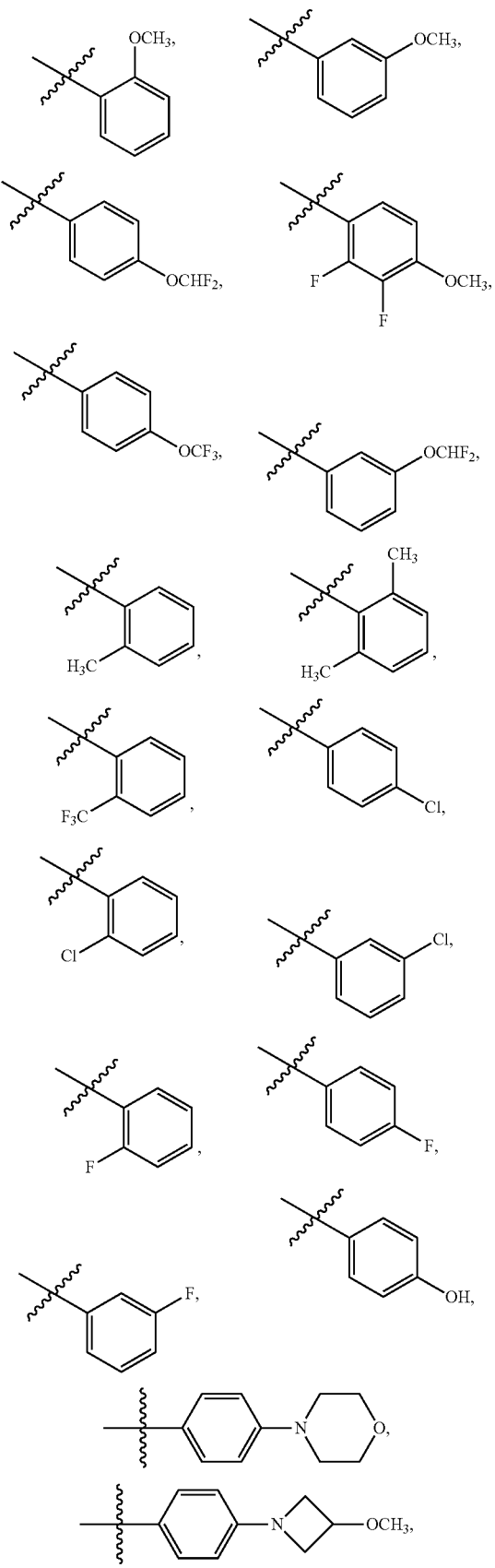

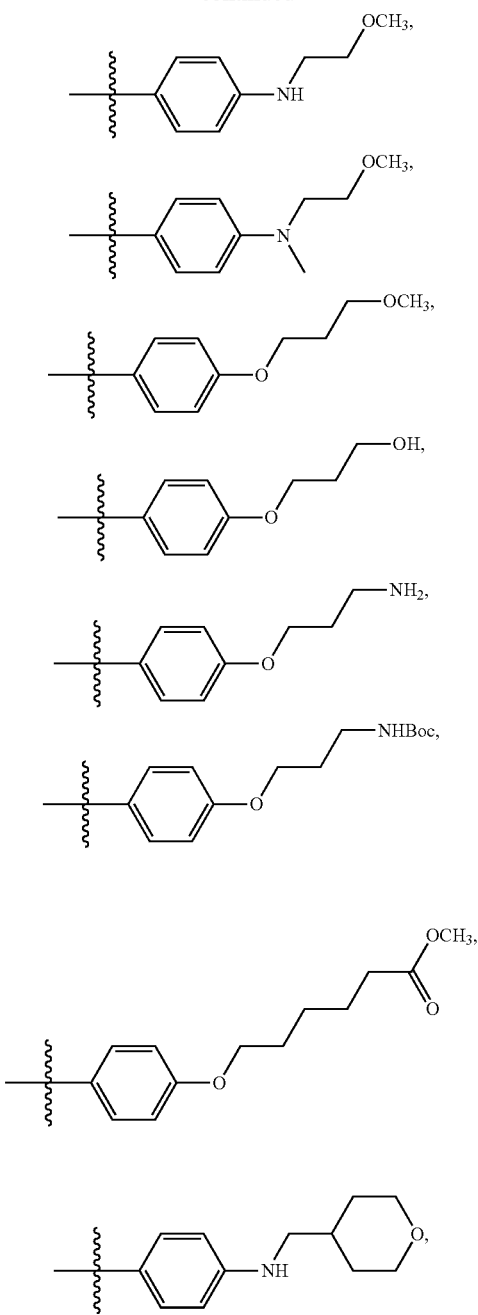
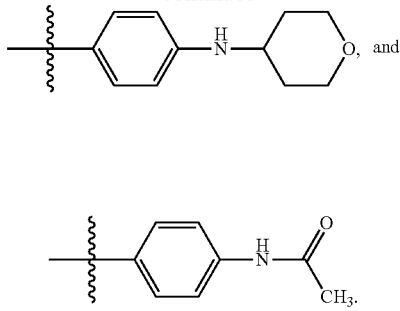

In a further particular embodiment, $R_3$ is an aryl fused to a dioxole, preferably a benzo[1,3]dioxole optionally substituted by at least one fluorine.

In a further particular embodiment, $R_3$ is a heteroaryl, preferably a pyridinyl optionally substituted by at least one radical selected in the group consisting of a methoxy, a methyl, and a morpholinyl, preferably a methoxy.

In a further particular embodiment, $R_3$ is a cycloalkyl, preferably a cyclohexyl, optionally substituted by a $(C_1\text{-}C_6)$ alkyl, preferably a methyl.

In a further particular embodiment, $R_3$ is a heterocycloalkyl, preferably a piperidinyl.

In a further particular embodiment, $R_3$ is a $(C_1\text{-}C_6)$alkyl, preferably a tert-butyl or a methyl substituted by a phenyl (i.e., a benzyl).

In a preferred embodiment,
X represents a —$CR_{1b}R_{1b'}$ unit;
n is 1;
$R_{1a}$, $R_{1a'}$, $R_{1c}$, $R_{1c'}$, $R_{1d}$, and $R_{1d'}$ represent a hydrogen, and one of $R_{1b}$ and $R_{1b'}$ represents a $(C_1\text{-}C_6)$alkyl, preferably a tert-butyl, or a phenyl, and the other is a hydrogen; and
$R_3$ represents a phenyl optionally substituted by at least one radical selected in the group consisting of a halogen, a difluoromethyloxy, a trifluoromethyloxy, a —O—$(CH_2)_2$—$OCH_3$, a —O—$(CH_2)_2$—OH, and a methoxy.

In a further preferred embodiment,
X represents a —N—$R_{1b}$ unit;
n is 1;
$R_{1a}$, $R_{1a'}$, $R_{1c}$, $R_{1c'}$, $R_{1d}$, and $R_{1d'}$ represent a hydrogen, and $R_{1b''}$ represents a phenyl optionally substituted by at least one $(C_1\text{-}C_6)$alkyl, preferably a methyl, and/or a halogen, preferably a fluorine; and
$R_3$ represents a phenyl optionally substituted by at least one radical selected in the group consisting of a halogen, a difluoromethyloxy, a trifluoromethyloxy, a —O—$(CH_2)_2$—$OCH_3$, a —O—$(CH_2)_2$—OH, and a methoxy, preferably a methoxy.

In a more preferred embodiment, a compound for use of formula (I) according to the present invention is selected in the group consisting of compounds of the table A below:

TABLE A

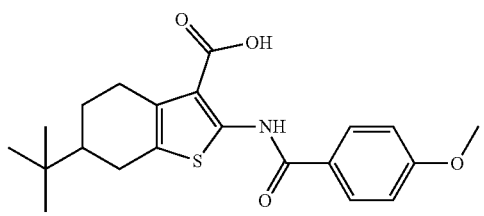 [SMILES: COc1ccc(C(=O)Nc2sc3c(c2C(=O)O)CCC(C(C)(C)C)C3)cc1]

Compound #1

TABLE A-continued
| | |
|---|---|
| 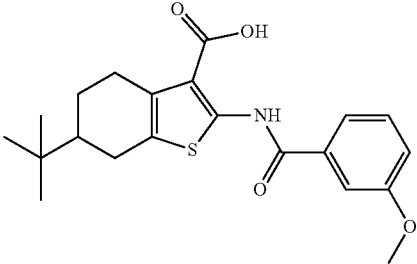 [SMILES: COc1cccc(C(=O)Nc2sc3c(c2C(=O)O)CCC(C(C)(C)C)C3)c1] | Compound #2 |
| 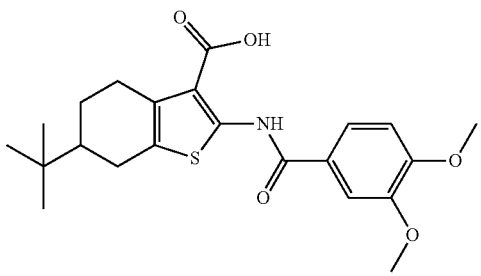 [SMILES: COc1ccc(C(=O)Nc2sc3c(c2C(=O)O)CCC(C(C)(C)C)C3)cc1OC] | Compound #3 |
| 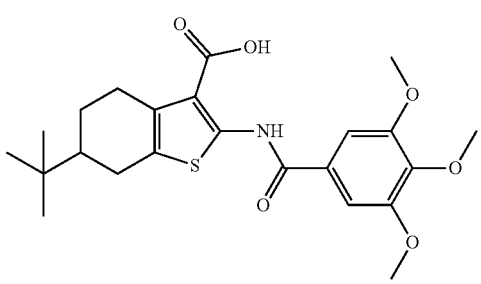 [SMILES: COc1cc(C(=O)Nc2sc3c(c2C(=O)O)CCC(C(C)(C)C)C3)cc(OC)c1OC] | Compound #4 |
| 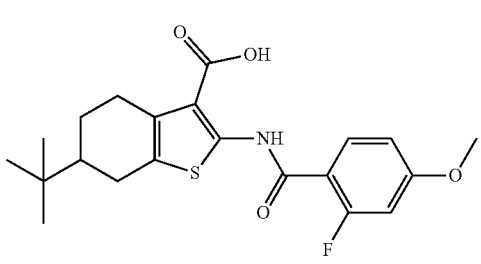 [SMILES: COc1ccc(C(=O)Nc2sc3c(c2C(=O)O)CCC(C(C)(C)C)C3)c(F)c1] | Compound #5 |
| 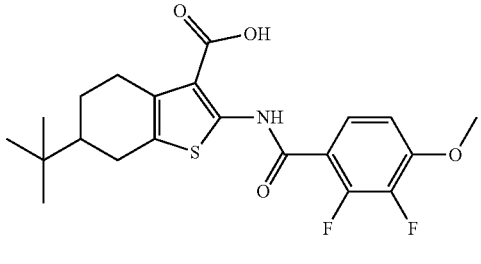 [SMILES: COc1ccc(C(=O)Nc2sc3c(c2C(=O)O)CCC(C(C)(C)C)C3)c(F)c1F] | Compound #6 |
| 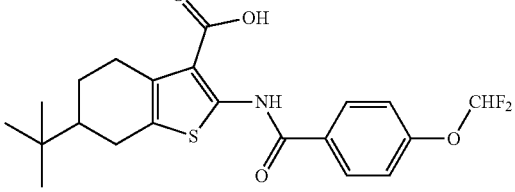 | Compound #7 |

TABLE A-continued

| | |
|---|---|
| (structure) | Compound #8 |
| (structure) | Compound #9 |
| (structure) | Compound #10 |
| (structure) | Compound #11 |
| (structure) | Compound #12 |
| (structure) | Compound #45 |
| (structure) | Compound #46 |

TABLE A-continued
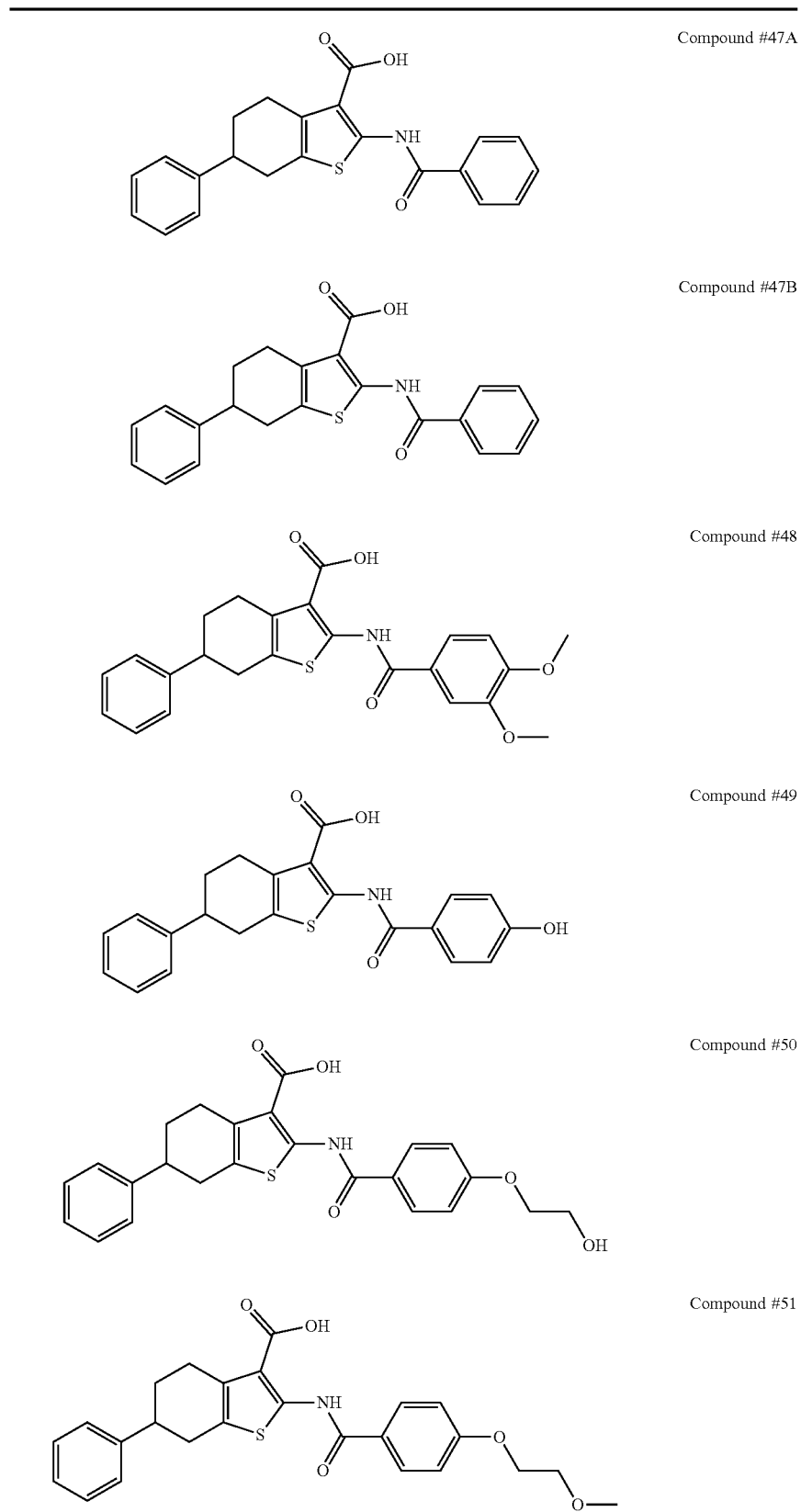
Compound #47A
Compound #47B
Compound #48
Compound #49
Compound #50
Compound #51

TABLE A-continued

| Structure | |
|---|---|
| (6-phenyl-4,5,6,7-tetrahydrothieno[2,3-c]pyridine-3-carboxylic acid, 2-benzamido) | Compound #52 |
| (6-(4-fluoro-2-methylphenyl)-4,5,6,7-tetrahydrothieno[2,3-c]pyridine-3-carboxylic acid, 2-benzamido) | Compound #53 |
| (6-(4-fluoro-2-methylphenyl)-4,5,6,7-tetrahydrothieno[2,3-c]pyridine-3-carboxylic acid, 2-(3,4-dimethoxybenzamido)) | Compound #54 |
| (6-(4-fluoro-2-methylphenyl)-4,5,6,7-tetrahydrothieno[2,3-c]pyridine-3-carboxylic acid, 2-(2-fluoro-4-methoxybenzamido)) | Compound #55 |
| (6-(2,4-difluorophenyl)-4,5,6,7-tetrahydrothieno[2,3-c]pyridine-3-carboxylic acid, 2-benzamido) | Compound #56 |
| (6-(2-methylphenyl)-4,5,6,7-tetrahydrothieno[2,3-c]pyridine-3-carboxylic acid, 2-benzamido) | Compound #57 |

TABLE A-continued
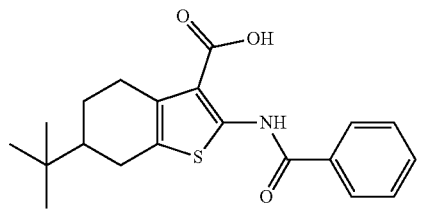 [SMILES: CC(C)(C)C1CCc2c(sc(NC(=O)c3ccccc3)c2C(=O)O)C1]
Compound #66
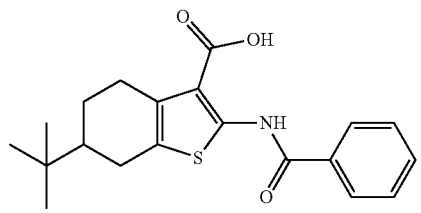 [SMILES: CC(C)(C)C1CCc2c(sc(NC(=O)c3ccccc3)c2C(=O)O)C1]
Compound #67
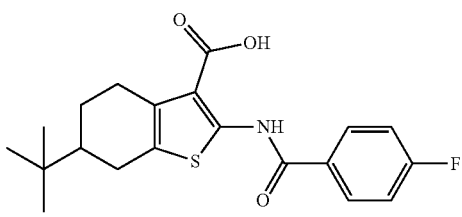 [SMILES: CC(C)(C)C1CCc2c(sc(NC(=O)c3ccc(F)cc3)c2C(=O)O)C1]
Compound #68
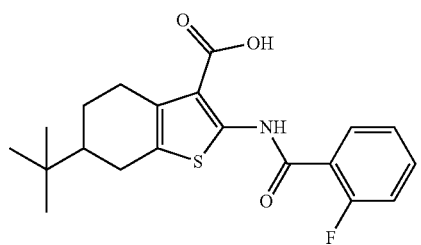 [SMILES: CC(C)(C)C1CCc2c(sc(NC(=O)c3ccccc3F)c2C(=O)O)C1]
Compound #69
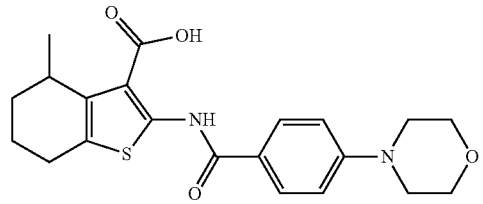 [SMILES: CC1CCCc2sc(NC(=O)c3ccc(N4CCOCC4)cc3)c(C(=O)O)c21]
Compound #70
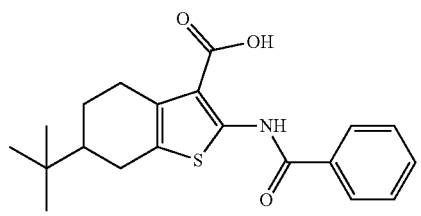 [SMILES: CC(C)(C)C1CCc2c(sc(NC(=O)c3ccccc3)c2C(=O)O)C1]
Compound #71
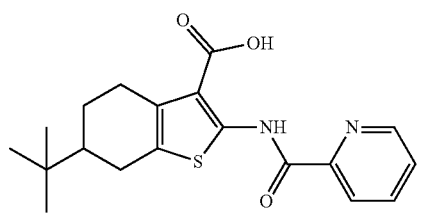 [SMILES: CC(C)(C)C1CCc2c(sc(NC(=O)c3ccccn3)c2C(=O)O)C1]
Compound #72

TABLE A-continued

| Structure | Compound |
|---|---|
| (tert-butyl-tetrahydrobenzothiophene-carboxylic acid with 2-fluorobenzamide) | Compound #73 |
| (4-methyl-tetrahydrobenzothiophene-carboxylic acid with benzamide) | Compound #74 |
| (4-methyl-tetrahydrobenzothiophene-carboxylic acid with 4-(difluoromethoxy)benzamide) | Compound #75 |
| (4-methyl-tetrahydrobenzothiophene-carboxylic acid with 2-fluoro-4-methoxybenzamide) | Compound #76 |
| (tetrahydrobenzothiophene-carboxylic acid with benzamide) | Compound #77 |
| (4-methyl-tetrahydrobenzothiophene-carboxylic acid with benzamide) | Compound #79 |
| (4-methyl-tetrahydrobenzothiophene-carboxylic acid with 3,4-dimethoxybenzamide) | Compound #81 |

TABLE A-continued
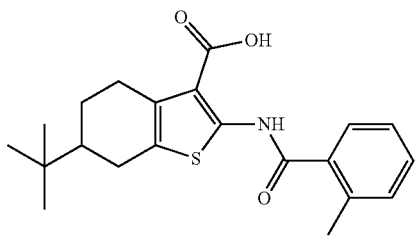 [SMILES: Cc1ccccc1C(=O)Nc1sc2c(c1C(=O)O)CCC(C(C)(C)C)C2] Compound #82
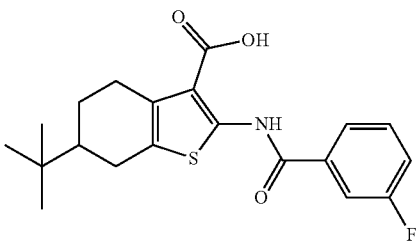 [SMILES: CC(C)(C)C1CCc2c(sc(NC(=O)c3cccc(F)c3)c2C(=O)O)C1] Compound #83
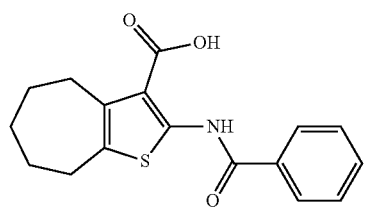 [SMILES: O=C(Nc1sc2c(c1C(=O)O)CCCCC2)c1ccccc1] Compound #84
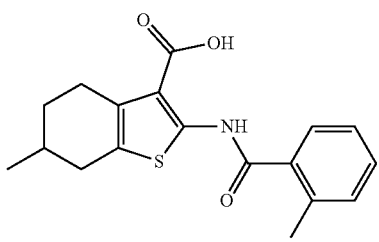 [SMILES: Cc1ccccc1C(=O)Nc1sc2c(c1C(=O)O)CCC(C)C2] Compound #86
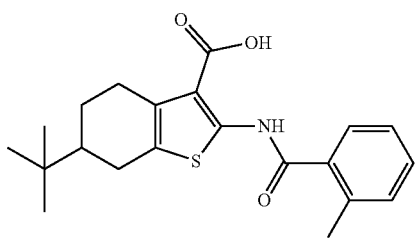 [SMILES: Cc1ccccc1C(=O)Nc1sc2c(c1C(=O)O)CCC(C(C)(C)C)C2] Compound #87
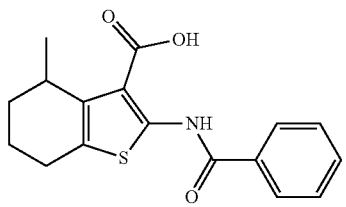 [SMILES: CC1CCCc2sc(NC(=O)c3ccccc3)c(C(=O)O)c21] Compound #88
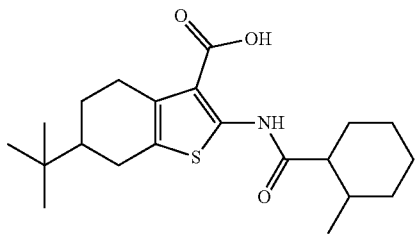 [SMILES: CC1CCCCC1C(=O)Nc1sc2c(c1C(=O)O)CCC(C(C)(C)C)C2] Compound #89

TABLE A-continued
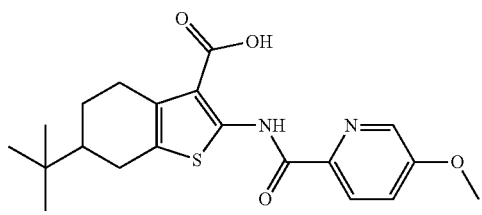 [SMILES: COc1ccc(C(=O)Nc2sc3c(c2C(=O)O)CCC(C(C)(C)C)C3)nc1]
Compound #91
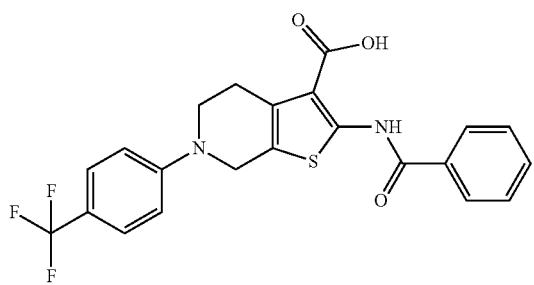 [SMILES: O=C(Nc1sc2c(c1C(=O)O)CCN(c1ccc(C(F)(F)F)cc1)C2)c1ccccc1]
Compound #92
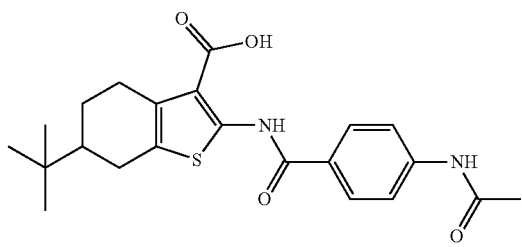 [SMILES: CC(=O)Nc1ccc(C(=O)Nc2sc3c(c2C(=O)O)CCC(C(C)(C)C)C3)cc1]
Compound #93
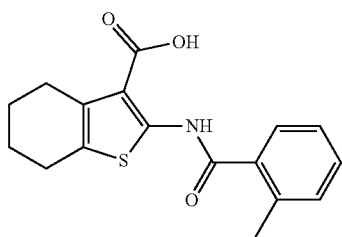 [SMILES: Cc1ccccc1C(=O)Nc1sc2c(c1C(=O)O)CCCC2]
Compound #95
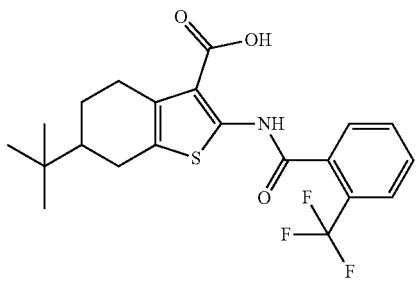 [SMILES: CC(C)(C)C1CCc2c(sc(NC(=O)c3ccccc3C(F)(F)F)c2C(=O)O)C1]
Compound #97
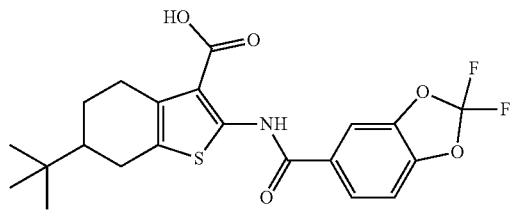 [SMILES: CC(C)(C)C1CCc2c(sc(NC(=O)c3ccc4c(c3)OC(F)(F)O4)c2C(=O)O)C1]
Compound #99

TABLE A-continued
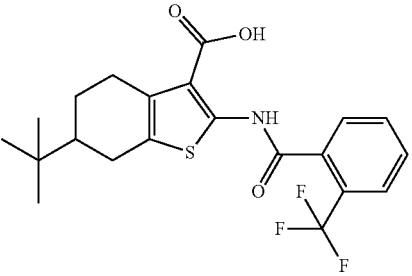 [SMILES: CC(C)(C)C1CCc2c(sc(NC(=O)c3ccccc3C(F)(F)F)c2C(=O)O)C1] Compound #100
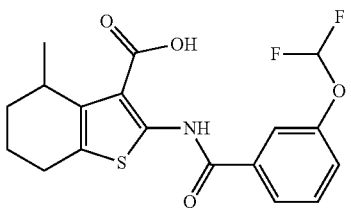 [SMILES: CC1CCCc2sc(NC(=O)c3cccc(OC(F)F)c3)c(C(=O)O)c21] Compound #102
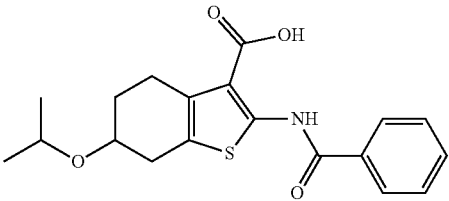 [SMILES: CC(C)OC1CCc2c(sc(NC(=O)c3ccccc3)c2C(=O)O)C1] Compound #103
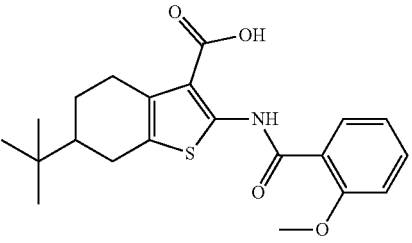 [SMILES: COc1ccccc1C(=O)Nc1sc2c(c1C(=O)O)CCC(C(C)(C)C)C2] Compound #104
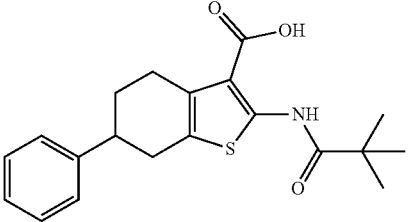 [SMILES: CC(C)(C)C(=O)Nc1sc2c(c1C(=O)O)CCC(c1ccccc1)C2] Compound #106
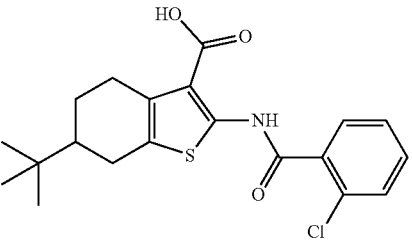 [SMILES: CC(C)(C)C1CCc2c(sc(NC(=O)c3ccccc3Cl)c2C(=O)O)C1] Compound #107

TABLE A-continued
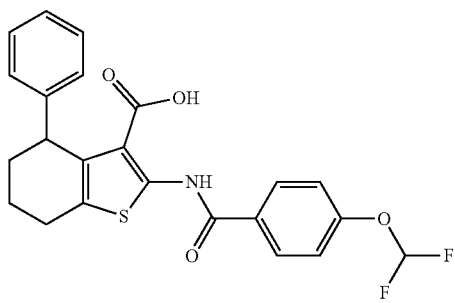 [SMILES: O=C(Nc1sc2c(c1C(=O)O)C(c1ccccc1)CCC2)c1ccc(OC(F)F)cc1]
Compound #108
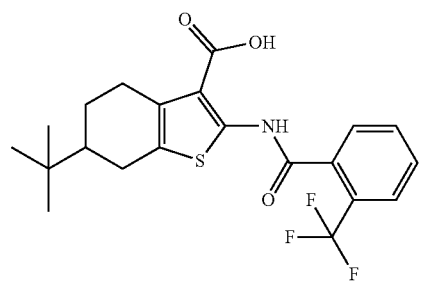 [SMILES: CC(C)(C)C1CCc2c(sc(NC(=O)c3ccccc3C(F)(F)F)c2C(=O)O)C1]
Compound #109
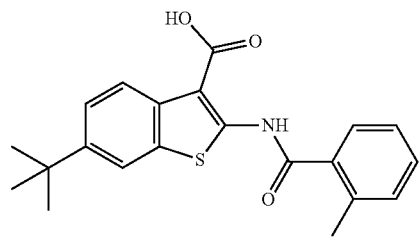 [SMILES: Cc1ccccc1C(=O)Nc1sc2cc(C(C)(C)C)ccc2c1C(=O)O]
Compound #111
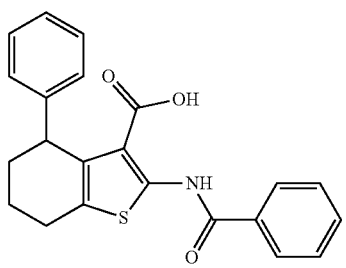 [SMILES: O=C(Nc1sc2c(c1C(=O)O)C(c1ccccc1)CCC2)c1ccccc1]
Compound #112
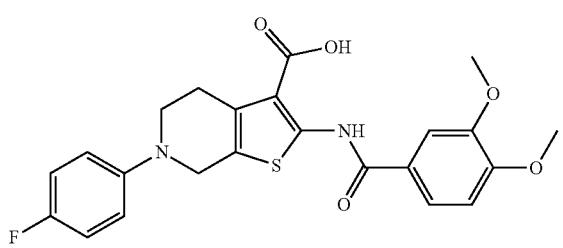 [SMILES: COc1ccc(C(=O)Nc2sc3c(c2C(=O)O)CCN(c2ccc(F)cc2)C3)cc1OC]
Compound #113
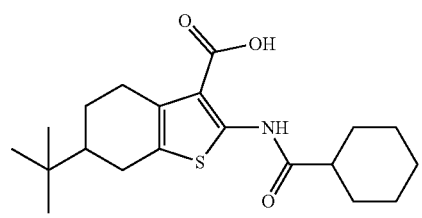 [SMILES: CC(C)(C)C1CCc2c(sc(NC(=O)C3CCCCC3)c2C(=O)O)C1]
Compound #115

TABLE A-continued
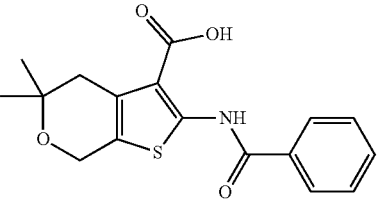 [SMILES: CC1(C)Cc2c(sc(NC(=O)c3ccccc3)c2C(=O)O)CO1] Compound #116
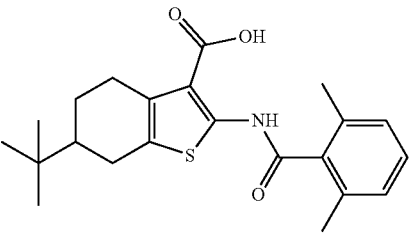 [SMILES: Cc1cccc(C)c1C(=O)Nc1sc2c(c1C(=O)O)CCC(C(C)(C)C)C2] Compound #118
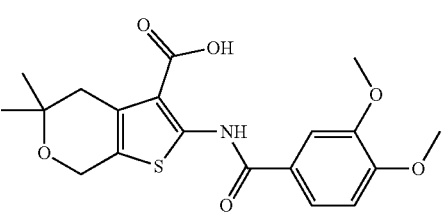 Compound #119
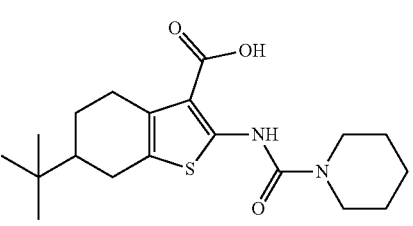 [SMILES: CC(C)(C)C1CCc2c(sc(NC(=O)N3CCCCC3)c2C(=O)O)C1] Compound #120
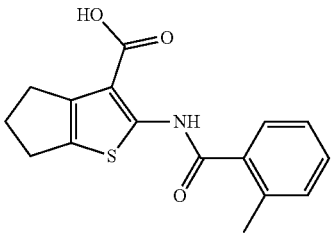 [SMILES: Cc1ccccc1C(=O)Nc1sc2c(c1C(=O)O)CCC2] Compound #121
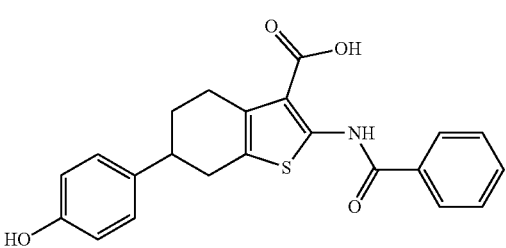 [SMILES: O=C(Nc1sc2c(c1C(=O)O)CCC(c1ccc(O)cc1)C2)c1ccccc1] Compound #122
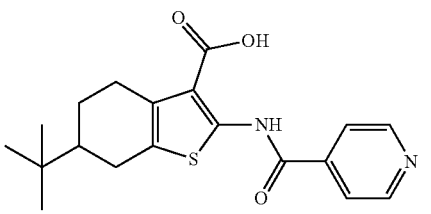 [SMILES: CC(C)(C)C1CCc2c(sc(NC(=O)c3ccncc3)c2C(=O)O)C1] Compound #123

TABLE A-continued
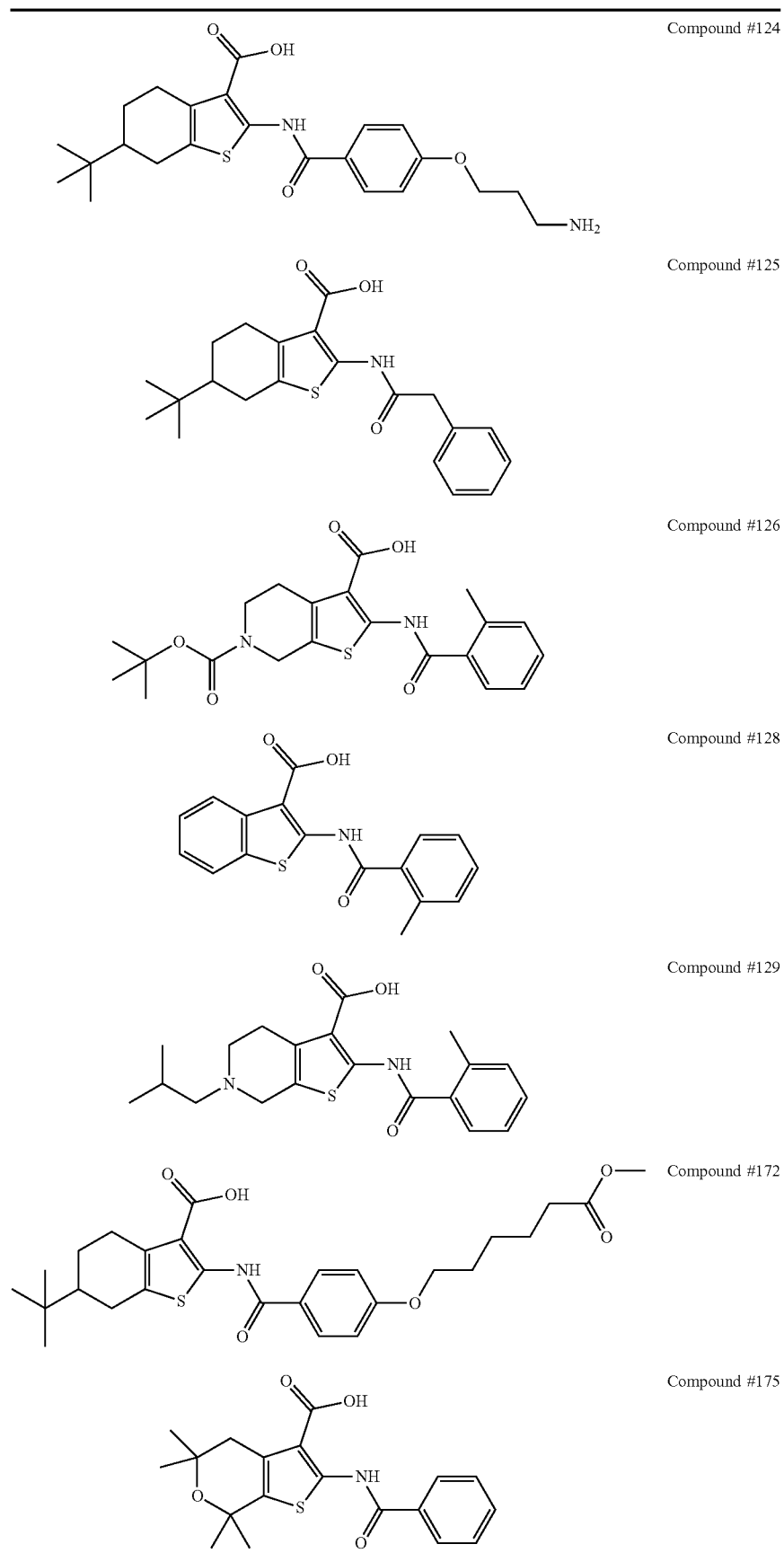
Compound #124
Compound #125
Compound #126
Compound #128
Compound #129
Compound #172
Compound #175

TABLE A-continued
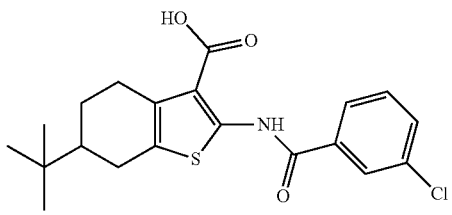 [SMILES: CC(C)(C)C1CCc2c(sc(NC(=O)c3cccc(Cl)c3)c2C(=O)O)C1] Compound #177
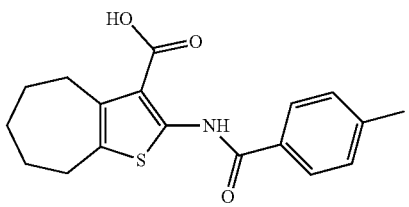 [SMILES: Cc1ccc(C(=O)Nc2sc3c(c2C(=O)O)CCCCC3)cc1] Compound #184
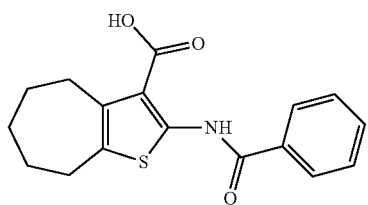 [SMILES: O=C(Nc1sc2c(c1C(=O)O)CCCCC2)c1ccccc1] Compound #185
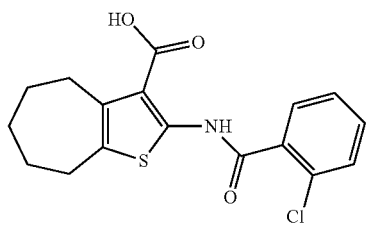 [SMILES: O=C(Nc1sc2c(c1C(=O)O)CCCCC2)c1ccccc1Cl] Compound #186
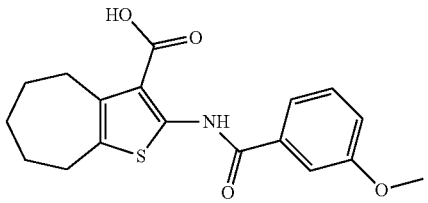 [SMILES: COc1cccc(C(=O)Nc2sc3c(c2C(=O)O)CCCCC3)c1] Compound #187
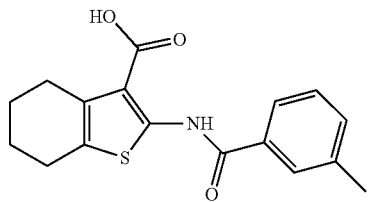 [SMILES: Cc1cccc(C(=O)Nc2sc3c(c2C(=O)O)CCCC3)c1] Compound #188
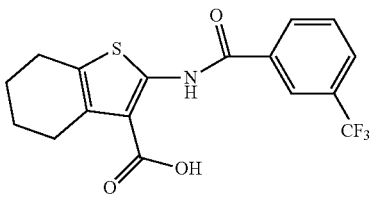 [SMILES: O=C(Nc1sc2c(c1C(=O)O)CCCC2)c1cccc(C(F)(F)F)c1] Compound #192

TABLE A-continued

| Structure | Compound |
|---|---|
| (4,5,6,7-tetrahydrobenzo[b]thiophene-3-carboxylic acid, 2-[[4-(trifluoromethyl)benzoyl]amino]-) | Compound #193 |
| (4,5,6,7-tetrahydrobenzo[b]thiophene-3-carboxylic acid, 2-[(4-isopropylbenzoyl)amino]-) | Compound #197 |
| (4,5,6,7-tetrahydrobenzo[b]thiophene-3-carboxylic acid, 2-[[2-(thiophen-3-yl)acetyl]amino]-) | Compound #198 |
| (4,5,6,7-tetrahydrobenzo[b]thiophene-3-carboxylic acid, 2-[[2-(thiophen-2-yl)acetyl]amino]-) | Compound #199 |
| (cyclopenta[b]thiophene-3-carboxylic acid, 2-[[4-(3-methoxyazetidin-1-yl)benzoyl]amino]-) | Compound #207 |
| (cyclopenta[b]thiophene-3-carboxylic acid, 2-(benzoylamino)-) | Compound #210 |
| (cyclopenta[b]thiophene-3-carboxylic acid, 2-[[4-[(tetrahydro-2H-pyran-4-yl)methylamino]benzoyl]amino]-) | Compound #211 |

TABLE A-continued

| | |
|---|---|
| (structure) | Compound #215 |
| (structure) | Compound #216 |
| (structure) | Compound #217 |
| (structure) | Compound #231 |
| (structure) | Compound #232 |
| (structure) | Compound #233 |
| (structure) | Compound #234 |

TABLE A-continued

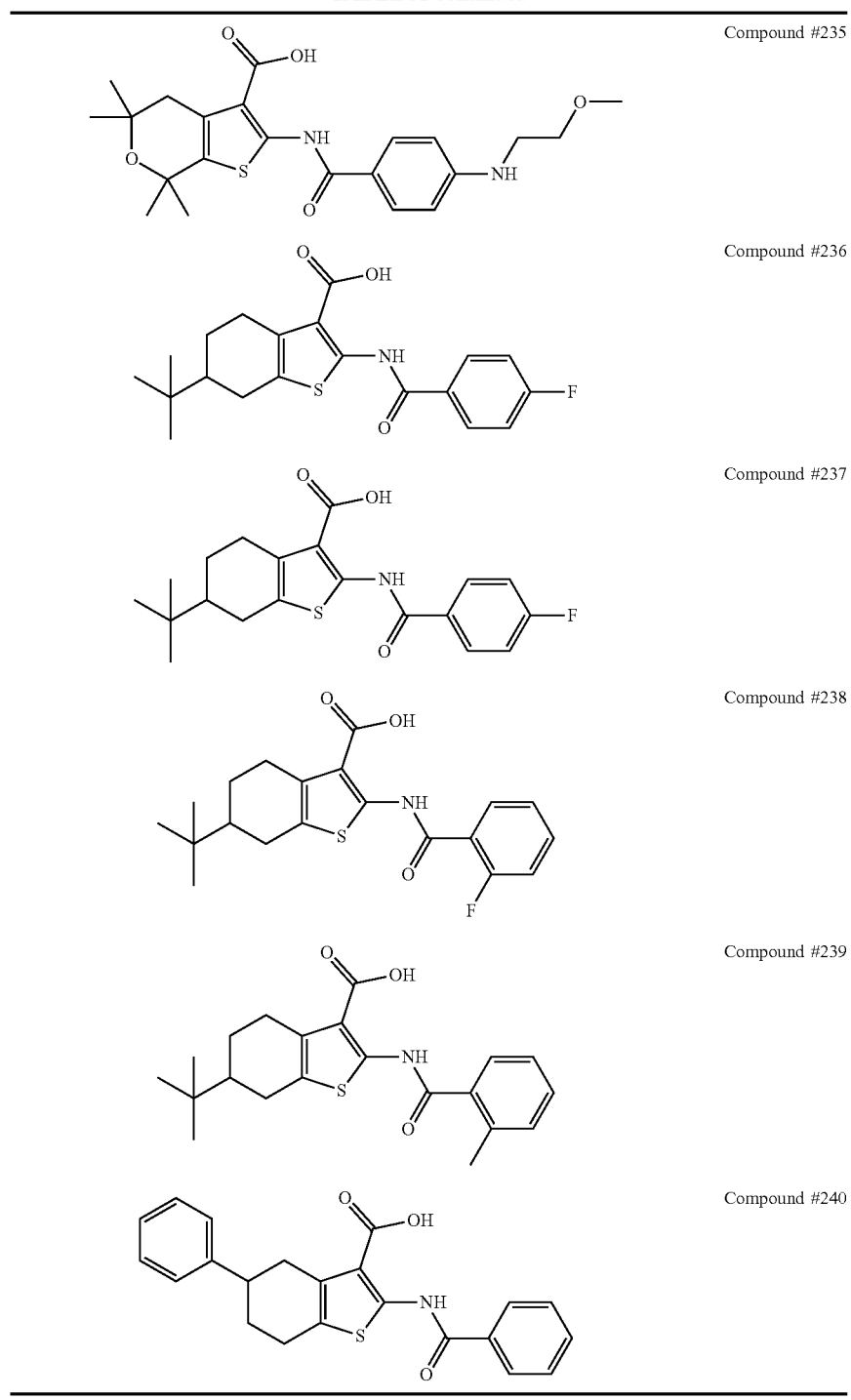

Compound #235

Compound #236

Compound #237

Compound #238

Compound #239

Compound #240

According to the invention, $R_2$ represents —COOH.

It is also described herein compounds of formula (I) as described above in any particular embodiments in which $R_2$ represents:

a —$CO_2R_4$ with $R_4$ being a ($C_1$-$C_6$)alkyl; or a 5-10 membered ring, saturated or unsaturated selected in the group consisting of an aryl, a heteroaryl, a cycloalkyl, and a heterocycloalkyl, said 5-10 membered ring is optionally substituted by a hydroxy, a halogen, or a ($C_1$-$C_6$)alkyl optionally substituted by at least one halogen, preferably optionally substituted by at least one fluorine, and n, $R_{1a}$, $R_{1a'}$, $R_{1c}$, $R_{1c'}$, $R_{1d}$, $R_{1d'}$ and $R_3$ are such as defined herein.

In one embodiment, the 5-10 membered ring is selected so as to be an (bio)isostere of a carboxyl group.

In a preferred embodiment, $R_2$ represents a heteroaryl, preferably a tetrazolyl, an aryl optionally substituted by a hydroxy, preferably a phenyl substituted by a hydroxy, or a —$CO_2R_4$ with $R_4$ being a hydrogen or a ($C_1$-$C_6$)alkyl, preferably an ethyl. In a more preferred embodiment, $R_2$ represents a —$CO_2R_4$ with $R_4$ being a hydrogen, i.e. —COOH.

For instance, compounds according to this embodiment include Compound #178, Compound #179, Compound #180, Compound #181, Compound #182, Compound #183, Compound #189, Compound #190, Compound #191, Compound #194, Compound #195, Compound #196 and Compound #200.

TABLE A'

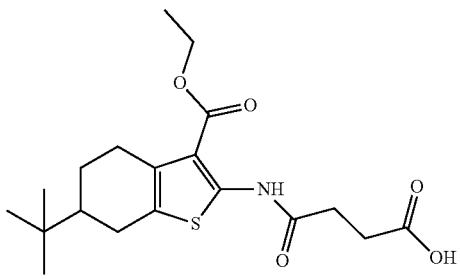 [SMILES: CCOC(=O)c1c(NC(=O)CCC(=O)O)sc2c1CCC(C(C)(C)C)C2]

Compound #178

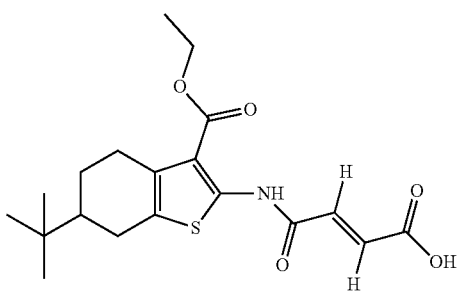 [SMILES: CCOC(=O)c1c(NC(=O)/C=C/C(=O)O)sc2c1CCC(C(C)(C)C)C2]

Compound #179

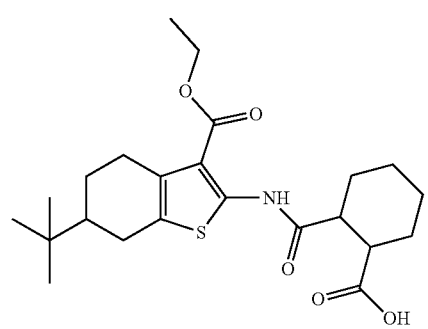 [SMILES: CCOC(=O)c1c(NC(=O)C2CCCCC2C(=O)O)sc2c1CCC(C(C)(C)C)C2]

Compound #180

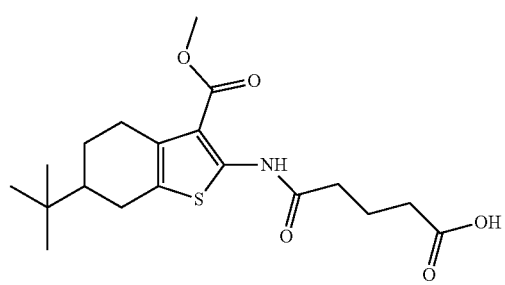 [SMILES: COC(=O)c1c(NC(=O)CCCC(=O)O)sc2c1CCC(C(C)(C)C)C2]

Compound #181

TABLE A'-continued
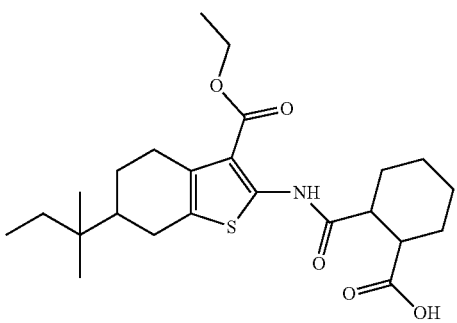 [SMILES: CCOC(=O)c1c(NC(=O)C2CCCCC2C(=O)O)sc2c1CCC(C(C)(C)CC)C2]
Compound #182
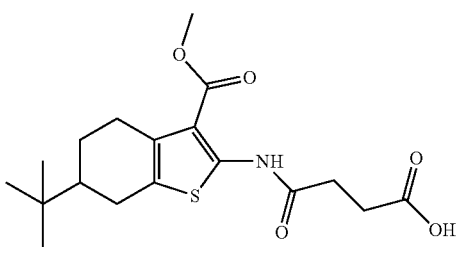 [SMILES: COC(=O)c1c(NC(=O)CCC(=O)O)sc2c1CCC(C(C)(C)C)C2]
Compound #183
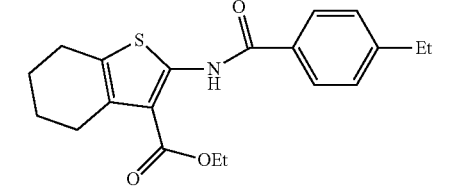 [SMILES: CCOC(=O)c1c(NC(=O)c2ccc(CC)cc2)sc2c1CCCC2]
Compound #189
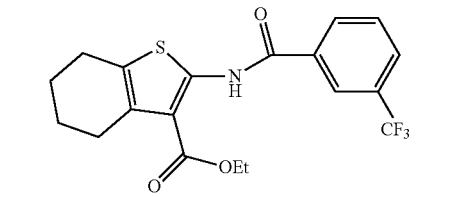 [SMILES: CCOC(=O)c1c(NC(=O)c2cccc(C(F)(F)F)c2)sc2c1CCCC2]
Compound #190
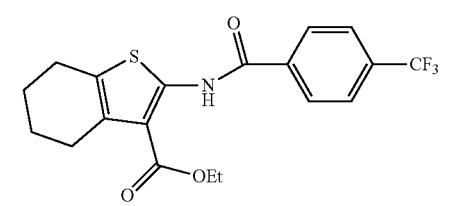 [SMILES: CCOC(=O)c1c(NC(=O)c2ccc(C(F)(F)F)cc2)sc2c1CCCC2]
Compound #191
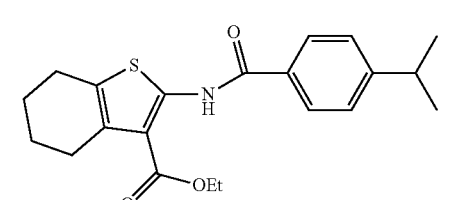
Compound #194
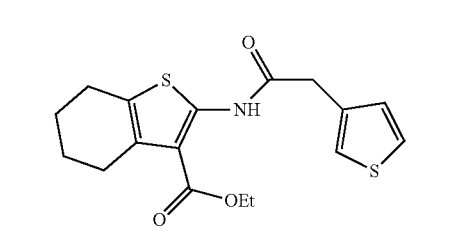 [SMILES: CCOC(=O)c1c(NC(=O)Cc2ccsc2)sc2c1CCCC2]
Compound #195

TABLE A'-continued

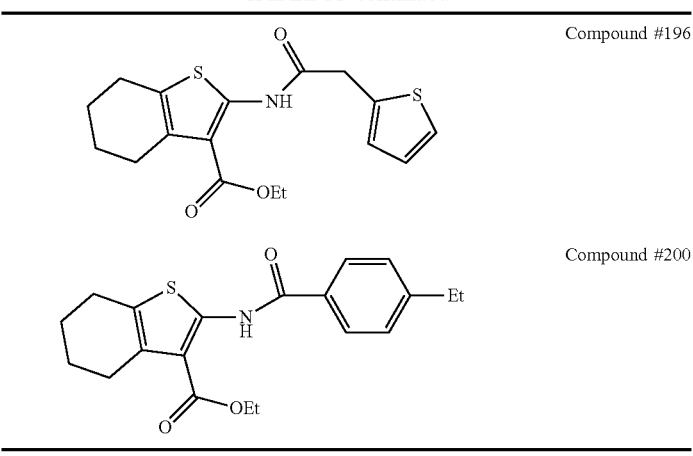

Compound #196

Compound #200

In a further more preferred embodiment, a compound for use of formula (I) according to the present invention is selected in the group consisting of:
Compounds of the above table A,
Compounds of the above table A',

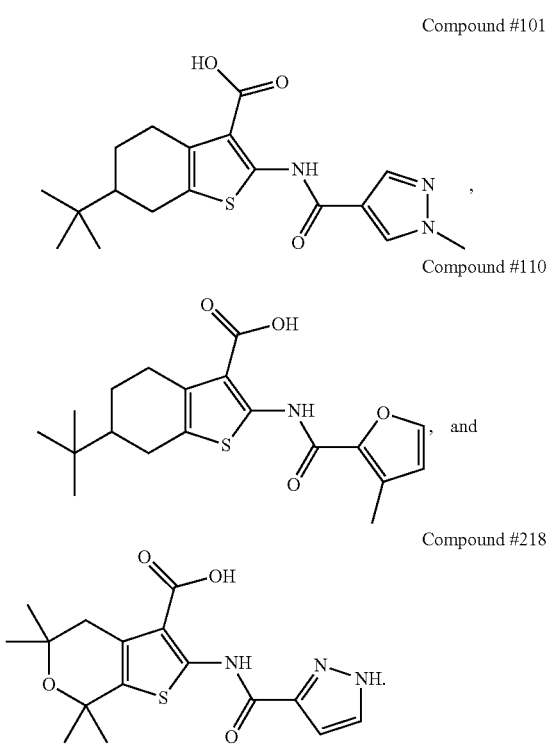

Compound #101

Compound #110

Compound #218

In a particular embodiment, the compounds for use of formula (I) according to the present invention is selected in the group consisting of compound #1, compound #2, compound #3, compound #5, compound #6, compound #7, compound #8, compound #9, compound #10, compound #47A and B, compound #48, compound #50, compound #51, compound #52, compound #54, compound #66, compound #67.

A particular aspect of the present invention relates to any pharmaceutically acceptable salt of the compounds as disclosed above and any enantiomer or diastereoisomer of the compounds as disclosed above.

A more particular aspect relates to any enantiomer of the compounds as disclosed above. These enantiomers can be obtained from the corresponding carboxylate compound which is purified by chiral SFC (in particular the Chiral SFC purification method of table 3) to give a first enantiomer carboxylate compound and a second enantiomer carboxylate compound follow by a step of deprotecting the carboxylate to give the corresponding enantiomer 1 and 2. The first enantiomer carboxylate compound corresponds to the first compound eluted from the chiral SFC. The second enantiomer carboxylate compound corresponds to the second compound eluted from the chiral SFC. After the deprotection step, the first enantiomer carboxylate compound gives a so called "first enantiomer" and the second enantiomer carboxylate compound gives a so called "second enantiomer".

These enantiomers can also be obtained from the corresponding racemate which is purified by chiral SFC (in particular the Chiral SFC purification method of table 3) to give a first enantiomer compound and a second enantiomer compound. The first enantiomer compound corresponds to the first compound eluted from the chiral SFC. The second enantiomer compound corresponds to the second compound eluted from the chiral SFC.

More particularly, the present invention relates to the following enantiomers:
  first enantiomer of compound #46: compound #47A;
    second enantiomer of compound #46: compound #47B;
  first enantiomer of compound #71: compound #67; second enantiomer of compound #71: compound #66;
  first enantiomer of compound #236: compound #237; second enantiomer of compound #236: compound #68; and
  first enantiomer of compound #73: compound #69; second enantiomer of compound #73: compound #238.

New Compounds of the Invention

The inventors have also provided new compounds and the stereoisomers and the pharmaceutical salts thereof of formula (I):

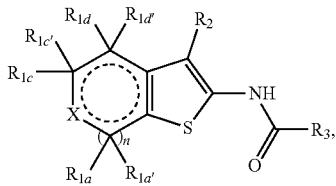 (I)

wherein:

X represents:
a —$CR_{1b}R_{1b'}$ unit,
a N—$R_{1b''}$ unit, or
an oxygen atom;

n is 0, 1, or 2;

when X is a —$CR_{1b}R_{1b'}$ unit, and n is 0 or 2, then one of $R_{1a}$, $R_{1a'}$, $R_{1b}$, $R_{1b'}$, $R_{1c}$, $R_{1c'}$, $R_{1d}$, and $R_{1d'}$ represents:
a halogen,
a ($C_1$-$C_6$)alkyl, optionally substituted by at least one halogen, preferably a fluorine,
a ($C_1$-$C_6$)alkyloxy optionally substituted by at least one halogen, preferably a fluorine,
a cyano, or
an aryl optionally substituted by at least one radical selected in the group consisting of:
a halogen,
a ($C_1$-$C_6$)alkyl optionally substituted by at least one halogen, preferably a fluorine,
a hydroxy,
a ($C_1$-$C_6$)alkyloxy optionally substituted by at least one halogen, preferably a fluorine, and the others represent a hydrogen;

when X is a N—$R_{1b''}$ unit, then $R_{1a}$, $R_{1a'}$, $R_{1c}$, $R_{1c'}$, $R_{1d}$, and $R_{1d'}$ represent independently:
a hydrogen,
a halogen,
a ($C_1$-$C_6$)alkyl, optionally substituted by at least one halogen, preferably a fluorine,
a ($C_1$-$C_6$)alkyloxy optionally substituted by at least one halogen, preferably a fluorine,
a cyano,
an aryl optionally substituted by at least one radical selected in the group consisting of:
a halogen,
a ($C_1$-$C_6$)alkyl optionally substituted by at least one halogen, preferably a fluorine,
a hydroxy, or
a ($C_1$-$C_6$)alkyloxy optionally substituted by at least one halogen, preferably a fluorine;

and $R_{1b''}$ represents:
an aryl optionally substituted by at least one radical selected in the group consisting of:
a halogen,
a ($C_1$-$C_6$)alkyl optionally substituted by at least one halogen, preferably a fluorine,
a hydroxy, and
a ($C_1$-$C_6$)alkyloxy optionally substituted by at least one halogen, preferably a fluorine, or
a ($C_1$-$C_6$)alkyl optionally substituted by at least one halogen, preferably a fluorine, or
a —$CO_2$—$R_8$ with $R_8$ being a ($C_1$-$C_6$)alkyl; and when X is an oxygen atom, then at least one of $R_{1a}$, $R_{1a'}$, $R_{1c}$, $R_{1c'}$, $R_{1d}$, and $R_{1d'}$ represents:
a halogen,
a ($C_1$-$C_6$)alkyl, optionally substituted by at least one halogen, preferably a fluorine,
a ($C_1$-$C_6$)alkyloxy optionally substituted by at least one halogen, preferably a fluorine,
a cyano, or
an aryl optionally substituted by at least one radical selected in the group consisting of:
a halogen,
a ($C_1$-$C_6$)alkyl optionally substituted by at least one halogen, preferably a fluorine,
a hydroxy,
a ($C_1$-$C_6$)alkyloxy optionally substituted by at least one halogen, preferably a fluorine,
and the other represent a hydrogen;

$R_2$ represents —COOH; and $R_3$ represents:
a 5-10 membered ring, saturated or unsaturated selected in the group consisting of:
an aryl optionally fused to a dioxole,
a heteroaryl,
a cycloalkyl,
a heterocycloalkyl, and
a 5-10 membered bridged carbocyclyl or heterocyclyl, said 5-10 membered ring is optionally substituted by at least one radical selected in the group consisting of:
a halogen,
a ($C_1$-$C_6$)alkyl optionally substituted by at least one halogen, preferably a fluorine, or a ($C_1$-$C_6$)alkyloxy,
a —NH—($C_1$-$C_6$)alkyl or a —N—(($C_1$-$C_6$)alkyl)$_2$, optionally substituted by a heterocycloalkyl or a ($C_1$-$C_6$)alkyloxy,
a —NH-heterocycloalkyl, a —NH-cycloalkyl, a —N(($C_1$-$C_6$)alkyl)-heterocycloalkyl or a —N(($C_1$-$C_6$)alkyl)-cycloalkyl, optionally substituted by a ($C_1$-$C_6$)alkyloxy or a —CO—$R_4$ with $R_4$ being a hydrogen or a ($C_1$-$C_6$)alkyl,
a hydroxy, a —CO—$R_4$ or a —$CO_2R_4$ with $R_4$ being a hydrogen or a ($C_1$-$C_6$)alkyl,
a ($C_1$-$C_6$)alkyloxy optionally substituted by at least one radical selected in the group consisting of a halogen, preferably a fluorine, a hydroxy, a ($C_1$-$C_6$)alkyloxy, a —$NR_5R_6$ with $R_5$ and $R_6$ are independently a hydrogen or a ($C_1$-$C_6$)alkyl, a —$NHCOR_7$, a —$NHCO_2R_7$, with $R_7$ being a ($C_1$—$C_6$)alkyl, a —$CO_2R_4$ with $R_4$ being a hydrogen or a ($C_1$-$C_6$)alkyl, and a heterocycle,
a —$NHCOR_7$ or —$NHCO_2R_7$ with $R_7$ being a ($C_1$-$C_6$)alkyl, and
a heterocycloalkyl, a heterocycloalkyloxy or a spiroheterocycloalkyl, optionally substituted by a ($C_1$-$C_6$)alkyloxy, a hydroxy, a halogen or a ($C_1$-$C_6$)alkyl optionally substituted by a ($C_1$-$C_6$)alkyloxy, or
a ($C_1$-$C_6$)alkyl or a ($C_2$-$C_6$)alkenyl, optionally substituted by a 5-10 membered ring as defined above or a —$CO_2R_4$ with $R_4$ being a hydrogen or a ($C_1$-$C_6$) alkyl.

In a particular aspect, the new compound is such that $R_3$ is not a 5-membered heteroaryl.

Particularly, X, n, $R_{1a}$, $R_{1a'}$, $R_{1b}$, $R_{1b'}$, $R_{1b''}$, $R_{1c}$, $R_{1c'}$, $R_{1d}$, $R_{1d'}$, $R_2$, and $R_3$ are such as above defined including the particular and/or preferred embodiments disclosed for the compounds for use. In one particular aspect, X is a N—R$_{1b''}$ unit or an oxygen atom and n, R$_{1a}$, R$_{1a'}$, R$_{1b}$, R$_{1b'}$, R$_{1b''}$, R$_{1c}$, R$_{1c'}$, R$_{1d}$, R$_{1d'}$, R$_2$, and R$_3$ are such as above defined including the particular and/or preferred embodiments disclosed for the compounds for use.

More particularly, a new compound of formula (I) is selected in the group consisting of:
2-Benzamido-6-phenyl-5,7-dihydro-4H-thieno[2,3-c]pyridine-3-carboxylic acid (Compound #52);
2-Benzamido-6-(4-fluoro-2-methylphenyl)-5,7-dihydro-4H-thieno[2,3-c]pyridine-3-carboxylic acid (Compound #53);
2-[(3,4-Dimethoxybenzoyl)amino]-6-(4-fluoro-2-methylphenyl)-5,7-dihydro-4H-thieno[2,3-c]pyridine-3-carboxylic acid (Compound #54);
2-[(2-Fluoro-4-methoxybenzoyl)amino]-6-(4-fluoro-2-methyl-phenyl)-5,7-dihydro-4H-thieno[2,3-c]pyridine-3-carboxylic acid (Compound #55);
2-Benzamido-6-(2,4-difluorophenyl)-5,7-dihydro-4H-thieno[2,3-c]pyridine-3-carboxylic acid (Compound #56);
2-Benzamido-6-(o-tolyl)-5,7-dihydro-4H-thieno[2,3-c]pyridine-3-carboxylic acid (Compound #57);
2-Benzamido-6-[4-(trifluoromethyl)phenyl]-5,7-dihydro-4H-thieno[2,3-c]pyridine-3-carboxylic acid (Compound #92);
2-[(3,4-Dimethoxybenzoyl)amino]-6-(4-fluorophenyl)-5,7-dihydro-4H-thieno[2,3-c]pyridine-3-carboxylic acid (Compound #113);
2-Benzamido-5,5-dimethyl-4,7-dihydrothieno[2,3-c]pyran-3-carboxylic acid (Compound #116);
2-[(3,4-Dimethoxybenzoyl)amino]-5,5-dimethyl-4,7-dihydrothieno[2,3-c]pyran-3-carboxylic acid (Compound #119);
6-tert-Butoxycarbonyl-2-[(2-methylbenzoyl)amino]-5,7-dihydro-4H-thieno[2,3-c]pyridine-3-carboxylic acid (Compound #126);
6-iso-Butyl-2-[(2-methylbenzoyl)amino]-5,7-dihydro-4H-thieno[2,3-c]pyridine-3-carboxylic acid formate salt (Compound #129);
2-Benzamido-5,5,7,7-tetramethyl-4H-thieno[2,3-c]pyran-3-carboxylic acid (Compound #175);
2-[[4-(3-Methoxyazetidin-1-yl)benzoyl]amino]-5,5,7,7-tetramethyl-4H-thieno[2,3-c]pyran-3-carboxylic acid (Compound #217);
5,5,7,7-Tetramethyl-2-(1H-pyrazole-3-carbonylamino)-4H-thieno[2,3-c]pyran-3-carboxylic acid (Compound #218);
5,5,7,7-Tetramethyl-2-[[4-(tetrahydropyran-4-ylamino)benzoyl]amino]-4H-thieno[2,3-c]pyran-3-carboxylic acid (Compound #232);
5,5,7,7-Tetramethyl-2-[[4-(tetrahydropyran-4-ylmethylamino) benzoyl]amino]-4H-thieno[2,3-c]pyran-3-carboxylic acid (Compound #233);
2-[[4-(2-Methoxyethylamino)benzoyl]amino]-5,5,7,7-tetramethyl-4H-thieno[2,3-c]pyran-3-carboxylic acid (Compound #234); and
2-[[4-[2-Methoxyethyl(methyl)amino]benzoyl]amino]-5,5,7,7-tetramethyl-4H-thieno[2,3-c]pyran-3-carboxylic acid (Compound #235).

The inventors have also provided new compounds and the stereoisomers and the pharmaceutical salts thereof selected in the group consisting of:
6-tert-Butyl-2-[(4-methoxybenzoyl)amino]-4,5,6,7-tetrahydrobenzothiophene-3-carboxylic acid (Compound #1);
6-tert-Butyl-2-[(3-methoxybenzoyl)amino]-4,5,6,7-tetrahydrobenzothiophene-3-carboxylic acid (Compound #2);
6-tert-Butyl-2-[(3,4-dimethoxybenzoyl)amino]-4,5,6,7-tetrahydrobenzothiophene-3-carboxylic acid (Compound #3);
6-tert-Butyl-2-[(3,4,5-trimethoxybenzoyl)amino]-4,5,6,7-tetrahydrobenzo thiophene-3-carboxylic acid (Compound #4);
6-tert-Butyl-2-[(2-fluoro-4-methoxybenzoyl)amino]-4,5,6,7-tetrahydrobenzothiophene-3-carboxylic acid (Compound #5);
6-tert-Butyl-2-[(2,3-difluoro-4-methoxy-benzoyl)amino]-4,5,6,7-tetrahydrobenzothiophene-3-carboxylic acid (Compound #6);
6-tert-Butyl-2-[[4-(difluoromethoxy)benzoyl]amino]-4,5,6,7-tetrahydrobenzothiophene-3-carboxylic acid (Compound #7);
6-tert-Butyl-2-[[4-(trifluoromethoxy)benzoyl]amino]-4,5,6,7-tetrahydrobenzothiophene-3-carboxylic acid (Compound #8);
6-tert-Butyl-2-[(4-morpholinobenzoyl)amino]-4,5,6,7-tetrahydrobenzothiophene-3-carboxylic acid (Compound #9);
6-tert-Butyl-2-[(4-chlorobenzoyl)amino]-4,5,6,7-tetrahydrobenzothiophene-3-carboxylic acid (Compound #10);
2-[[4-[3-(tert-Butoxycarbonylamino)propoxy]benzoyl]amino]-6-tert-butyl-4,5,6,7-tetrahydrobenzothiophene-3-carboxylic acid (Compound #11);
6-tert-Butyl-2-[[4-(2-hydroxyethoxy)benzoyl]amino]-4,5,6,7-tetrahydrobenzothiophene-3-carboxylic acid (Compound #12);
2-[(2-Methylbenzoyl)amino]-6-phenyl-4,5,6,7-tetrahydrobenzothiophene-3-carboxylic acid (Compound #45);
2-Benzamido-6-phenyl-4,5,6,7-tetrahydrobenzothiophene-3-carboxylic acid (Compound #46);
2-[(3,4-Dimethoxybenzoyl)amino]-6-phenyl-4,5,6,7-tetrahydrobenzothiophene-3-carboxylic acid (Compound #48);
2-[(4-Hydroxybenzoyl)amino]-6-phenyl-4,5,6,7-tetrahydrobenzothiophene-3-carboxylic acid (Compound #49);
2-[[4-(2-Hydroxyethoxy)benzoyl]amino]-6-phenyl-4,5,6,7-tetrahydrobenzothiophene-3-carboxylic acid (Compound #50);
2-[[4-(2-Methoxyethoxy)benzoyl]amino]-6-phenyl-4,5,6,7-tetrahydrobenzothiophene-3-carboxylic acid (Compound #51);
2-Benzamido-6-tert-butyl-4,5,6,7-tetrahydrobenzothiophene-3-carboxylic acid (Compound #71);
6-tert-Butyl-2-[(4-fluorobenzoyl)amino]-4,5,6,7-tetrahydrobenzothiophene-3-carboxylic acid (Compound #236);
6-tert-Butyl-2-[(2-fluorobenzoyl)amino]-4,5,6,7-tetrahydrobenzothiophene-3-carboxylic acid (Compound #73);
4-Methyl-2-[(4-morpholinobenzoyl)amino]-4,5,6,7-tetrahydrobenzothiophene-3-carboxylic acid (Compound #70);
6-tert-Butyl-2-(pyridine-2-carbonylamino)-4,5,6,7-tetrahydrobenzothiophene-3-carboxylic acid (Compound #72);
2-Benzamido-4-methyl-4,5,6,7-tetrahydrobenzothiophene-3-carboxylic acid (Compound #74);
2-[[4-(Difluoromethoxy)benzoyl]amino]-4-methyl-4,5,6,7-tetrahydrobenzothiophene-3-carboxylic acid (Compound #75);
2-[(2-Fluoro-4-methoxybenzoyl)amino]-4-methyl-4,5,6,7-tetrahydrobenzothiophene-3-carboxylic acid (Compound #76);
2-[(3,4-Dimethoxybenzoyl)amino]-4-methyl-4,5,6,7-tetrahydrobenzothiophene-3-carboxylic acid (Compound #81);
6-tert-Butyl-2-[(2-methylbenzoyl)amino]-4,5,6,7-tetrahydrobenzothiophene-3-carboxylic acid (Compound #82);

6-tert-Butyl-2-[(3-fluorobenzoyl)amino]-4,5,6,7-tetrahydrobenzothiophene-3-carboxylic acid (Compound #83);
6-Methyl-2-[(2-methylbenzoyl)amino]-4,5,6,7-tetrahydrobenzothiophene-3-carboxylic acid (Compound #86);
6-tert-Butyl-2-[(2-methylcyclohexanecarbonyl)amino]-4,5,6,7-tetrahydrobenzothiophene-3-carboxylic acid (Compound #89);
6-tert-Butyl-2-[(5-methoxypyridine-2-carbonyl)amino]-4,5,6,7-tetrahydrobenzothiophene-3-carboxylic acid (Compound #91);
2-[(4-Acetamidobenzoyl)amino]-6-tert-butyl-4,5,6,7-tetrahydrobenzothiophene-3-carboxylic acid (Compound #93);
6-tert-Butyl-2-[[2-(trifluoromethyl)benzoyl]amino]-4,5,6,7-tetrahydrobenzothiophene-3-carboxylic acid (Compound #100);
6-tert-Butyl-2-[(2,2-difluoro-1,3-benzodioxole-5-carbonyl)amino]-4,5,6,7-tetrahydrobenzothiophene-3-carboxylic acid (Compound #99);
6-tert-Butyl-2-[(1-methylpyrazole-4-carbonyl)amino]-4,5,6,7-tetrahydrobenzothiophene-3-carboxylic acid (Compound #101);
2-[[3-(Difluoromethoxy)benzoyl]amino]-4-methyl-4,5,6,7-tetrahydrobenzothiophene-3-carboxylic acid (Compound #102);
2-Benzamido-6-iso-propoxy-4,5,6,7-tetrahydrobenzothiophene-3-carboxylic acid (Compound #103);
6-tert-Butyl-2-[(2-methoxybenzoyl)amino]-4,5,6,7-tetrahydrobenzothiophene-3-carboxylic acid (Compound #104);
2-(2,2-Dimethylpropanoylamino)-6-phenyl-4,5,6,7-tetrahydrobenzothiophene-3-carboxylic acid (Compound #106);
6-tert-Butyl-2-[(2-chlorobenzoyl)amino]-4,5,6,7-tetrahydrobenzothiophene-3-carboxylic acid (Compound #107);
2-[[4-(Difluoromethoxy)benzoyl]amino]-4-phenyl-4,5,6,7-tetrahydrobenzothiophene-3-carboxylic acid (Compound #108);
6-tert-Butyl-2-[(3-methylfuran-2-carbonyl)amino]-4,5,6,7-tetrahydrobenzothiophene-3-carboxylic acid (Compound #110);
6-tert-Butyl-2-[(2-methylbenzoyl)amino]benzothiophene-3-carboxylic acid (Compound #111);
2-Benzamido-4-phenyl-4,5,6,7-tetrahydrobenzothiophene-3-carboxylic acid (Compound #112);
6-tert-Butyl-2-(cyclohexanecarbonylamino)-4,5,6,7-tetrahydrobenzothiophene-3-carboxylic acid (Compound #115);
6-tert-Butyl-2-[(2,6-dimethylbenzoyl)amino]-4,5,6,7-tetrahydrobenzothiophene-3-carboxylic acid (Compound #118);
6-tert-Butyl-2-(piperidine-1-carbonylamino)-4,5,6,7-tetrahydrobenzothiophene-3-carboxylic acid (Compound #120);
2-Benzamido-6-(4-hydroxyphenyl)-4,5,6,7-tetrahydrobenzothiophene-3-carboxylic acid (Compound #122);
6-tert-Butyl-2-(pyridine-4-carbonylamino)-4,5,6,7-tetrahydrobenzothiophene-3-carboxylic acid (Compound #123);
2-[[4-(3-Aminopropoxy)benzoyl]amino]-6-tert-butyl-4,5,6,7-tetrahydrobenzothiophene-3-carboxylic acid hydrochloride salt (Compound #124);
6-tert-Butyl-2-[(2-phenylacetyl)amino]-4,5,6,7-tetrahydrobenzothiophene-3-carboxylic acid (Compound #125);
6-tert-Butyl-2-[[4-(6-methoxy-6-oxo-hexoxy)benzoyl]amino]-4,5,6,7-tetrahydrobenzothiophene-3-carboxylic acid (Compound #172); and
2-Benzamido-5-phenyl-4,5,6,7-tetrahydrobenzothiophene-3-carboxylic acid (Compound #240).

Therapeutic Uses of Compounds

The present invention relates to a pharmaceutical or veterinary composition comprising a new compound according to the invention. Preferably, the pharmaceutical composition further comprises a pharmaceutically or veterinary acceptable carrier or excipient. The present invention relates to the use of a new compound according to the invention as a drug. The invention further relates to a method for treating a disease in a subject, wherein a therapeutically effective amount of a new compound according to the invention, is administered to said subject in need thereof. The invention also relates to the use of a new compound according to the invention, for the manufacture of a medicine.

In addition, the present invention relates to a method for treating an infectious disease, preferably a viral disease, in a subject, wherein a therapeutically effective amount of a compound according to the invention, is administered to said subject suffering of an infectious disease, preferably a viral disease. The present invention relates to the use of the compounds according to the invention as an anti-infectious agent, preferably an antiviral agent. The invention also relates to the use of the compounds according to the invention, for the manufacture of a medicine for the treatment of an infectious disease, preferably a viral infection. The invention relates to a compound according to the invention for use in the treatment of an infectious disease, preferably a viral infection.

The present invention further relates to a method for treating a cancer in a subject, wherein a therapeutically effective amount of a compound according to the invention is administered to said subject suffering of a cancer. The present invention relates to the use of the compounds according to the invention as an antitumor agent. The invention also relates to the use of the compounds according to the invention, for the manufacture of a medicine for the treatment of a cancer. The invention relates to a compound according to the invention for use in the treatment of a cancer.

The present invention further relates to a method for treating a metabolic disorder or disease in a subject, wherein a therapeutically effective amount of a compound according to the invention is administered to said subject suffering of a metabolic disorder or disease. The invention also relates to the use of the compounds according to the invention, for the manufacture of a medicine for the treatment of a metabolic disorder or disease. The invention relates to a compound according to the invention for use in the treatment of a metabolic disorder or disease.

The present invention further relates to a method for treating a cardiovascular disease in a subject, wherein a therapeutically effective amount of a compound according to the invention is administered to said subject suffering of a cardiovascular disease. The invention also relates to the use of the compounds according to the invention, for the manufacture of a medicine for the treatment of a cardiovascular disease. The invention relates to a compound according to the invention for use in the treatment of a cardiovascular disease.

The present invention further relates to a method for treating an inflammatory disease or disorder in a subject, wherein a therapeutically effective amount of a compound according to the invention is administered to said subject suffering of an inflammatory disease or disorder. The invention also relates to the use of the compounds according to the invention, for the manufacture of a medicine for the treatment of an inflammatory disease or disorder. The invention relates to a compound according to the invention for use in the treatment of an inflammatory disease or disorder.

The present invention also relates to a phytosanitary composition comprising a compound according to the invention, preferably a new compound according to the invention. It also relates to the use of a compound according to the invention, preferably a new compound according to the invention, as a phytosanitary agent. Thereby, the compound according to the invention. It further relates to a method for treating a plant against infection, especially infection by a virus, comprising contacting the plant with an efficient amount of a compound according to the invention, preferably a new compound according to the invention.

The present invention further relates to a method for treating aging or a neurodegenerative disease or disorder in a subject, wherein a therapeutically effective amount of a new compound according to the invention is administered to said subject suffering of aging or a neurodegenerative disease or disorder. The invention also relates to the use of a new compound according to the invention, for the manufacture of a medicine for the treatment of aging or a neurodegenerative disease or disorder. The invention relates to a new compound according to the invention for use in the treatment of aging or a neurodegenerative disease or disorder.

Antiviral Agents

The present invention relates to the use of a compound according to the invention as an antiviral agent. The present invention also relates to a compound of the present invention for use in the treatment of viral infections, the use of a compound of the present invention for the manufacture of a medicine for the treatment of viral infections, and to a method for treating a viral infection in a subject, comprising administering a therapeutically effective amount of a compound according to the invention to the subject.

The present invention also relates to the use of a compound of the present invention as a research tool, especially for studying viral infections. It further relates to a method for blocking viral infection in a cell, a tissue or a subject.

The viral agent can be a DNA virus or a RNA virus. The viral agent can be selected from the group consisting of Alphaviridae, Flaviviridae, Hepadnaviridae, Herpesviridae, Orthomyxoviridae, Papovaviridae, Paramyxoviridae, Picornaviridae, Polyomaviridae, Reoviridae, Retroviridae, Rhabdoviridae, and Tobamoviruses.

In one embodiment, the Alphaviridae is selected from the group consisting of Barmah Forest virus, Middelburg virus, Ndumu virus, Bebaru virus, Chikungunya virus, Mayaro virus, O'nyong'nyong virus, Ross River virus, Semliki Forest virus, Sindbis virus, Una virus, Eastern equine encephalitis virus, Tonate virus, Venezuelan equine encephalitis virus, Cabassou virus, Everglades virus, Mosso das Pedras virus, Mucambo virus, Parmana virus, Pixuna virus, Rio Negro virus, Trocara virus, Aura virus, Babanki virus, Kyzylagach virus, Ockelbo virus, Whataroa virus, Sleeping disease virus, Samon pancreatic disease virus, Southern elephant seal virus, and Western equine encephalitis virus; preferably selected from the group consisting of Barmah Forest virus, Chikungunya virus, Mayaro virus, O'nyong'nyong virus, Ross River virus, Semliki Forest virus, Sindbis virus, Una virus, Eastern equine encephalitis virus, Tonate virus, Venezuelan equine encephalitis virus and Western equine encephalitis virus.

In one embodiment, the Flaviviridae is selected from the group consisting of dengue virus, Hepatitis C virus, Japanese encephalitis virus, West Nile virus, yellow fever virus, Zika virus, Tick-borne encephalitis virus, Kyasanur forest disease virus, Murray Valley encephalitis virus, and Saint Louis encephalitis virus.

In one embodiment, the Hepadnaviridae is selected from the group consisting of Hepatitis B virus.

In one embodiment, the Herpesviridae is selected from the group consisting of Herpes Simplex virus 1 (HSV-1), Herpes Simplex virus 2 (HSV-2), Varicella zoster virus (VZV), Epstein-Barr virus (EBV), Cytomegalovirus (CMV), Roseolovirus (HHV-6A and 6B), HHV-7 and Kaposi's sarcoma-associated herpesvirus (KSHV).

In one embodiment, the Orthomyxoviridae is selected from the group consisting of Influenza virus A, Influenza virus B, Influenza virus C, Isavirus, Thogotovirus and Quaranjavirus, preferably selected from the group consisting of Influenza virus A and Influenza virus B. In one embodiment, the Influenza virus A is selected from the subtypes consisting of H1N1, H1N2, H2N2, H3N1, H3N2, H3N8, H5N1, H5N2, H5N3, H5N8, H5N9, H7N1, H7N2, H7N3, H7N4, H7N7, H7N9, H9N2, and H10N7.

In one embodiment, the Papovaviridae is selected from the group consisting of Papillomavirus (HPC) and Polyomavirus, especially Simian virus 40, Merkel cell polyomavirus, Trichodysplasia spinulosa polyomavirus, BK polyomavirus, JC polyomavirus and Human polyomavirus 7.

In one embodiment, the Paramyxoviridae is selected from the group consisting of Rubulavirus, Morbillivirus, Pneumovirus, Metapneumovirus, Avulavirus, Ferlavirus, Henipavirus, and Respirovirus. In a particular embodiment, the Paramyxoviridae is the mumps virus, measles virus, human parainfluenza viruses (HPIV), especially HPIV-1, HPIV-2, HPIV-3 or HPIV-4, respiratory syncytial virus (RSV), in particular Human respiratory syncytial virus (HRSV), canine distemper virus, phocine distemper virus, cetacean morbillivirus, Newcastle disease virus, rinderpest virus, Hendra virus and Nipah virus.

In one embodiment, the Picornaviridae is selected from the group consisting of Aphthovirus, Aquamavirus, Avihepatovirus, Cardiovirus, Cosavirus, Dicipivirus, Enterovirus, Erbovirus, Hepatovirus, Kobuvirus, Megrivirus, Parechovirus, Piscevirus, Rhinovirus, Salivirus, Sapelovirus, Senecavirus, Techovirus, and Tremovirus. In a particular embodiment, the Picornaviridae is a Rhinovirus, for instance a Rhinovirus A, Rhinovirus B or Rhinovirus C.

In one embodiment, the Retroviridae is selected from the group consisting of Alpharetrovirus; especially Avian leukosis virus and Rous sarcoma virus; Betaretrovirus, especially Mouse mammary tumour virus; Gammaretrovirus, especially Murine leukemia virus and Feline leukemia virus; Deltaretrovirus, especially Bovine leukemia virus and Human T-lymphotropic virus; Epsilonretrovirus, especially Walleye dermal sarcoma virus; Lentivirus, especially Human immunodeficiency virus 1 and Simian, Feline immunodeficiency viruses; Spumavirus, especially Simian foamy virus.

In one embodiment, the Rhabdoviridae is selected from the group consisting of vesiculovirus, especially vesicular stomatitis virus, lyssavirus, Ephemerovirus, novirhabdovirus, cytorhabdovirus and nucleorhabdovirus.

In one preferred embodiment, the viral agent according to the invention is selected from the group consisting in Herpesviridae such as Varicella zoster virus (VZV), Epstein-Barr (EB) virus, Herpes simplex virus of type 1 (HSV-1), Kaposis sarcoma herpesvirus (KSHV), murine γ-HV68 virus (γ-MHV68), or human cytomegalovirus (HCMV); Hepadnaviridae such as Hepatitis virus B (HBV); Papovaviridae such as Human papillomavirus type 16 (HPV16);

Parvoviridae such as Human parvovirus B19; Polyomaviridae such as Simian virus 40; Retroviridae such has Human immunodeficiency virus 1 (HIV-1), or Simian immunodeficiency virus type 1 (SIV 1); Orthomyxoviridae such as Influenza A virus; Flaviviridae such as Dengue virus, or Hepatitis C virus; Picornaviridae such as Poliovirus, Coxsakievirus B3 (CVB3), or Coxsakievirus B4 (CVB4); Reoviridae such as Rotavirus; Alphaviridae such as Sindbis virus; Tobamoviruses such as Tabacco mosaic virus; Rhabdoviridae such as vesicular stomatitis virus. More preferably, the viral agent according to the invention is an influenza virus. Still preferably, the viral agent according to the invention is an influenza virus A or B, even more preferably an influenza virus A.

In another preferred embodiment, the viral agent according to the invention presents an antiviral resistance to classic antiviral drugs. The terms "antiviral resistance", "antiviral agent resistance" or "antiviral drug resistance", as used herein, are equivalent and refer to the ability of viruses to resist the effects of an antiviral agent previously used to treat them. Antiviral resistance can be defined by a decreased susceptibility to a drug through either a minimally effective, or completely ineffective, treatment response to prevent associated illnesses from a particular virus.

In one embodiment, the compound of the invention can be used in combination with another antiviral drug, for instance and non-exhaustively, an agent selected from the group consisting of neuraminidase inhibitors, M2 inhibitors, RNA polymerase inhibitors, interferons (immune system modulators interferon alpha-2a and PEGylated interferon alpha-2a (Pegasys) and interferon alpha-2b (ViraferonPeg ou Introna)), antiviral vaccine, antigenic polypeptides or neutralizing antibodies directed to a viral antigenic polypeptide.

Antibacterial Agents

The present invention relates to the use of a compound according to the invention as an antibacterial agent. The present invention also relates to a compound of the present invention for use in the treatment of bacterial infections, the use of a compound of the present invention for the manufacture of a medicine for the treatment of bacterial infections, and to a method for treating a bacterial infection in a subject, comprising administering a therapeutically effective amount of a compound according to the invention to the subject.

The bacterium can be gram-negative and gram-positive bacteria, preferably an infectious bacterium. Such gram-positive bacteria include, but are not limited to, *Pasteurella* species, Staphylococci species, and *Streptococcus* species.

Specific examples of bacteria include but are not limited to, *Helicobacter pylori, Burkholderia cepacia, Pseudomonas aeruginosa, Pseudomonas fluorescens, Pseudomonas acidovorans, Pseudomonas alcaligenes, Pseudomonas putida, Stenotrophomonas maltophilia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella parapertussis, Bordetella bronchiseptica, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Campylobacter fetus, Campylobacter jejuni, Campylobacter coli, Borrelia burgdorferi, Vibrio cholerae, Vibrio parahaemolyticus, Listeria monocytogenes, Neisseria gonorrhoeae, Neisseria meningitidis, Kingella denitrificans, Kingella indologenes, Kingella kingae, Kingella oralis, Legionella pneumophila, Moraxella bovis, Moraxella catarrhalis, Moraxella lacunata, Gardnerella vaginalis, Bacteroides fragilis, Bacteroides distasonis, Bacteroides vulgatus, Bacteroides ovalus, Bacteroides thetaiotaomicron, Bacteroides uniformis, Bacteroides eggerthii, Bacteroides splanchnicus, Clostridium difficile, Clostridium tetani, Mycobacterium species, Corynebacterium ulcerans, Streptococcus agalactiae, Gardnerella vaginitis, Streptococcus pyogenes, Enterococcus faecalis, Enterococcus faecium, Fusobacterium nucleatum, Porphyromonas gingivalis, Vibrio vulnificus, Clostridium botulinum, Corynebacterium diptheriae, Staphylococcus aureus, Staphylococcus epidermidis, Staphylococcus saprophyticus, Staphylococcus intermedius, Staphylococcus hyicus, Staphylococcus haemolyticus, Staphylococcus hominis,* or *Staphylococcus saccharolyticus.*

In a particular embodiment, the bacterium is a *Mycobacterium*, for instance *Mycobacterium* species is selected from the group consisting of *M. africanum, M. bovis, M. bovis* BCG, *M. canetti, M. caprae, M. microti, M. mungi, M. orygis, M. pinnipedii, M. suricattae, M. tuberculosis, M. avium, M. avium* paratuberculosis, *M. avium silvaticum, M. avium* "hominissuis", *M. colombiense, M. indicus pranii, M. asiaticum, M. gordonae, M. gastri* and *M. kansasii, M. hiberniae, M. nonchromogenicum, M. terrae, M. triviale, M. ulcerans, M. pseudoshottsii, M. shottsii, M. triplex, M. genavense, M. florentinum, M. lentiflavum, M. palustre, M. kubicae, M. parascrofulaceum, M. heidelbergense, M. interjectum, M. simiae, M. bohemicum, M. botniense, M. branderi, M. celatum, M. chimaera, M. conspicuum, M. cookie, M. doricum, M. farcinogenes, M. haemophilum, M. heckeshornense, M. intracellular, M. lacus, M. leprae, M. lepraemurium, M. lepromatosis, M. liflandii, M. malmoense, M. marinum, M. monacense, M. montefiorense, M. murale, M. nebraskense, M. saskatchewanense, M. scrofulaceum, M. shimoidei, M. szulgai, M. tusciae, M. xenopi, M. yongonense, M. intermedium, M. abscessus, M. chelonae, M. bolletii, M. fortuitum, M. fortuitum subsp. Acetamidolyticum, M. boenickei, M. peregrinum, M. porcinum, M. senegalense, M. septicum, M. neworleansense, M. houstonense, M. mucogenicum, M. mageritense, M. brisbanense, M. cosmeticum, M. parafortuitum, M. austroafricanum, M. diernhoferi, M. hodleri, M. neoaurum, M. frederiksbergense, M. aurum, M. vaccae, M. chitae, M. fallax, M. confluentis, M. flavescens, M. madagascariense, M. phlei, M. smegmatis, M. goodie, M. wolinskyi, M. thermoresistibile, M. gadium, M. komossense, M. obuense, M. sphagni, M. agri, M. aichiense, M. alvei, M. arupense, M. brumae, M. canariasense, M. chubuense, M. conceptionense, M. duvalii, M. elephantis, M. gilvum, M. hassiacum, M. holsaticum, M. immunogenum, M. massiliense, M. moriokaense, M. psychrotolerans, M. pyrenivorans, M. vanbaalenii, M. pulveris, M. arosiense, M. aubagnense, M. caprae, M. chlorophenolicum, M. fluoroanthenivorans, M. kumamotonense, M. novocastrense, M. parmense, M. phocaicum, M. poriferae, M. rhodesiae, M. seoulense,* and *M. tokaiense,* preferably *Mycobacterium tuberculosis, Mycobacterium leprae,* or *Mycobacterium ulcerans.*

In another preferred embodiment, the bacterium according to the invention presents a resistance to classic antibacterial drugs. The terms "antibacterial resistance", "antibacterial agent resistance" or "antibacterial drug resistance", as used herein, are equivalent and refer to the ability of bacteria to resist the effects of an antibacterial agent previously used to treat them. Antibacterial resistance can be defined by a decreased susceptibility to a drug through either a minimally effective, or completely ineffective, treatment response to prevent associated illnesses from a particular bacterium.

In one embodiment, the compound of the invention can be used in combination with another antibacterial drug.

NEET Proteins Modulators

Compounds of the present invention are able to modulate NEET proteins. In particular, the compounds can be a NEET protein stabiliser. Alternatively, the compounds can be a NEET protein destabiliser.

The NEET protein family includes three class of proteins encoded by the CISD1, CISD2 and CISD3 genes.

CISD1 gene encodes the protein mitoNEET. It was previously called C10orf70 or ZCD1 or MDS029. The gene encoding the protein is described in databases GeneCards GCID GC10P058269; HGNC: 30880; Entrez Gene: 55847; and UniGene: Hs.370102. The protein is described in UniProtKB under: Q9NZ45. Amino acid and nucleotide reference sequences of mitoNEET are disclosed in GenPept and Genbank under NP_060934.1 and NM_018464.4, respectively.

CISD2 gene encodes the protein NAF-1 (nutrient-deprivation autophagy factor-1). It was previously called WFS2 or ZCD2 and is also called Miner1, ERIS (endoplasmic reticulum intermembrane small protein) and mitoNEET related 1. The gene encoding the protein is described in databases GeneCards GCID GC04P102868; HGNC: 24212; Entrez Gene: 493856; and UniGene: Hs.444955. and Hs.745013. The protein is described in UniProtKB under: Q8N5K1. Amino acid and nucleotide reference sequences of NAF-1 are disclosed in GenPept and Genbank under NP_001008389.1 and NM_001008388.4, respectively.

CISD3 gene encodes the protein Miner2. It is also called mitoNEET-Related protein 2 or mitochondrial matrix-localized mitochondrial inner NEET protein (MiNT). The gene encoding the protein is described in databases GeneCards GCID GC17P038730; HGNC: 27578; Entrez Gene: 284106; and UniGene: Hs.713595. The protein is described in UniProtKB under ID P0C7P0. Amino acid and nucleotide reference sequences of Miner2 are disclosed in GenPept and Genbank under NP_001129970.1 and NM_001136498.1, respectively. NEET proteins are important for human health and disease. For instance, they are involved in oncology (Holt et al, 2016, J Cell Sci, 129, 155-165; Bai et al, 2015, Proc Natl Acad Sci USA, 112, 3698-3703; Tamir et al, 2014, Proc Natl Acad Sci USA, 111, 5177-5182; Sohn et al, 2013, Proc Natl Acad Sci USA, 110, 14676-14681; Darash-Yahana et al, 2016, Proc Natl Acad Sci USA, 113, 10890-10895), especially apoptosis and autophagy; in metabolic disorders and diseases (Tamir et al, 2015, Biochim Biophys Acta, 1853, 1294-1315; Takahashi et al, Journal of Pharmacology and experimental therapeutics, 2015, 352, 338-345); cardiovascular diseases (Du et al, 2015, Cell Biol Int, 39, 816-823; Habener et al, 2016, PLoS One, 11, e0156054); inflammatory diseases and disorders (Taminelli et al, 2008, Biochem Biophys Res Commun, 365, 856-862); iron storage disorders (REF); aging (Chen et al, 2009, Genes Dev, 23, 1183-1194) and neurodegenerative diseases or disorders (He et al, 2016, Sci Rep, 6, 35205). Studies demonstrated a role for mitoNEET and NAF-1 in the regulation of cellular iron, calcium and ROS homeostasis, and a key role for NEET proteins in critical processes, such as cancer cell proliferation and tumor growth, lipid and glucose homeostasis in obesity and diabetes, control of autophagy, longevity in mice, and senescence in plants (Tamir et al, 2015, Biochim Biophys Acta, 1853, 1294-1315). Abnormal regulation of NEET proteins was consequently found to result in multiple health conditions. For instance, missplicing of NAF-1 causes Wolfram syndrome 2. NAF-1 is also functionally linked to the regulation of autophagy in cancer and aging.

Cancers

The compounds of the present invention are able to kill tumor cells. In addition, the compounds of the present invention are also able to modulate NEET proteins (Holt et al, 2016, J Cell Sci, 129, 155-165; Bai et al, 2015, Proc Natl Acad Sci USA, 112, 3698-3703; Tamir et al, 2014, Proc Natl Acad Sci USA, 111, 5177-5182; Sohn et al, 2013, Proc Natl Acad Sci USA, 110, 14676-14681; Darash-Yahana et al, 2016, Proc Natl Acad Sci USA, 113, 10890-10895). NEET proteins are involved in the regulation of apoptosis/autophagy in cancer biology. Accordingly, the present invention relates to the use of a compound of the present invention as an antitumor agent. The present invention also relates to a compound of the present invention for use for treating a cancer, the use of a compound of the present invention for the manufacture of a medicine for treating a cancer, and to a method for treating a cancer in a subject, comprising administering an effective amount of a compound of the present invention to the subject.

In one aspect, the cancer can be a solid tumor or a hematopoietic cancer. For instance, the cancer can be selected from the group consisting of bone cancer, gastro-intestinal cancer, liver cancer, pancreatic cancer, gastric cancer, colorectal cancer, esophageal cancer, oro-pharyngeal cancer, laryngeal cancer, salivary gland carcinoma, thyroid cancer, lung cancer, cancer of the head or neck, skin cancer, squamous cell cancer, melanoma, uterine cancer, cervical cancer, endometrial carcinoma, vulvar cancer, ovarian cancer, breast cancer, prostate cancer, cancer of the endocrine system, sarcoma of soft tissue, bladder cancer, kidney cancer, glioblastoma and various types of cancers of the central nervous system, lymphoma and leukemia. In a preferred embodiment, the cancer is a breast cancer, in particular a triple-negative breast cancer, prostate cancer and ovarian cancer. In one particular embodiment, the cancer is a breast cancer.

Optionally, the compound of the present invention used for treating cancer is a modulator of mitoNEET and/or NAF-1. In one aspect, the compound is a modulator of CISD-1. In another aspect, the compound is a modulator of NAF-1. In a further aspect, the compound is a modulator of mitoNEET and NAF-1.

In this aspect, the compound of the present invention can be combined with radiotherapy, immunotherapy, hormonotherapy, or chemotherapy, all well-known by the person skilled in the field.

Metabolic Disorders and Diseases

NEET proteins are involved in metabolic disorders and diseases (Tamir et al, 2015, Biochim Biophys Acta, 1853, 1294-1315). Accordingly, the present invention further relates to a method for treating a metabolic disorder or disease in a subject, wherein a therapeutically effective amount of a compound according to the invention is administered to said subject suffering of a metabolic disorder or disease. The invention also relates to the use of the compounds according to the invention, for the manufacture of a medicine for the treatment of a metabolic disorder or disease. The invention relates to a compound according to the invention for use in the treatment of a metabolic disorder or disease.

The metabolic disorders and diseases can be selected in the group consisting of diabetes mellitus, insulin resistance, insulin deficiency, hepatic steatosis, nonalcoholic fatty liver disease, Nonalcoholic steatohepatitis (NASH), glucose intolerance, obesity, lipodystrophy, coronary heart disease, diabetic retinopathy, diabetic neuropathy, diabetic nephropathy, hypoglycemia, hyperglycemia, beta cell dysfunction or hyperinsulinaemia, Wolfram syndrome, Polycystic ovary syndrome, pyruvate dehydrogenase deficiency, Albright hereditary osteodystrophy, cystinosis, fructose intolerance, Walker-Warburg syndrome, hypobetalipoproteinemia, Alström syndrome, and cirrhosis.

In one aspect, the metabolic disease or disorder can be selected from the group consisting of diabetes, in particular diabetes type I or diabetes type II, ateroslerosis, obesity, diabetic neuropathies, lysosomal storage diseases, severe insulin resistance, hyperinsulinemia, hyperlipidemia, Rabson-Mendenhall syndrome, leprechaunism, lipoatrophic diabetes, acute and chronic renal insufficiency, end-stage chronic renal failure, glomerulonephritis, interstitial nephritis, pyelonephritis, glomerulosclerosis, and lipoatrophic diabetes, hepatic steatosis, nonalcoholic fatty liver disease, Nonalcoholic steatohepatitis (NASH), glucose intolerance, lipodystrophy, coronary heart disease, diabetic retinopathy, diabetic neuropathy, diabetic nephropathy, hypoglycemia, hyperglycemia, beta cell dysfunction or hyperinsulinaemia, Wolfram syndrome, Polycystic ovary syndrome, pyruvate dehydrogenase deficiency, Albright hereditary osteodystrophy, cystinosis, fructose intolerance, Walker-Warburg syndrome, hypobetalipoproteinemia, Alström syndrome, and cirrhosis.

In another aspect, the metabolic disease or disorder can be selected from the group consisting of activator deficiency/GM2 gangliosidosis, alpha-mannosidosis, aspartylglucoaminuria, cholesteryl ester storage disease, chronic hexosaminidase A deficiency, cystinosis, Danon disease, Fabry disease, Farber disease, fucosidosis, galactosialidosis, Gaucher Disease (Types I, II and III), GM1 Ganliosidosis, including infantile, late infantile/juvenile and adult/chronic), Hunter syndrome (MPS II), Mucolipidosis II, Infantile Free Sialic Acid Storage Disease (ISSD), Juvenile Hexosaminidase A Deficiency, Krabbe disease, Lysosomal acid lipase deficiency, Metachromatic Leukodystrophy, Hurler syndrome, Scheie syndrome, Hurler-Scheie syndrome, Sanfilippo syndrome, Morquio Type A and B, Maroteaux-Lamy, Sly syndrome, mucolipidosis, multiple sulfate deficiency, Niemann-Pick disease, Neuronal ceroid lipofuscinoses, CLN6 disease, Jansky-Bielschowsky disease, pycnodysostosis, Sandhoff disease, Schindler disease, and Tay-Sachs or Wolman disease.

In a preferred embodiment, metabolic disorders and diseases can be selected in the group consisting of diabetes mellitus, insulin resistance, obesity and Wolfram syndrome.

Optionally, the compound of the present invention used for treating metabolic diseases or disorders is a modulator of mitoNEET, NAF-1 and/or MiNT. In particular, it can be a modulator of a combination of NEET proteins, such as mitoNEET and NAF-1, mitoNEET and MiNT, NAF-1 and MiNT or mitoNEET, NAF-1 and MiNT. Alternatively, it can be a modulator of mitoNEET, NAF-1 or MiNT.

The compound of the present invention can be combined with other drugs known for their uses in the treatment of metabolic diseases or disorders.

Cardiovascular Diseases

NEET proteins have been disclosed to be involved in cardiovascular diseases and disorders (Du et al, 2015, Cell Biol Int, 39, 816-823; Habener et al, 2016, PLoS One, 11, e0156054; Tamir et al, 2015, Biochim Biophys Acta, 1853, 1294-1315). Therefore, the present invention further relates to a method for treating a cardiovascular disease in a subject, wherein a therapeutically effective amount of a compound according to the invention is administered to said subject suffering of a cardiovascular disease. The invention also relates to the use of the compounds according to the invention, for the manufacture of a medicine for the treatment of a cardiovascular disease. The invention relates to a compound according to the invention for use in the treatment of a cardiovascular disease.

In one aspect, the cardiovascular disease is selected from the group consisting of myocardial injury, Ischemia, Ischemia reperfusion injury and hypertension. In one embodiment, the cardiovascular disease is myocardial injury.

Optionally, the compound of the present invention used for treating a cardiovascular disease is a modulator of mitoNEET and/or NAF-1. In one aspect, the compound is a modulator of mitoNEET. In another aspect, the compound is a modulator of NAF-1. In a further aspect, the compound is a modulator of mitoNEET and NAF-1.

The compound of the present invention can be combined with other drugs known for their uses in the treatment of cardiovascular diseases or disorders.

Inflammatory Diseases

NEET proteins have been disclosed to be involved in inflammation (Tamir et al, 2015, Biochim Biophys Acta, 1853, 1294-1315).

In one aspect, the inflammatory disease or disorder can be selected from the group consisting of Crohn disease, inflammatory bowel disease, asthma, chronic obtrusive pulmonary disease (COPD), systemic lupus erythematosus, cystic fibrosis, psoriasis, infectious arthritis, and multiple sclerosis.

Optionally, the compound of the present invention used for treating inflammatory diseases or disorders is a modulator of mitoNEET.

In one particular embodiment, the inflammatory disease or disorder is cystic fibrosis (Taminelli et al, 2008, Biochem Biophys Res Commun, 365, 856-862). Optionally, the compound of the present invention used for treating cystic fibrosis is a modulator of mitoNEET.

The compound of the present invention can be combined with other drugs known for their uses in the treatment of inflammatory diseases or disorders.

Iron Storage Disorders

NEET proteins are involved in iron homeostasis. The compounds of the present invention are able to modulate the NEET protein binding to iron, for instance by stabilizing and destabilizing this binding.

Accordingly, the present invention relates to a compound of the present invention for use for treating an iron storage disorder, the use of a compound of the present invention for the manufacture of a medicine for treating an iron storage disorder, and to a method for treating an iron storage disorder in a subject, comprising administering an effective amount of a compound of the present invention to the subject.

The iron storage disorder or disease can be associated to an iron deficiency or to an iron overload.

The iron storage disorders or diseases include, but are not limited thereto, Ferroportin Deficiency, Hereditary Hemochromatosis, including Hereditary Hemochromatosis due to HFE mutations and Hereditary Hemochromatosis due to transferrin receptor 2 mutations, Juvenile Hemochromatosis, including Juvenile Hemochromatosis due to hepcidin mutations and Juvenile Hemochromatosis due to hemojuvelin mutations, Iron Overload, including African Iron Overload, Iron Overload secondary to atransferrinemia and Iron Overload secondary to aceruloplasminemia, Thalassemia, Myelodysplastic Syndromes, Congenital Dyserythropoietic Anemias, Sickle Cell Disease and other Hemoglobinopathies, Red Cell Enzyme Deficiencies and Multiple Blood Transfusions.

Aging and Neurodegenerative Diseases

It is known that NEET proteins are involved in aging (Chen et al, 2009, Genes Dev, 23, 1183-1194) and in neurodegenerative diseases and disorders (He et al, 2016, Sci Rep, 6, 35205).

Therefore, a compound of the present invention, in particular a new compound of the present invention, can be used for the treatment of aging or a neurodegenerative disease or disorder. Accordingly, the present invention relates to a method for treating aging or a neurodegenerative disease or disorder in a subject, wherein a therapeutically effective amount of a compound according to the invention, preferably a new one, is administered to said subject suffering of aging or a neurodegenerative disease or disorder. The invention also relates to the use of a compound according to the invention, preferably a new one, for the manufacture of a medicine for the treatment of aging or a neurodegenerative disease or disorder. The invention relates to a compound according to the invention, preferably a new one, for use in the treatment of aging or a neurodegenerative disease or disorder.

In one embodiment, the compound of the present invention used for treating aging or treating or preventing aging damage. Optionally, the compound of the present invention used for treating aging is a modulator of NAF-1.

In another embodiment, the compound of the present invention used for treating a neurodegenerative disease or disorder. The neurodegenerative disease can be selected from the group consisting of Adrenal Leukodystrophy, Alexander's disease, Alper's disease, Alzheimer's disease, Amyotrophic lateral sclerosis, ataxia telangiectasia, Batten disease, bovine spongiform encephalopathy, Canavan disease, cerebral palsy, corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy body dementia, neuroborreliosis, Machado-Joseph disease, multiple system atrophy, multiple sclerosis, narcolepsy, Niemann Pick disease, Parkinson's disease, Pelizaeus-Merzbacher disease, Pick's disease, primary lateral sclerosis, prion diseases, progressive supranuclear palsy, Refsum's disease, Sandhoff disease, Schilder's disease, subacute combined degeneration of spinal cord secondary to pernicious anaemia, Spielmeyer-Vogt-Sjogren-Batten disease, spinocerebellar ataxia, spinal muscular atrophy, Steele-Richardson-Olszewski disease, Tabes *dorsalis* and toxic encephalopathy. Preferably, the neurodegenerative disease or disorder can be selected from the group consisting of multiple sclerosis, Alzheimer's disease, Parkinson's disease and amyotrophic lateral sclerosis.

The neurodegenerative disease or disorder also includes central nervous system (CNS) injury.

Optionally, the compound of the present invention used for treating a neurodegenerative disease or disorder is a modulator of mitoNEET.

The compound of the present invention can be combined with other drugs known for their uses in the treatment of neurodegenerative diseases or disorders.

Pharmaceutical Composition

The present invention also relates to a pharmaceutical composition comprising a compound of the present invention, preferably a new compound of the present invention. The composition further comprises at least one pharmaceutically acceptable carrier or excipient.

In a particular embodiment, the pharmaceutical composition according to the invention further comprises at least another active ingredient, preferably selected from the group consisting in an antiviral agent, an anti-cancerous agent, an antibiotic, or a molecule aimed to treat metabolic diseases, cardiovascular diseases, inflammatory diseases, aging, muscle diseases, neurodegenerative diseases or iron storage disorders. Preferably, the other active ingredient is an antiviral agent. More preferably, the other active ingredient is an antiviral agent against an influenza virus, preferably an influenza A virus.

In a particular embodiment, the pharmaceutical composition according to the invention further comprises an antiviral agent, for instance and non-exhaustively, an agent selected from the group consisting of neuraminidase inhibitors, M2 inhibitors, RNA polymerase inhibitors, interferons (immune system modulators interferon alpha-2a and PEGylated interferon alpha-2a (Pegasys) and interferon alpha-2b (ViraferonPeg ou Introna)), antiviral vaccine, antigenic polypeptides or neutralizing antibodies directed to a viral antigenic polypeptide.

The invention also concerns the pharmaceutical composition of the invention for use in the treatment of a disease. The invention also relates to the use of a pharmaceutical composition according to the invention for the manufacture of a medicine for treating a disease in a subject. The invention further relates to a method for treating a disease in a subject, wherein a therapeutically effective amount of a pharmaceutical composition according to the invention is administered to said subject suffering from said disease.

The subject according to the invention is an animal, preferably a mammal, even more preferably a human. However, the term "subject" can also refer to non-human animals, in particular mammals such as dogs, cats, horses, cows, pigs, sheep, donkeys, rabbits, ferrets, gerbils, hamsters, chinchillas, rats, mice, guinea pigs and non-human primates, among others, that are in need of treatment.

The human subject according to the invention may be a human at the prenatal stage, a new-born, a child, an infant, an adolescent or an adult.

In a preferred embodiment, the subject has been diagnosed with a disease. Preferably, the subject has been diagnosed with a disease selected from the group consisting in viral infections, bacterial infections, cancers, metabolic diseases or disorders, cardiovascular diseases or disorders, inflammatory diseases or disorders, iron storage disorders, aging and neurodegenerative diseases or disorders. Diagnostic methods of these diseases are well known by the man skilled in the art.

The compound according to the invention or the pharmaceutical composition according to the invention may be administered by any conventional route of administration. In particular, the compound or the pharmaceutical composition of the invention can be administered by a topical, enteral, oral, parenteral, intranasal, intravenous, intra-arterial, intramuscular, intratumoral, subcutaneous or intraocular administration and the like.

In particular, the compound according to the invention or the pharmaceutical composition according to the invention can be formulated for a topical, enteral, oral, parenteral, intranasal, intravenous, intra-arterial, intramuscular, intratumoral, subcutaneous or intraocular administration and the like.

Preferably, the compound according to the invention or the pharmaceutical composition according to the invention is administered by enteral or parenteral route of administration. When administered parenterally, the compound according to the invention or the pharmaceutical composition according to the invention is preferably administered by intravenous route of administration. When administered enterally, the compound according to the invention or the pharmaceutical composition according to the invention is preferably administered by oral route of administration.

The pharmaceutical composition comprising the molecule is formulated in accordance with standard pharmaceutical practice (Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

For oral administration, the composition can be formulated into conventional oral dosage forms such as tablets, capsules, powders, granules and liquid preparations such as syrups, elixirs, and concentrated drops. Nontoxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials, are also necessary. For example, starch, gelatine, sugars such as lactose or dextrose, and natural or synthetic gums can be used as binders. Disintegrants are also necessary in the tablets to facilitate break-up of the tablet. Disintegrants include starches, clays, celluloses, algins, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Pharmaceutical compositions according to the invention may be formulated to release the active drug substantially immediately upon administration or at any predetermined time or time period after administration.

Preferably, the treatment with the compound according to the invention or the pharmaceutical composition according to the invention start no longer than a month, preferably no longer than a week, after the diagnosis of the disease. In a most preferred embodiment, the treatment starts the day of the diagnosis.

The compound according to the invention or the pharmaceutical composition according to the invention may be administered as a single dose or in multiple doses.

Preferably, the treatment is administered regularly, preferably between every day and every month, more preferably between every day and every two weeks, more preferably between every day and every week, even more preferably the treatment is administered every day. In a particular embodiment, the treatment is administered several times a day, preferably 2 or 3 times a day, even more preferably 3 times a day.

The duration of treatment with the compound according to the invention or the pharmaceutical composition according to the invention is preferably comprised between 1 day and 20 weeks, more preferably between 1 day and 10 weeks, still more preferably between 1 day and 4 weeks, even more preferably between 1 day and 2 weeks. In a particular embodiment, the duration of the treatment is of about 1 week. Alternatively, the treatment may last as long as the disease persists.

The amount of compound according to the invention or of pharmaceutical composition according to the invention to be administered has to be determined by standard procedure well known by those of ordinary skills in the art. Physiological data of the patient (e.g. age, size, and weight) and the routes of administration have to be taken into account to determine the appropriate dosage, so as a therapeutically effective amount will be administered to the patient.

In a preferred embodiment, the total compound dose for each administration of the compound according to the invention or of the pharmaceutical composition according to the invention is comprised between 0.00001 and 1 g, preferably between 0.01 and 10 mg.

The form of the pharmaceutical compositions, the route of administration and the dose of administration of the compound according to the invention, or the pharmaceutical composition according to the invention can be adjusted by the man skilled in the art according to the type and severity of the disease, and to the patient, in particular its age, weight, sex, and general physical condition.

Kit and Use of a Kit

The present invention also relates to the combined use of a compound of the present invention with at least another active ingredient, preferably selected from the group consisting in an antiviral agent, an anti-cancerous agent, an anti-apoptotic agent, an anti-autophagy agent, an autophagy inducing agent, an antibiotic, an antiparasitic agent, an antifungal agent, or a molecule aimed to treat neurodegenerative diseases, inflammatory diseases, autoimmune diseases, liver diseases, aging, muscle diseases, or metabolic diseases for the treatment of a disease selected from the group consisting of cancer, infectious diseases, in particular viral diseases, metabolic diseases or disorders, cardiovascular diseases or disorders, inflammatory diseases, iron storage disorders, aging, and neurodegenerative diseases.

The present invention also relates to a product comprising a compound of the present invention, and another active ingredient, as a combined preparation for simultaneous, separate or sequential use, in particular for use for the treatment of a disease selected from the group consisting of cancer, infectious diseases, in particular viral diseases, metabolic diseases or disorders, cardiovascular diseases or disorders, inflammatory diseases, iron storage disorders, aging, and neurodegenerative diseases. Preferably, the other active ingredient is selected from the group consisting in an antiviral agent, an anti-cancerous agent, an anti-apoptotic agent, an anti-autophagy agent, an autophagy inducing agent, an antibiotic, an antiparasitic agent, an antifungal agent, or a molecule aimed to treat cancer, infectious diseases, in particular viral diseases, metabolic diseases or disorders, cardiovascular diseases or disorders, inflammatory diseases, iron storage disorders, aging, and neurodegenerative diseases. Preferably, the other active ingredient is an antiviral.

Further aspects and advantages of the present invention will be described in the following examples, which should be regarded as illustrative and not limiting.

EXAMPLES

Example A—Chemistry

Abbreviations

Aq Aqueous
br s Broad singlet
$CDCl_3$ Deuterated chloroform
d Doublet
DAD Diode Array Detector
DCM Dichloromethane (methylene chloride)
dd Doublet of doublets
ddd Doublet of doublets of doublets
ddt Doublet of doublets of triplets
DIPEA N,N-Diisopropylethylamine
DMAP 4-Dimethylaminopyridine
DMF N,N-Dimethylformamide
DMSO Dimethyl sulfoxide
dq Doublet of quartets
dt Doublet of triplets
EtOAc Ethyl acetate
$Et_2O$ Diethyl ether
EtOH Ethanol
g Gram(s)
h Hour(s)
HCl Hydrochloric acid
HPLC High-pressure liquid chromatography
i-PrOH Isopropanol
LC/MS Liquid chromatography/mass spectrometry
LiOH Lithium hydroxide
m Multiplet
M Molar
MeCN Acetonitrile
MeOH Methyl alcohol
$MgSO_4$ Magnesium sulfate
min Minute(s)
mmol Millimole
MHz MegaHertz
MS Mass spectrometry
N Normal
$NaHCO_3$ Sodium bicarbonate
$Na_2SO_4$ Sodium sulfate
$NH_4Cl$ Ammonium chloride
NMR Nuclear magnetic resonance
p para
PDA Photodiode Array
PG Protecting group
ppm Parts per million
q Quartet
qd Quartet of doublets
quin Quintet
RP-HPLC Reverse-phase high-pressure liquid chromatography
$R_t$ Retention time
RT Room temperature
s Singlet
t Triplet
td Triplet of doublets
tert- Tertiary THF Tetrahydrofuran General Synthetic Schemes Compounds of the invention may be prepared using the synthetic transformations illustrated in Schemes I-VII. Starting materials are commercially available or may be prepared by the procedures described herein, by literature procedures, or by procedures that would be well known to one skilled in the art of organic chemistry. Unless stated, all aqueous solutions are saturated.

Methods for preparing 2-[(benzoyl)amino]-4,5-disubstituted-thiophene-3-carboxylicacid compounds of the invention containing various substitutions on the bicyclic scaffold and on the benzamides are illustrated in Schemes I-II. In Scheme I, step a, the 2-aminothiophene-3-carboxylate scaffold 3 can be commercially available or synthesised from commercially available cyclic ketones 1 and cyanoacetate 2 in a 3-component reaction using sulfur and a suitable base. This reaction, called a Gewald reaction (as described in Ber., 1966, 99, 94-100), can be carried out using for example one of the procedures described in Example #21, Example #85, Example #93 and Preparation #4, or by methods known to one skilled in the art (for example, *European Journal of Medicinal Chemistry*, 2016, 123, 31-47) to provide the 2-aminothiophene-3-carboxylate compounds 3. 2-Aminothiophene derivatives 3 may react with substituted benzoyl chloride as described in Scheme I, step b using conditions such as those described in Example #1, or by methods known to one skilled in the art (for instance, *J. Med. Chem.*, 2013, 56(24), 10118-10131) to give 2-(benzamido)thiophene-3-carboxylate derivatives 4. Acyl chlorides can be commercially available or synthesised as described for example in Example #52 and Example #61 or by methods known to one skilled in the art (for example, *J. Med. Chem.*, 2016, 59(13), 6201-6220). In Scheme I, step b, 2-aminothiophenes 3 may also react with substituted benzoic acids in the presence of a coupling reagent, such as 2-chloro-1-methylpyridinium iodide (also called Mukaiyama's reagent), as described in Preparation #2, or by methods known to one skilled in the art (for example, *European Journal of Medicinal Chemistry*, 2014, 76, 110-117) to give 2-(benzamido)thiophene-3-carboxylate derivatives 4. In Scheme I, step c, the ester of 2-(benzamido)thiophene-3-carboxylate derivatives 4 may be hydrolysed to the 2-(benzamido)thiophene-3-carboxylic acids 5 using conditions such as those described in Example #1 and Example #10 or by methods known to one skilled in the art (for example, *J. Med. Chem.*, 2013, 56(24), 10118-10131).

Scheme I

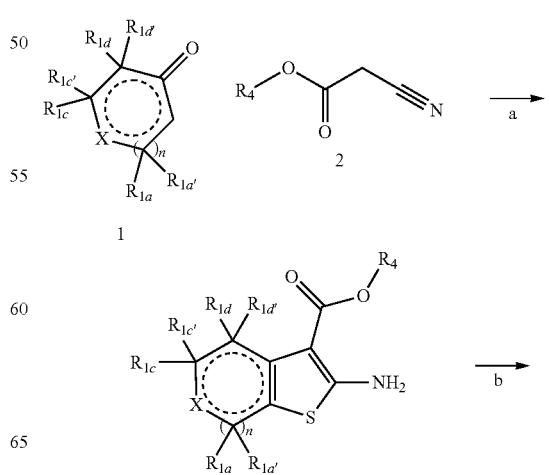

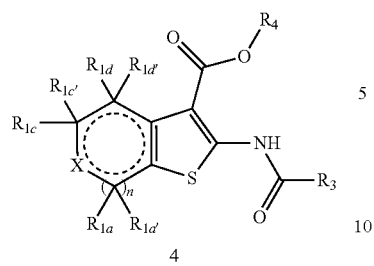

4

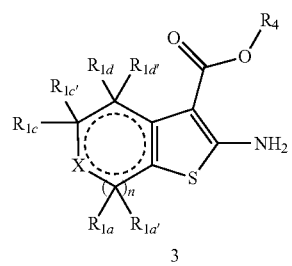

3

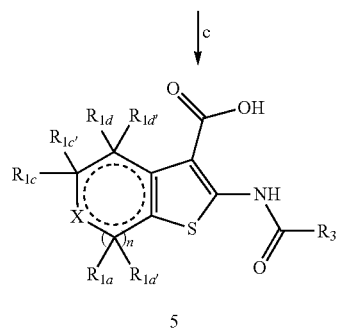

5

In Scheme II, an alternative method for preparing 2-aminothiophene-3-carboxylate derivatives 3 is reported. In Scheme II, step d, 2-cyano-2-(cyclohexylidene)acetate compounds 6 can be synthesised from commercially available cyclic ketones 1 and cyanoacetate 2 using ammonium acetate, as described in Preparation #6 or by methods known to one skilled in the art (for example, *Synthetic Communications*, 2006, 36(22), 3305-3317). This reaction is generally known for those skilled in the art as Knoevenagel condensation. In Scheme II, step e, 2-cyano-2-(cyclohexylidene) acetate compounds 6 may react with sulfur and a base to give 2-aminothiophenes 3 as described in Preparation #6 or by methods known to one skilled in the art (for example, *J. Med. Chem.*, 2005, 48(26), 8270-8288).

Compounds of general structure 4 may be modified later in the synthesis as described in Scheme III. 2-Aminothiophene derivatives 3 may react with 0-protected benzoyl chloride derivatives as described in Scheme III, step b using, for example, similar conditions described in Scheme I, step b. A suitable protecting group (PG) may be, for instance, the acetoxy, as shown in Preparation #3, Step A. In Scheme III, step f, a suitable protecting group (PG) may be cleaved to give 2-(4-hydroxybenzamido)thiophene-3-carboxylate ester derivatives 8 using appropriate conditions such as those described in Preparation #3, Step A, for example, or by methods known to one skilled in the art (for example, *ACS Medicinal Chemistry Letters*, 2014, 5(1), 84-88). In Scheme III, step c, the ester of 2-(4-hydroxybenzamido)thiophene-3-carboxylate derivatives 8 may be hydrolysed to the 2-(4-hydroxybenzamido)thiophene-3-carboxylic acids 9 using conditions such as those described in Scheme I, step c.

Scheme III

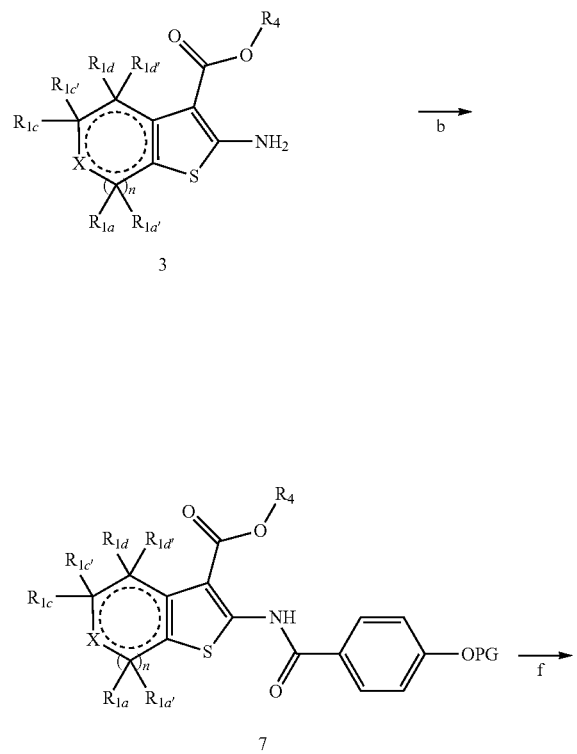

Scheme II

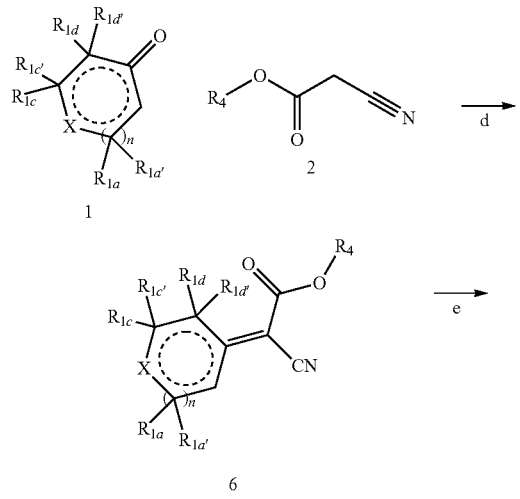

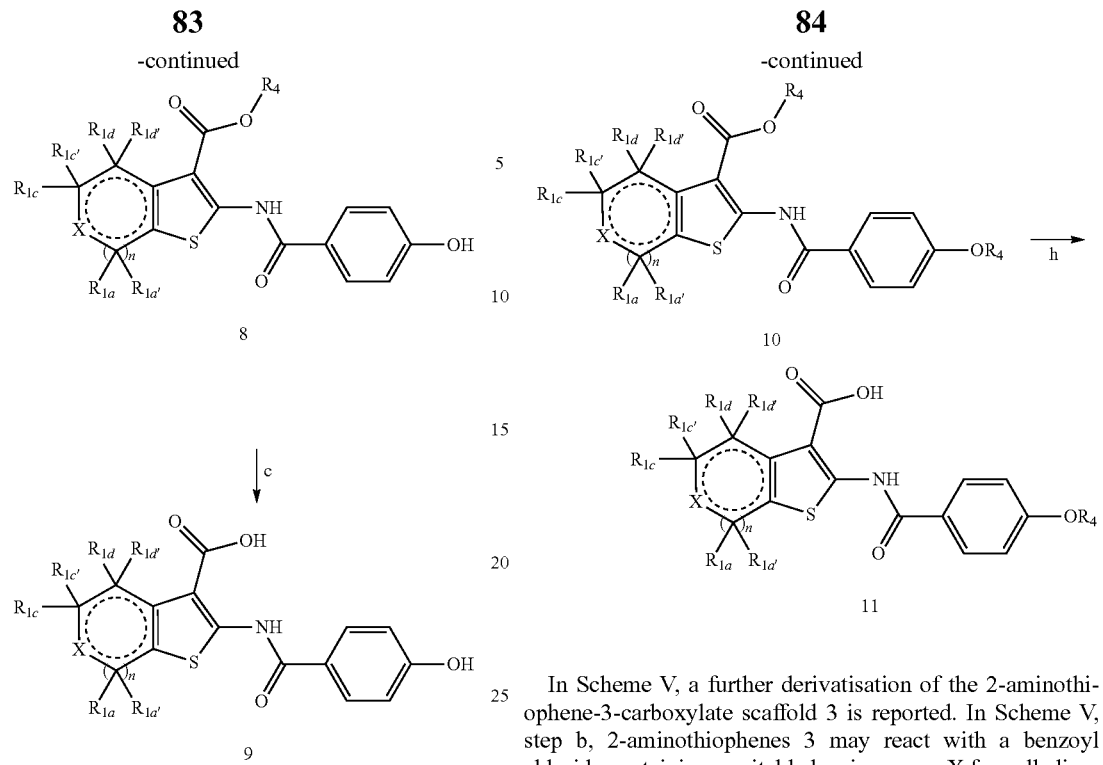

Scheme IV, step g, shows a further modification of 2-(4-hydroxybenzamido)thiophene-3-carboxylate ester derivatives 8, which may react with an electrophile to give ethers of general structure 10. This transformation has been described for example in Example #20 and Preparation #3, Step B or can be achieved by methods known to one skilled in the art (for example, *ACS Medicinal Chemistry Letters*, 2014, 5(11), 1230-1234). In Scheme IV, step h, compounds of general structure 10 may also undergo further derivatisation. Suitable manipulation may be, for instance, deprotection of an appropriate protection group, as described for example in Example #12 and Example #79 or by methods known to one skilled in the art (for example, WO2014031784 and *Journal of Medicinal Chemistry*, 2003, 46(24), 5238-5248). Further derivatisation may include the hydrolysis of 2-(benzamido)thiophene-3-carboxylate ester derivatives 10 to the corresponding 2-(benzamido)thiophene-3-carboxylic acid compounds 11, as shown in Example #11, Example #12 and Example #20, or using conditions such as those described in Scheme I, step c.

In Scheme V, a further derivatisation of the 2-aminothiophene-3-carboxylate scaffold 3 is reported. In Scheme V, step b, 2-aminothiophenes 3 may react with a benzoyl chloride containing a suitable leaving group X for palladium catalysed reactions, such as an halide, to give 2-(benzamido)thiophene-3-carboxylate derivatives 12. Typical procedures have been described in Scheme I, step b. In Scheme V, step i, 2-(halobenzamido)thiophene-3-carboxylate derivatives 12 may react with amines to give 2-(aminobenzamido)thiophene-3-carboxylate ester derivatives 13 using a suitable palladium catalyst, as described for example in Example #36 or by methods known to one skilled in the art (for example, *J. Med. Chem.*, 2014, 57(7), 3094-3116). In Scheme V, step c, 2-(aminobenzamido)thiophene-3-carboxylate derivatives 13 may be hydrolysed to the 2-(aminobenzamido)thiophene-3-carboxylic acids 14 using conditions such as those described in Scheme I, step c.

Scheme V

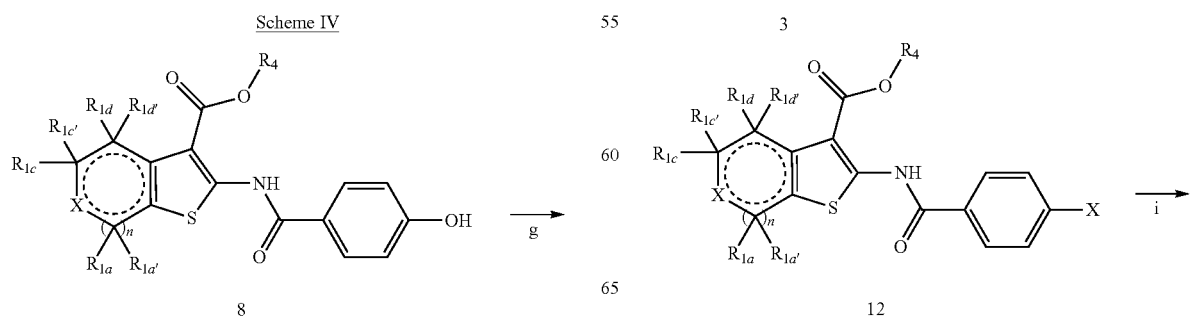

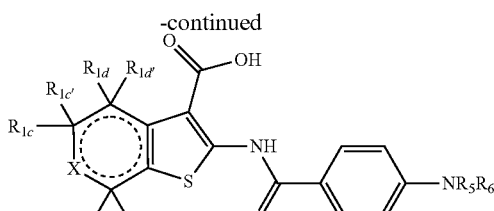

14

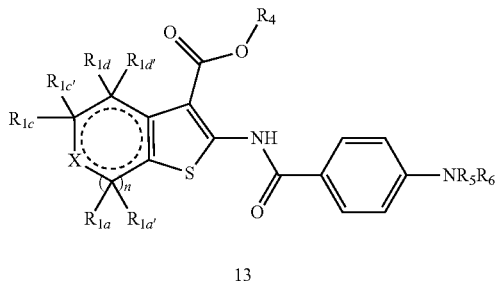

13

↓ c

Analytical Methods

Analytical data is included within the procedures below, in the illustrations of the general procedures, or in the tables of examples. Unless otherwise stated, all $^1$H NMR data were collected on a Bruker Avance 400 MHz equipped with 5 mm QNP probe or Bruker Avance III 400 MHz, 5 mm BBFO Plus probe instruments and chemical shifts are quoted in parts per million (ppm). LC/MS was performed on Acquity UPLC (binary pump/PDA detector) coupled to Waters ZQ Mass Spectrometer or Acquity i-Class (quaternary pump/PDA detector) coupled to Quattro Micro Mass Spectrometer. LC/MS data is referenced to LC/MS conditions using the method number provided in Table 1. Chiral SFC data is referenced to SFC conditions using the method number provided in Table 1.

TABLE 1

LC/MS and Chiral SFC analysis methods

| Method | Conditions |
|---|---|
| A | LC/MS analysis condition: Column: Acquity UPLC BEH C18 1.7 μm, 100 × 2.1 mm, maintained at 40° C. Mobile phase: MeCN (0.1% formic acid) in water (0.1% formic acid), from 5% to 95% within 6 min; Flow rate: 0.4 ml/min; Wavelength: 200-500 nm DAD. ZQ Mass Spectrometer |
| B | LC/MS analysis condition: Column: Acquity UPLC BEH C18 1.7 μm, 100 × 2.1 mm, maintained at 40° C. Mobile phase: MeCN (0.1% formic acid) in water (0.1% formic acid), from 5% to 95% within 6 min; Flow rate: 0.4 ml/min; Wavelength: 200-500 nm DAD. Quattro Micro Mass Spectrometer |
| C | LC/MS analysis condition: Column: Acquity UPLC BEH Shield RP18 1.7 μm, 100 × 2.1 mm plus guard cartridge, maintained at 40° C. Mobile phase: MeCN in water (with 10 mM ammonium bicarbonate), from 5% to 95% within 6 min; Flow rate: 0.5 ml/min; Wavelength: 210-400 nm DAD. Waters DAD + Waters SQD2, single quadrapole UPLC-MS |
| D | LC/MS analysis condition: Column: Acquity UPLC HSS C18 1.8 μm, 100 × 2.1 mm plus guard cartridge, maintained at 40° C. Mobile phase: MeCN (0.1% formic acid) in water (0.1% formic acid), from 5% to 95% within 6 min; Flow rate: 0.5 ml/min; Wavelength: 210-400 nm DAD. Waters DAD + Waters SQD2, single quadrapole UPLC-MS |
| E | LC/MS analysis condition: Column: Acquity UPLC HSS C18 1.8 μm, 100 × 2.1 mm plus guard cartridge, maintained at temp. Mobile phase: MeCN (0.1% formic acid) in water (0.1% formic acid), from 5% to 95% within 8 min; Flow rate: 0.4 ml/min; Wavelength: 210-400 nm DAD. Waters DAD + Waters SQD2, single quadrapole UPLC-MS |
| F | LC/MS analysis condition: Column: Acquity UPLC BEH Shield RP18 1.7 μm, 100 × 2.1 mm plus guard cartridge, maintained at temp. Mobile phase: MeCN in water (with 10 mM ammonium bicarbonate), from 5% to 95% within 8 min; Flow rate: 0.4 ml/min; Wavelength: 210-400 nm DAD. Waters DAD + Waters SQD2, single quadrapole UPLC-MS |
| G | Chiral SFC analysis condition: Column: YMC Cellulose-C 5 μm, 150 × 2 mm, 120 bar, maintained at 40° C. Mobile phase: 20/80 MeOH (0.1% DEA)/CO$_2$; Flow rate: 0.95 ml/min; Wavelength: 230 nm DAD |
| H | Chiral SFC analysis condition: Column: YMC Amylose-C 5 μm, 250 mm, 120 bar, maintained at 40° C. Mobile phase: 20/80 MeOH (0.1% DEA)/CO$_2$; Flow rate: 0.95 ml/min; Wavelength: 230-235 nm DAD |
| I | Chiral SFC analysis condition: Column: YMC Cellulose-SC 5 μm, 150 × 2 mm, 120 bar, maintained at 40° C. Mobile phase: 20/80 i-PrOH (0.1% DEA)/CO$_2$; Flow rate: 0.95 ml/min; Wavelength: 335 nm DAD |
| J | Chiral SFC analysis condition: Column: YMC Cellulose-C 5 μm, 250 × 4.6 mm, 120 bar, maintained at 40° C. Mobile phase: 30/70 MeCN (0.1% DEA)/CO$_2$; Flow rate: 5.0 ml/min; Wavelength: 230 nm DAD |

TABLE 1-continued

LC/MS and Chiral SFC analysis methods

| Method | Conditions |
|---|---|
| K | Chiral SFC analysis condition: Column: YMC Amylose-C 5 μm, 150 × 2 mm, 120 bar, maintained at 40° C. Mobile phase: 40/60 i-PrOH (0.1% DEA)/$CO_2$; Flow rate: 0.95 ml/min; Wavelength: 230 nm DAD |

Purification Methods

For the general procedures, intermediate and final compounds may be purified by any technique or combination of techniques known to one skilled in the art. Some examples that are not limiting include flash chromatography with a solid phase (i.e. silica gel, alumina, etc.) and a solvent (or combination of solvents, i.e. heptane, EtOAc, DCM, MeOH, MeCN, water, etc.) that elutes the desired compounds; RP-HPLC purification performed on Agilent Technologies 1260 Infinity purification system and Agilent 6120 series Single Quadrupole Mass Spectrometer (see Table 2 for some non-limiting conditions); recrystallization from an appropriate solvent (i.e. MeOH, EtOH, i-PrOH, EtOAc, toluene, etc.) or combination of solvents (i.e. EtOAc/heptane, EtOAc/MeOH, etc.); precipitation from a combination of solvents (i.e. DMF/water, DMSO/DCM, EtOAc/heptane, etc.); trituration with an appropriate solvent (i.e. EtOAc, DCM, MeCN, MeOH, EtOH, i-PrOH, n-PrOH, etc.); extractions by dissolving a compound in a liquid and washing with an appropriately immiscible liquid (i.e. DCM/water, EtOAc/water, DCM/saturated $NaHCO_3$, EtOAc/saturated $NaHCO_3$, DCM/10% aqueous HCl, EtOAc/10% aqueous HCl, etc.); distillation (i.e. simple, fractional, Kugelrohr, etc.). Descriptions of these techniques can be found in the following references: Gordon, A. J. and Ford, R. A., "The Chemist's Companion", 1972; Palleros, D. R. "Experimental Organic Chemistry", 2000; Still, W. C., Kahn and M. Mitra, A. *J. Org. Chem.* 1978, 43(14), 2923-2925; Yan, B. "Analysis and Purification Methods in Combinatorial Chemistry" 2003; Harwood, L. M., Moody, C. J. and Percy, J. M. "Experimental Organic Chemistry: Standard and Microscale, $2^{nd}$ Edition", 1999.

TABLE 2

RP-HPLC purification methods

| Method | Conditions |
|---|---|
| A | RP-HPLC purification condition: Column XSELECT CSH Prep C18 5 μm, 19 × 250 mm. Mobile phase: MeCN in water (0.1% formic acid); Flow rate: 20 ml/min; Wavelength: 210-260 nm DAD. Sample injected in DMSO (+optional formic acid and water), 22 min non-linear gradient from 10% to 95% MeCN, centered around a specific focused gradient |
| B | RP-HPLC purification condition: Column Waters Sunfire C18 10 μm, 150 × 19 mm. Mobile phase: MeCN in water (0.1% ammonium bicarbonate); Flow rate: 20 ml/min; Wavelength: 210-400 nm DAD. Sample injected in DMSO, 25 min non-linear gradient from 5% to 95% MeCN, centered around a specific focused gradient |

Chiral SFC purification is referenced to SFC conditions using the method number provided in Table 3.

TABLE 3

Chiral SFC purification method

| Method | Conditions |
|---|---|
| A | Chiral SFC purification condition: Column: YMC CELLULOSE-SB 5 μm, 250 × 20 mm, 120 bar, maintained at 40° C. Mobile phase: 20/80 MeOH (0.1% DEA)/$CO_2$; Flow rate: 100 ml/min; Wavelength: 230 nm DAD |

PREPARATIONS AND EXAMPLES

All starting materials are commercially available from Sigma-Aldrich (including Fluka and Discovery CPR) or Acros unless otherwise noted after the chemical name. Reagent/reactant names given are as named on the commercial bottle or asgenerated by IUPAC conventions or ChemDraw 16.0. None of the specific conditions and reagents noted herein is to be construed as limiting the scope of the invention and are provided for illustrative purposes only.

Example #1. 6-tert-Butyl-2-[(4-methoxybenzoyl)amino]-4,5,6,7-tetrahydrobenzothiophene-3-carboxylic acid (Compound #1)

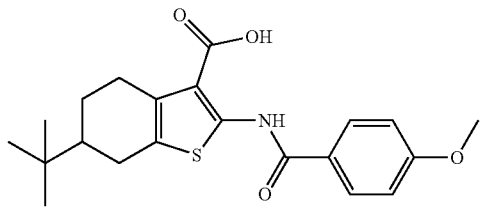 [SMILES: COc1ccc(C(=O)Nc2sc3c(c2C(=O)O)CCC(C(C)(C)C)C3)cc1]

To a solution of methyl 2-amino-6-tert-butyl-4,5,6,7-tetrahydro-1-benzothiophene-3-carboxylate (CAS: 213192-26-8, 250 mg, 0.94 mmol) in DCM (20 ml) was added DIPEA (CAS: 7087-68-5, 700 μl, 4.0 mmol) and 4-methoxybenzoyl chloride (CAS: 100-07-2, 255 mg, 1.5 mmol). The reaction mixture was stirred at RT overnight. The reaction was partitioned between DCM and saturated aqueous NaHCO$_3$ solution. The two phases were separated. The organic phase was washed with a 0.1N aqueous HCl solution and dried over MgSO$_4$. The solvent was removed under reduced pressure. Crystallisation from MeOH afforded methyl 6-(tert-butyl)-2-(4-methoxybenzamido)-4,5,6,7-tetrahydrobenzo[b]thiophene-3-carboxylate as an off-white solid (300 mg, yield 79%), which was dissolved in THF (7.0 ml) and MeOH (7.0 ml). To the solution was added LiOH aq. (CAS: 1310-66-3, 0.7M, 153 mg, 3.70 mmol). The reaction mixture was stirred at 60° C. for 30 minutes. The reaction was allowed to cool to RT. The reaction was next acidified with 0.1N aqueous HCl solution and extracted with EtOAc. The organic phase was dried over MgSO$_4$ and the solvent was removed under reduced pressure. The residue was triturated with a 1:1 mixture of EtOAc/isohexane to give 6-(tert-butyl)-2-(4-methoxybenzamido)-4,5,6,7-tetrahydrobenzo[b]thiophene-3-carboxylic acid as a white solid (190 mg, yield 49%). $^1$H NMR (DMSO-d$_6$, 400 MHz): δ=13.23 (br s, 1H), 12.32 (br s, 1H), 7.86 (d, J=8.9 Hz, 2H), 7.15 (d, J=8.9 Hz, 2H), 3.86 (s, 3H), 3.05 (dd, J=17.3, 4.2 Hz, 1H), 2.69 (dd, J=15.6, 4.2 Hz, 1H), 2.51-2.35 (m, 2H, partially obscured by the DMSO peak), 1.98 (d, J=9.1 Hz, 1H), 1.44 (td, J=11.8, 3.8 Hz, 1H), 1.28-1.18 (m, 1H), 0.92 (s, 9H). LC/MS (Table 1, Method A) R$_t$=6.07 min; MS m/z: 388 [M+H]$^+$.

Example #2. 6-tert-Butyl-2-[(3-methoxybenzoyl)amino]-4,5,6,7-tetrahydrobenzothiophene-3-carboxylic acid (Compound #2)

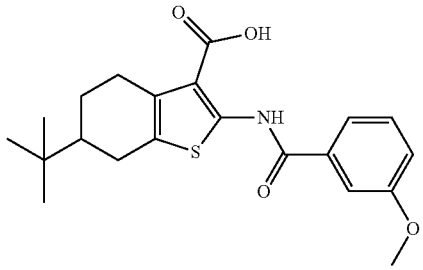 [SMILES: COc1cccc(C(=O)Nc2sc3c(c2C(=O)O)CCC(C(C)(C)C)C3)c1]

The title compound was synthesized according to the procedure described in Example #1 using 3-methoxybenzoyl chloride (CAS: 1711-05-3) as a starting material (off-white solid, yield 93%). $^1$H NMR (DMSO-d$_6$, 400 MHz): δ=13.31 (s, 1H), 12.37 (s, 1H), 7.56 (t, J=7.9 Hz, 1H), 7.47-7.43 (m, 2H), 7.25 (ddd, J=8.2, 2.6, 0.9 Hz, 1H), 3.85 (s, 3H), 3.05 (dd, J=17.1, 4.8 Hz, 1H), 2.71 (dd, J=16.0, 4.6 Hz, 1H), 2.57-2.50 (m, 1H, partially obscured by the DMSO peak), 2.40 (t, J=13.0 Hz, 1H), 2.00-1.96 (m, 1H), 1.44 (td, J=11.7, 3.4 Hz, 1H), 1.23 (qd, J=12.4, 4.9 Hz, 1H), 0.94 (s, 9H). LC/MS (Table 1, Method A) R$_t$=6.14 min; m/z: 388 [M+H]$^+$.

Example #3. 6-tert-Butyl-2-[(3,4-dimethoxybenzoyl)amino]-4,5,6,7-tetrahydrobenzothiophene-3-carboxylic acid (Compound #3)

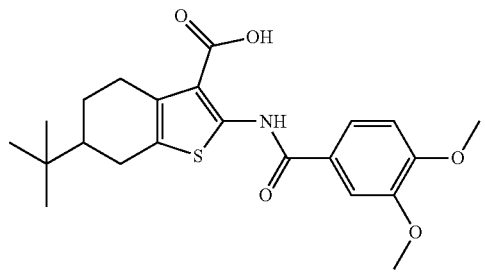 [SMILES: COc1ccc(C(=O)Nc2sc3c(c2C(=O)O)CCC(C(C)(C)C)C3)cc1OC]

The title compound was synthesized according to the procedure described in Example #1 using 3,4-dimethoxybenzoyl chloride (CAS: 3535-37-3) as a starting material (white solid, yield 60%). $^1$H NMR (DMSO-d$_6$, 400 MHz): δ=13.31 (s, 1H), 12.38 (s, 1H), 7.50-7.46 (m, 2H), 7.18 (d, J=8.4 Hz, 1H), 3.86 (s, 3H), 3.85 (s, 3H), 3.05 (dd, J=17.0, 4.0 Hz, 1H), 2.72-2.66 (m, 1H), 2.56-2.51 (m, 1H, partially obscured by the DMSO peak), 2.42-2.35 (m, 1H), 1.98 (d, J=8.9 Hz, 1H), 1.44 (td, J=11.8, 3.8 Hz, 1H), 1.23 (qd, J=12.3, 4.8 Hz, 1H), 0.92 (s, 9H). LC/MS (Table 1, Method A) R$_t$=5.88 min; MS m/z: 418 [M+H]$^+$.

Example #4. 6-tert-Butyl-2-[(3,4,5-trimethoxybenzoyl)amino]-4,5,6,7-tetrahydrobenzothiophene-3-carboxylic acid (Compound #4)

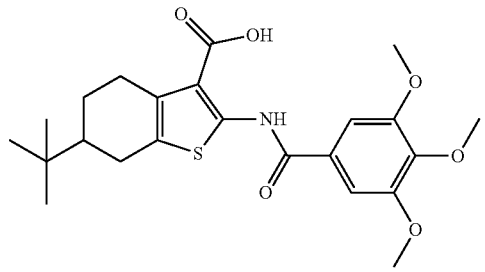 [SMILES: COc1cc(C(=O)Nc2sc3c(c2C(=O)O)CCC(C(C)(C)C)C3)cc(OC)c1OC]

The title compound was synthesized according to the procedure described in Example #1 using 3,4,5-trimethoxybenzoyl chloride (CAS: 4521-61-3) as a starting material (white solid, yield 21%). $^1$H NMR (DMSO-d$_6$, 400 MHz): δ=13.42 (s, 1H), 12.47 (s, 1H), 7.21 (s, 2H), 3.89 (s, 6H), 3.75 (s, 3H), 3.05 (d, J=12.9 Hz, 1H), 2.79-2.67 (m, 1H), 2.57-2.51 (m, 1H, partially obscured by the DMSO peak), 2.43-2.35 (m, 1H), 1.98 (d, J=9.1 Hz, 1H), 1.48-1.41 (m, 1H), 1.23 (qd, J=12.5, 5.0 Hz, 1H), 0.92 (s, 9H). LC/MS (Table 1, Method A) $R_t$=6.02 min; MS m/z: 448 [M+H]$^+$.

Example #5. 6-tert-Butyl-2-[(2-fluoro-4-methoxy-benzoyl)amino]-4,5,6,7-tetrahydrobenzothiophene-3-carboxylic acid (Compound #5)

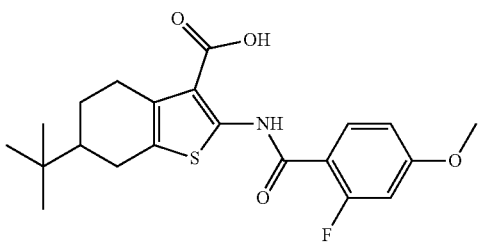 [SMILES: COc1ccc(C(=O)Nc2sc3c(c2C(=O)O)CCC(C(C)(C)C)C3)c(F)c1]

The title compound was synthesized according to the procedure described in Example #1 using 2-fluoro-4-methoxybenzoyl chloride (CAS: 321-24-4) as a starting material (white solid, yield 71%). $^1$H NMR (DMSO-d$_6$, 400 MHz): δ=13.18 (s, 1H), 12.38 (s, 1H), 8.00 (t, J=9.0 Hz, 1H), 7.09 (d, J=14.3 Hz, 1H), 6.98 (dd, J=8.8, 2.1 Hz, 1H), 3.88 (s, 3H), 3.04 (d, J=17.1 Hz, 1H), 2.71-2.66 (m, 1H), 2.55-2.50 (m, 1H, partially obscured by the DMSO peak), 2.41-2.34 (m, 1H), 1.97 (d, J=9.6 Hz, 1H), 1.47-1.40 (m, 1H), 1.27-1.18 (m, 1H), 0.93 (s, 9H). LC/MS (Table 1, Method A) $R_t$=6.16 min; MS m/z: 406 [M+H]$^+$.

Example #6. 6-tert-Butyl-2-[(2,3-difluoro-4-methoxy-benzoyl)amino]-4,5,6,7-tetrahydrobenzo-thiophene-3-carboxylic acid (Compound #6)

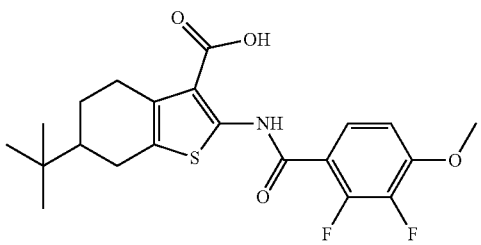 [SMILES: COc1ccc(C(=O)Nc2sc3c(c2C(=O)O)CCC(C(C)(C)C)C3)c(F)c1F]

The title compound was synthesized according to the procedure described in Example #1 using 2,3-difluoro-4-methoxybenzoyl chloride (CAS: 849632-69-5) as a starting material (pale yellow solid, yield 21%). $^1$H NMR (DMSO-d$_6$, 400 MHz): δ=13.26 (br s, 1H), 12.47 (br s, 1H), 7.87-7.81 (m, 1H), 7.25 (dd, J=8.0, 8.0 Hz, 1H), 3.97 (s, 3H), 3.05 (dd, J=4.2, 17.2 Hz, 1H), 2.73-2.65 (m, 1H), 2.57-2.52 (m, 1H, partially obscured by the DMSO peak), 2.42-2.33 (m, 1H), 1.98 (d, J=9.2 Hz, 1H), 1.47-1.38 (m, 1H), 1.28-1.16 (m, 1H), 0.92 (s, 9H). LC/MS (Table 1, Method A) $R_t$=6.12 min; MS m/z: 424 [M+H]$^+$.

Example #7. 6-tert-Butyl-2-[[4-(difluoromethoxy)benzoyl]amino]-4,5,6,7-tetrahydrobenzothiophene-3-carboxylic acid (Compound #7)

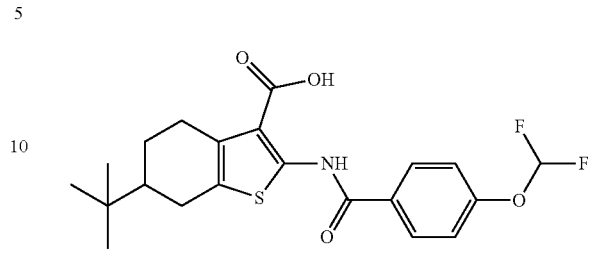

The title compound was synthesized according to the procedure described in Example #1 using 4-(difluoromethoxy)benzoyl chloride (CAS: 57320-63-5) as a starting material (pale yellow solid, yield 65%). $^1$H NMR (DMSO-d$_6$, 400 MHz): δ=13.02 (s, 1H), 8.16-7.95 (m, 2H), 7.59-7.22 (m, 4H), 3.09 (dd, J=17.0, 4.0 Hz, 1H), 2.72-2.67 (m, 1H), 2.54-2.50 (m, 1H, partially obscured by the DMSO peak), 2.43-2.35 (m, 1H), 1.99-1.96 (m, 1H), 1.48-1.41 (m, 1H), 1.22 (qd, J=12.3, 5.0 Hz, 1H), 0.92 (s, 9H). LC/MS (Table 1, Method A) $R_t$=6.14 min; MS m/z: 424 [M+H]$^+$.

Example #8. 6-tert-Butyl-2-[[4-(trifluoromethoxy)benzoyl]amino]-4,5,6,7-tetrahydrobenzothiophene-3-carboxylic acid (Compound #8)

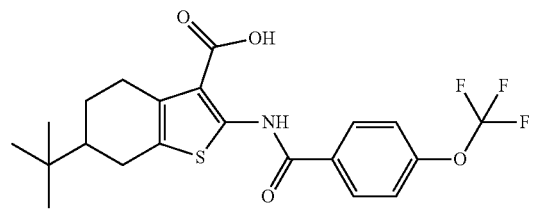 [SMILES: CC(C)(C)C1CCc2c(sc(NC(=O)c3ccc(OC(F)(F)F)cc3)c2C(=O)O)C1]

The title compound was synthesized according to the procedure described in Example #1 using 4-(trifluoromethoxy)benzoyl chloride (CAS: 36823-88-8) as a starting material (pale yellow solid, yield 40%). $^1$H NMR (DMSO-ds, 400 MHz): δ=13.36 (s, 1H), 12.46 (s, 1H), 8.05-8.01 (m, 2H), 7.53 (d, J=8.0 Hz, 2H), 3.06 (dd, J=17.1, 4.4 Hz, 1H), 2.71 (dd, J=15.8, 4.4 Hz, 1H), 2.58-2.54 (m, 1H, partially obscured by the DMSO peak), 2.43-2.36 (m, 1H), 2.01-1.96 (m, 1H), 1.48-1.41 (m, 1H), 1.23 (qd, J=12.3, 5.0 Hz, 1H), 0.92 (s, 9H). LC/MS (Table 1, Method A) $R_t$=6.51 min; MS m/z: 442 [M+H]$^+$.

Example #9. 6-tert-Butyl-2-[(4-morpholinobenzoyl)amino]-4,5,6,7-tetrahydrobenzothiophene-3-carboxylic acid (Compound #9)

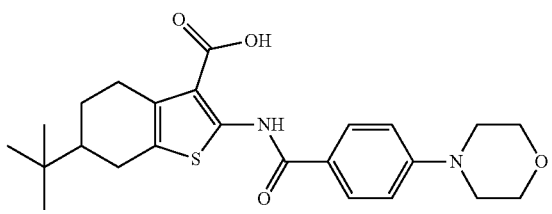 [SMILES: CC(C)(C)C1CCc2c(sc(NC(=O)c3ccc(N4CCOCC4)cc3)c2C(=O)O)C1]

To a solution of methyl 6-(tert-butyl)-2-(4-morpholino-benzamido)-4,5,6,7-tetrahydrobenzo[b]thiophene-3-carboxylate (Preparation #1, 62 mg, 0.14 mmol) in THF (1.0 ml) and MeOH (1.0 ml) was added LiOH aq. (CAS: 1310-66-3, 0.7M, 28 mg, 0.68 mmol). The reaction mixture was stirred at RT for 6 hours. The reaction was acidified to pH ~3 with 1N aqueous HCl solution. The reaction mixture was then extracted with DCM (×2). The combined organic phases were dried over MgSO$_4$ and the solvent was removed under reduced pressure. The residue was triturated with MeOH to give 6-tert-butyl-2-[(4-morpholinobenzoyl)amino]-4,5,6,7-tetrahydrobenzothiophene-3-carboxylic acid as a yellow solid (13 mg, yield 22%). $^1$H NMR (CDCl$_3$, 400 MHz): δ=11.99 (s, 1H), 7.87 (d, J=8.7 Hz, 2H), 6.99 (d, J=8.7 Hz, 2H), 3.91-3.88 (m, 4H), 3.33-3.31 (m, 4H), 3.16-3.09 (m, 1H), 2.76-2.59 (m, 2H), 2.47-2.40 (m, 1H), 2.07-2.02 (m, 1H), 1.55-1.27 (m, 2H), 0.96 (s, 9H), one exchangeable proton not observed. LC/MS (Table 1, Method A) R$_t$=5.94 min; MS m/z: 443 [M+H]$^+$.

Example #10. 6-tert-Butyl-2-[(4-chlorobenzoyl)amino]-4,5,6,7-tetrahydrobenzothiophene-3-carboxylic acid (Compound #10)

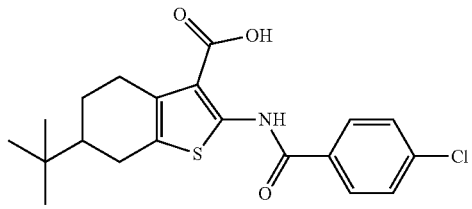 [SMILES: CC(C)(C)C1CCc2c(sc(NC(=O)c3ccc(Cl)cc3)c2C(=O)O)C1]

To a solution of methyl 6-(tert-butyl)-2-(4-chlorobenzamido)-4,5,6,7-tetrahydrobenzo[b]thiophene-3-carboxylate (Preparation #2, 81 mg, 0.20 mmol) in THF (1.5 ml) and MeOH (1.5 ml) was added LiOH aq. (CAS: 1310-66-3, 0.7M, 42 mg, 1.00 mmol). The reaction mixture was stirred at 50° C. overnight. The reaction was allowed to cool to RT. The volatiles were removed under reduced pressure and the residue was partitioned between a 1N aqueous HCl solution and DCM. The two phases were separated. The organic phase was dried over MgSO$_4$ and the solvent was removed under reduced pressure. The residue was triturated with MeOH to give 6-tert-butyl-2-[(4-chlorobenzoyl)amino]-4,5,6,7-tetrahydrobenzothiophene-3-carboxylic acid as a pale yellow solid (33 mg, yield 42%). $^1$H NMR (CDCl$_3$, 400 MHz): δ=12.10 (s, 1H), 7.94-7.91 (m, 2H), 7.53-7.50 (m, 2H), 3.16-3.10 (m, 1H), 2.77-2.59 (m, 2H), 2.49-2.41 (m, 1H), 2.09-2.04 (m, 1H), 1.58-1.29 (m, 2H, partially obscured by the water peak), 0.96 (s, 9H), one exchangeable proton not observed. LC/MS (Table 1, Method A) R$_t$=6.55 min; MS m/z: 392 [M+H]$^+$.

Example #11. 2-[[4-[3-(tert-Butoxycarbonylamino)propoxy]benzoyl]amino]-6-tert-butyl-4,5,6,7-tetrahydrobenzothiophene-3-carboxylic acid (Compound #11)

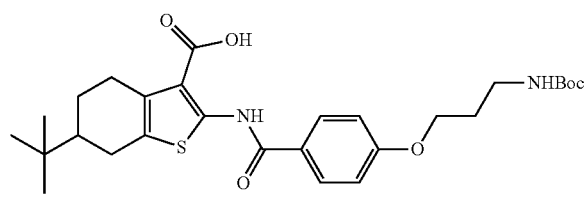 [SMILES: CC(C)(C)OC(=O)NCCCOc1ccc(C(=O)Nc2sc3c(c2C(=O)O)CCC(C(C)(C)C)C3)cc1]

The title compound was synthesized according to the procedure described in Example #10 using methyl 2-(4-(3-((tert-butoxycarbonyl)amino)propoxy)benzamido)-6-(tert-butyl)-4,5,6,7-tetrahydrobenzo[b]thiophene-3-carboxylate (Preparation #3) as a starting material (white solid, yield 85%). $^1$H NMR (DMSO-d$_6$, 400 MHz): δ=14.09 (br s, 1H), 7.84 (d, J=8.8 Hz, 2H), 7.09 (d, J=8.8 Hz, 2H), 6.91 (br s, 1H), 4.06 (t, J=6.2 Hz, 2H), 3.18-3.07 (m, 3H), 2.68-2.63 (m, 1H), 2.50-2.34 (m, 2H, partially obscured by the DMSO peak), 1.98-1.93 (m, 1H), 1.85 (q, J=6.5 Hz, 2H), 1.46-1.36 (m, 10H), 1.26-1.16 (m, 1H), 0.92 (s, 9H), one exchangeable proton not observed. LC/MS (Table 1, Method A) R$_t$=6.35 min; MS m/z: 531 [M+H]$^+$.

Example #12. 6-tert-Butyl-2-[[4-(2-hydroxyethoxy)benzoyl]amino]-4,5,6,7-tetrahydrobenzothiophene-3-carboxylic acid (Compound #12)

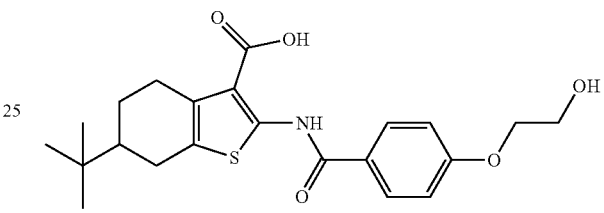

To a solution of methyl 6-(tert-butyl)-2-(4-hydroxybenzamido)-4,5,6,7-tetrahydrobenzo[b]thiophene-3-carboxylate (Preparation #3, Step A, 116 mg, 0.30 mmol) in acetonitrile (5.0 ml) was added Cs$_2$CO$_3$ (CAS: 534-17-8, 117 mg, 0.36 mmol), 2-(2-bromoethoxy)tetrahydro-2H-pyran (CAS: 17739-45-6, 75 mg, 0.36 mmol) and potassium iodide (CAS: 7681-11-0, 2 mg, 0.012 mmol). The reaction mixture was set to stir at RT and next heated at 65° C. for 45 minutes. Another aliquot of 2-(2-bromoethoxy)tetrahydro-2H-pyran (200 mg, 0.96 mmol) was added. The reaction was heated at 65° C. for 45 minutes (1.5 hours in total). An additional aliquot of Cs$_2$CO$_3$ (120 mg, 0.36 mmol) was added and the reaction was maintained at 65° C. for a further 1 hour (2.5 hours in total). The reaction was allowed to cool to RT. The mixture was partitioned between EtOAc and a 0.1N aqueous HCl solution. The two phases were separated. The organic phase was washed with water and dried over MgSO$_4$. The solvent was removed under reduced pressure. Purification by flash chromatography on silica gel (eluting with EtOAc/isohexane 1:4 to 1:3) afforded methyl 6-(tert-butyl)-2-(4-(2-((tetrahydro-2H-pyran-2-yl)oxy)ethoxy)benzamido)-4,5,6,7-tetrahydrobenzo[b]thiophene-3-carboxylate as a colourless oil (90 mg, yield 58%). Methyl 6-(tert-butyl)-2-(4-(2-((tetrahydro-2H-pyran-2-yl)oxy)ethoxy)benzamido)-4,5,6,7-tetrahydrobenzo[b]thiophene-3-carboxylate (90 mg, 0.17 mmol) was suspended in MeOH (10 ml) and p-toluenesulfonic acid monohydrate (CAS: 6192-52-5, 1.7 mg, 8.7 μmol) was added. The reaction mixture was set to stir at RT and next heated at 60° C. for 30 minutes. The reaction was allowed to cool to RT and the solvent was removed under reduced pressure. Purification by flash chromatography on silica gel (eluting with EtOAc/isohexane 1:4 to 1:2) afforded methyl 6-(tert-butyl)-2-(4-(2-hydroxyethoxy)benzamido)-4,5,6,7-tetrahydrobenzo[b]thiophene-3-carboxylate as a white solid (43 mg, yield 57%). Methyl 6-(tert-butyl)-2-(4-(2-hydroxyethoxy)benzamido)-4,5,6,7-tetrahydrobenzo[b]thiophene-3-carboxylate was hydrolysed to give 6-tert-butyl-2-[[4-(2-hydroxyethoxy)benzoyl]amino]-4,5,6,7- tetrahydrobenzothiophene-3-carboxylic acid according to the procedure described in Example #10 (white solid, yield 71%). ¹H NMR (DMSO-d₆, 400 MHz): δ=13.24 (s, 1H), 12.32 (s, 1H), 7.85 (d, J=8.9 Hz, 2H), 7.16 (d, J=8.9 Hz, 2H), 4.94 (t, J=5.4 Hz, 1H), 4.09 (t, J=5.0 Hz, 2H), 3.75 (q, J=5.0 Hz, 2H), 3.05-3.02 (m, 1H), 2.72-2.67 (m, 1H), 2.56-2.35 (m, 2H, partially obscured by the DMSO peak), 2.00-1.96 (m, 1H), 1.48-1.41 (m, 1H), 1.28-1.18 (m, 1H), 0.92 (s, 9H). LC/MS (Table 1, Method A) R$_t$=5.48 min; m/z: 418 [M+H]⁺.

Example #13. 2-[(2-Methylbenzoyl)amino]-6-phenyl-4,5,6,7-tetrahydrobenzothiophene-3-carboxylic acid (Compound #45)

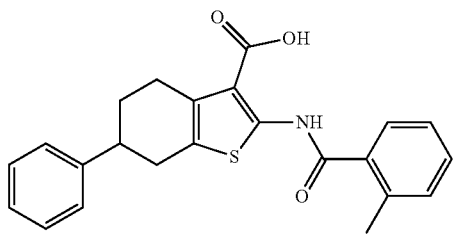 [SMILES: Cc1ccccc1C(=O)Nc1sc2c(c1C(=O)O)CCC(c1ccccc1)C2]

The title compound was synthesized according to the procedure described in Example #1 using methyl 2-amino-6-phenyl-4,5,6,7-tetrahydrobenzo[b]thiophene-3-carboxylate (Preparation #4) and 2-methylbenzoyl chloride (CAS: 933-88-0) as starting materials (white solid, yield 31%). ¹H NMR (DMSO-d₆, 400 MHz): δ=13.28 (s, 1H), 11.87 (s, 1H), 7.64-7.61 (m, 1H), 7.49 (dt, J=1.2, 7.5 Hz, 1H), 7.41-7.29 (m, 6H), 7.26-7.20 (m, 1H), 3.07-2.89 (m, 3H), 2.82-2.70 (m, 2H), 2.47 (s, 3H), 2.03 (d, J=12.7 Hz, 1H), 1.96-1.84 (m, 1H). LC/MS (Table 1, Method B) R$_t$=5.74 min; MS m/z: 392 [M+H]⁺.

Example #14. 2-Benzamido-6-phenyl-4,5,6,7-tetrahydrobenzothiophene-3-carboxylic acid (Compound #46)

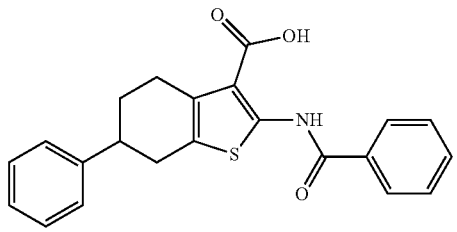 [SMILES: O=C(Nc1sc2c(c1C(=O)O)CCC(c1ccccc1)C2)c1ccccc1]

The title compound was synthesized according to the procedure described in Example #1 using methyl 2-amino-6-phenyl-4,5,6,7-tetrahydrobenzo[b]thiophene-3-carboxylate (Preparation #4) and benzoyl chloride (CAS: 98-88-4) as starting materials (pale yellow solid, yield 70%). ¹H NMR (DMSO-d₆, 400 MHz): δ=13.37 (s, 1H), 12.44 (s, 1H), 7.95-7.91 (m, 2H), 7.72-7.60 (m, 3H), 7.33-7.29 (m, 4H), 7.26-7.20 (m, 1H), 3.06-2.90 (m, 3H), 2.81-2.73 (m, 2H), 2.03 (dd, J=4.8, 10.4 Hz, 1H), 1.95-1.85 (m, 1H). LC/MS (Table 1, Method A) R$_t$=5.64 min; MS m/z: 378 [M+H]⁺.

Example #15. 2-Benzamido-6-phenyl-4,5,6,7-tetrahydrobenzothiophene-3-carboxylic acid (Enantiomer 1) (Compound #47A)

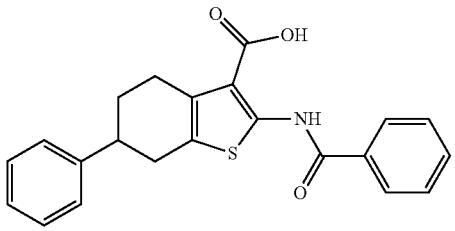 [SMILES: O=C(Nc1sc2c(c1C(=O)O)CCC(c1ccccc1)C2)c1ccccc1]

2-Benzamido-6-phenyl-4,5,6,7-tetrahydrobenzothiophene-3-carboxylic acid (Example #14, 200 mg) was resolved in its constituent enantiomers by chiral SFC purification (Table 3, Method A). The wet fractions pertaining to Enantiomer 1 were combined and the solvent was removed under reduced pressure to give 2-benzamido-6-phenyl-4,5,6,7-tetrahydrobenzothiophene-3-carboxylic acid diethylamine salt (Enantiomer 1). The residue was dissolved in EtOAc and washed with 0.1N aqueous HCl solution. The organic phase was dried over MgSO₄ and the solvent was removed under reduced pressure. The residue was triturated with EtOAc/isohexane to give 2-benzamido-6-phenyl-4,5,6,7-tetrahydrobenzothiophene-3-carboxylic acid (Enantiomer 1) as white solid (60 mg, yield 30%). ¹H NMR (DMSO-d₆, 400 MHz): δ=13.39 (s, 1H), 12.60 (s, 1H), 7.95-7.92 (m, 2H), 7.72-7.60 (m, 3H), 7.35-7.30 (m, 4H), 7.26-7.20 (m, 1H), 3.08-3.92 (m, 3H), 2.83-2.73 (m, 2H), 2.03 (dd, J=3.5, 9.9 Hz, 1H), 1.95-1.85 (m, 1H). LC/MS (Table 1, Method A) R$_t$=5.62 min; MS m/z: 378 [M+H]⁺. Chiral SFC (Table 1, Method G) R$_t$=6.6 min; e.e. 97.9%, first eluting enantiomer.

Example #16. 2-Benzamido-6-phenyl-4,5,6,7-tetrahydrobenzothiophene-3-carboxylic acid (Enantiomer 2) (Compound #47B)

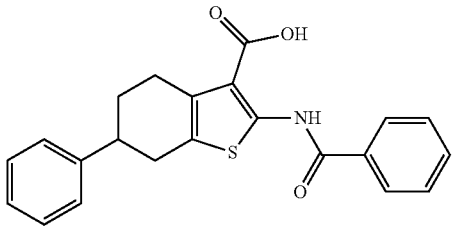 [SMILES: O=C(Nc1sc2c(c1C(=O)O)CCC(c1ccccc1)C2)c1ccccc1]

2-Benzamido-6-phenyl-4,5,6,7-tetrahydrobenzothiophene-3-carboxylic acid (Example #14, 200 mg) was resolved in its constituent enantiomers by chiral SFC purification (Table 3, Method A). The wet fractions pertaining to Enantiomer 2 were combined and the solvent was removed under reduced pressure to give 2-benzamido-6-phenyl-4,5,6,7-tetrahydrobenzothiophene-3-carboxylic acid diethylamine salt (Enantiomer 2). The residue was dissolved in EtOAc and washed with a 0.1N aqueous HCl solution. The organic phase was dried over MgSO₄ and the solvent was removed under reduced pressure. The residue was triturated with EtOAc/isohexane to give 2-benzamido-6-phenyl-4,5,6,7-tetrahydrobenzothiophene-3-carboxylic acid (Enantiomer 2) as white solid (40 mg, yield 20%). ¹H NMR (DMSO-d₆, 400

MHz): δ=13.38 (s, 1H), 12.55 (s, 1H), 7.95-7.91 (m, 2H), 7.71-7.61 (m, 3H), 7.36-7.30 (m, 4H), 7.26-7.20 (m, 1H), 3.07-2.91 (m, 3H), 2.82-2.75 (m, 2H), 2.03 (dd, J=5.0, 10.5 Hz, 1H), 1.95-1.85 (m, 1H). LC/MS (Table 1, Method A) $R_t$=5.62 min; MS m/z: 378 [M+H]$^+$. Chiral SFC (Table 1, Method G) $R_t$=7.5 min; e.e. 93.6%, second eluting enantiomer.

Example #17. 2-[(3,4-Dimethoxybenzoyl)amino]-6-phenyl-4,5,6,7-tetrahydrobenzothiophene-3-carboxylic acid (Compound #48)

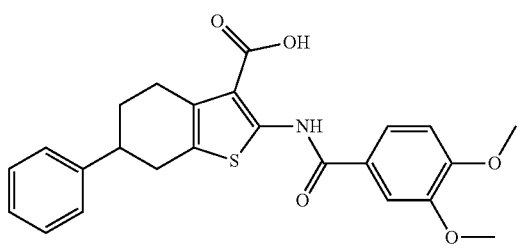 [SMILES: COc1ccc(C(=O)Nc2sc3c(c2C(=O)O)CCC(c2ccccc2)C3)cc1OC]

The title compound was synthesized according to the procedure described in Example #1 using methyl 2-amino-6-phenyl-4,5,6,7-tetrahydrobenzo[b]thiophene-3-carboxylate (Preparation #4) and 3,4-dimethozybenzoyl chloride (CAS: 3535-37-3) as starting materials (white solid, yield 4%). $^1$H NMR (DMSO-d$_6$, 400 MHz): δ=12.69 (s, 1H), 7.54 (dt, J=2.0, 8.6 Hz, 2H), 7.41-7.34 (m, 4H), 7.31-7.21 (m, 2H), 3.92 (s, 3H), 3.90 (s, 3H), 3.13-2.93 (m, 3H), 2.88-2.73 (m, 2H), 2.11-2.06 (m, 1H), 1.95 (dq, J=4.9, 11.6 Hz, 1H), one exchangeable proton not observed. LC/MS (Table 1, Method C) $R_t$=2.88 min; MS m/z: 438 [M+H]$^+$.

Example #18. 2-[(4-Hydroxybenzoyl)amino]-6-phenyl-4,5,6,7-tetrahydrobenzothiophene-3-carboxylic acid (Compound #49)

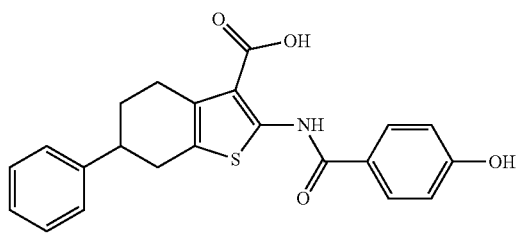 [SMILES: O=C(Nc1sc2c(c1C(=O)O)CCC(c1ccccc1)C2)c1ccc(O)cc1]

To a solution of methyl 2-amino-6-phenyl-4,5,6,7-tetrahydrobenzo[b]thiophene-3-carboxylate (Preparation #4, 1.15 g, 4.00 mmol) in DCM (70 ml) was added DIPEA (CAS: 7087-68-5, 3.50 ml, 20.0 mmol) and 4-acetoxybenzoyl chloride (CAS: 27914-73-4, 953 mg, 4.80 mmol). The reaction mixture was stirred at RT overnight. The reaction was partitioned between DCM and a 0.1M aqueous HCl solution. The two phases were separated and the organic phase was dried over MgSO$_4$. The solvent was removed under reduced pressure. The residue was suspended in THF (25 ml) and MeOH (25 ml) and LiOH aq. (CAS: 1310-66-3, 0.8M, 336 mg, 8.00 mmol) was added. The reaction was set to stir at RT and next heated at 40° C. for 30 minutes. The reaction was allowed to cool to RT and next acidified to pH ~3 with 1N aqueous HCl solution. The organic solvents were removed under reduced pressure and the aqueous suspension was filtered to afford methyl 2-(4-hydroxybenzamido)-6-phenyl-4,5,6,7-tetrahydrobenzo[b]thiophene-3-carboxylate as a white solid (1.60 g, yield 98%). Methyl 2-(4-hydroxybenzamido)-6-phenyl-4,5,6,7-tetrahydrobenzo[b]thiophene-3-carboxylate was finally hydrolysed to give 2-[(4-hydroxybenzoyl)amino]-6-phenyl-4,5,6,7-tetrahydrobenzothiophene-3-carboxylic acid according to the procedure described in Example #10 (white solid, yield 96%). $^1$H NMR (DMSO-d$_6$, 400 MHz): δ=13.27 (s, 1H), 12.32 (s, 1H), 10.42 (s, 1H), 7.80-7.75 (m, 2H), 7.35-7.29 (m, 4H), 7.26-7.20 (m, 1H), 6.98-6.93 (m, 2H), 3.06-2.88 (m, 3H), 2.76 (dd, J=11.0, 14.2 Hz, 2H), 2.02 (d, J=11.0 Hz, 1H), 1.94-1.84 (m, 1H). LC/MS (Table 1, Method A) $R_t$=5.07 min; MS m/z: 394 [M+H]$^+$.

Example #19. 2-[[4-(2-Hydroxyethoxy)benzoyl]amino]-6-phenyl-4,5,6,7-tetrahydrobenzothiophene-3-carboxylic acid (Compound #50)

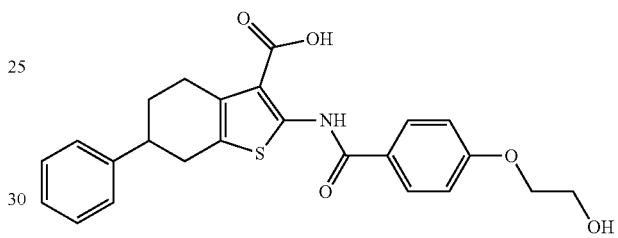

The title compound was synthesized according to the procedure described in Example #12 using methyl 2-(4-hydroxybenzamido)-6-phenyl-4,5,6,7-tetrahydrobenzo[b]thiophene-3-carboxylate (synthesized in Example #18) as a starting material (white solid, yield 41%). $^1$H NMR (DMSO-d$_6$, 400 MHz): δ=13.31 (s, 1H), 12.35 (s, 1H), 7.89-7.84 (m, 2H), 7.36-7.30 (m, 4H), 7.26-7.20 (m, 1H), 7.19-7.14 (m, 2H), 4.94 (t, J=5.4 Hz, 1H), 4.10 (t, J=4.9 Hz, 2H), 3.75 (q, J=4.8 Hz, 2H), 3.07-2.88 (m, 3H), 2.81-2.73 (m, 2H), 2.02 (d, J=9.8 Hz, 1H), 1.90 (dq, J=5.4, 11.8 Hz, 1H). LC/MS (Table 1, Method A) $R_t$=5.02 min; MS m/z: 438 [M+H]$^+$.

Example #20. 2-[[4-(2-Methoxyethoxy)benzoyl]amino]-6-phenyl-4,5,6,7-tetrahydrobenzothiophene-3-carboxylic acid (Compound #51)

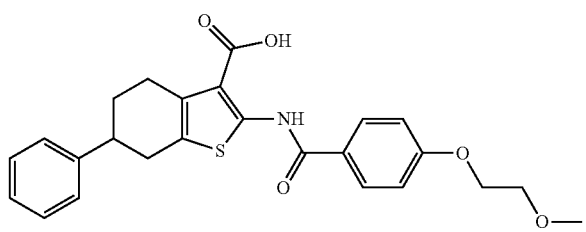 [SMILES: COCCOc1ccc(C(=O)Nc2sc3c(c2C(=O)O)CCC(c2ccccc2)C3)cc1]

To a suspension of methyl 2-(4-hydroxybenzamido)-6-phenyl-4,5,6,7-tetrahydrobenzo[b]thiophene-3-carboxylate (synthesized in Example #18, 204 mg, 0.50 mmol) and Cs$_2$CO$_3$ (CAS: 534-17-8, 244 mg, 0.75 mmol) in acetonitrile (10 ml) was added 2-bromoethyl methyl ether (CAS: 6482-24-2, 104 mg, 0.75 mmol). The reaction mixture was set to stir at RT and next heated at 60° C. for 1 hour. The reaction was allowed to cool to RT. Additional Cs$_2$CO$_3$ (200 mg, 0.62 mmol), 2-bromoethyl methyl ether (150 mg, 1.08 mmol) and potassium iodide (CAS: 7681-11-0, 3 mg) were added. The reaction mixture was again set to stir at RT and next heated at 60° C. for a further 5 hours (6 hours in total). The reaction was allowed to cool to RT. The mixture was partitioned between EtOAc and 0.1N aqueous HCl solution. The two phases were separated, the organic phase was dried over MgSO$_4$ and the solvent was removed under reduced pressure. Trituration with EtOAc/isohexane afforded methyl 2-(4-(2-methoxyethoxy)benzamido)-6-phenyl-4,5,6,7-tetrahydrobenzo[b]thiophene-3-carboxylate as a yellow solid (170 mg, 73%). Methyl 2-(4-(2-methoxyethoxy)benzamido)-6-phenyl-4,5,6,7-tetrahydrobenzo[b]thiophene-3-carboxylate was hydrolysed to give 2-[[4-(2-methoxyethoxy)benzoyl]amino]-6-phenyl-4,5,6,7-tetrahydrobenzothiophene-3-carboxylic acid following the procedure described in Example #10 (white solid, yield 58%). $^1$H NMR (DMSO-d$_6$, 400 MHz): δ=13.32 (s, 1H), 12.35 (s, 1H), 7.86 (d, J=8.9 Hz, 2H), 7.34-7.29 (m, 4H), 7.25-7.20 (m, 1H), 7.17 (d, J=8.9 Hz, 2H), 4.23-4.19 (m, 2H), 3.71-3.68 (m, 2H), 3.32 (s, 3H), 3.06-2.89 (m, 3H), 2.77 (dd, J=10.9, 14.2 Hz, 2H), 2.02 (d, J=10.1 Hz, 1H), 1.94-1.84 (m, 1H). LC/MS (Table 1, Method A) R$_t$=5.61 min; MS m/z: 452 [M+H]$^+$.

Example #21. 2-Benzamido-6-phenyl-5,7-dihydro-4H-thieno[2,3-c]pyridine-3-carboxylic acid (Compound #52)

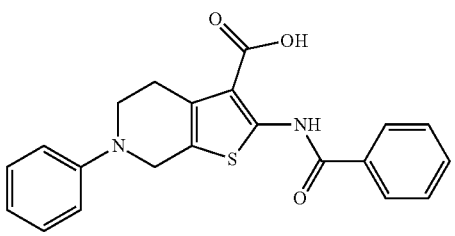

A reaction vessel was charged with 1-phenylpiperidin-4-one (CAS: 19125-34-9, 526 mg, 3.00 mmol), methyl cyanoacetate (CAS: 105-34-0, 290 µl, 3.30 mmol), diethylamine (CAS: 109-89-7,160 µl, 1.50 mmol) and sulfur (CAS: 7704-34-9,115 mg, 3.60 mmol) and solvated in methanol (4.0 ml). The reaction was set to stir at RT. The reaction mixture was stirred at RT overnight. The volatiles were removed under reduced pressure. The residue was partitioned between water and EtOAc and the two phases were separated. The aqueous phase was further extracted with EtOAc. The combined organic phases were washed with brine and dried over Na$_2$SO$_4$. The solvent was removed under reduced pressure. Purification by flash chromatography on silica gel (eluting with 0-30% EtOAc in isohexane) afforded methyl 2-amino-6-phenyl-4,5,6,7-tetrahydrothieno[2,3-c]pyridine-3-carboxylate as an orange solid (870 mg, quant.). The title compound was then synthesized according to the procedure described in Example #1 using methyl 2-amino-6-phenyl-4,5,6,7-tetrahydrothieno[2,3-c]pyridine-3-carboxylate and benzoyl chloride (CAS: 98-88-4) as starting materials (yellow solid, yield 27%). $^1$H NMR (DMSO-d$_6$, 400 MHz): δ=13.48 (br s, 1H), 12.37 (s, 1H), 7.96-7.91 (m, 2H), 7.73-7.61 (m, 3H), 7.36-7.27 (m, 4H), 6.97 (br s, 1H), 4.49 (s, 2H), 3.67 (t, J=5.2 Hz, 2H), 3.03 (br s, 2H). LC/MS (Table 1, Method A) R$_t$=5.05 min; MS m/z: 379 [M+H]$^+$.

Example #22. 2-Benzamido-6-(4-fluoro-2-methylphenyl)-5,7-dihydro-4H-thieno[2,3-c]pyridine-3-carboxylic acid (Compound #53)

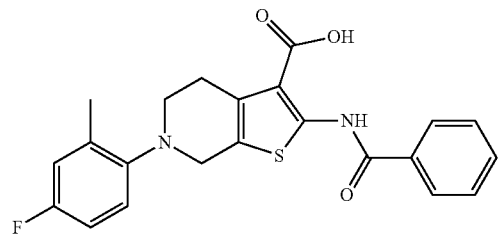 [SMILES: Cc1cc(F)ccc1N1CCc2c(sc(NC(=O)c3ccccc3)c2C(=O)O)C1]

A suspension of 1-benzyl-1-methyl-4-oxopiperidium iodide (CAS: 77542-27-9, 1.00 g, 3.02 mmol), 4-fluoro-2-methylaniline (CAS: 452-71-1, 378 mg, 3.02 mmol), potassium carbonate (CAS: 584-08-7, 63 mg, 0.45 mmol) in EtOH (7.0 ml) and water (5.0 ml) was heated at reflux for 3 hours. The reaction mixture was allowed to cool to RT. The reaction was partitioned between DCM and water. The two phases were separated and the organic phase was dried over MgSO$_4$. The solvent was removed under reduced pressure. Purification by flash chromatography on silica gel (eluting with 30% EtOAc in isohexane) afforded 1-(4-fluoro-2-methylphenyl)piperidin-4-one as a pale yellow oil (320 mg, 51%). The title compound was then synthesized according to the procedure described in Example #21 using 1-(4-fluoro-2-methylphenyl)piperidin-4-one as a starting material (yellow solid, yield 17%). $^1$H NMR (DMSO-d$_6$, 400 MHz): δ=13.44 (s, 1H), 12.39 (s, 1H), 7.96-7.92 (m, 2H), 7.73-7.61 (m, 3H), 7.13 (dd, J=5.5, 8.7 Hz, 1H), 7.06 (dd, J=3.0, 9.7 Hz, 1H), 6.98 (ddd, J=8.5, 8.5, 3.1 Hz, 1H), 4.04 (s, 2H), 3.13 (t, J=5.5 Hz, 2H), 2.92 (t, J=5.3 Hz, 2H), 2.29 (s, 3H). LC/MS (Table 1, Method A) R$_t$=5.60 min; m/z: 411 [M+H]$^+$.

Example #23. 2-[(3,4-Dimethoxybenzoyl)amino]-6-(4-fluoro-2-methylphenyl)-5,7-dihydro-4H-thieno[2,3-c]pyridine-3-carboxylic acid (Compound #54)

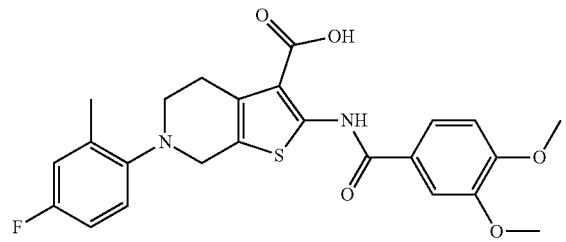 [SMILES: COc1ccc(C(=O)Nc2sc3c(c2C(=O)O)CCN(c2ccc(F)cc2C)C3)cc1OC]

The title compound was synthesized according to the procedure described in Example #21 using 1-(4-fluoro-2-methylphenyl)piperidin-4-one (as synthesized in Example #22) and 3,4-dimethoxybenzoyl chloride (CAS: 3535-37-3) as starting materials (yellow solid, yield 4%). $^1$H NMR (DMSO-d$_6$, 400 MHz): δ=13.25 (s, 1H), 7.52 (dt, J=2.1, 8.9 Hz, 2H), 7.18 (d, J=8.5 Hz, 1H), 7.14 (dd, J=5.4, 8.9 Hz, 1H), 7.07 (dd, J=3.0, 9.6 Hz, 1H), 6.98 (dt, J=3.1, 8.5 Hz, 1H), 4.03 (s, 2H), 3.87 (s, 6H), 3.12 (t, J=5.6 Hz, 2H), 2.94 (t, J=5.3 Hz, 2H), 2.31 (s, 3H), one exchangeable proton not observed. LC/MS (Table 1, Method C) R$_t$=2.94 min; MS m/z: 471 [M+H]$^+$.

Example #24. 2-[(2-Fluoro-4-methoxybenzoyl)amino]-6-(4-fluoro-2-methyl-phenyl)-5,7-dihydro-4H-thieno[2,3-c]pyridine-3-carboxylic acid (Compound #55)

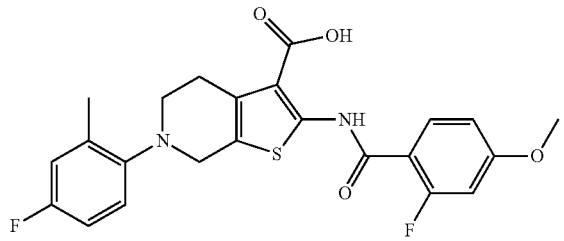 [SMILES: COc1ccc(C(=O)Nc2sc3c(c2C(=O)O)CCN(c2ccc(F)cc2C)C3)c(F)c1]

The title compound was synthesized according to the procedure described in Example #21 using 1-(4-fluoro-2-methylphenyl)piperidin-4-one (as synthesized in Example #22) and 2-fluoro-4-methoxybenzoyl chloride (CAS: 321-24-4) as starting materials (yellow solid, yield 10%). $^1$H NMR (DMSO-d$_6$, 400 MHz): δ=12.71 (s, 1H), 8.01 (t, J=9.0 Hz, 1H), 7.15-7.04 (m, 3H), 7.02-6.94 (m, 2H), 4.02 (s, 2H), 3.89 (s, 3H), 3.13 (t, J=5.6 Hz, 2H), 2.93 (t, J=5.2 Hz, 2H), 2.30 (s, 3H), one exchangeable proton not observed. LC/MS (Table 1, Method C) R$_t$=2.98 min; MS m/z: 459 [M+H]$^+$.

Example #25. 2-Benzamido-6-(2,4-difluorophenyl)-5,7-dihydro-4H-thieno[2,3-c]pyridine-3-carboxylic acid (Compound #56)

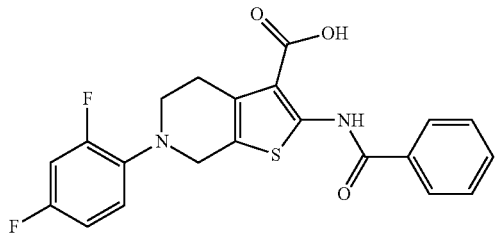 [SMILES: O=C(Nc1sc2c(c1C(=O)O)CCN(c1ccc(F)cc1F)C2)c1ccccc1]

The title compound was synthesized according to the procedure described in Example #22 using 1-benzyl-1-methyl-4-oxopiperidium iodide (CAS: 77542-27-9) and 2,4-difluoroaniline (CAS: 367-25-9) as starting materials (white solid, yield 6%). $^1$H NMR (DMSO-d$_6$, 400 MHz): δ=13.46 (s, 1H), 12.40 (s, 1H), 7.95-7.91 (m, 2H), 7.73-7.61 (m, 3H), 7.24 (ddd, J=3.1, 9.1, 12.3 Hz, 1H), 7.14-7.07 (m, 1H), 7.03-6.97 (m, 1H), 4.22 (s, 2H), 3.36-3.34 (m, 2H, partially covered by the water peak), 2.90 (t, J=5.3 Hz, 2H). LC/MS (Table 1, Method A) R$_t$=5.28 min; m/z: 415 [M+H]$^+$.

Example #26. 2-Benzamido-6-(o-tolyl)-5,7-dihydro-4H-thieno[2,3-c]pyridine-3-carboxylic acid (Compound #57)

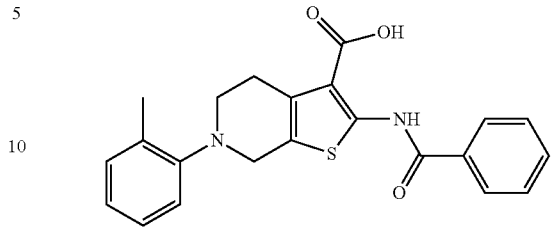

The title compound was synthesized according to the procedure described in Example #22 using 1-benzyl-1-methyl-4-oxopiperidium iodide (CAS: 77542-27-9) and o-toluidine (CAS: 95-53-4) as starting materials (yellow solid, yield 21%). $^1$H NMR (DMSO-d$_6$, 400 MHz): δ=13.47 (s, 1H), 12.51 (s, 1H), 8.00 (d, J=7.2 Hz, 2H), 7.78-7.66 (m, 3H), 7.27-7.12 (m, 3H), 7.04 (t, J=7.3 Hz, 1H), 4.13 (s, 2H), 3.21 (t, J=5.2 Hz, 2H), 2.99 (t, J=5.1 Hz, 2H), 2.34 (s, 3H). LC/MS (Table 1, Method C) R$_t$=2.94 min; MS m/z: 393 [M+H]$^+$.

Example #27. 2-Benzamido-6-tert-butyl-4,5,6,7-tetrahydrobenzothiophene-3-carboxylic acid (Compound #71)

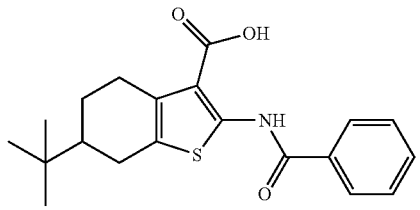 [SMILES: CC(C)(C)C1CCc2c(sc(NC(=O)c3ccccc3)c2C(=O)O)C1]

The title compound was synthesized according to the procedure described in Example #1 using methyl 2-amino-6-tert-butyl-4,5,6,7-tetrahydro-1-benzothiophene-3-carboxylate (CAS: 213192-26-8) and benzoyl chloride (CAS: 98-88-4) as starting materials (white solid, yield 30%). $^1$H NMR (DMSO-d$_6$, 400 MHz): δ=13.29 (br s, 1H), 12.44 (s, 1H), 7.94-7.89 (m, 2H), 7.72-7.60 (m, 3H), 3.05 (dd, J=4.1, 17.4 Hz, 1H), 2.70 (dd, J=4.5, 16.1 Hz, 1H), 2.59-2.51 (m, 1H, partially obscured by the DMSO peak), 2.43-2.34 (m, 1H), 2.02-1.94 (m, 1H), 1.49-1.40 (m, 1H), 1.27-1.17 (m, 1H), 0.92 (s, 9H). LC/MS (Table 1, Method A) R$_t$=6.09 min; m/z: 358 [M+H]$^+$.

Example #28. 2-Benzamido-6-tert-butyl-4,5,6,7-tetrahydrobenzothiophene-3-carboxylic acid (Enantiomer 1) (Compound #67)

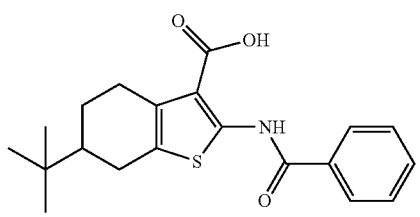 [SMILES: CC(C)(C)C1CCc2c(sc(NC(=O)c3ccccc3)c2C(=O)O)C1]

The title compound was synthesized according to the procedure described in Example #15 using 2-benzamido-6-tert-butyl-4,5,6,7-tetrahydrobenzothiophene-3-carboxylic acid (Example #27) as a starting material (white solid, yield 34%). ¹H NMR (DMSO-d₆, 400 MHz): δ=13.30 (br s, 1H), 12.44 (s, 1H), 7.94-7.89 (m, 2H), 7.71-7.60 (m, 3H), 3.05 (dd, J=4.4, 17.2 Hz, 1H), 2.71 (dd, J=4.6, 16.0 Hz, 1H), 2.58-2.52 (m, 1H, partially obscured by the DMSO peak), 2.45-2.34 (m, 1H), 2.02-1.94 (m, 1H), 1.49-1.39 (m, 1H), 1.30-1.17 (m, 1H), 0.93 (s, 9H). LC/MS (Table 1, Method A) $R_t$=6.09 min; MS m/z: 358 [M+H]⁺. Chiral SFC (Table 1, Method H) $R_t$=3.3 min; e.e. 98.8%, first eluting enantiomer.

Example #29. 2-Benzamido-6-tert-butyl-4,5,6,7-tetrahydrobenzothiophene-3-carboxylic acid (Enantiomer 2) (Compound #66)

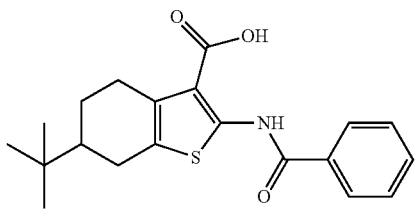 [SMILES: CC(C)(C)C1CCc2c(sc(NC(=O)c3ccccc3)c2C(=O)O)C1]

The title compound was synthesized according to the procedure described in Example #16 using 2-benzamido-6-tert-butyl-4,5,6,7-tetrahydrobenzothiophene-3-carboxylic acid (Example #27) as a starting material (white solid, yield 28%). ¹H NMR (DMSO-d₆, 400 MHz): δ=13.40 (br s, 1H), 12.75 (br s, 1H), 7.94-7.90 (m, 2H), 7.70-7.58 (m, 3H), 3.08 (dd, J=3.7, 17.0 Hz, 1H), 2.70 (dd, J=4.4, 15.8 Hz, 1H), 2.57-2.52 (m, 1H, partially obscured by the DMSO peak), 2.43-2.36 (m, 1H), 2.00-1.95 (m, 1H), 1.48-1.40 (m, 1H), 1.28-1.18 (m, 1H), 0.93 (s, 9H). LC/MS (Table 1, Method A) $R_t$=6.09 min, MS m/z: 358 [M+H]⁺. Chiral SFC (Table 1, Method H) $R_t$=4.0 min; e.e. 98.1%, second eluting enantiomer.

Example #30. 6-tert-Butyl-2-[(4-fluorobenzoyl)amino]-4,5,6,7-tetrahydrobenzothiophene-3-carboxylic acid (Compound #236)

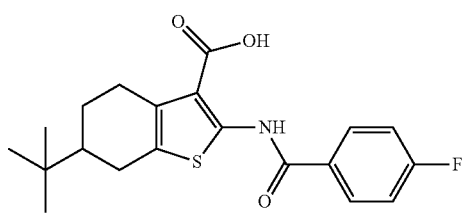 [SMILES: CC(C)(C)C1CCc2c(sc(NC(=O)c3ccc(F)cc3)c2C(=O)O)C1]

The title compound was synthesized according to the procedure described in Example #1 using 4-fluorobenzoyl chloride (CAS: 403-43-0) as a starting material (off-white solid, yield 51%). ¹H NMR (DMSO-d₆, 400 MHz): δ=13.29 (br s, 1H), 12.49 (br s, 1H), 8.00-7.95 (m, 2H), 7.49-7.44 (m, 2H), 3.09-3.03 (m, 1H), 2.73-2.67 (m, 1H), 2.57-2.51 (m, 1H, partially obscured by the DMSO peak), 2.43-2.34 (m, 1H), 2.00-1.95 (m, 1H), 1.48-1.42 (m, 1H), 1.26-1.21 (m, 1H), 0.93 (s, 9H). LC/MS (Table 1, Method A) $R_t$=6.14 min. m/z: 376 [M+H]+.

Example #31. 6-tert-Butyl-2-[(4-fluorobenzoyl)amino]-4,5,6,7-tetrahydrobenzothiophene-3-carboxylic acid (Enantiomer 1) (Compound #237)

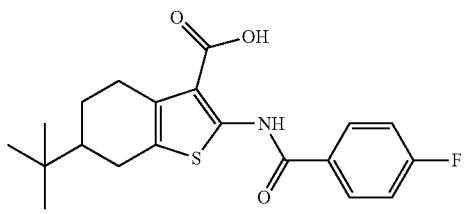 [SMILES: CC(C)(C)C1CCc2c(sc(NC(=O)c3ccc(F)cc3)c2C(=O)O)C1]

The title compound was synthesized according to the procedure described in Example #15 using 6-tert-butyl-2-[(4-fluorobenzoyl)amino]-4,5,6,7-tetrahydrobenzothiophene-3-carboxylic acid (Example #30) as a starting material (white solid, yield 37%). ¹H NMR (DMSO-d₆, 400 MHz): δ=13.25 (br s, 1H), 12.52 (br s, 1H), 8.00-7.95 (m, 2H), 7.49-7.43 (m, 2H), 3.09-3.03 (m, 1H), 2.73-2.67 (m, 1H), 2.57-2.52 (m, 1H, partially obscured by the DMSO peak), 2.43-2.36 (m, 1H), 2.01-1.96 (m, 1H), 1.48-1.41 (m, 1H), 1.25-1.17 (m, 1H), 0.92 (s, 9H). LC/MS (Table 1, Method A) $R_t$=6.14 min, MS m/z: 376 [M+H]⁺. Chiral SFC (Table 1, Method I) $R_t$=7.7 min; e.e. 93.2%, first eluting enantiomer.

Example #32. 6-tert-Butyl-2-[(4-fluorobenzoyl)amino]-4,5,6,7-tetrahydrobenzothiophene-3-carboxylic acid (Enantiomer 2) (Compound #68)

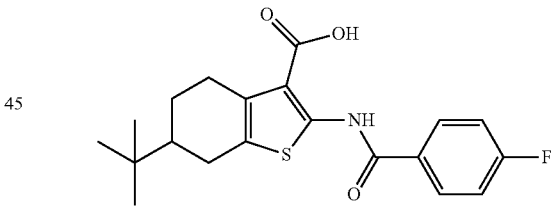

The title compound was synthesized according to the procedure described in Example #16 using 6-tert-butyl-2-[(4-fluorobenzoyl)amino]-4,5,6,7-tetrahydrobenzothiophene-3-carboxylic acid (Example #30) as a starting material (pale yellow solid, yield 45%). ¹H NMR (DMSO-d₆, 400 MHz): δ=13.29 (br s, 1H), 12.49 (br s, 1H), 8.00-7.95 (m, 2H), 7.49-7.44 (m, 2H), 3.09-3.03 (m, 1H), 2.73-2.67 (m, 1H), 2.57-2.51 (m, 1H, partially obscured by the DMSO peak), 2.43-2.34 (m, 1H), 2.00-1.95 (m, 1H), 1.48-1.42 (m, 1H), 1.26-1.21 (m, 1H), 0.93 (s, 9H). LC/MS (Table 1, Method A) $R_t$=6.14 min, MS m/z: 376 [M+H]⁺. Chiral SFC (Table 1, Method I) $R_t$=9.6 min; e.e. 93.6%, second eluting enantiomer.

Example #33. 6-tert-Butyl-2-[(2-fluorobenzoyl)amino]-4,5,6,7-tetrahydrobenzothiophene-3-carboxylic acid (Compound #73)

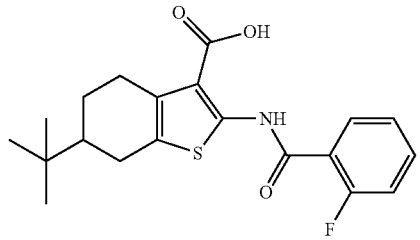 [SMILES: CC(C)(C)C1CCc2c(sc(NC(=O)c3ccccc3F)c2C(=O)O)C1]

The title compound was synthesized according to the procedure described in Example #1 using methyl 2-amino-6-tert-butyl-4,5,6,7-tetrahydro-1-benzothiophene-3-carboxylate (CAS: 213192-26-8) and 2-fluorobenzoyl chloride (CAS: 393-52-2) as starting materials (off-white solid, yield 48%). $^1$H NMR (DMSO-$d_6$, 400 MHz): δ=13.24 (br s, 1H), 12.51 (br s, 1H), 8.09-8.03 (m, 1H), 7.74-7.68 (m, 1H), 7.49-7.41 (m, 2H), 3.10-3.04 (m, 1H), 2.74-2.66 (m, 1H), 2.58-2.52 (m, 1H, partially obscured by the DMSO peak), 2.45-2.36 (m, 1H), 2.02-1.94 (m, 1H), 1.49-1.39 (m, 1H), 1.29-1.17 (m, 1H), 0.92 (s, 9H). LC/MS (Table 1, Method A) $R_t$=6.13 min; m/z: 376 [M+H]$^+$.

Example #34. 6-tert-Butyl-2-[(2-fluorobenzoyl)amino]-4,5,6,7-tetrahydrobenzothiophene-3-carboxylic acid (Enantiomer 1) (Compound #69)

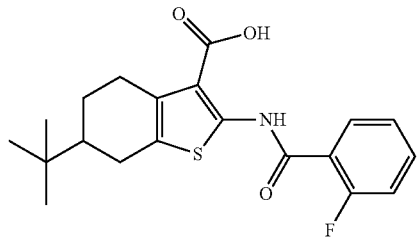 [SMILES: CC(C)(C)C1CCc2c(sc(NC(=O)c3ccccc3F)c2C(=O)O)C1]

The title compound was synthesized according to the procedure described in Example #15 using 6-tert-butyl-2-[(2-fluorobenzoyl)amino]-4,5,6,7-tetrahydrobenzothiophene-3-carboxylic acid (Example #33) as a starting material (white solid, yield 29%). $^1$H NMR (DMSO-$d_6$, 400 MHz): δ=13.25 (br s, 1H), 12.49 (br s, 1H), 8.09-8.03 (m, 1H), 7.75-7.69 (m, 1H), 7.49-7.41 (m, 2H), 3.09-3.03 (m, 1H), 2.74-2.66 (m, 1H), 2.55-2.50 (m, 1H, partially obscured by the DMSO peak), 2.43-2.33 (m, 1H), 2.01-1.95 (m, 1H), 1.48-1.41 (m, 1H), 1.28-1.18 (m, 1H), 0.92 (s, 9H). LC/MS (Table 1, Method A) $R_t$=6.12 min, MS m/z: 376 [M+H]$^+$. Chiral SFC (Table 1, Method H) $R_t$=4.1 min; e.e. 100%, first eluting enantiomer.

Example #35. 6-tert-Butyl-2-[(2-fluorobenzoyl)amino]-4,5,6,7-tetrahydrobenzothiophene-3-carboxylic acid (Enantiomer 2) (Compound #238)

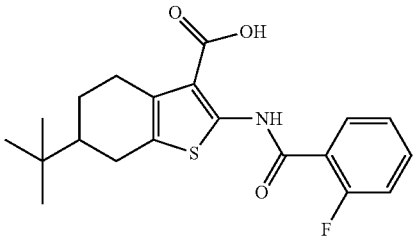

The title compound was synthesized according to the procedure described in Example #16 using 6-tert-butyl-2-[(2-fluorobenzoyl)amino]-4,5,6,7-tetrahydrobenzothiophene-3-carboxylic acid (Example #33) as a starting material (white solid, yield 29%). $^1$H NMR (DMSO-$d_6$, 400 MHz): δ=13.24 (br s, 1H), 12.55 (br s, 1H), 8.08-8.03 (m, 1H), 7.74-7.68 (m, 1H), 7.49-7.41 (m, 2H), 3.09-3.03 (m, 1H), 2.72-2.68 (m, 1H), 2.57-2.51 (m, 1H, partially obscured by the DMSO peak), 2.44-2.36 (m, 1H), 2.01-1.95 (m, 1H), 1.47-1.41 (m, 1H), 1.28-1.19 (m, 1H), 0.92 (s, 9H). LC/MS (Table 1, Method A) $R_t$=6.12 min, MS m/z: 376 [M+H]$^+$. Chiral SFC (Table 1, Method H) $R_t$=4.8 min; e.e. 100%, second eluting enantiomer.

Example #36. 4-Methyl-2-[(4-morpholinobenzoyl)amino]-4,5,6,7-tetrahydrobenzothiophene-3-carboxylic acid (Compound #70)

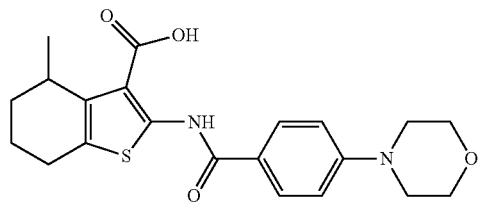 [SMILES: CC1CCCc2sc(NC(=O)c3ccc(N4CCOCC4)cc3)c(C(=O)O)c21]

Ethyl 2-(4-bromobenzamido)-4-methyl-4,5,6,7-tetrahydrobenzo[b]thiophene-3-carboxylate (Preparation #5, 338 mg, 0.80 mmol), morpholine (CAS: 110-91-8, 63 mg, 0.32 mmol), RuPhos Pd G2 (CAS: 1375325-68-0, 33 mg, 0.04 mmol) and Cs$_2$CO$_3$ (CAS: 534-17-8, 175 mg, 0.54 mmol) were suspended in dioxane (3.0 ml). The reaction mixture was degassed with nitrogen for 10 minutes. The reaction was set to stir at RT and next heated at 75° C. overnight. The reaction was allowed to cool to RT. The reaction was diluted with DCM and filtered through a pad of Celite®. The solvent was removed under reduced pressure. The residue was triturated with MeOH to afford ethyl 4-methyl-2-(4-morpholinobenzamido)-4,5,6,7-tetrahydrobenzo[b]thiophene-3-carboxylate as an off-white solid (304 mg, yield 91%). Ethyl 4-methyl-2-(4-morpholinobenzamido)-4,5,6,7-tetrahydrobenzo[b]thiophene-3-carboxylate (304 mg, 0.71 mmol) was dissolved in THF (5.0 ml), MeOH (5.0 ml) and water (3.6 ml). To the solution was added lithium hydroxide monohydrate (CAS: 1310-66-3, 149 mg, 3.55 mmol). The reaction mixture was stirred at 50° C. overnight. The reaction was allowed to cool to RT. The reaction was partitioned between DCM and 1N aqueous HCl solution. The two phases were separated and the aqueous phase was extracted with DCM (×2). The combined organic phases were passed through a phase separator and the solvent was removed under reduced pressure. Purification by RP-HPLC (Table 2, Method A) afforded 4-methyl-2-[(4-morpholinobenzoyl) amino]-4,5,6,7-tetrahydrobenzothiophene-3-carboxylic acid as an off-white solid (40 mg, yield 12%). $^1$H NMR (DMSO-$d_6$, 400 MHz): δ=13.07 (br s, 1H), 7.82 (d, J=8.7 Hz, 2H), 7.18 (br s, 1H), 7.14 (d, J=8.6 Hz, 2H), 3.82-3.77 (m, 4H), 3.44-3.29 (m, 5H, partially obscured by the water peak), 2.75-2.59 (m, 2H), 1.92-1.66 (m, 4H), 1.21 (d, J=6.7 Hz, 3H). LC/MS (Table 1, Method C) $R_t$=2.70 min; MS m/z: 401 [M+H]$^+$.

Example #37. 6-tert-Butyl-2-(pyridine-2-carbonylamino)-4,5,6,7-tetrahydrobenzothiophene-3-carboxylic acid (Compound #72)

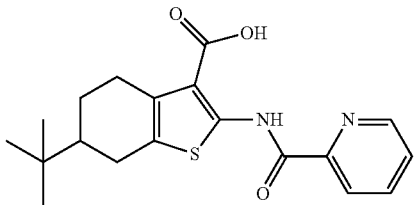 [SMILES: CC(C)(C)C1CCc2c(sc(NC(=O)c3ccccn3)c2C(=O)O)C1]

To a solution of methyl 2-amino-6-tert-butyl-4,5,6,7-tetrahydro-1-benzothiophene-3-carboxylate (CAS: 213192-26-8, 134 mg, 0.50 mmol) in acetonitrile (3.0 ml) was added 2-picolinic acid (CAS: 98-98-6, 80 mg, 0.65 mmol), 2-chloromethylpyridinium iodide (CAS: 14338-32-0, 166 mg, 0.65 mmol), DMAP (CAS: 1122-58-3, 18 mg, 0.15 mmol) and TEA (CAS: 121-44-8, 210 µl, 1.50 mmol). The reaction mixture was set to stir at RT and next stirred at 60° C. for 20 hours. The reaction was partitioned between EtOAc and saturated NH$_4$Cl aqueous solution and the two phases were separated. The aqueous phase was extracted with EtOAc (×2). The combined organic phases were dried over MgSO$_4$ and the solvent was removed under reduced pressure to afford methyl 6-(tert-butyl)-2-(picolinamido)-4,5,6,7-tetrahydrobenzo[b]thiophene-3-carboxylate (186 mg, yield quant.). The title compound was then synthesized according to the procedure described in Example #10 using methyl 6-(tert-butyl)-2-(picolinamido)-4,5,6,7-tetrahydrobenzo[b] thiophene-3-carboxylate as a starting material (yellow solid, yield 7%). $^1$H NMR (DMSO-$d_6$, 400 MHz): δ=13.06 (br s, 2H), 8.77-8.74 (m, 1H), 8.20-8.17 (m, 1H), 8.10 (ddd, J=7.7, 7.7, 1.7 Hz, 1H), 7.72 (ddd, J=1.3, 4.7, 7.5 Hz, 1H), 3.07 (dd, J=4.5, 17.3 Hz, 1H), 2.75-2.68 (m, 1H), 2.59-2.52 (m, 1H, partially obscured by the DMSO peak), 2.46-2.36 (m, 1H), 2.02-1.95 (m, 1H), 1.49-1.40 (m, 1H), 1.30-1.18 (m, 1H), 0.92 (s, 9H). LC/MS (Table 1, Method A) $R_t$=5.85 min; MS m/z: 359 [M+H]$^+$.

Example #38. 2-Benzamido-4-methyl-4,5,6,7-tetrahydrobenzothiophene-3-carboxylic acid (Compound #74)

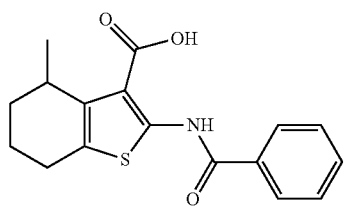 [SMILES: CC1CCCc2sc(NC(=O)c3ccccc3)c(C(=O)O)c21]

The title compound was synthesized according to the procedure described in Example #1 using ethyl 2-amino-4-methyl-4,5,6,7-tetrahydrobenzo[b]thiophene-3-carboxylate (Preparation #5, Step A) and benzoyl chloride (CAS: 98-88-4) as starting materials (off-white solid, yield 7%). $^1$H NMR (DMSO-$d_6$, 400 MHz): δ=13.39 (br s, 1H), 12.50 (s, 1H), 7.94-7.89 (m, 2H), 7.72-7.59 (m, 3H), 3.40-3.34 (m, 1H, partially obscured by the water peak), 2.77-2.56 (m, 2H), 1.88-1.61 (m, 4H), 1.17 (d, J=6.8 Hz, 3H). LC/MS (Table 1, Method C) $R_t$=2.73 min; m/z: 316 [M+H]$^+$.

Example #39. 2-[[4-(Difluoromethoxy)benzoyl] amino]-4-methyl-4,5,6,7-tetrahydrobenzothiophene-3-carboxylic acid (Compound #75)

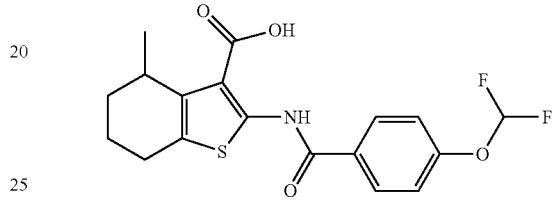

The title compound was synthesized according to the procedure described in Example #1 using ethyl 2-amino-4-methyl-4,5,6,7-tetrahydrobenzo[b]thiophene-3-carboxylate (Preparation #5, Step A) and 4-(difluoromethoxy)benzoyl chloride (CAS: 57320-63-5) as starting materials (white solid, yield 3%). $^1$H NMR (DMSO-$d_6$, 400 MHz): δ=14.18 (br s, 1H), 7.99 (d, J=8.8 Hz, 2H), 7.40 (t, J=73.6 Hz, 1H), 7.37 (d, J=8.7 Hz, 2H), 7.25 (br s, 1H), 3.48-3.40 (m, 1H, partially obscured by the water peak), 2.72-2.54 (m, 2H), 1.90-1.62 (m, 4H), 1.18 (d, J=6.7 Hz, 3H). LC/MS (Table 1, Method D) $R_t$=3.76 min; m/z: 382 [M+H]$^+$.

Example #40. 2-[(2-Fluoro-4-methoxybenzoyl) amino]-4-methyl-4,5,6,7-tetrahydrobenzothiophene-3-carboxylic acid (Compound #76)

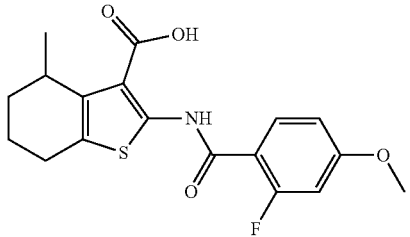 [SMILES: COc1ccc(C(=O)Nc2sc3c(c2C(=O)O)C(C)CCC3)c(F)c1]

The title compound was synthesized according to the procedure described in Example #1 using ethyl 2-amino-4-methyl-4,5,6,7-tetrahydrobenzo[b]thiophene-3-carboxylate (Preparation #5, Step A) and 2-fluoro-4-methoxybenzoyl chloride (CAS: 321-24-4) as starting materials (white solid, yield 3%). $^1$H NMR (DMSO-$d_6$, 400 MHz): δ=13.52 (br s, 1H), 12.63 (d, J=9.3 Hz, 1H), 8.21 (t, J=9.1 Hz, 1H), 7.31-7.18 (m, 2H), 4.09 (s, 3H), 3.59-3.56 (m, 1H, partially obscured by the water peak), 2.94-2.76 (m, 2H), 2.08-1.81 (m, 4H), 1.36 (d, J=6.7 Hz, 3H). LC/MS (Table 1, Method D) $R_t$=3.76 min; MS m/z: 386 [M+Na]$^+$.

Example #41. 2-Benzamido-4,5,6,7-tetrahydrobenzothiophene-3-carboxylic acid (Compound #77)

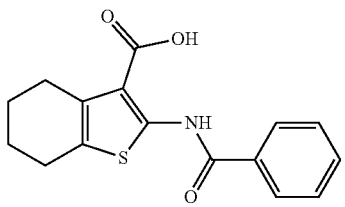

The title compound was synthesized according to the procedure described in Example #1 using methyl 2-amino-4,5,6,7-tetrahydro-1-benzothiophene-3-carboxylate (CAS: 108354-78-5) and benzoyl chloride (CAS: 98-88-4) as starting materials (pale yellow solid, yield 38%). $^1$H NMR (DMSO-d$_6$, 400 MHz): δ=13.30 (br s, 1H), 12.48 (s, 1H), 7.94-7.90 (m, 2H), 7.71-7.60 (m, 3H), 2.79-2.73 (m, 2H), 2.67-2.63 (m, 2H), 1.78-1.69 (m, 4H). LC/MS (Table 1, Method A) R$_t$=4.98 min; MS m/z: 302 [M+H]$^+$.

Example #42. 2-Benzamido-4-methyl-4,5,6,7-tetrahydrobenzothiophene-3-carboxylic acid (Enantiomer 1) (Compound #79)

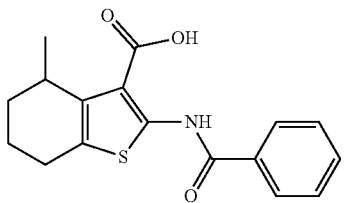

The title compound was synthesized according to the procedure described in Example #15 using 2-benzamido-4-methyl-4,5,6,7-tetrahydrobenzothiophene-3-carboxylic acid (Example #38) as a starting material (off-white solid, yield 32%). $^1$H NMR (DMSO-d$_6$, 400 MHz): δ=13.46 (br s, 1H), 12.56 (br s, 1H), 8.00-7.95 (m, 2H), 7.78-7.66 (m, 3H), 3.45-3.40 (m, 1H, partially obscured by the water peak), 2.78-2.61 (m, 2H), 1.92-1.70 (m, 4H), 1.23 (d, J=6.9 Hz, 3H). LC/MS (Table 1, Method C) R$_t$=2.72 min; MS m/z: 316 [M+H]$^+$. Chiral SFC (Table 1, Method J) R$_t$=4.9 min: e.e. 91.1%, first eluting enantiomer.

Example #43. 2-Benzamido-4-methyl-4,5,6,7-tetrahydrobenzothiophene-3-carboxylic acid (Enantiomer 2) (Compound #88)

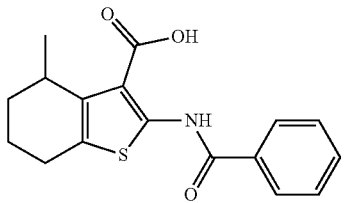

The title compound was synthesized according to the procedure described in Example #16 using 2-benzamido-4-methyl-4,5,6,7-tetrahydrobenzothiophene-3-carboxylic acid (Example #38) as a starting material (off-white solid, yield 27%). $^1$H NMR (DMSO-d$_6$, 400 MHz): δ=13.44 (br s, 1H), 12.53 (s, 1H), 7.98-7.94 (m, 2H), 7.77-7.65 (m, 3H), 3.43-3.38 (m, 1H, partially obscured by the water peak), 2.80-2.62 (m, 2H), 1.91-1.69 (m, 4H), 1.22 (d, J=6.7 Hz, 3H). LC/MS (Table 1, Method C) R$_t$=2.72 min; m/z: 316 [M+H]$^+$. Chiral SFC (Table 1, Method J) R$_t$=6.0 min; e.e. 95.8%, second eluting enantiomer.

Example #44. 2-[(3,4-Dimethoxybenzoyl)amino]-4-methyl-4,5,6,7-tetrahydrobenzothiophene-3-carboxylic acid (Compound #81)

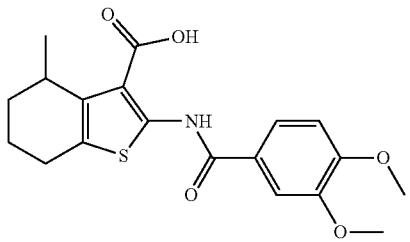 [SMILES: COc1ccc(C(=O)Nc2sc3c(c2C(=O)O)C(C)CCC3)cc1OC]

The title compound was synthesized according to the procedure described in Example #1 using ethyl 2-amino-4-methyl-4,5,6,7-tetrahydrobenzo[b]thiophene-3-carboxylate (Preparation #5, Step A) and 3,4-dimethoxybenzoyl chloride (CAS: 3535-37-3) as starting materials (white solid, yield 47%). $^1$H NMR (DMSO-d$_6$, 400 MHz): δ=13.60 (br s, 1H), 12.65 (s, 1H), 7.71-7.64 (m, 2H), 7.38 (d, J=8.4 Hz, 1H), 4.06 (s, 3H), 4.05 (s, 3H), 3.58-3.53 (m, 1H, partially obscured by the water peak), 2.93-2.73 (m, 2H), 2.04-1.80 (m, 4H), 1.35 (d, J=6.6 Hz, 3H). LC/MS (Table 1, Method D) R$_t$=3.63 min; MS m/z: 376 [M+H]$^+$.

Example #45. 6-tert-Butyl-2-[(2-methylbenzoyl)amino]-4,5,6,7-tetrahydrobenzothiophene-3-carboxylic acid (Compound #82)

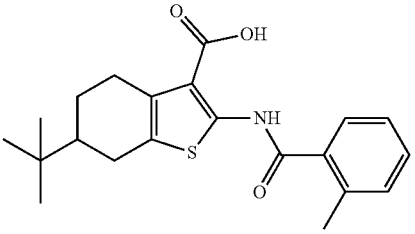 [SMILES: Cc1ccccc1C(=O)Nc1sc2c(c1C(=O)O)CCC(C(C)(C)C)C2]

The title compound was synthesized according to the procedure described in Example #1 using methyl 2-amino-6-tert-butyl-4,5,6,7-tetrahydro-1-benzothiophene-3-carboxylate (CAS: 213192-26-8) and 2-methylbenzoyl chloride (CAS: 933-88-0) as starting materials (off-white solid, yield 32%). $^1$H NMR (DMSO-d$_6$, 400 MHz): δ=13.22 (br s, 1H), 11.86 (s, 1H), 7.62-7.59 (m, 1H), 7.51-7.46 (m, 1H), 7.40-7.34 (m, 2H), 3.05 (dd, J=4.3, 17.1 Hz, 1H), 2.74-2.66 (m, 1H), 2.57-2.52 (m, 1H, partially obscured by the DMSO peak), 2.47 (s, 3H), 2.44-2.35 (m, 1H), 2.02-1.94 (m, 1H), 1.48-1.39 (m, 1H), 1.28-1.16 (m, 1H), 0.93 (s, 9H). LC/MS (Table 1, Method B) R$_t$=6.16 min; MS m/z: 372 [M+H]$^+$.

Example #46. 6-tert-Butyl-2-[(3-fluorobenzoyl)amino]-4,5,6,7-tetrahydrobenzothiophene-3-carboxylic acid (Compound #83)

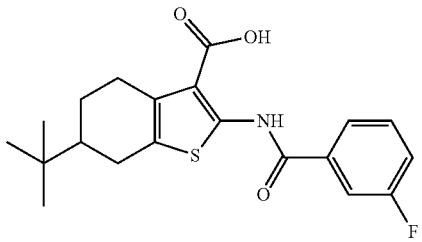 [SMILES: CC(C)(C)C1CCc2c(sc(NC(=O)c3cccc(F)c3)c2C(=O)O)C1]

The title compound was synthesized according to the procedure described in Example #1 using methyl 2-amino-6-tert-butyl-4,5,6,7-tetrahydro-1-benzothiophene-3-carboxylate (CAS: 213192-26-8) and 3-fluorobenzoyl chloride (CAS: 1711-07-5) as starting materials (white solid, yield 36%). $^1$H NMR (DMSO-d$_6$, 400 MHz): δ=13.34 (br s, 1H), 12.48 (s, 1H), 7.75-7.65 (m, 3H), 7.57-7.51 (m, 1H), 3.05 (dd, J=4.5, 17.0 Hz, 1H), 2.74-2.66 (m, 1H), 2.58-2.52 (m, 1H, partially obscured by the DMSO peak), 2.45-2.35 (m, 1H), 2.02-1.94 (m, 1H), 1.49-1.39 (m, 1H), 1.29-1.18 (m, 1H), 0.93 (s, 9H). LC/MS (Table 1, Method A) R$_t$=6.24 min; m/z: 376 [M+H]$^+$.

Example #47. 2-Benzamido-5,6,7,8-tetrahydro-4H-cyclohepta[b]thiophene-3-carboxylic acid (Compound #84)

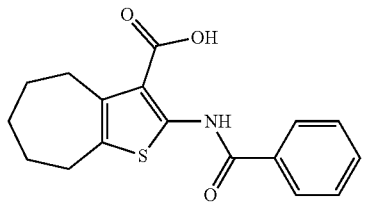 [SMILES: O=C(Nc1sc2c(c1C(=O)O)CCCCC2)c1ccccc1]

The title compound was synthesized according to the procedure described in Example #21 using cycloheptanone (CAS: 502-42-1) and benzoyl chloride (CAS: 98-88-4) as starting materials (off-white solid, yield 52%). $^1$H NMR (DMSO-d$_6$, 400 MHz): δ=13.52 (br s, 1H), 12.37 (br s, 1H), 7.92-7.88 (m, 2H), 7.71-7.58 (m, 3H), 3.10-3.07 (m, 2H), 2.77-2.71 (m, 2H), 1.86-1.78 (m, 2H), 1.65-1.51 (m 4H). LC/MS (Table 1, Method A) R$_t$=5.20 min: m/z: 316 [M+H]$^+$.

Example #48. 6-Methyl-2-[(2-methylbenzoyl)amino]-4,5,6,7-tetrahydrobenzothiophene-3-carboxylic acid (Compound #86)

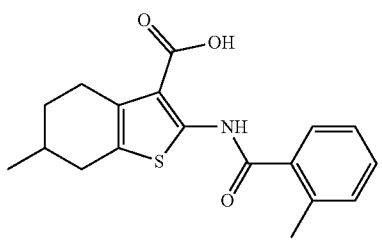 [SMILES: Cc1ccccc1C(=O)Nc1sc2c(c1C(=O)O)CCC(C)C2]

The title compound was synthesized according to the procedure described in Example #1 using ethyl 2-amino-6-methyl-4,5,6,7-tetrahydro-1-benzothiophene-3-carboxylate (CAS: 76981-71-0) and 2-methylbenzoyl chloride (CAS: 933-88-0) as starting materials (off-white solid, yield 28%). $^1$H NMR (DMSO-d$_6$, 400 MHz): δ=13.20 (br s, 1H), 11.87 (s, 1H), 7.62-7.59 (m, 1H), 7.48 (ddd, J=7.5, 7.5, 1.3 Hz, 1H), 7.39-7.34 (m, 2H), 2.97-2.88 (m, 1H), 2.74 (dd, J=4.7, 16.0 Hz, 1H), 2.69-2.57 (m, 1H), 2.46 (s, 3H), 2.29-2.20 (m, 1H), 1.89-1.78 (m, 2H), 1.39-1.27 (m, 1H), 1.04 (d, J=6.5 Hz, 3H). LC/MS (Table 1, Method A) R$_t$=5.49 min; MS m/z: 330 [M+H]$^+$.

Example #49. 6-tert-Butyl-2-[(2-methylbenzoyl)amino]-4,5,6,7-tetrahydrobenzothiophene-3-carboxylic acid (Enantiomer 1) (Compound #87)

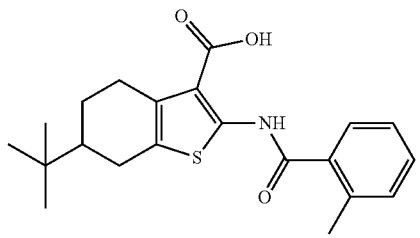 [SMILES: Cc1ccccc1C(=O)Nc1sc2c(c1C(=O)O)CCC(C(C)(C)C)C2]

The title compound was synthesized according to the procedure described in Example #15 using 6-tert-butyl-2-[(2-methylbenzoyl)amino]-4,5,6,7-tetrahydrobenzothiophene-3-carboxylic acid (Example #45) as a starting material (white solid, yield 32%). $^1$H NMR (DMSO-d$_6$, 400 MHz): δ=13.20 (br s, 1H), 11.84 (s, 1H), 7.62-7.60 (m, 1H), 7.51-7.46 (m, 1H), 7.40-7.34 (m, 2H), 3.04 (dd, J=4.3, 17.2 Hz, 1H), 2.74-2.66 (m, 1H), 2.57-2.51 (m, 1H, partially obscured by the DMSO peak), 2.46 (s, 3H), 2.44-2.34 (m, 1H), 2.02-1.94 (m, 1H), 1.48-1.39 (m, 1H), 1.29-1.16 (m, 1H), 0.93 (s, 9H). LC/MS (Table 1, Method A) R$_t$=6.21 min; m/z: 372 [M+H]$^+$. Chiral SFC (Table 1, Method K) R$_t$=1.8 min: e.e. 100%, first eluting enantiomer.

Example #50. 6-tert-Butyl-2-[(2-methylbenzoyl)amino]-4,5,6,7-tetrahydrobenzothiophene-3-carboxylic acid (Enantiomer 2) (Compound #239)

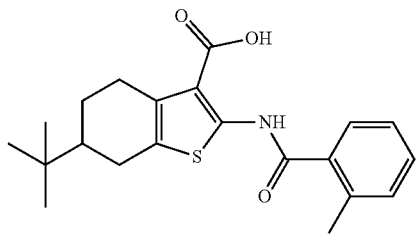 [SMILES: Cc1ccccc1C(=O)Nc1sc2c(c1C(=O)O)CCC(C(C)(C)C)C2]

The title compound was synthesized according to the procedure described in Example #15 using 6-tert-butyl-2-[(2-methylbenzoyl)amino]-4,5,6,7-tetrahydrobenzothiophene-3-carboxylic acid (Example #45) as a starting material (white solid, yield 76%). $^1$H NMR (DMSO-d$_6$, 400 MHz): δ=13.21 (s, 1H), 11.84 (s, 1H), 7.62-7.60 (m, 1H), 7.50-7.46 (m, 1H), 7.39-7.34 (m, 2H), 3.04 (dd, J=4.3, 17.2 Hz, 1H), 2.74-2.66 (m, 1H), 2.57-2.52 (m, 1H, partially obscured by the DMSO peak), 2.46 (s, 3H), 2.44-2.32 (m, 1H), 2.00-1.97 (m, 1H), 1.47-1.39 (m, 1H), 1.29-1.17 (m, 1H), 0.93 (s, 9H). LC/MS (Table 1, Method A) $R_t$=6.21 min; MS m/z: 372 [M+H]$^+$. Chiral SFC (Table 1, Method K) $R_t$=2.8 min; e.e. 100%, second eluting enantiomer.

Example #51. 6-tert-Butyl-2-[(2-methylcyclohexanecarbonyl)amino]-4,5,6,7-tetrahydrobenzothiophene-3-carboxylic acid (Compound #89)

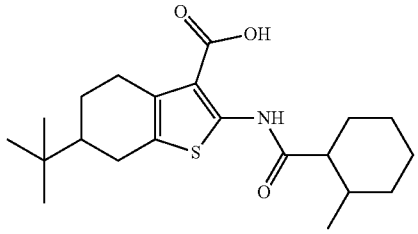 [SMILES: CC1CCCCC1C(=O)Nc1sc2c(c1C(=O)O)CCC(C(C)(C)C)C2]

The title compound was synthesized according to the procedure described in Example #37 using methyl 2-amino-6-tert-butyl-4,5,6,7-tetrahydro-1-benzothiophene-3-carboxylate (CAS: 213192-26-8) and 2-methyl-1-cyclohexanecarboxylic acid (CAS: 56586-13-1) as starting materials (yellow solid, yield 88%). $^1$H NMR (DMSO-d$_6$, 400 MHz): δ=13.02 (br s, 1H), 11.42 (br s, 1H), 3.01 (dd, J=4.2, 17.1 Hz, 1H), 2.69-2.59 (m, 2H), 2.48-2.42 (m, 1H), 2.39-2.29 (m, 1H), 2.20-2.13 (m, 1H), 1.99-1.91 (m, 1H), 1.75-1.16 (m, 10H), 0.91 (s, 9H), 0.82 (d, J=7.0 Hz, 3H). LC/MS (Table 1, Method A) $R_t$=6.48 min: m/z: 378 [M+H]$^+$.

Example #52. 6-tert-Butyl-2-[(5-methoxypyridine-2-carbonyl)amino]-4,5,6,7-tetrahydrobenzothiophene-3-carboxylic acid (Compound #91)

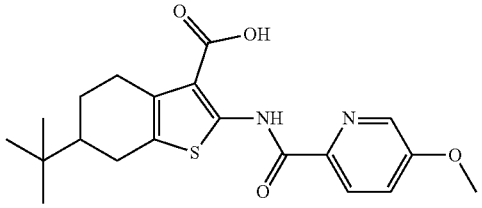 [SMILES: COc1ccc(C(=O)Nc2sc3c(c2C(=O)O)CCC(C(C)(C)C)C3)nc1]

A reaction vessel was charged with 5-methoxypicolinic acid (CAS: 29082-92-6, 300 mg, 1.96 mmol) and solvated in thionyl chloride (CAS: 7719-09-7, 0.71 ml, 27.4 mmol). The reaction was set to stir at RT and next heated at 50° C. for 3 hours. The reaction was stopped and allowed to cool to RT. The solvent was removed under reduced pressure to give 5-methoxypicolinoyl chloride as a yellow oil (336 mg, yield quant.). The title compound was then synthesized according to the procedure described in Example #1 using methyl 2-amino-6-tert-butyl-4,5,6,7-tetrahydro-1-benzothiophene-3-carboxylate (CAS: 213192-26-8) and 5-methoxypicolinoyl chloride as starting materials (off-white solid, yield 2%). $^1$H NMR (CDCl$_3$, 400 MHz): δ=12.85 (s, 1H), 8.37 (d, J=2.7 Hz, 1H), 8.23 (d, J=8.6 Hz, 1H), 7.34 (dd, J=2.8, 8.7 Hz, 1H), 3.94 (s, 3H), 3.20-3.12 (m, 1H), 2.79-2.62 (m, 2H), 2.51-2.42 (m, 1H), 2.09-2.03 (m, 1H), 1.57-1.48 (m, 1H), 1.41-1.29 (m, 1H), 0.96 (s, 9H), one exchangeable proton not observed. LC/MS (Table 1, Method A) $R_t$=5.88 min; MS m/z: 389 [M+H]$^+$.

Example #53. 2-Benzamido-6-[4-(trifluoromethyl)phenyl]-5,7-dihydro-4H-thieno[2,3-c]pyridine-3-carboxylic acid (Compound #92)

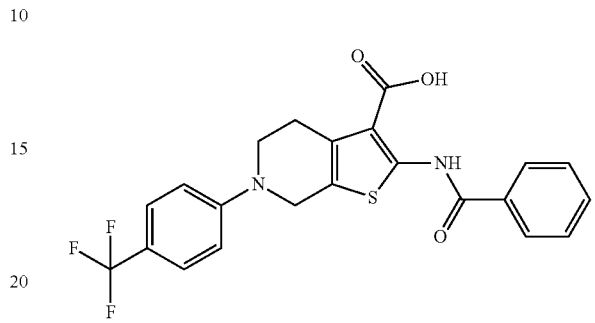

The title compound was synthesized according to the procedure described in Example #21 using 1-[4-(trifluoromethyl)phenyl]piperidin-4-one (CAS: 120807-29-6) and benzoyl chloride (CAS: 98-88-4) as starting materials (yellow solid, yield 19%). $^1$H NMR (DMSO-d$_6$, 400 MHz): δ=13.48 (br s, 1H), 12.41 (br s, 1H), 7.95-7.90 (m, 2H), 7.72-7.61 (m, 3H), 7.52 (d, J=8.7 Hz, 2H), 7.17 (d, J=8.8 Hz, 2H), 4.54 (s, 2H), 3.73 (t, J=5.7 Hz, 2H), 2.94 (t, J=5.1 Hz, 2H). LC/MS (Table 1, Method A) $R_t$=5.58 min: MS m/z: 447 [M+H]$^+$.

Example #54. 2-[(4-Acetamidobenzoyl)amino]-6-tert-butyl-4,5,6,7-tetrahydrobenzothiophene-3-carboxylic acid (Compound #93)

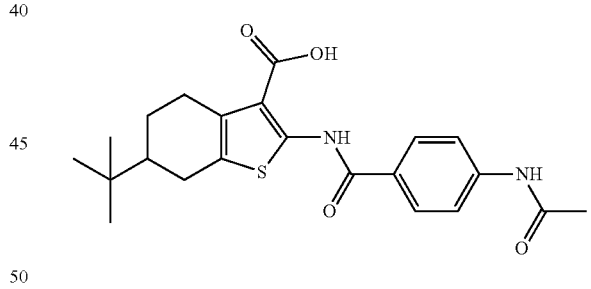

The title compound was synthesized according to the procedure described in Example #37 using methyl 2-amino-6-tert-butyl-4,5,6,7-tetrahydro-1-benzothiophene-3-carboxylate (CAS: 213192-26-8) and 4-acetamidobenzoic acid (CAS: 556-08-1) as starting materials (white solid, yield 36%). $^1$H NMR (DMSO-d$_6$, 400 MHz): δ=13.27 (br s, 1H), 12.37 (br s, 1H), 10.35 (s, 1H), 7.85 (d, J=8.5 Hz, 2H), 7.80 (d, J=8.7 Hz, 2H), 3.06 (d, J=16.0 Hz, 1H), 2.70 (d, J=14.3 Hz, 1H), 2.60-2.53 (m, 1H, partially obscured by the DMSO peak), 2.43-2.34 (m, 1H), 2.11 (s, 3H), 2.00-1.96 (m, 1H), 1.47-1.40 (m, 1H), 1.29-1.18 (m, 1H), 0.94 (s, 9H). LC/MS (Table 1, Method A) $R_t$=5.45 min; MS m/z: 415 [M+H]$^+$.

Example #55. 2-[(2-Methylbenzoyl)amino]-4,5,6,7-tetrahydrobenzothiophene-3-carboxylic acid (Compound #95)

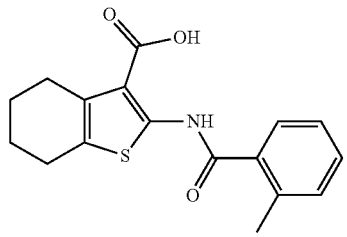 [SMILES: Cc1ccccc1C(=O)Nc1sc2c(c1C(=O)O)CCCC2]

The title compound was synthesized according to the procedure described in Example #1 using methyl 2-amino-4,5,6,7-tetrahydro-1-benzothiophene-3-carboxylate (CAS: 108354-78-5) and 2-methylbenzoyl chloride (CAS: 933-88-0) as starting materials (white solid, yield 60%). $^1$H NMR (DMSO-$d_6$, 400 MHz): δ=13.22 (br s, 1H), 11.86 (br s, 1H), 7.63-7.60 (m, 1H), 7.51-7.46 (m, 1H), 7.40-7.34 (m, 2H), 2.77-2.61 (m, 4H), 2.46 (s, 3H), 1.80-1.68 (m, 4H). LC/MS (Table 1, Method B) $R_t$=5.13 min: MS m/z: 316 [M+H]$^+$.

Example #56. 6-tert-Butyl-2-[[2-(trifluoromethyl)benzoyl]amino]-4,5,6,7-tetrahydrobenzothiophene-3-carboxylic acid (Compound #100)

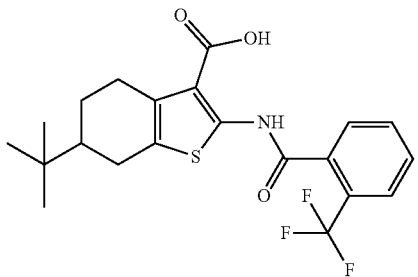 [SMILES: CC(C)(C)C1CCc2c(sc(NC(=O)c3ccccc3C(F)(F)F)c2C(=O)O)C1]

The title compound was synthesized according to the procedure described in Example #1 using methyl 2-amino-6-tert-butyl-4,5,6,7-tetrahydro-1-benzothiophene-3-carboxylate (CAS: 213192-26-8) and 2-(trifluoromethyl)benzoyl chloride (CAS: 312-94-7) as starting materials (white solid, yield 23%). $^1$H NMR (DMSO-$d_6$, 400 MHz): δ=13.24 (br s, 1H), 11.78 (s, 1H), 7.92 (d, J=7.7 Hz, 1H), 7.88-7.77 (m, 3H), 3.03 (dd, J=4.5, 17.1 Hz, 1H), 2.72 (dd, J=4.5, 15.9 Hz, 1H), 2.57-2.52 (m, 1H, partially obscured by the DMSO peak), 2.44-2.37 (m, 1H), 2.02-1.94 (m, 1H), 1.49-1.39 (m, 1H), 1.30-1.20 (m, 1H), 0.93 (s, 9H). LC/MS (Table 1, Method A) $R_t$=6.04 min; MS m/z: 426 [M+H]$^+$.

Example #57. 6-tert-Butyl-2-[[2-(trifluoromethyl)benzoyl]amino]-4,5,6,7-tetrahydrobenzothiophene-3-carboxylic acid diethylamine salt (Enantiomer 1) (Compound #109)

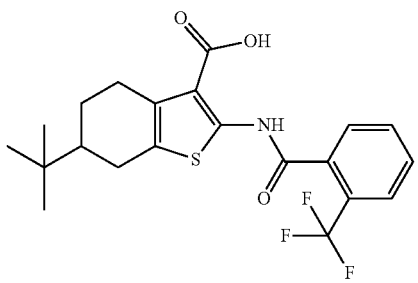 [SMILES: CC(C)(C)C1CCc2c(sc(NC(=O)c3ccccc3C(F)(F)F)c2C(=O)O)C1]

The title compound was synthesized according to the procedure described in Example #15 using 6-tert-butyl-2-[[2-(trifluoromethyl)benzoyl]amino]-4,5,6,7-tetrahydrobenzothiophene-3-carboxylic acid (Example #56) as a starting material (white solid, yield 28%). $^1$H NMR (DMSO-$d_6$, 400 MHz): δ=15.39 (br s, 1H), 8.54 (br s, 1H), 7.82 (d, J=7.6 Hz, 1H), 7.79-7.74 (m, 1H), 7.68 (t, J=7.3 Hz, 2H), 3.24-3.15 (m, 1H), 2.89 (q, J=7.2 Hz, 4H), 2.62 (dd, J=4.7, 15.7 Hz, 1H), 2.46-2.31 (m, 2H), 1.97-1.91 (m, 1H), 1.46-1.37 (m, 1H), 1.23-1.11 (m, 7H), 0.92 (s, 9H). LC/MS (Table 1, Method A) $R_t$=6.04 min; MS m/z: 426 [M+H]$^+$. Chiral SFC (Table 1, Method J) $R_t$=2.2 min: e.e. 100%, first eluting enantiomer.

Example #58. 6-tert-Butyl-2-[[2-(trifluoromethyl)benzoyl]amino]-4,5,6,7-tetrahydrobenzothiophene-3-carboxylic acid (Enantiomer 2) (Compound #97)

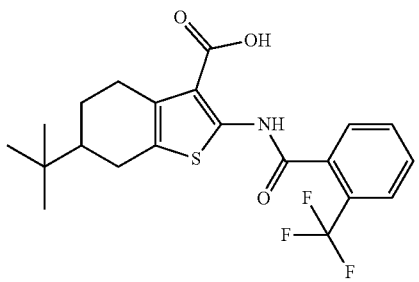 [SMILES: CC(C)(C)C1CCc2c(sc(NC(=O)c3ccccc3C(F)(F)F)c2C(=O)O)C1]

The title compound was synthesized according to the procedure described in Example #16 using 6-tert-butyl-2-[[2-(trifluoromethyl)benzoyl]amino]-4,5,6,7-tetrahydrobenzothiophene-3-carboxylic acid (Example #56) as a starting material (white solid, yield 30%). $^1$H NMR (DMSO-$d_6$, 400 MHz): δ=13.27 (br s, 1H), 11.75 (s, 1H), 7.93 (d, J=7.7 Hz, 1H), 7.88-7.78 (m, 3H), 3.04 (dd, J=4.3, 17.2 Hz, 1H), 2.72 (dd, J=4.2, 15.8 Hz, 1H), 2.57-2.52 (m, 1H, partially obscured by the DMSO peak), 2.45-2.37 (m, 1H), 2.01-1.96 (m, 1H), 1.48-1.40 (m, 1H), 1.28-1.17 (m, 1H), 0.93 (s, 9H). LC/MS (Table 1, Method A) $R_t$=6.04 min; MS m/z: 426 [M+H]$^+$. Chiral SFC (Table 1, Method J) $R_t$=3.7 min; e.e. 98.6%, second eluting enantiomer.

Example #59. 6-tert-Butyl-2-[(2,2-difluoro-1,3-benzodioxole-5-carbonyl)amino]-4,5,6,7-tetrahydrobenzothiophene-3-carboxylic acid (Compound #99)

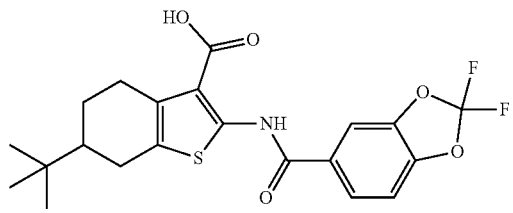 [SMILES: CC(C)(C)C1CCc2c(sc(NC(=O)c3ccc4c(c3)OC(F)(F)O4)c2C(=O)O)C1]

The title compound was synthesized according to the procedure described in Example #52 using methyl 2-amino-6-tert-butyl-4,5,6,7-tetrahydro-1-benzothiophene-3-carboxylate (CAS: 213192-26-8) and 2,2-difluorobenzodioxole-5-carboxylic acid (CAS: 656-46-2) as starting materials (off-white solid, yield 60%). $^1$H NMR (CDCl$_3$, 400 MHz):

δ=12.09 (s, 1H), 7.78-7.74 (m, 2H), 7.21 (d, J=8.2 Hz, 1H), 3.13 (dd, J=5.0, 17.2 Hz, 1H), 2.75 (dd, J=4.5, 15.9 Hz, 1H), 2.70-2.59 (m, 1H), 2.49-2.40 (m, 1H), 2.08-2.03 (m, 1H), 1.55-1.48 (m, 1H), 1.39-1.30 (m, 1H), 0.96 (s, 9H), one exchangeable proton not observed. LC/MS (Table 1, Method A) $R_t$=6.50 min; m/z: 438 [M+H]$^+$.

Example #60. 6-tert-Butyl-2-[(1-methylpyrazole-4-carbonyl)amino]-4,5,6,7-tetrahydrobenzothiophene-3-carboxylic acid (Compound #101)

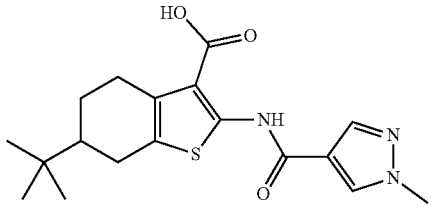 [SMILES: Cn1cc(C(=O)Nc2sc3c(c2C(=O)O)CCC(C(C)(C)C)C3)cn1]

The title compound was synthesized according to the procedure described in Example #37 using methyl 2-amino-6-tert-butyl-4,5,6,7-tetrahydro-1-benzothiophene-3-carboxylate (CAS: 213192-26-8) and 1-methyl-1H-pyrazole-4-carboxylic acid (CAS: 5952-92-1) as starting materials (off-white solid, yield 12%). $^1$H NMR (DMSO-d$_6$, 400 MHz): δ=13.18 (br s, 1H), 11.95 (br s, 1H), 8.34 (s, 1H), 7.85 (d, J=0.7 Hz, 1H), 3.92 (s, 3H), 3.05 (dd, J=4.2, 17.2 Hz, 1H), 2.68 (dd, J=4.3, 15.6 Hz, 1H), 2.56-2.45 (m, 1H, partially obscured by the DMSO peak), 2.42-2.33 (m, 1H), 2.01-1.93 (m, 1H), 1.48-1.38 (m, 1H), 1.28-1.16 (m, 1H), 0.92 (s, 9H). LC/MS (Table 1, Method A) $R_t$=5.18 min; MS m/z: 362 [M+H]$^+$.

Example #61. 2-[[3-(Difluoromethoxy)benzoyl]amino]-4-methyl-4,5,6,7-tetrahydrobenzothiophene-3-carboxylic acid (Compound #102)

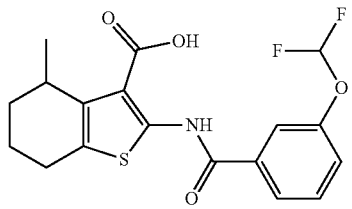 [SMILES: CC1CCCc2sc(NC(=O)c3cccc(OC(F)F)c3)c(C(=O)O)c21]

To a stirred solution of 3-(difluoromethoxy)benzoic acid (CAS: 4837-19-8, 311 mg, 1.50 mmol) in DCM (10 ml) was added oxalyl chloride (CAS: 79-37-8, 160 µl, 1.84 mmol) and DMF (7 µl, 0.08 mmol). The reaction mixture was stirred at RT for 2.5 hours. The reaction was poured to a solution of ethyl 2-amino-4-methyl-4,5,6,7-tetrahydrobenzo[b]thiophene-3-carboxylate (Preparation #5, Step A, 200 mg, 0.84 mmol) and DIPEA (CAS: 7087-68-5, 0.58 ml, 3.34 mmol). The reaction mixture was stirred at RT for 20 hours. The reaction mixture was partitioned between DCM and a saturated aqueous NaHCO$_3$ solution. The two phases were separated and the aqueous phase was extracted with DCM (×3). The combined organic phases were passed through a phase separator and the solvent was removed under reduced pressure. Trituration with MeOH afforded ethyl 2-(3-(difluoromethoxy)benzamido)-4-methyl-4,5,6,7-tetrahydrobenzo[b]thiophene-3-carboxylate as a yellow solid (223 mg, yield 54%). The title compound was then synthesized according to the procedure described in Example #10 using ethyl 2-(3-(difluoromethoxy)benzamido)-4-methyl-4,5,6,7-tetrahydrobenzo[b]thiophene-3-carboxylate as a starting material (yellow solid, yield 9%). $^1$H NMR (DMSO-d$_6$, 400 MHz): δ=13.07 (br s, 1H), 7.78 (d, J=7.9 Hz, 1H), 7.72-7.66 (m, 2H), 7.49 (dd, J=2.2, 8.2 Hz, 1H), 7.38 (t, J=73.6 Hz, 1H), 3.45-3.26 (m, 1H, partially obscured by the water peak), 2.75-2.56 (m, 2H), 1.88-1.64 (m, 4H), 1.18 (d, J=6.7 Hz, 3H), one exchangeable proton not observed. LC/MS (Table 1, Method D) $R_t$=3.77 min; MS m/z: 382 [M+H]$^+$.

Example #62. 2-Benzamido-6-iso-propoxy-4,5,6,7-tetrahydrobenzothiophene-3-carboxylic acid (Compound #103)

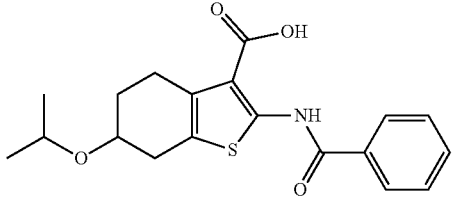 [SMILES: CC(C)OC1CCc2c(sc(NC(=O)c3ccccc3)c2C(=O)O)C1]

The title compound was synthesized according to the procedure described in Example #21 using 4-iso-propoxy-cyclohexanone (CAS: 69697-46-7) and benzoyl chloride (CAS: 98-88-4) as starting materials (white solid, yield 41%). $^1$H NMR (DMSO-d$_6$, 400 MHz): δ=13.36 (br s, 1H), 12.38 (s, 1H), 7.93-7.89 (m, 2H), 7.71-7.60 (m, 3H), 3.87-3.74 (m, 2H), 2.99-2.85 (m, 2H), 2.79-2.66 (m, 1H), 2.56-2.52 (m, 1H, partially obscured by the DMSO peak), 1.94-1.86 (m, 1H), 1.74-1.65 (m, 1H), 1.10 (d, J=6.0 Hz, 3H), 1.09 (d, J=6.0 Hz, 3H). LC/MS (Table 1, Method A) $R_t$=5.01 min; MS m/z: 360 [M+H]$^+$.

Example #63. 6-tert-Butyl-2-[(2-methoxybenzoyl)amino]-4,5,6,7-tetrahydrobenzothiophene-3-carboxylic acid (Compound #104)

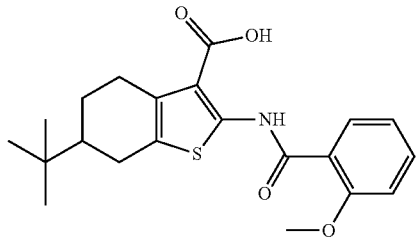

The title compound was synthesized according to the procedure described in Example #1 using methyl 2-amino-6-tert-butyl-4,5,6,7-tetrahydro-1-benzothiophene-3-carboxylate (CAS: 213192-26-8) and 2-methoxybenzoyl chloride (CAS: 21615-34-9) as starting materials (pale yellow solid, yield 6%). $^1$H NMR (DMSO-ds, 400 MHz): δ=13.05 (br s, 2H), 8.10 (dd, J=1.8, 7.8 Hz, 1H), 7.63 (ddd, J=1.5, 7.2, 8.5 Hz, 1H), 7.28 (d, J=8.4 Hz, 1H), 7.18-7.12 (m, 1H), 4.07 (s, 3H), 3.09-3.02 (m, 1H), 2.71-2.64 (m, 1H), 2.58-2.52 (m, 1H, partially obscured by the DMSO peak), 2.42-2.34 (m, 1H), 2.01-1.94 (m, 1H), 1.47-1.39 (m, 1H), 1.29-

1.17 (m, 1H), 0.92 (s, 9H). LC/MS (Table 1, Method A) R$_t$=6.14 min: MS m/z: 410 [M+Na]$^+$.

Example #64. 2-(2,2-Dimethylpropanoylamino)-6-phenyl-4,5,6,7-tetrahydrobenzothiophene-3-carboxylic acid (Compound #106)

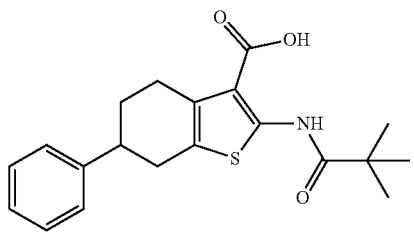 [SMILES: CC(C)(C)C(=O)Nc1sc2c(c1C(=O)O)CCC(c1ccccc1)C2]

The title compound was synthesized according to the procedure described in Example #1 using methyl 2-amino-6-phenyl-4,5,6,7-tetrahydrobenzo[b]thiophene-3-carboxylate (Preparation #4) and trimethylacetyl chloride (CAS: 3282-30-2) as starting materials (white solid, yield 39%). $^1$H NMR (DMSO-d$_6$, 400 MHz): δ=13.24 (br s, 1H), 11.77 (br s, 1H), 7.32 (d, J=4.4 Hz, 4H), 7.25-7.19 (m, 1H), 3.03-2.84 (m, 3H), 2.78-2.68 (m, 2H), 2.04-1.98 (m, 1H), 1.92-1.81 (m, 1H), 1.25 (s, 9H). LC/MS (Table 1, Method A) R$_t$=5.48 min; m/z: 358 [M+H]$^+$.

Example #65. 6-tert-Butyl-2-[(2-chlorobenzoyl)amino]-4,5,6,7-tetrahydrobenzothiophene-3-carboxylic acid (Compound #107)

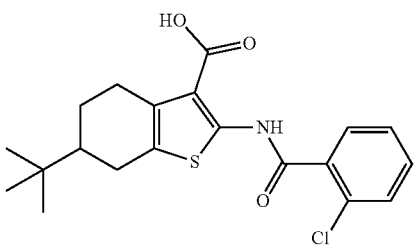 [SMILES: CC(C)(C)C1CCc2c(sc(NC(=O)c3ccccc3Cl)c2C(=O)O)C1]

The title compound was synthesized according to the procedure described in Example #1 using methyl 2-amino-6-tert-butyl-4,5,6,7-tetrahydro-1-benzothiophene-3-carboxylate (CAS: 213192-26-8) and 2-chlorobenzoyl chloride (CAS: 609-65-4) as starting materials (white solid, yield 32%). $^1$H NMR (DMSO-d$_6$, 400 MHz): δ=13.27 (br s, 1H), 11.99 (br s, 1H), 7.78 (dd, J=1.5, 7.6 Hz, 1H), 7.66-7.57 (m, 2H), 7.52 (dt, J=1.6, 7.3 Hz, 1H), 3.05 (dd, J=4.4, 17.2 Hz, 1H), 2.75-2.68 (m, 1H), 2.58-2.52 (m, 1H, partially obscured by the DMSO peak), 2.43-2.35 (m, 1H), 2.02-1.96 (m, 1H), 1.47-1.39 (m, 1H), 1.29-1.16 (m, 1H), 0.93 (s, 9H). LC/MS (Table 1, Method A) R$_t$=6.11 min: MS m/z: 414 [M+Na]$^+$.

Example #66. 2-[[4-(Difluoromethoxy)benzoyl]amino]-4-phenyl-4,5,6,7-tetrahydrobenzothiophene-3-carboxylic acid (Compound #108)

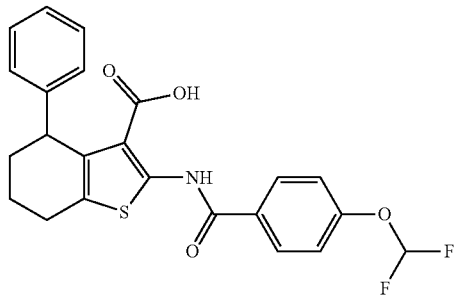 [SMILES: O=C(Nc1sc2c(c1C(=O)O)C(c1ccccc1)CCC2)c1ccc(OC(F)F)cc1]

The title compound was synthesized according to the procedure described in Example #1 using ethyl 2-amino-4-phenyl-4,5,6,7-tetrahydrobenzo[b]thiophene-3-carboxylate (Preparation #6) and 4-(difluoromethoxy)benzoyl chloride (CAS: 57320-63-5) as starting materials (yellow solid, yield 26%). $^1$H NMR (DMSO-d$_6$, 400 MHz): δ=12.85 (br s, 1H), 8.01 (d, J=8.8 Hz, 2H), 7.64-7.24 (m, 5H), 7.17 (t, J=7.2 Hz, 1H), 7.00 (d, J=7.6 Hz, 2H), 4.70 (s, 1H), 2.91-2.69 (m, 2H), 2.15-2.03 (m, 1H), 1.88 (d, J=13.2 Hz, 1H), 1.73-1.66 (m, 1H), 1.61-1.51 (m, 1H), one exchangeable proton not observed. LC/MS (Table 1, Method C) R$_t$=2.72 min; MS m/z: 444 [M+H]$^+$.

Example #67. 6-tert-Butyl-2-[(3-methylfuran-2-carbonyl)amino]-4,5,6,7-tetrahydrobenzothiophene-3-carboxylic acid (Compound #110)

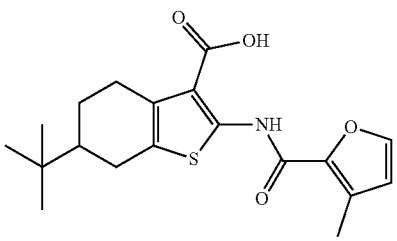 [SMILES: Cc1ccoc1C(=O)Nc1sc2c(c1C(=O)O)CCC(C(C)(C)C)C2]

The title compound was synthesized according to the procedure described in Example #37 using methyl 2-amino-6-tert-butyl-4,5,6,7-tetrahydro-1-benzothiophene-3-carboxylate (CAS: 213192-26-8) and 3-methyl-2-furoic acid (CAS: 4412-96-8) as starting materials (off-white solid, yield 23%). $^1$H NMR (DMSO-d$_6$, 400 MHz): δ=13.18 (br s, 1H), 12.16 (s, 1H), 7.88 (d, J=1.5 Hz, 1H), 6.65 (d, J=1.4 Hz, 1H), 3.05 (dd, J=4.4, 17.1 Hz, 1H), 2.67 (dd, J=4.6, 15.8 Hz, 1H), 2.57-2.51 (m, 1H, partially obscured by the DMSO peak), 2.41-2.33 (m, 4H), 2.01-1.95 (m, 1H), 1.46-1.38 (m, 1H), 1.29-1.16 (m, 1H), 0.92 (s, 9H). LC/MS (Table 1, Method A) R$_t$=6.11 min; MS m/z: 362 [M+H]$^+$.

Example #68. 6-tert-Butyl-2-[(2-methylbenzoyl)amino]benzothiophene-3-carboxylic acid (Compound #111)

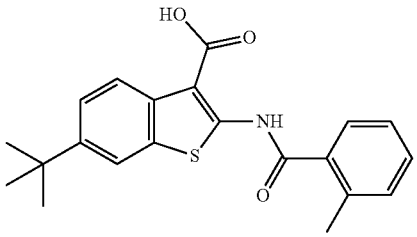 [SMILES: Cc1ccccc1C(=O)Nc1sc2cc(C(C)(C)C)ccc2c1C(=O)O]

The title compound was synthesized according to the procedure described in Example #1 using ethyl 2-amino-6-tert-butyl-1-benzothiophene-3-carboxylate (CAS: 438228-39-8) and 2-methylbenzoyl chloride (CAS: 933-88-0) as starting materials (off-white solid, yield 20%). $^1$H NMR (DMSO-d$_6$, 400 MHz): δ=13.74 (br s, 1H), 12.42 (br s, 1H), 8.23 (d, J=8.7 Hz, 1H), 7.95 (d, J=1.7 Hz, 1H), 7.75-7.70 (m, 1H), 7.55-7.50 (m, 2H), 7.44-7.38 (m, 2H), 2.53 (s, 3H), 1.35 (s, 9H). LC/MS (Table 1, Method A) R$_t$=5.92 min; MS m/z: 368 [M+H]$^+$.

Example #69. 2-Benzamido-4-phenyl-4,5,6,7-tetrahydrobenzothiophene-3-carboxylic acid (Compound #112)

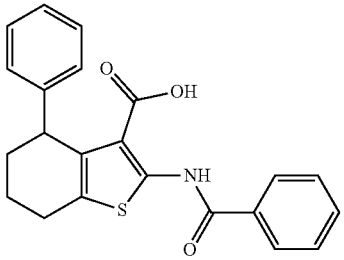 [SMILES: O=C(Nc1sc2c(c1C(=O)O)C(c1ccccc1)CCC2)c1ccccc1]

The title compound was synthesized according to the procedure described in Example #1 using ethyl 2-amino-4-phenyl-4,5,6,7-tetrahydrobenzo[b]thiophene-3-carboxylate (Preparation #6) and benzoyl chloride (CAS: 98-88-4) as starting materials (yellow solid, yield 38%). $^1$H NMR (DMSO-d$_6$, 400 MHz): δ=13.00 (br s, 1H), 12.55 (br s, 1H), 7.94-7.90 (m, 2H), 7.71-7.60 (m, 3H), 7.25 (t, J=7.5 Hz, 2H), 7.14 (t, J=7.2 Hz, 1H), 6.97 (d, J=7.4 Hz, 2H), 4.64 (s, 1H), 2.82 (dd, J=4.1, 16.8 Hz, 1H), 2.76-2.67 (m, 1H), 2.11-2.00 (m, 1H), 1.85 (d, J=12.6 Hz, 1H), 1.71-1.66 (m, 1H), 1.59-1.47 (m, 1H). LC/MS (Table 1, Method C) R$_t$=2.90 min; m/z: 378 [M+H]$^+$.

Example #70. 2-[(3,4-Dimethoxybenzoyl)amino]-6-(4-fluorophenyl)-5,7-dihydro-4H-thieno[2,3-c]pyridine-3-carboxylic acid (Compound #113)

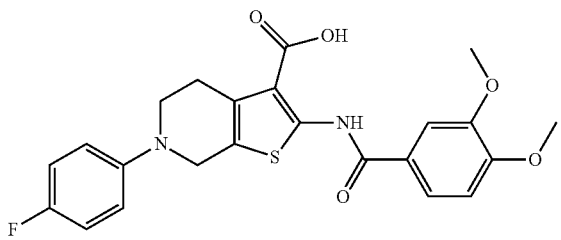 [SMILES: COc1ccc(C(=O)Nc2sc3c(c2C(=O)O)CCN(c2ccc(F)cc2)C3)cc1OC]

The title compound was synthesized according to the procedure described in Example #21 using 1-(4-fluorophenyl)piperidin-4-one (CAS: 116247-98-4) and 3,4-dimethoxybenzoyl chloride (CAS: 3535-37-3) as starting materials (pale yellow solid, yield 19%). $^1$H NMR (DMSO-d$_6$, 400 MHz): δ=13.45 (br s, 1H), 12.34 (s, 1H), 7.52-7.46 (m, 2H), 7.19 (d, J=8.5 Hz, 1H), 7.06-7.04 (m, 4H), 4.32 (s, 2H), 3.86 (s, 3H), 3.86 (s, 3H), 3.52 (t, J=5.6 Hz, 2H), 2.89 (t, J=6.0 Hz, 2H). LC/MS (Table 1, Method A) R$_t$=4.89 min; MS m/z: 457 [M+H]$^+$.

Example #71. 6-tert-Butyl-2-(cyclohexanecarbonylamino)-4,5,6,7-tetrahydrobenzothiophene-3-carboxylic acid (Compound #115)

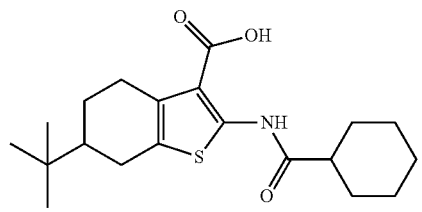 [SMILES: CC(C)(C)C1CCc2c(sc(NC(=O)C3CCCCC3)c2C(=O)O)C1]

The title compound was synthesized according to the procedure described in Example #1 using methyl 2-amino-6-tert-butyl-4,5,6,7-tetrahydro-1-benzothiophene-3-carboxylate (CAS: 213192-26-8) and cyclohexanecarbonyl chloride (CAS: 2719-27-9) as starting materials (white solid, yield 34%). $^1$H NMR (CDCl$_3$, 400 MHz): δ=11.13 (s, 1H), 3.12-3.06 (m, 1H), 2.72-2.56 (m, 2H), 2.43-2.36 (m, 2H), 2.05-1.98 (m, 3H), 1.87-1.82 (m, 2H), 1.73-1.69 (m, 1H), 1.60-1.24 (m, 7H), 0.95 (s, 9H), one exchangeable proton not observed. LC/MS (Table 1, Method A) R$_t$=6.23 min; MS m/z: 364 [M+H]$^+$.

Example #72. 2-Benzamido-5,5-dimethyl-4,7-dihydrothieno[2,3-c]pyran-3-carboxylic acid (Compound #116)

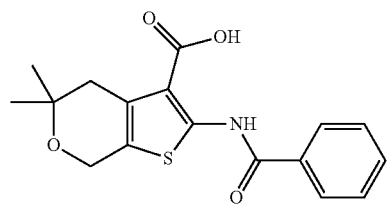 [SMILES: CC1(C)Cc2c(sc(NC(=O)c3ccccc3)c2C(=O)O)CO1]

The title compound was synthesized according to the procedure described in Example #21 using 2,2-dimethyl-tetrahydro-pyran-4-one (CAS: 1194-16-7) and benzoyl chloride (CAS: 98-88-4) as starting materials (white solid, yield 36%). $^1$H NMR (DMSO-d$_6$, 400 MHz): δ=13.47 (br s, 1H), 12.39 (s, 1H), 7.95-7.90 (m, 2H), 7.72-7.61 (m, 3H), 4.65 (s, 2H), 2.73 (s, 2H), 1.24 (s, 6H). LC/MS (Table 1, Method A) R$_t$=4.44 min; m/z: 332 [M+H]$^+$.

Example #73. 6-tert-Butyl-2-[(2,6-dimethylbenzoyl)amino]-4,5,6,7-tetrahydrobenzothiophene-3-carboxylic acid (Compound #118)

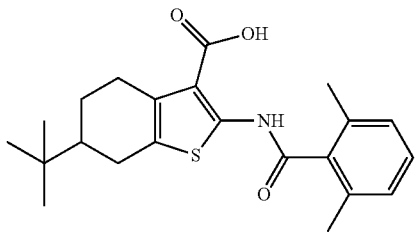 [SMILES: Cc1cccc(C)c1C(=O)Nc1sc2c(c1C(=O)O)CCC(C(C)(C)C)C2]

The title compound was synthesized according to the procedure described in Example #1 using methyl 2-amino-6-tert-butyl-4,5,6,7-tetrahydro-1-benzothiophene-3-carboxylate (CAS: 213192-26-8) and 2,6-dimethylbenzoyl chloride (CAS: 21900-37-8) as starting materials (yellow solid, yield 28%). $^1$H NMR (DMSO-$d_6$, 400 MHz): δ=13.19 (br s, 1H), 11.45 (s, 1H), 7.32-7.28 (m, 1H), 7.15 (d, J=7.7 Hz, 2H), 3.04 (dd, J=4.3, 17.3 Hz, 1H), 2.71 (dd, J=4.5, 15.9 Hz, 1H), 2.56-2.51 (m, 1H, partially obscured by the DMSO peak), 2.43-2.35 (m, 1H), 2.24 (s, 6H), 2.02-1.94 (m, 1H), 1.49-1.38 (m, 1H), 1.29-1.15 (m, 1H), 0.92 (s, 9H). LC/MS (Table 1, Method A) $R_t$=6.24 min; MS m/z: 386 [M+H]$^+$.

Example #74. 2-[(3,4-Dimethoxybenzoyl)amino]-5,5-dimethyl-4,7-dihydrothieno[2,3-c]pyran-3-carboxylic acid (Compound #119)

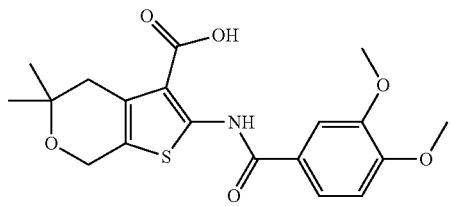

The title compound was synthesized according to the procedure described in Example #21 using 2,2-dimethyl-tetrahydro-pyran-4-one (CAS: 1194-16-7) and 3,4-dimethoxybenzoyl chloride (CAS: 3535-37-3) as starting materials (white solid, yield 21%). $^1$H NMR (DMSO-$d_6$, 400 MHz): δ=13.47 (br s, 1H), 12.35 (s, 1H), 7.51-7.47 (m, 2H), 7.19 (d, J=8.4 Hz, 1H), 4.64 (s, 2H), 3.87 (s, 3H), 3.85 (s, 3H), 2.72 (s, 2H), 1.23 (s, 6H). LC/MS (Table 1, Method A) $R_t$=4.25 min; MS m/z: 392 [M+H]$^+$.

Example #75. 6-tert-Butyl-2-(piperidine-1-carbonylamino)-4,5,6,7-tetrahydrobenzothiophene-3-carboxylic acid (Compound #120)

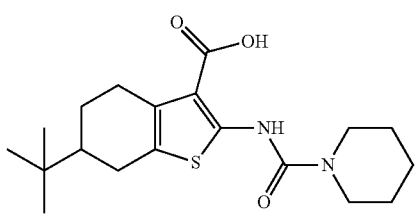 [SMILES: CC(C)(C)C1CCc2c(sc(NC(=O)N3CCCCC3)c2C(=O)O)C1]

To a stirred solution of methyl 2-amino-6-tert-butyl-4,5,6,7-tetrahydro-1-benzothiophene-3-carboxylate (CAS: 213192-26-8, 200 mg, 0.75 mmol) in MeCN (5.0 ml) at RT was added DIPEA (CAS: 7087-68-5, 0.20 ml, 1.12 mmol) and piperidine-1-carbonyl chloride (CAS: 13939-69-0, 0.10 ml, 0.90 mmol). The reaction mixture was next heated at 70° C. for 72 hours. The reaction was allowed to cool to RT. The solvent was removed under reduced pressure to give 6-(tert-butyl)-2-(piperidine-1-carboxamido)-4,5,6,7-tetrahydrobenzo[b]thiophene-3-carboxylic acid (283 mg, yield quant.). 6-(tert-Butyl)-2-(piperidine-1-carboxamido)-4,5,6,7-tetrahydrobenzo[b]thiophene-3-carboxylic acid (283 mg, 0.75 mmol) was dissolved in THF (4.0 ml) and methanol (2.0 ml). To the solution was added LiOH aq. (CAS: 1310-66-3, 2M, 1.5 ml, 2.99 mmol). The reaction mixture was set to stir at RT and next heated at 50° C. for 2 hours. The reaction was allowed to cool to RT. The reaction was partitioned between EtOAc and 1N aqueous HCl and the two phases were separated. The aqueous phase was extracted with EtOAc (×2). The combined organic phases were washed with brine and dried over MgSO$_4$. The solvent was removed under reduced pressure. Purification by RP-HPLC (Table 2, Method A) afforded 6-tert-butyl-2-(piperidine-1-carbonylamino)-4,5,6,7-tetrahydrobenzothiophene-3-carboxylic acid as a yellow solid (96 mg, yield 35%). $^1$H NMR (DMSO-$d_6$, 400 MHz): δ=12.82 (br s, 1H), 11.31 (br s, 1H), 3.43-3.38 (m, 4H), 3.00 (dd, J=4.3, 17.3 Hz, 1H), 2.59 (dd, J=4.4, 15.8 Hz, 1H), 2.48-2.41 (m, 1H, partially obscured by the DMSO peak), 2.36-2.26 (m, 1H), 1.98-1.92 (m, 1H), 1.63-1.48 (m, 6H), 1.44-1.35 (m, 1H), 1.23-1.13 (m, 1H), 0.91 (s, 9H). LC/MS (Table 1, Method A) $R_t$=5.71 min; m/z: 365 [M+H]$^+$.

Example #76. 2-[(2-Methylbenzoyl)amino]-5,6-dihydro-4H-cyclopenta[b]thiophene-3-carboxylic acid (Compound #121)

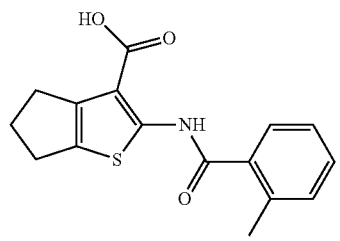 [SMILES: Cc1ccccc1C(=O)Nc1sc2c(c1C(=O)O)CCC2]

The title compound was synthesized according to the procedure described in Example #1 using ethyl 2-amino-5,6-dihydro-4H-cyclopenta[b]thiophene-3-carboxylate (CAS: 4815-29-6) and 2-methylbenzoyl chloride (CAS: 933-88-0) as starting materials (white solid, yield 49%). $^1$H NMR (DMSO-$d_6$, 400 MHz): δ=13.15 (br s, 1H), 11.60 (s, 1H), 7.64-7.61 (m, 1H), 7.49 (dt, J=1.3, 7.5 Hz, 1H), 7.40-7.35 (m, 2H), 2.88-2.80 (m, 4H), 2.47 (s, 3H), 2.37-2.29 (m, 2H). LC/MS (Table 1, Method A) $R_t$=4.94 min; MS m/z: 300 [M−H]$^-$.

Example #77. 2-Benzamido-6-(4-hydroxyphenyl)-4,5,6,7-tetrahydrobenzothiophene-3-carboxylic acid (Compound #122)

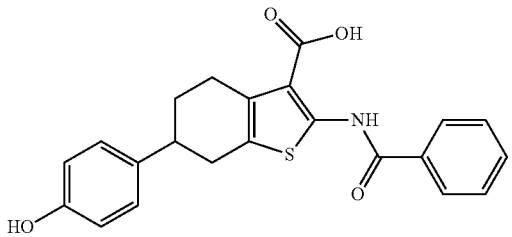 [SMILES: O=C(Nc1sc2c(c1C(=O)O)CCC(c1ccc(O)cc1)C2)c1ccccc1]

The title compound was synthesized according to the procedure described in Example #21 using 4-(4-hydroxyphenyl)cyclohexanone (CAS: 105640-07-1) and benzoyl chloride (CAS: 98-88-4) as starting materials (yellow solid, yield 11%). $^1$H NMR (DMSO-$d_6$, 400 MHz): δ=13.34 (br s, 1H), 12.42 (s, 1H), 9.19 (s, 1H), 7.95-7.90 (m, 2H), 7.72-7.61 (m, 3H), 7.11 (d, J=8.5 Hz, 2H), 6.71 (d, J=8.5 Hz, 2H), 3.07-2.98 (m, 1H), 2.92-2.66 (m, 4H), 2.02-1.94 (m, 1H), 1.88-1.73 (m, 1H). LC/MS (Table 1, Method A) $R_t$=4.56 min; MS m/z: 394 [M+H]$^+$.

Example #78. 6-tert-Butyl-2-(pyridine-4-carbonylamino)-4,5,6,7-tetrahydrobenzothiophene-3-carboxylic acid (Compound #123)

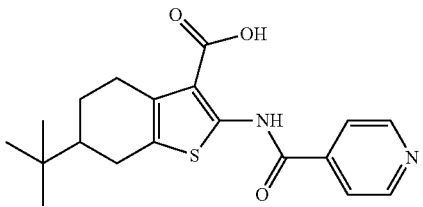 [SMILES: CC(C)(C)C1CCc2c(sc(NC(=O)c3ccncc3)c2C(=O)O)C1]

The title compound was synthesized according to the procedure described in Example #37 using methyl 2-amino-6-tert-butyl-4,5,6,7-tetrahydro-1-benzothiophene-3-carboxylate (CAS: 213192-26-8) and 4-pyridinecarboxylic acid (CAS: 55-22-1) as starting materials (yellow solid, yield 15%). $^1$H NMR (DMSO-$d_6$, 400 MHz): δ=13.41 (br s, 1H), 12.64 (br s, 1H), 8.87-8.84 (m, 2H), 7.81-7.78 (m, 2H), 3.07 (dd, J=4.3, 17.2 Hz, 1H), 2.71 (dd, J=4.5, 16.0 Hz, 1H), 2.59-2.52 (m, 1H, partially obscured by the DMSO peak), 2.46-2.35 (m, 1H), 2.03-1.94 (m, 1H), 1.49-1.40 (m, 1H), 1.30-1.18 (m, 1H), 0.92 (s, 9H). LC/MS (Table 1, Method A) $R_t$=5.45 min; MS m/z: 359 [M+H]$^+$.

Example #79. 2-[[4-(3-Aminopropoxy)benzoyl]amino]-6-tert-butyl-4,5,6,7-tetrahydrobenzothiophene-3-carboxylic acid hydrochloride salt (Compound #124)

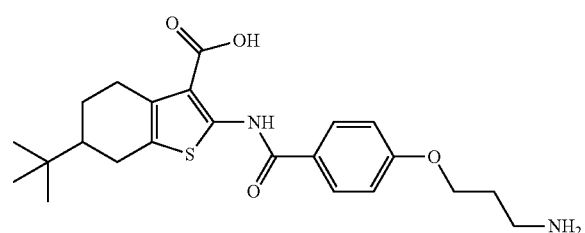

To 2-[[4-[3-(tert-butoxycarbonylamino)propoxy]benzoyl]amino]-6-tert-butyl-4,5,6,7-tetrahydrobenzothiophene-3-carboxylic acid (Example #11, 20 mg, 0.038 mmol) was added 4N HCl in dioxane (CAS: 7647-01-0, 2.0 ml). The reaction mixture was stirred at RT for 0.5 hours. The solvent was removed under reduced pressure. Trituration with Et$_2$O afforded 2-[[4-(3-aminopropoxy)benzoyl]amino]-6-tert-butyl-4,5,6,7-tetrahydrobenzothiophene-3-carboxylic acid hydrochloride salt as an off-white solid (10 mg, yield 63%). $^1$H NMR (DMSO-$d_6$, 400 MHz): δ=13.24 (br s, 1H), 12.35 (br s, 1H), 7.90 (br s, 3H), 7.88 (d, J=8.7 Hz, 2H), 7.16 (d, J=8.9 Hz, 2H), 4.18 (t, J=6.0 Hz, 2H), 3.08-2.96 (m, 3H), 2.72-2.67 (m, 1H), 2.42-2.33 (m, 2H), 2.05 (t, J=6.8 Hz, 2H), 2.00-1.96 (m, 1H), 1.48-1.40 (m, 1H), 1.28-1.19 (m, 1H), 0.92 (s, 9H). LC/MS (Table 1, Method A) $R_t$=4.10 min; MS m/z: 431 [M+H]$^+$.

Example #80. 6-tert-Butyl-2-[(2-phenylacetyl)amino]-4,5,6,7-tetrahydrobenzothiophene-3-carboxylic acid (Compound #125)

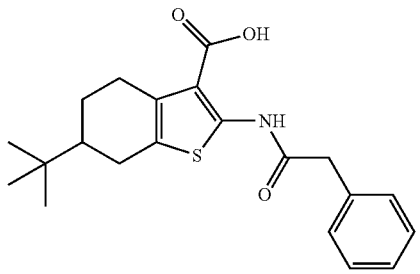 [SMILES: CC(C)(C)C1CCc2c(sc(NC(=O)Cc3ccccc3)c2C(=O)O)C1]

The title compound was synthesized according to the procedure described in Example #1 using methyl 2-amino-6-tert-butyl-4,5,6,7-tetrahydro-1-benzothiophene-3-carboxylate (CAS: 213192-26-8) and phenylacetyl chloride (CAS: 103-80-0) as starting materials (yellow solid, yield 15%). $^1$H NMR (DMSO-$d_6$, 400 MHz): δ=11.23 (br s, 1H), 7.38-7.29 (m, 5H), 3.86 (s, 2H), 2.98-2.93 (m, 1H), 2.62 (dd, J=4.4, 16.0 Hz, 1H), 2.47-2.27 (m, 2H), 1.95-1.89 (m, 1H), 1.42-1.34 (m, 1H), 1.23-1.11 (m, 1H), 0.90 (s, 9H), one exchangeable proton not observed. LC/MS (Table 1, Method A) $R_t$=5.80 min; MS m/z: 372 [M+H]$^+$.

Example #81. 6-tert-Butoxycarbonyl-2-[(2-methylbenzoyl)amino]-5,7-dihydro-4H-thieno[2,3-c]pyridine-3-carboxylic acid (Compound #126)

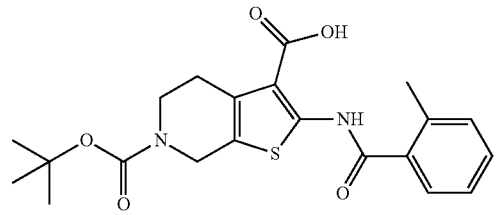 [SMILES: Cc1ccccc1C(=O)Nc1sc2c(c1C(=O)O)CCN(C(=O)OC(C)(C)C)C2]

The title compound was synthesized according to the procedure described in Example #1 using ethyl 6-Boc-2-amino-4,7-dihydro-5H-thieno[2,3-c]pyridine-3-carboxylate (CAS: 193537-14-3) and 2-methylbenzoyl chloride (CAS: 933-88-0) as starting materials (pale yellow solid, yield 55%). $^1$H NMR (DMSO-$d_6$, 400 MHz): δ=13.42 (br s, 1H), 11.88 (br s, 1H), 7.65-7.61 (m, 1H), 7.49 (dt, J=1.3, 7.5 Hz, 1H), 7.40-7.35 (m, 2H), 4.49 (s, 2H), 3.57 (t, J=5.7 Hz, 2H), 2.85-2.78 (m, 2H), 2.47 (s, 3H), 1.43 (s, 9H). LC/MS (Table 1, Method B) $R_t$=5.14 min; MS m/z: 417 [M+H]$^+$.

Example #82. 2-[(2-Methylbenzoyl)amino]benzothiophene-3-carboxylic acid (Compound #128)

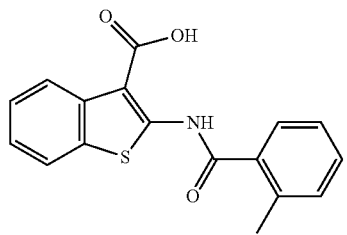 [SMILES: Cc1ccccc1C(=O)Nc1sc2ccccc2c1C(=O)O]

The title compound was synthesized according to the procedure described in Example #1 using ethyl 2-amino-1-benzothiophene-3-carboxylate (CAS: 7311-95-7) and 2-methylbenzoyl chloride (CAS: 933-88-0) as starting materials (off-white solid, yield 7%). $^1$H NMR (DMSO-d$_6$, 400 MHz): δ=13.82 (br s, 1H), 12.40 (br s, 1H), 8.33 (d, J=8.2 Hz, 1H), 7.98 (d, J=7.9 Hz, 1H), 7.75-7.72 (m, 1H), 7.56-7.32 (m, 5H), 2.53 (s, 3H). LC/MS (Table 1, Method A) $R_t$=5.00 min; MS m/z: 310 [M−H]$^−$.

Example #83. 6-iso-Butyl-2-[(2-methylbenzoyl)amino]-5,7-dihydro-4H-thieno[2,3-c]pyridine-3-carboxylic acid formate salt (Compound #129)

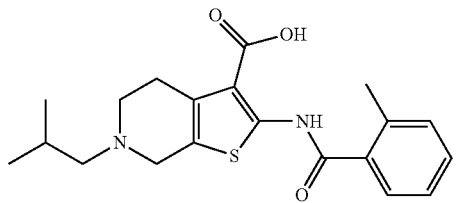 [SMILES: Cc1ccccc1C(=O)Nc1sc2c(c1C(=O)O)CCN(CC(C)C)C2]

To 6-(tert-butyl) 3-ethyl 2-benzamido-4,7-dihydrothieno[2,3-c]pyridine-3,6(5H)-dicarboxylate (prepared as described in Example #81, 2.00 g, 4.50 mmol) was added 4N HCl in dioxane (CAS: 7647-01-0, 40 ml). The reaction mixture was set to stit at RT and next stirred at 70° C. for 1 hour. The precipitate was filtered and dried in vacuo. The solid was dissolved in EtOAc and washed with saturated NaHCO$_3$ aqueous solution (×2). The organic phase was dried over NaSO$_4$ and the solvent was removed under reduced pressure to afford ethyl 2-benzamido-4,5,6,7-tetrahydrothieno[2,3-c]pyridine-3-carboxylate as a white solid (962 mg, yield 62%). To a stirred solution of ethyl 2-benzamido-4,5,6,7-tetrahydrothieno[2,3-c]pyridine-3-carboxylate (100 mg, 0.29 mmol) in dichloroethane (1.5 ml) under nitrogen was added iso-butyraldehyde (CAS: 78-84-2, 40 μl, 0.44 mmol). The reaction mixture was stirred at RT for 10 minutes. Sodium triacetoxyborohydride (CAS: 56553-60-7, 92 mg, 0.44 mmol) was added and the reaction mixture was stirred at RT for 16 hours. Additional iso-butyraldehyde (160 μl, 1.76 mmol) and sodium triacetoxyborohydride (350 mg, 1.67 mmol) were added and the reaction mixture was stirred at RT for a further 2 hours (18 hours in total). The solvent was removed under reduced pressure. The residue was partitioned between EtOAc and water. The two phases were separated. The organic phase was washed with brine and dried over Na$_2$SO$_4$. The solvent was removed under reduced pressure. The residue was dissolved in THF (0.5 ml) and methanol (0.5 ml). A solution of LiOH aq (CAS: 1310-66-3, 1M, 0.43 ml, 0.43 mmol) was added and the reaction mixture was heated at 70° C. for 2 hours. Additional LiOH aq (1M, 1.0 ml, 1.00 mmol) was added and the reaction was heated at 70° C. for a further 2 hours (4 hours in total). The reaction mixture was allowed to cool to RT. The reaction was quenched with the addition of formic acid (1.0 ml). The volatiles were removed under reduced pressure. The residue was purified by RP-HPLC (Table 2, Method A), followed by SCX II cartridge (eluting with 0-100% 2M NH$_3$ in MeOH). The fractions containing the product were concentrated in vacuo and the residue was acidified with formic acid. The solvent was removed under reduced pressure to give 6-isobutyl-2-[(2-methylbenzoyl)amino]-5, 7-dihydro-4H-thieno[2, 3-c]pyridine-3-carboxylic acid formate salt as a yellow solid (57 mg, yield 53%). $^1$H NMR (CDCl$_3$, 400 MHz): δ=12.15 (br s, 1H), 8.30 (s, 1H), 7.63-7.59 (m, 1H), 7.41-7.34 (m, 1H), 7.30-7.24 (m, 2H), 4.28 (s, 2H), 3.50-3.42 (m, 2H), 3.27-3.19 (m, 2H), 2.99 (d, J=7.2 Hz, 2H), 2.55 (s, 3H), 2.18-2.07 (m, 1H), 1.05 (d, J=6.6 Hz, 6H), one exchangeable proton not observed. LC/MS (Table 1, Method A) Rt=3.01 min; MS m/z: 373 [M+H]$^+$.

Example #84. 6-tert-Butyl-2-[[4-(6-methoxy-6-oxohexoxy)benzoyl]amino]-4,5,6,7-tetrahydrobenzothiophene-3-carboxylic acid (Compound #172)

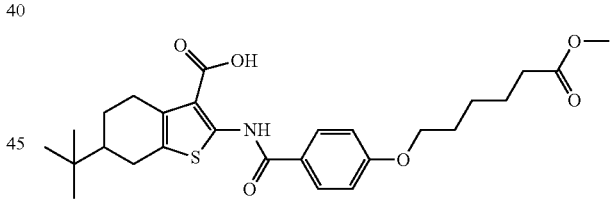

To a stirred solution of tert-butyl 6-(tert-butyl)-2-(4-((6-methoxy-6-oxohexyl)oxy)benzamido)-4,5,6,7-tetrahydrobenzo[b]thiophene-3-carboxylate (Preparation #7, 200 mg, 0.36 mmol) in DCM (5.0 ml) was added TFA (5.5 ml). The reaction mixture was stirred at RT for 4 hours. The solvents were removed in vacuo and the residue was azeotroped with toluene (×3). The residue was triturated with acetonitrile and washed with MeOH to give 6-tert-butyl-2-[[4-(6-methoxy-6-oxo-hexoxy)benzoyl]amino]-4,5,6,7-tetrahydrobenzothiophene-3-carboxylic acid as a white solid (87 mg, yield 48%). $^1$H NMR (DMSO-d$_6$, 400 MHz): δ=13.24 (br s, 1H), 12.35 (s, 1H), 7.89 (d, J=8.6 Hz, 2H), 7.17 (d, J=8.7 Hz, 2H), 4.11 (t, J=6.3 Hz, 2H), 3.64 (s, 3H), 3.10 (d, J=15.0 Hz, 1H), 2.74 (d, J=16.2 Hz, 1H), 2.59-2.50 (m, 1H, partially covered by the solvent peak), 2.49-2.37 (m, 3H), 2.02 (d, J=11.1 Hz, 1H), 1.85-1.59 (m, 4H), 1.53-1.43 (m, 3H), 1.34-1.21 (m, 1H), 0.98 (s, 9H). LC/MS (Table 1, Method C) $R_t$=3.28 min: MS m/z: 502 [M+H]$^+$.

Example #85. 2-Benzamido-5,5,7,7-tetramethyl-4H-thieno[2,3-c]pyran-3-carboxylic acid (Compound #175)

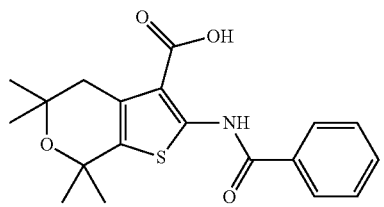 [SMILES: CC1(C)Cc2c(sc(NC(=O)c3ccccc3)c2C(=O)O)C(C)(C)O1]

A reaction vessel was charged with 2,2,6,6-tetramethyl-tetrahydropyran-4-one (CAS: 1197-66-6, 5.00 g, 32.0 mmol), ethyl cyanoacetate (CAS: 105-56-6, 3.4 ml, 32.0 mmol), morpholine (CAS: 110-91-8, 8.4 ml, 96.0 mmol) and sulfur (CAS: 7704-34-9, 1.03 g, 32.0 mmol) and solvated in ethanol (70 ml). The reaction was set to stir at RT and next heated at 80° C. overnight. The reaction was allowed to cool to RT and the solvent was removed under reduced pressure. The residue was partitioned between EtOAc and brine. The two phases were separated and the organic phase was washed with brine. The organic phase was dried over $MgSO_4$ and the solvent was removed under reduced pressure. Purification by flash chromatography on silica gel (eluting with 0-40% EtOAc in isohexane) afforded ethyl 2-amino-5,5,7,7-tetramethyl-4,7-dihydro-5H-thieno[2,3-c]pyran-3-carboxylate as a yellow oil (7.60 g, yield 84%). The title compound was then synthesized according to the procedure described in Example #1 using ethyl 2-amino-5,5,7,7-tetramethyl-4,7-dihydro-5H-thieno[2,3-c]pyran-3-carboxylate and benzoyl chloride (CAS: 98-88-4) as starting materials (off-white solid, yield 16%). $^1$H NMR (DMSO-$d_6$, 400 MHz): δ=13.53 (br s, 1H), 12.40 (s, 1H), 7.97 (d, J=7.5 Hz, 2H), 7.78-7.65 (m, 3H), 2.83 (s, 2H), 1.52 (s, 6H), 1.28 (s, 6H). LC/MS (Table 1, Method C) $R_t$=2.69 min; MS m/z: 360 [M+H]$^+$.

Example #86. 2-[[4-(3-Methoxyazetidin-1-yl)benzoyl]amino]-5,6-dihydro-4H-cyclopenta[b]thiophene-3-carboxylic acid (Compound #207)

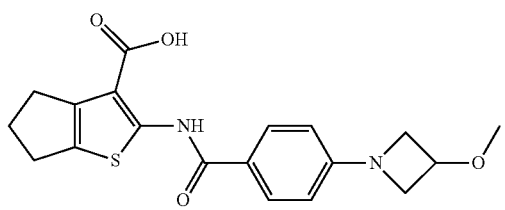 [SMILES: COC1CN(c2ccc(C(=O)Nc3sc4c(c3C(=O)O)CCC4)cc2)C1]

The title compound was synthesized according to the procedure described in Example #36 using ethyl 2-(4-bromobenzamido)-5,6-dihydro-4H-cyclopenta[b]thiophene-3-carboxylate (Preparation #8) and 3-methoxyazetidine hydrochloride (CAS: 148644-09-1) as starting materials (yellow solid, yield 71%). $^1$H NMR (DMSO-$d_6$, 400 MHz): δ=13.16 (br s, 1H), 12.26 (br s, 1H), 7.79 (d, J=8.9 Hz, 2H), 6.61 (d, J=8.6 Hz, 2H), 4.45-4.39 (m, 2H), 4.22 (t, J=7.4 Hz, 2H), 3.82 (dd, J=3.7, 8.7 Hz, 2H), 3.33 (s, 3H), 2.92-2.83 (m, 4H), 2.43-2.35 (m, 2H). LC/MS (Table 1, Method D) $R_t$=3.53 min: MS m/z: 373 [M+H]$^+$.

Example #87. 2-Benzamido-5,6-dihydro-4H-cyclopenta[b]thiophene-3-carboxylic acid (Compound #210)

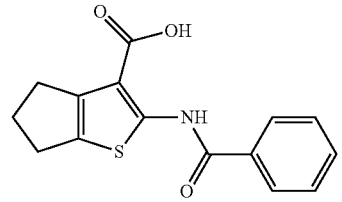 [SMILES: O=C(Nc1sc2c(c1C(=O)O)CCC2)c1ccccc1]

The title compound was then synthesized according to the procedure described in Example #1 using ethyl 2-amino-5,6-dihydro-4H-cyclopenta[b]thiophene-3-carboxylate (CAS: 4815-29-6) and benzoyl chloride (CAS: 98-88-4) as starting materials (pale yellow solid, yield 41%). $^1$H NMR (CDCl$_3$, 400 MHz): δ=11.82 (s, 1H), 8.00 (d, J=7.3 Hz, 2H), 7.63-7.51 (m, 3H), 2.98 (t, J=7.3 Hz, 2H), 2.90 (t, J=7.1 Hz, 2H), 2.48-2.39 (m, 2H), one exchangeable proton not observed. LC/MS (Table 1, Method D) $R_t$=3.51 min; m/z: 288 [M+H]$^+$.

Example #88. 2-[[4-(Tetrahydropyran-4-ylmethylamino)benzoyl]amino]-5,6-dihydro-4H-cyclopenta[b]thiophene-3-carboxylic acid (Compound #211)

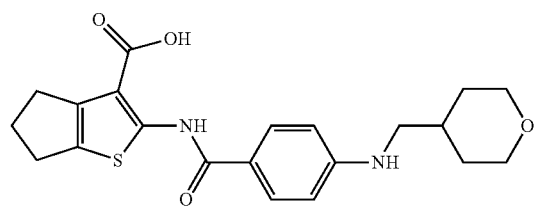 [SMILES: O=C(Nc1sc2c(c1C(=O)O)CCC2)c1ccc(NCC2CCOCC2)cc1]

The title compound was synthesized according to the procedure described in Example #36 using ethyl 2-(4-bromobenzamido)-5,6-dihydro-4H-cyclopenta[b]thiophene-3-carboxylate (Preparation #8) and tetrahydropyran-4-ylmethanamine (CAS: 130290-79-8) as starting materials (yellow solid, yield 71%). $^1$H NMR (CDCl$_3$, 400 MHz): δ=11.66 (s, 1H), 7.82 (d, J=8.4 Hz, 2H), 6.61 (d, J=8.3 Hz, 2H), 4.01 (dd, J=3.2, 11.1 Hz, 2H), 3.39 (t, J=11.2 Hz, 2H), 3.09 (d, J=6.9 Hz, 2H), 2.98-2.92 (m, 2H), 2.91-2.83 (m, 2H), 2.45-2.35 (m, 2H), 1.86 (s, 1H), 1.68 (d, J=12.7 Hz, 2H), 1.38 (ddt, J=4.1, 12.4, 12.3 Hz, 2H), two exchangeable protons not observed. LC/MS (Table 1, Method D) $R_t$=3.47 min; MS m/z: 401 [M+H]$^+$.

Example #89. 2-[[4-(3-Methoxyazetidin-1-yl)benzoyl]amino]-4,5,6,7-tetrahydrobenzothiophene-3-carboxylic acid (Compound #215)

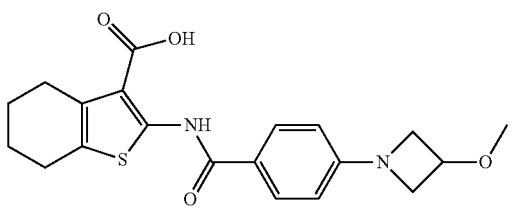 [SMILES: COC1CN(c2ccc(C(=O)Nc3sc4c(c3C(=O)O)CCCC4)cc2)C1]

The title compound was synthesized according to the procedure described in Example #36 using ethyl 2-(4-bromobenzamido)-4,5,6,7-tetrahydrobenzo[b]thiophene-3-carboxylate (Preparation #9) and 3-methoxyazetidine hydrochloride (CAS: 148644-09-1) as starting materials (yellow solid, yield 70%). $^{1}$H NMR (DMSO-$d_6$, 400 MHz): δ=13.21 (br s, 1H), 12.33 (s, 1H), 7.77 (d, J=8.7 Hz, 2H), 6.60 (d, J=8.5 Hz, 2H), 4.45-4.38 (m, 1H), 4.21 (t, J=7.3 Hz, 2H), 3.81 (dd, J=4.0, 8.6 Hz, 2H), 3.33 (s, 3H), 2.81 (s, 2H), 2.67 (s, 2H), 1.79 (s, 4H). LC/MS (Table 1, Method C) $R_t$=2.75 min; MS m/z: 387 [M+H]$^+$.

Example #90. 2-[[4-(Tetrahydropyran-4-ylmethylamino)benzoyl]amino]-4,5,6,7-tetrahydrobenzothiophene-3-carboxylic acid (Compound #216)

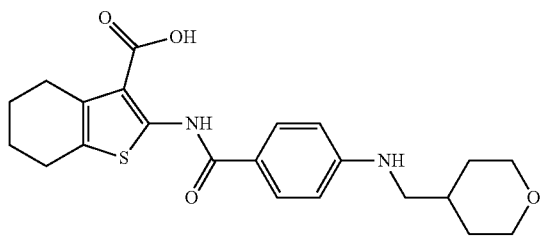 [SMILES: O=C(Nc1sc2c(c1C(=O)O)CCCC2)c1ccc(NCC2CCOCC2)cc1]

The title compound was synthesized according to the procedure described in Example #36 using ethyl 2-(4-bromobenzamido)-4,5,6,7-tetrahydrobenzo[b]thiophene-3-carboxylate (Preparation #9) and tetrahydropyran-4-ylmethanamine (CAS: 130290-79-8) as starting materials (pale yellow solid, yield 40%). $^{1}$H NMR (CDCl$_3$, 400 MHz): δ=11.97 (s, 1H), 7.82 (d, J=8.7 Hz, 2H), 6.60 (d, J=8.7 Hz, 2H), 4.01 (dd, J=3.5, 11.2 Hz, 2H), 3.39 (dt, J=1.6, 11.8 Hz, 2H), 3.08 (d, J=6.8 Hz, 2H), 2.87-2.81 (m, 2H), 2.70-2.65 (m, 2H), 1.86-1.76 (m, 5H), 1.69 (d, J=13.1 Hz, 2H), 1.43-1.32 (m, 2H), two exchangeable protons not observed. LC/MS (Table 1, Method D) $R_t$=3.57 min; MS m/z: 415 [M+H]$^+$.

Example #91. 2-[[4-(3-Methoxyazetidin-1-yl)benzoyl]amino]-5,5,7,7-tetramethyl-4H-thieno[2,3-c]pyran-3-carboxylic acid (Compound #217)

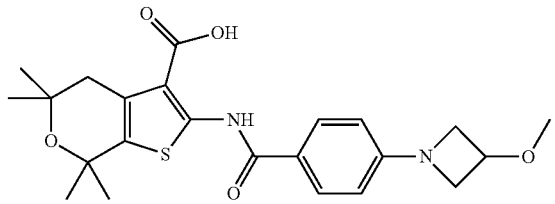

The title compound was synthesized according to the procedure described in Example #36 using ethyl 2-(4-bromobenzamido)-5,5,7,7-tetramethyl-4,7-dihydro-5H-thieno[2,3-c]pyran-3-carboxylate (Preparation #10) and 3-methoxyazetidine hydrochloride (CAS: 148644-09-1) as starting materials (white solid, yield 49%). $^{1}$H NMR (CDCl$_3$, 400 MHz): δ=13.40 (br s, 1H), 12.27 (s, 1H), 7.78 (d, J=8.7 Hz, 2H), 6.61 (d, J=8.7 Hz, 2H), 4.45-4.39 (m, 1H), 4.23 (t, J=7.3 Hz, 2H), 3.81 (dd, J=3.7, 8.5 Hz, 2H), 3.31 (s, 3H), 2.81 (s, 2H), 1.51 (s, 6H), 1.27 (s, 6H). LC/MS (Table 1, Method D) $R_t$=3.66 min: MS m/z: 445 [M+H]$^+$.

Example #92. 5,5,7,7-Tetramethyl-2-(1H-pyrazole-3-carbonylamino)-4H-thieno[2,3-c]pyran-3-carboxylic acid (Compound #218)

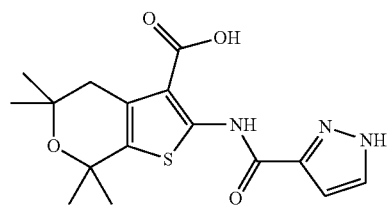 [SMILES: CC1(C)Cc2c(sc(NC(=O)c3cc[nH]n3)c2C(=O)O)C(C)(C)O1]

The title compound was synthesized according to the procedure described in Example #37 using ethyl 2-amino-5,5,7,7-tetramethyl-4,7-dihydro-5H-thieno[2,3-c]pyran-3-carboxylate (prepared as described in Example #85) and 1H-pyrazole-3-carboxylic acid (CAS: 1621-91-6) as starting materials (white solid, yield 31%). $^{1}$H NMR (CDCl$_3$, 400 MHz): δ=12.42 (s, 1H), 7.59 (s, 1H), 6.84 (s, 1H), 2.89 (d, J=3.8 Hz, 2H), 1.55 (s, 3H), 1.52 (s, 3H), 1.31 (s, 3H), 1.27 (s, 3H), two exchangeable protons not observed. LC/MS (Table 1, Method C) $R_t$=2.53 min; m/z: 350 [M+H]$^+$.

Example #93. 2-[[4-(2-Methoxyethylamino)benzoyl]amino]-5,6-dihydro-4H-cyclopenta[b]thiophene-3-carboxylic acid (Compound #231)

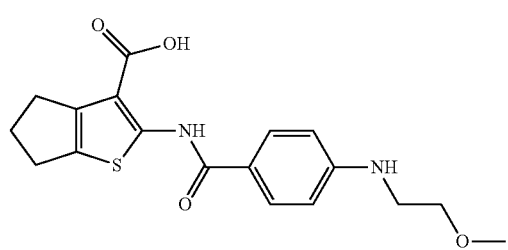 [SMILES: COCCNc1ccc(C(=O)Nc2sc3c(c2C(=O)O)CCC3)cc1]

The title compound was synthesized according to the procedure described in Example #36 using ethyl 2-(4-bromobenzamido)-5,6-dihydro-4H-cyclopenta[b]thiophene-3-carboxylate (Preparation #8) and 2-methoxyethanamine (CAS: 109-85-3) as starting materials (pale yellow solid, yield 20%). $^{1}$H NMR (DMSO-$d_6$, 400 MHz): δ=13.05 (s, 1H), 12.03 (s, 1H), 7.69-7.63 (m, 2H), 6.74 (d, J=8.7 Hz, 2H), 6.64 (t, J=5.5 Hz, 1H), 3.52 (t, J=5.6 Hz, 2H), 3.34-3.28 (m, 5H), 2.89-2.78 (m, 4H), 2.38-2.29 (m, 2H). LC/MS (Table 1, Method E) $R_t$=4.72 min; MS m/z: 361 [M+H]$^+$.

Example #94. 5,5,7,7-Tetramethyl-2-[[4-(tetrahydro-pyran-4-ylamino)benzoyl]amino]-4H-thieno[2,3-c]pyran-3-carboxylic acid (Compound #232)

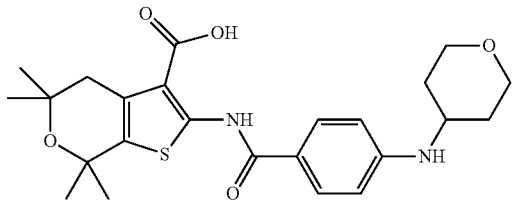 [SMILES: CC1(C)Cc2c(sc(NC(=O)c3ccc(NC4CCOCC4)cc3)c2C(=O)O)C(C)(C)O1]

The title compound was synthesized according to the procedure described in Example #36 using ethyl 2-(4-bromobenzamido)-5,5,7,7-tetramethyl-4,7-dihydro-5H-thieno[2,3-c]pyran-3-carboxylate (Preparation #10) and 4-aminotetrahydropyran (CAS: 38041-19-9) as starting materials (pale yellow solid, yield 44%). $^1$H NMR (CDCl$_3$, 400 MHz): δ=11.92 (s, 1H), 7.84 (d, J=8.4 Hz, 2H), 6.65 (d, J=8.5 Hz, 2H), 4.03 (d, J=11.5 Hz, 3H), 3.63-3.48 (m, 4H), 2.86 (s, 2H), 2.05 (d, J=12.8 Hz, 2H), 1.56 (s, 6H), 1.32 (s, 6H), two exchangeable protons not observed. LC/MS (Table 1, Method F) R$_t$=3.12 min; MS m/z: 459 [M+H]$^+$.

Example #95. 5,5,7,7-Tetramethyl-2-[[4-(tetrahydro-pyran-4-ylmethylamino) benzoyl]amino]-4H-thieno[2,3-c]pyran-3-carboxylicacid (Compound #233)

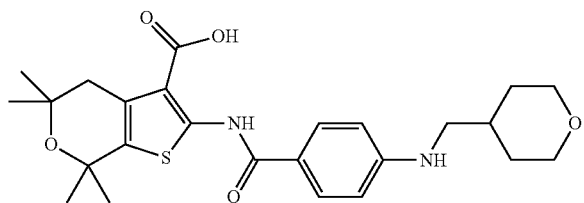 [SMILES: CC1(C)Cc2c(sc(NC(=O)c3ccc(NCC4CCOCC4)cc3)c2C(=O)O)C(C)(C)O1]

The title compound was synthesized according to the procedure described in Example #36 using ethyl 2-(4-bromobenzamido)-5,5,7,7-tetramethyl-4,7-dihydro-5H-thieno[2,3-c]pyran-3-carboxylate (Preparation #10) and tetrahydropyran-4-ylmethanamine (CAS: 130290-79-8) as starting materials (white solid, yield 35%). $^1$H NMR (CDCl$_3$, 400 MHz): δ=11.94 (s, 1H), 7.83 (d, J=8.6 Hz, 2H), 6.63 (d, J=8.3 Hz, 2H), 4.01 (dd, J=3.8, 11.2 Hz, 2H), 3.40 (t, J=11.5 Hz, 2H), 3.11 (d, J=6.7 Hz, 2H), 2.86 (s, 2H), 1.93-1.82 (m, 1H), 1.71 (d, J=12.4 Hz, 2H), 1.56 (s, 6H), 1.45-1.32 (m, 8H), two exchangeable protons not observed. LC/MS (Table 1, Method F) R$_t$=3.26 min; MS m/z: 473 [M+H]$^+$.

Example #96. 2-[[4-(2-Methoxyethylamino)benzoyl]amino]-5,5,7,7-tetramethyl-4H-thieno[2,3-c]pyran-3-carboxylic acid (Compound #234)

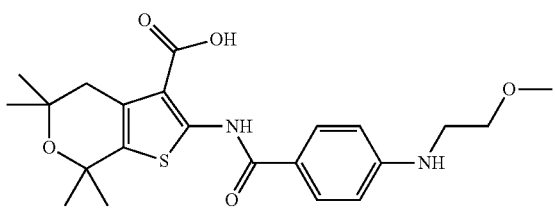

The title compound was synthesized according to the procedure described in Example #36 using ethyl 2-(4-bromobenzamido)-5,5,7,7-tetramethyl-4,7-dihydro-5H-thieno[2,3-c]pyran-3-carboxylate (Preparation #10) and 2-methoxyethanamine (CAS: 109-85-3) as starting materials (white solid, yield 49%). $^1$H NMR (CDCl$_3$, 400 MHz): δ=11.96 (s, 1H), 7.85 (d, J=8.5 Hz, 2H), 6.68 (d, J=8.6 Hz, 2H), 3.67 (t, J=4.6 Hz, 2H), 3.43 (s, 3H), 3.38 (t, J=4.6 Hz, 2H), 2.86 (s, 2H), 1.54 (s, 6H), 1.31 (s, 6H), two exchangeable protons not observed. LC/MS (Table 1, Method F) R$_t$=3.09 min: MS m/z: 433 [M+H]$^+$.

Example #97. 2-[[4-[2-Methoxyethyl(methyl)amino]benzoyl]amino]-5,5,7,7-tetramethyl-4H-thieno[2,3-c]pyran-3-carboxylic acid (Compound #235)

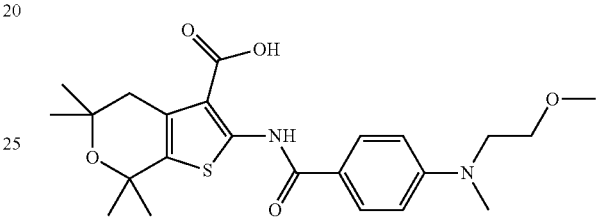

The title compound was synthesized according to the procedure described in Example #36 using ethyl 2-(4-bromobenzamido)-5,5,7,7-tetramethyl-4,7-dihydro-5H-thieno[2,3-c]pyran-3-carboxylate (Preparation #10) and 2-methoxy-N-methyl-ethanamine (CAS: 38256-93-8) as starting materials (white solid, yield 46%). $^1$H NMR (CDCl$_3$, 400 MHz): δ=11.95 (s, 1H), 7.86 (d, J=8.7 Hz, 2H), 6.72 (d, J=8.2 Hz, 2H), 3.58 (s, 4H), 3.35 (s, 3H), 3.04 (s, 3H), 2.87 (s, 2H), 1.55 (s, 6H), 1.30 (s, 6H), one proton exchangeable not observed. LC/MS (Table 1, Method F) R$_t$=3.31 min; MS m/z: 447 [M+H]$^+$.

Example #98. 2-Benzamido-5-phenyl-4,5,6,7-tetrahydrobenzothiophene-3-carboxylic acid (Compound #240)

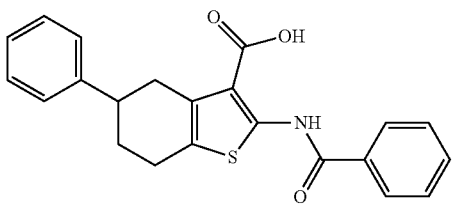 [SMILES: O=C(Nc1sc2c(c1C(=O)O)CC(c1ccccc1)CC2)c1ccccc1]

The title compound was synthesized according to the procedure described in Example #20 using 3-phenylcyclohexanone (CAS: 20795-53-3) and benzoyl chloride (CAS: 98-88-4) as starting materials (off-white solid, yield 19%). $^1$H NMR (DMSO-d$_6$, 400 MHz): δ=13.78 (br s, 1H), 7.94-7.91 (m, 2H), 7.65-7.57 (m, 3H), 7.34-7.31 (m, 4H), 7.26-7.13 (m, 2H), 3.29-3.21 (m, 1H, partially obscured by the water peak), 2.96-2.88 (m, 1H), 2.79-2.78 (m, 2H), 2.70-2.61 (m, 1H), 2.05-1.90 (m, 2H). LC/MS (Table 1, Method C) R$_t$=5.94 min, MS n/z: 378 [M+H]$^+$.

Preparation #1. Methyl 6-(tert-butyl)-2-(4-morpholinobenzamido)-4,5,6,7-tetrahydrobenzo[b]thiophene-3-carboxylate

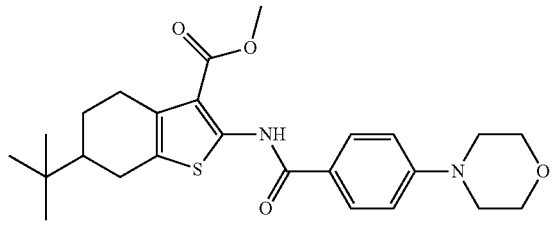 [SMILES: COC(=O)c1c(NC(=O)c2ccc(N3CCOCC3)cc2)sc2c1CCC(C(C)(C)C)C2]

A reaction vessel was charged with 4-morpholinobenzoic acid (CAS: 7470-38-4, 300 mg, 1.45 mmol) and solvated in thionyl chloride (CAS: 7719-09-7, 1.5 ml). The reaction was set to stir at RT and next heated at 50° C. for 3 hours. The reaction mixture was allowed to cool to RT and the volatiles were removed under reduced pressure to afford 4-morpholinobenzoyl chloride. To a solution of methyl 2-amino-6-tert-butyl-4,5,6,7-tetrahydro-1-benzothiophene-3-carboxylate (CAS: 213192-26-8, 97 mg, 0.36 mmol) in DCM (3 ml) was added DIPEA (190 µl, 1.09 mmol) and 4-morpholinobenzoyl chloride (98 mg, 0.43 mmol). The reaction mixture was stirred at RT overnight. The resulting mixture was partitioned between DCM and water. The two phases were separated and the organic phase was dried over MgSO$_4$. The solvent was removed under reduced pressure. Purification by flash chromatography on silica gel (eluting with 0-60% DCM in isohexane) gave methyl 6-(tert-butyl)-2-(4-morpholinobenzamido)-4,5,6,7-tetrahydrobenzo[b]thiophene-3-carboxylate (62 mg, yield 37%). $^1$H NMR (CDCl$_3$, 400 MHz): δ=12.16 (s, 1H), 7.94 (d, J=9.0 Hz, 2H), 6.94 (d, J=9.0 Hz, 2H), 3.90 (s, 3H), 3.89-3.86 (m, 4H), 3.31-3.29 (m, 4H), 3.18-3.15 (m, 1H), 3.07-3.00 (m, 1H), 2.74-2.38 (m, 2H), 2.03-1.97 (m, 1H), 1.51-1.24 (m, 2H), 0.95 (s, 9H).

Preparation #2. Methyl 6-(tert-butyl)-2-(4-chlorobenzamido)-4,5,6,7-tetrahydrobenzo[b]thiophene-3-carboxylate

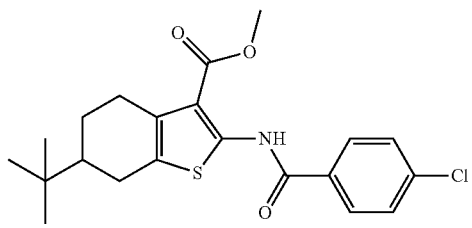 [SMILES: COC(=O)c1c(NC(=O)c2ccc(Cl)cc2)sc2c1CCC(C(C)(C)C)C2]

To a solution of methyl 2-amino-6-tert-butyl-4,5,6,7-tetrahydro-1-benzothiophene-3-carboxylate (CAS: 213192-26-8, 144 mg, 0.54 mmol) in acetonitrile (2.0 ml) was added 4-chlorobenzoic acid (CAS: 74-11-3, 81 µl, 0.70 mmol), 2-chloromethylpyridinium iodide (CAS: 14338-32-0, 193 mg, 0.76 mmol), DMAP (CAS: 1122-58-3.20 mg, 0.16 mmol) and TEA (CAS: 121-44-8,230 µl, 1.63 mmol). The reaction was set to stir at RT and next heated at 60° C. for 24 hours. The reaction mixture was allowed to cool to RT and next partitioned between DCM and water. The two phases were separated and the organic phase was dried over MgSO$_4$. The solvent was removed under reduced pressure. Purification by flash chromatography on silica gel (eluting with 0-60% DCM in isohexane) gave methyl 6-(tert-butyl)-2-(4-chlorobenzamido)-4,5,6,7-tetrahydrobenzo[b]thiophene-3-carboxylate (81 mg, yield 37%). $^1$H NMR (CDCl$_3$, 400 MHz): δ=12.28 (s, 1H), 7.97-7.93 (m, 2H), 7.50-7.47 (m, 2H), 3.91 (s, 3H), 3.07-3.01 (m, 1H), 2.75-2.70 (m, 1H), 2.62-2.55 (m, 1H), 2.47-2.39 (m, 1H), 2.05-2.00 (m, 1H), 1.53-1.26 (m, 2H), 0.95 (s, 9H).

Preparation #3. Methyl 2-(4-(3-((tert-butoxycarbonyl)amino)propoxy)benzamido)-6-(tert-butyl)-4,5,6,7-tetrahydrobenzo[b]thiophene-3-carboxylate

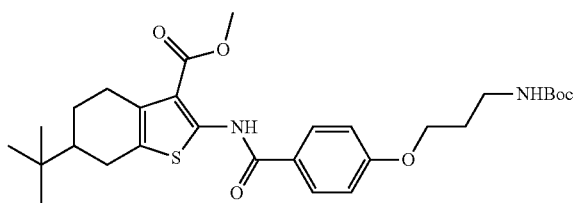 [SMILES: COC(=O)c1c(NC(=O)c2ccc(OCCCNC(=O)OC(C)(C)C)cc2)sc2c1CCC(C(C)(C)C)C2]

Step A. Methyl 6-(tert-butyl)-2-(4-hydroxybenzamido)-4,5,6,7-tetrahydrobenzo[b]thiophene-3-carboxylate

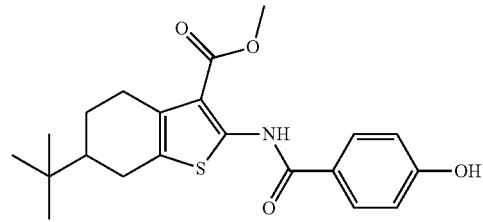 [SMILES: COC(=O)c1c(NC(=O)c2ccc(O)cc2)sc2c1CCC(C(C)(C)C)C2]

To a solution of methyl 2-amino-6-tert-butyl-4,5,6,7-tetrahydro-1-benzothiophene-3-carboxylate (CAS: 213192-26-8, 800 mg, 2.99 mmol) in DCM (70 ml) was added DIPEA (CAS: 7087-68-5, 2.10 ml, 11.97 mmol) and 4-acetoxybenzoyl chloride (CAS: 27914-73-4, 772 mg, 3.89 mmol). The reaction mixture was stirred at RT overnight. The resulting mixture was diluted with DCM. The organic phase was washed with an aqueous 1M HCl solution and dried over MgSO$_4$. The solvent was removed under reduced pressure. The residue was purified by trituration with Et$_2$O/isohexane to give methyl 2-(4-acetoxybenzamido)-6-(tert-butyl)-4,5,6,7-tetrahydrobenzo[b]thiophene-3-carboxylate as white solid (1.20 g, yield 93%). Methyl 2-(4-acetoxybenzamido)-6-(tert-butyl)-4,5,6,7-tetrahydrobenzo[b]thiophene-3-carboxylate (430 mg, 1.00 mmol) was suspended in THF (10 ml) and MeOH (10 ml) and LiOH aq. (CAS: 1310-66-3, 1M, 126 mg, 3.0 mmol) was added. The reaction mixture was stirred at RT for 5 minutes and then acidified with 1N aqueous HCl solution. The precipitate was filtered off and washed with MeOH/H$_2$O to afford methyl 6-(tert-butyl)-2-(4-hydroxybenzamido)-4,5,6,7-tetrahydrobenzo[b]thiophene-3-carboxylate as a white solid (330 mg, yield 85%). $^1$H NMR (DMSO-d$_6$, 400 MHz): δ=11.92 (s, 1H), 10.44 (s, 1H), 7.79 (d, J=8.7 Hz, 2H), 6.96 (d, J=8.7 Hz, 2H), 3.86 (s, 3H), 2.99 (dd, J=16.5, 3.8 Hz, 1H), 2.69 (dd, J=16.0, 4.0 Hz, 1H), 2.55-2.47 (m, 1H, partially obscured by the DMSO peak), 2.41-2.34 (m, 1H), 2.00-1.95 (m, 1H), 1.43 (td, J=11.4, 3.6 Hz, 1H), 1.22 (qd, J=12.5, 5.1 Hz, 1H), 0.92 (s, 9H).

Step B. Methyl 2-(4-(3-((tert-butoxycarbonyl) amino)propoxy)benzamido)-6-(tert-butyl)-4,5,6,7-tetrahydrobenzo[b]thiophene-3-carboxylate

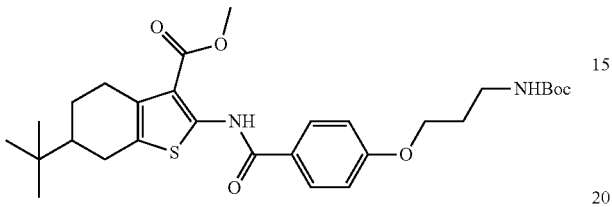

To a solution of methyl 6-(tert-butyl)-2-(4-hydroxybenzamido)-4,5,6,7-tetrahydrobenzo[b]thiophene-3-carboxylate (Preparation #3, Step A, 116 mg, 0.30 mmol) in acetonitrile (5.0 ml) was added $Cs_2CO_3$ (CAS: 534-17-8, 117 mg, 0.36 mmol) and 3-(Boc-amino)propyl bromide (CAS: 83948-53-2, 86 mg, 0.36 mmol). The reaction mixture was set to stir at RT and next heated at 60° C. for 15 minutes. Potassium iodide (CAS: 7681-11-0, 2 mg, 0.012 mmol) was added and the reaction mixture was heated at 60° C. for 2 hours. The reaction was allowed to cool to RT and water was added. The precipitate was filtered, the solid was washed with $MeCN/H_2O$ and dried under reduced pressure to give methyl 2-(4-(3-((tert-butoxycarbonyl)amino)propoxy)benzamido)-6-(tert-butyl)-4,5,6,7-tetrahydrobenzo[b]thiophene-3-carboxylate as a white solid (148 mg, yield 91%). $^1$H NMR (DMSO-$d_6$, 400 MHz): δ=11.97 (s, 1H), 7.88 (d, J=8.6 Hz, 2H), 7.14 (d, J=8.4 Hz, 2H), 6.94 (br s, 1H), 4.08 (t, J=5.8 Hz, 2H), 3.87 (s, 3H), 3.11 (q, J=6.1 Hz, 2H), 3.03-2.97 (m, 1H), 2.72-2.67 (m, 1H), 2.57-2.35 (m, 2H, partially obscured by the DMSO peak), 2.01-1.96 (m, 1H), 1.85 (quin, J=6.4 Hz, 2H), 1.47-1.34 (m, 10H), 1.29-1.18 (m, 1H), 0.92 (s, 9H).

Preparation #4. Methyl 2-amino-6-phenyl-4,5,6,7-tetrahydrobenzo[b]thiophene-3-carboxylate

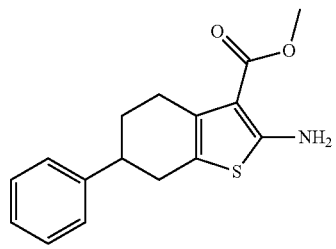 [SMILES: COC(=O)c1c(N)sc2c1CCC(c1ccccc1)C2]

A solution of 4-phenylcyclohexanone (CAS: 4894-75-1, 2.00 g, 11.5 mmol), methyl cyanoacetate (CAS: 105-34-0, 1.11 ml, 12.6 mmol), diethylamine (CAS: 109-89-7, 0.59 ml, 5.70 mmol) and sulfur (CAS: 7704-34-9, 121 mg, 3.78 mmol) in methanol (20 ml) was stirred at RT for 5 hours. The reaction was left standing for 16 hours and then the precipitate was collected to afford methyl 2-amino-6-phenyl-4,5,6,7-tetrahydrobenzo[b]thiophene-3-carboxylate as a white solid mixture (2.00 g, yield 61%). $^1$H NMR (CDCl$_3$, 400 MHz): δ=7.35-7.30 (m, 2H), 7.28-7.20 (m, 3H), 5.96 (s, 2H), 3.80 (s, 3H), 3.03-2.93 (m, 2H), 2.80-2.63 (m, 3H), 2.12-2.06 (m, 1H), 1.95-1.83 (m, 1H).

Preparation #5. Ethyl 2-(4-bromobenzamido)-4-methyl-4,5,6,7-tetrahydrobenzo[b]thiophene-3-carboxylate

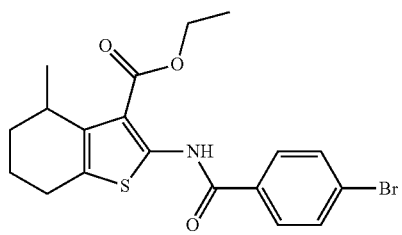 [SMILES: CCOC(=O)c1c(NC(=O)c2ccc(Br)cc2)sc2c1C(C)CCC2]

Step A. Ethyl 2-amino-4-methyl-4,5,6,7-tetrahydrobenzo[b]thiophene-3-carboxylate

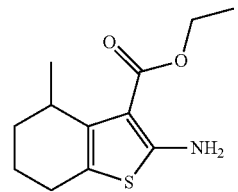 [SMILES: CCOC(=O)c1c(N)sc2c1C(C)CCC2]

The title compound was synthesized according to the procedure described in Preparation #4 using 2-methylcyclohexanone (CAS: 583-60-8) as a starting material (603 mg, yield 28%). $^1$H NMR (CDCl$_3$, 400 MHz): δ=5.96 (br s, 2H), 4.34-4.22 (m, 2H), 3.28-3.24 (m, 1H), 2.51-2.47 (m, 2H), 1.90-1.73 (m, 3H), 1.66-1.59 (m, 1H), 1.35 (t, J=7.1 Hz, 3H), 1.16 (d, J=6.8 Hz, 3H).

Step B. Ethyl 2-(4-bromobenzamido)-4-methyl-4,5,6,7-tetrahydrobenzo[b]thiophene-3-carboxylate

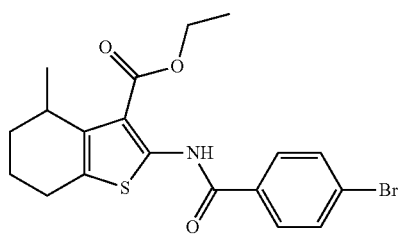 [SMILES: CCOC(=O)c1c(NC(=O)c2ccc(Br)cc2)sc2c1C(C)CCC2]

To a solution of ethyl 2-amino-4-methyl-4,5,6,7-tetrahydrobenzo[b]thiophene-3-carboxylate (Preparation #5, Step A, 200 mg, 0.84 mmol) in DCM (10 ml) was added DIPEA (CAS: 7087-68-5, 0.29 ml, 1.67 mmol) and 4-bromobenzoyl chloride (CAS: 586-75-4, 248 mg, 1.13 mmol). The reaction mixture was stirred at RT for 72 hours. The reaction was partitioned between DCM and saturated aqueous NaHCO$_3$ solution. The organic phase was separated and passed through a phase separator. The solvent was removed under reduced pressure. Trituration with MeOH gave ethyl 2-(4-bromobenzamido)-4-methyl-4,5,6,7-tetrahydrobenzo[b]thiophene-3-carboxylate as an off-white solid (338 mg, yield 96%). ¹H NMR (CDCl₃, 400 MHz): δ=12.44 (s, 1H), 7.88 (d, J=8.3 Hz, 2H), 7.66 (d, J=8.3 Hz, 2H), 4.48-4.34 (m, 2H), 3.39-3.35 (m, 1H), 2.76-2.60 (m, 2H), 1.84-1.81 (m 3H), 1.73-1.69 (m 1H), 1.43 (t, J=7.2 Hz, 3H), 1.20 (d, J=6.8 Hz, 3H).

Preparation #6. Ethyl 2-amino-4-phenyl-4,5,6,7-tetrahydrobenzo[b]thiophene-3-carboxylate

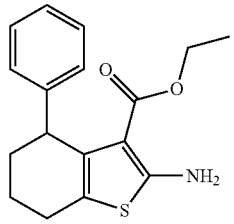 [SMILES: CCOC(=O)c1c(N)sc2c1C(c1ccccc1)CCC2]

To a stirred solution of 2-phenylcyclohexanone (CAS: 1444-65-1, 500 mg, 2.87 mmol) in toluene (10 ml) was added ethyl cyanoacetate (CAS: 105-56-6, 0.31 ml, 2.87 mmol), ammonium acetate (CAS: 631-61-8, 155 mg, 2.01 mmol) and acetic acid (0.3 ml). The reaction mixture was heated at 110° C. for 24 hours. The reaction was allowed to cool to RT and then it was partitioned between EtOAc and brine. The two phases were separated. The aqueous phase was extracted with EtOAc (×3) and the combined organic phases were washed with brine. The organic phase was dried over MgSO₄ and the solvent was removed under reduced pressure. Purification by flash chromatography on silica gel (eluting with 0-20% EtOAc in isohexane) afforded ethyl 2-cyano-2-(2-phenylcyclohexylidene)acetate as a colourless oil (455 mg, yield 58%). Ethyl 2-cyano-2-(2-phenylcyclohexylidene)acetate (200 mg, 0.74 mmol) was dissolved in DMF (4.0 ml). To the solution was added sulfur (CAS: 7704-34-9.26 mg, 0.82 mmol) and morpholine (CAS: 110-91-8, 71 µl, 0.82 mmol). The reaction mixture was heated at 100° C. for 4 hours. The reaction was allowed to cool to RT. The mixture was partitioned between EtOAc and saturated aqueous NaHCO₃ solution and the two phases were separated. The aqueous phase was extracted with EtOAc (×3). The combined organic phases were dried over MgSO₄ and the solvent was removed under reduced pressure. Purification by flash chromatography on silica gel (eluting with 0-20% EtOAc in isohexane) afforded ethyl 2-amino-4-phenyl-4,5,6,7-tetrahydrobenzo[b]thiophene-3-carboxylate as a pale yellow oil (177 mg, yield 79%). ¹H NMR (CDCl₃, 400 MHz): δ=7.24-7.19 (m, 2H), 7.16-7.09 (m, 1H), 7.03-7.01 (m, 2H), 6.01 (br s, 2H), 4.45-4.42 (m, 1H), 3.94-3.87 (m, 2H), 2.62-2.56 (m, 2H), 2.08-2.00 (m, 1H), 1.91-1.80 (m, 1H), 1.67-1.60 (m, 2H), 0.90 (t, J=7.2 Hz, 3H).

Preparation #7. tert-Butyl 6-(tert-butyl)-2-(4-((6-methoxy-6-oxohexyl)oxy)benzamido)-4,5,6,7-tetrahydrobenzo[b]thiophene-3-carboxylate

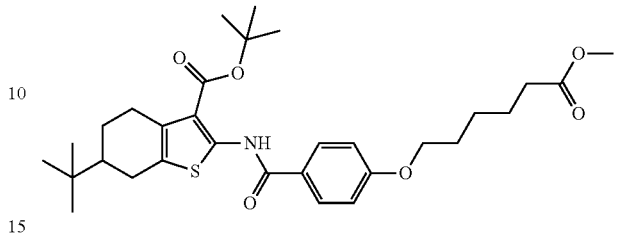

A solution of 4-tert-butylcyclohexanone (CAS: 98-53-3, 2.00 g, 12.97 mmol), tert-butyl cyanoacetate (CAS: 1116-98-9, 1.83 g, 12.97 mmol) and morpholine (CAS: 110-91-8, 3.39 g, 38.90 mmol) in ethanol (15 ml) was heated at 50° C. for 30 minutes. Sulfur (CAS: 7704-34-9, 416 mg, 12.97 mmol) was added and the reaction mixture was stirred at 80° C. for 16 hours. The volatiles were removed under reduced pressure and the residue was partitioned between EtOAc and brine. The organic phase was separated and dried over MgSO₄. The solvent was removed under reduced pressure. Purification by flash chromatography on silica gel (eluting with 0-30% EtOAc in isohexane) afforded tert-butyl 2-amino-6-(tert-butyl)-4,5,6,7-tetrahydrobenzo[b]thiophene-3-carboxylate (2.29 g, yield 57%). The residue was dissolved in DCM (50 ml) and DIPEA (CAS: 7087-68-5, 2.60 ml, 14.80 mmol) and 4-acetoxybenzoyl chloride (CAS: 27914-73-4, 2.21 g, 11.10 mmol) were added. The reaction mixture was stirred at RT overnight. The resulting mixture was diluted with DCM. The organic phase was washed with an aqueous 1M HCl solution and dried over MgSO₄. The solvent was removed under reduced pressure. Purification by flash chromatography on silica gel (eluting with 0-30% EtOAc in isohexane) afforded tert-butyl 2-(4-acetoxybenzamido)-6-(tert-butyl)-4,5,6,7-tetrahydrobenzo[b]thiophene-3-carboxylate (3.35 µg, yield 96%). tert-Butyl 2-(4-acetoxybenzamido)-6-(tert-butyl)-4,5,6,7-tetrahydrobenzo[b]thiophene-3-carboxylate was then suspended in methanol (30 ml), THF (30 ml), water (30 ml) and then lithium hydroxide monohydrate (CAS: 1310-66-3, 600 mg, 14.21 mmol) was added. The reaction mixture was stirred at RT for 2 hours. The reaction was partitioned between EtOAc and aqueous 1M HCl solution and the two phases were separated. The organic phase was washed with brine and dried over MgSO₄. The solvent was removed under reduced pressure. The residue was suspended in acetonitrile (50 ml) and then potassium carbonate (CAS: 584-08-7, 1.67 g, 12.07 mmol) and methyl 6-bromohexanoate (CAS: 14273-90-6, 2.52 g, 12.07 mmol) were added. The reaction mixture was stirred at RT for 16 hours and then it was heated at 60° C. for 24 hours. The reaction was allowed to cool to RT and next partitioned between EtOAc and water. The precipitate was filtered and the two phases were separated. The organic phase was dried over MgSO₄ and the solvent was removed under reduced pressure. The residue was combined with the precipitated solid and then triturated with isohexane to give tert-butyl 6-(tert-butyl)-2-(4-((6-methoxy-6-oxohexyl)oxy)benzamido)-4,5,6,7-tetrahydrobenzo[b]thiophene-3-carboxylate as a white solid (2.6 g, yield 66%). ¹H NMR (CDCl₃, 400 MHz): δ=12.28 (s, 1H), 7.96 (d, J=8.9 Hz, 2H), 6.98 (d, J=8.7 Hz, 2H), 4.03 (t, J=6.4 Hz, 2H), 3.68 (s, 3H), 3.03 (dd, J=4.4, 17.2 Hz, 1H), 2.71 (dd, J=3.6, 15.8 Hz, 1H), 2.57 (t, J=13.9 Hz, 1H), 2.44 (d, J=14.1 Hz, 1H), 2.37 (t, J=7.4 Hz, 2H), 2.02 (d, J=10.5 Hz, 1H), 1.89-1.79 (m, 2H), 1.77-1.67 (m, 2H), 1.61 (s, 9H), 1.55-1.43 (m, 3H), 1.31 (dq, J=5.1, 12.2 Hz, 1H), 0.95 (s, 9H).

Preparation #8. Ethyl 2-(4-bromobenzamido)-5,6-dihydro-4H-cyclopenta[b]thiophene-3-carboxylate

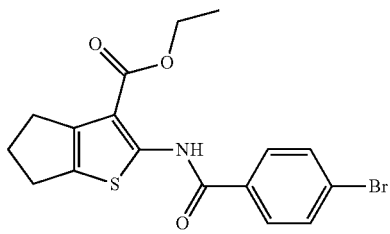 [SMILES: CCOC(=O)c1c(NC(=O)c2ccc(Br)cc2)sc2c1CCC2]

The title compound was synthesized according to the procedure described in Preparation #5 (Step B) using ethyl 2-amino-5,6-dihydro-4H-cyclopenta[b]thiophene-3-carboxylate (CAS: 4815-29-6) and 4-bromobenzoyl chloride (CAS: 586-75-4) as starting materials (yellow solid, 1.28 g, yield 98%). $^1$H NMR (CDCl$_3$, 400 MHz): δ=12.04 (s, 1H), 7.88 (d, J=8.5 Hz, 2H), 7.66 (d, J=8.7 Hz, 2H), 4.36 (q, J=7.1 Hz, 2H), 2.96-2.87 (m, 4H), 2.45-2.36 (m, 2H), 1.40 (t, J=7.1 Hz, 3H).

Preparation #9. Ethyl 2-(4-bromobenzamido)-4,5,6,7-tetrahydrobenzo[b]thiophene-3-carboxylate

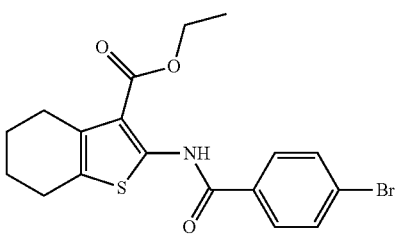 [SMILES: CCOC(=O)c1c(NC(=O)c2ccc(Br)cc2)sc2c1CCCC2]

The title compound was synthesized according to the procedure described in Preparation #5 (Step B) using ethyl 2-amino-4,5,6,7-tetrahydrobenzothiophene-3-carboxylate (CAS: 4506-71-2) and 4-bromobenzoyl chloride (CAS: 586-75-4) as starting materials (yellow solid, 980 mg, yield 77%). $^1$H NMR (CDCl$_3$, 400 MHz): δ=12.35 (s, 1H), 7.88 (d, J=8.5 Hz, 2H), 7.66 (d, J=8.6 Hz, 2H), 4.38 (q, J=7.1 Hz, 2H), 2.81 (br s, 2H), 2.70 (br s, 2H), 1.81 (br s, 4H), 1.41 (t, J=7.1 Hz, 3H).

Preparation #10. Ethyl 2-(4-bromobenzamido)-5,5,7,7-tetramethyl-4,7-dihydro-5H-thieno[2,3-c]pyran-3-carboxylate

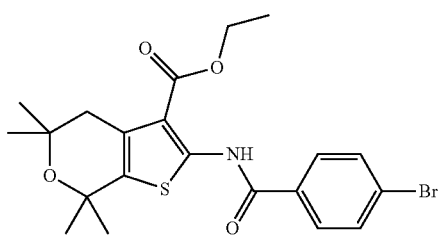 [SMILES: CCOC(=O)c1c(NC(=O)c2ccc(Br)cc2)sc2c1CC(C)(C)OC2(C)C]

A solution of 2,2,6,6-tetramethyltetrahydropyran-4-one (CAS: 1197-66-6, 5.00 g, 32.0 mmol), ethyl cyanoacetate (CAS: 105-56-6, 3.4 ml, 32.0 mmol), morpholine (CAS: 110-91-8, 8.4 ml, 96.0 mmol) and sulfur (CAS: 7704-34-9, 1.03 mg, 32.0 mmol) in ethanol (70 ml) was heated at 80° C. overnight. The reaction mixture was allowed to cool to RT and the solvent was removed under reduced pressure. The residue was partitioned between EtOAc and brine. The two phases were separated and the organic phase was washed with brine. The organic phase was dried over MgSO$_4$ and the solvent was removed under reduced pressure. Purification by flash chromatography on silica gel (eluting with 0-40% EtOAc in isohexane) afforded ethyl 2-amino-5,5,7,7-tetramethyl-4,7-dihydro-5H-thieno[2,3-c]pyran-3-carboxylate (7.60 g, yield 84%). The title compound was then synthesized according to the procedure described in Preparation #5 (Step B) using ethyl 2-amino-5,5,7,7-tetramethyl-4,7-dihydro-5H-thieno[2,3-c]pyran-3-carboxylate and 4-bromobenzoyl chloride (CAS: 586-75-4) as starting materials (yield quant). $^1$H NMR (CDCl$_3$, 400 MHz): δ=12.33 (s, 1H), 7.88 (d, J=8.6 Hz, 2H), 7.67 (d, J=8.4 Hz, 2H), 4.40 (q, J=7.2 Hz, 2H), 2.80 (s, 2H), 1.55 (s, 3H), 1.53 (s, 3H), 1.43 (t, J=7.1 Hz, 3H), 1.30 (s, 6H).

Example B—Biology

Example B1—Antiviral Effect

The antiviral effect of the compounds of the invention has been tested on A549 cell lines infected with H1N1 (influenza A/New Caledonia/20/99).

IC50 are reported in the following Table 1. The results show that the compounds of the present invention present an antiviral effect.

TABLE 1

| Compound | IC50 (μM) | Compound | IC50 (μM) | Compound | IC50 (μM) |
|---|---|---|---|---|---|
| #10 | 0.026 | #7 | 0.0346 | #51 | 0.038 |
| #8 | 0.0385 | #47A | 0.04 | #1 | 0.0548 |
| #3 | 0.055 | #54 | 0.06 | #5 | 0.06 |
| #66 | 0.0693 | #9 | 0.07 | #47B | 0.07 |
| #2 | 0.07 | #52 | 0.09 | #48 | 0.09 |
| #67 | 0.0917 | #50 | 0.09 | #6 | 0.09 |
| #68 | 0.12 | #69 | 0.12 | #53 | 0.14 |
| #11 | 0.14 | #70 | 0.1455 | #46 | 0.15 |
| #71 | 0.16 | #72 | 0.17 | #73 | 0.18 |
| #74 | 0.1815 | #56 | 0.15 | #76 | 0.2182 |
| #75 | 0.21 | #57 | 0.21 | #77 | 0.26 |
| #79 | 0.2917 | #45 | 0.3376 | #81 | 0.3391 |
| #82 | 0.3487 | #83 | 0.38 | #84 | 0.4 |
| #86 | 0.41 | #49 | 0.41 | #55 | 0.41 |
| #87 | 0.445 | #12 | 0.45 | #88 | 0.5471 |
| #89 | 0.59 | #91 | 0.62 | #92 | 0.66 |
| #93 | 0.66 | #95 | 0.7226 | #97 | 0.8 |
| #99 | 0.83 | #100 | 0.8734 | #101 | 0.9432 |
| #102 | 0.97 | #103 | 0.97 | #104 | 1.05 |
| #4 | 1.07 | #113 | 1.37 | #115 | 1.47 |
| #106 | 1.1 | #107 | 1.15 | #108 | 1.17 |
| #109 | 1.2 | #110 | 1.2 | #13 | 1.2 |
| #28 | 1.27 | #111 | 1.37 | #112 | 1.37 |
| #116 | 1.7 | #172 | 0.51 | #118 | 1.95 |
| #119 | 2.2 | #120 | 2.27 | #121 | 2.35 |
| #122 | 2.37 | #123 | 2.7 | #124 | 2.7 |
| #125 | 2.8 | #126 | 2.9 | #14 | 3.17 |
| #127 | 3.4 | #128 | 5 | #129 | 16.6 |
| #130 | 19.1 | #175 | 0.74 | #207 | 0.38 |
| #210 | 0.817 | #211 | 0.26 | #215 | 0.11 |
| #216 | 0.06 | #217 | 0.51 | | |
| #231 | 0.89 | #232 | 1.38 | #233 | 0.22 |
| #234 | 0.98 | #235 | 0.42 | #236 | 0.131 |

TABLE 1-continued

| Compound | IC50 (µM) | Compound | IC50 (µM) | Compound | IC50 (µM) |
|---|---|---|---|---|---|
| #237 | 0.211 | #238 | 0.31 | #239 | 0.548 |
| #240 | ND | | | | |

Materials and Methods

Human A549 cells (80,000 cells/well in a 96 well plate) were treated with a range of concentration of test molecules and immediately infected by H1N1 A/New Caledonia/20/99 virus (clinical isolate) at MOI of 0.1 in DMEM/1% Penicillin/streptomycin supplemented with 0.25 µg/ml TPCK trypsin (Sigma) and incubated at 37° C. in 5% $CO_2$. 48 h post-infection, supernatants (25 µl) were collected and transferred into a 96-well black flat-bottom plate, mixed with 25 µl PBS with Ca++/Mg++(Thermo Fisher) and 50 µl of 2'-(4-Methylumbelliferyl)-α-D-N-acetylneuraminic acid sodium salt hydrate stock-solution (20 µM, MUNANA, Sigma). Plates were incubated 1 h at 37° C. and reaction is stopped by adding 100 µl of Stop Solution (glycine 0.1 M pH10.7/25% ethanol). The amount of fluorescent product released by MUNANA hydrolysis (4-MU) was measured in a Tecan spectrophotometer with excitation and emission wavelengths of 365 and 450 nm respectively.

Example B2—Modulators of NEET Proteins

The modulator effect on the NEET proteins encoded by human CISD1, CISD2, and CISD3 genes by the compounds of the invention has been tested and is reported below. Particularly, the biochemical function of the NEET proteins is measured by the stability of Fe—S cluster binding of the purified NEET proteins.

The Fe—S cluster binding capacity of NEET proteins is known to be coordinated by four amino-acids in a stretch of 16 (three Cysteine and one Histidine). As the lability of the Fe—S cluster of NEET proteins is sensitive to the environment, cluster stability measurements are one of the measures of interactions of NEET proteins with small molecules and compounds. NEET protein/2Fe-2S cluster stability can be assessed by monitoring the decay in absorbance of its characteristic 458-nm peak (characteristic of the oxidized 2Fe-2S cluster) over time. Each NEET protein (mitoNEET, NAF-1 and Miner 2) was tested for its Fe—S binding in the absence or presence of a compound according to the invention (see table 2 below). The rate of cluster release (time in minutes to achieve 50% loss of bound Fe—S cluster) was compared for each NEET protein in the presence of one of the compounds of the invention (in a 1:3 protein:compound molar ratio) relative to each protein alone.

At pH 6, all the three NEET proteins (mitoNEET, NAF-1 and Miner 2) have a characteristic rate of loss of the bound Fe—S cluster that can be measured by the decrease of absorbance at wavelength 458 nm over time, using a spectrophotometer. Thus, Bis-Tris buffer (100 mM Bis-Tris pH6, 100 mM Nacl) was used at pH 6 to dilute either DMSO (Blank sample: Bis-Tris Buffer pH 6, 6 µM DMSO), DMSO and one of the three NEET proteins (Control sample: Bis-Tris Buffer pH 6, 6 µM DMSO, 2 µM purified NEET protein) or DMSO, one of the three NEET proteins and a compound of the invention (Test sample: Bis-Tris Buffer pH 6, 6 µM DMSO, 20 µM purified NEET protein, 6 µM compound of the invention).

A reaction mix containing DMSO diluted in the Bis-Tris Buffer with or without a compound of the invention was prepared. The purified NEET protein was the last component added to the reaction mix which was then aliquoted into 4 replicates in 96 wells plates. The absorbance at wavelength 458 nm was taken at 5 minutes intervals at 37° C. with a spectrofluorimeter. The assay run time for CISD2 gene product (NAF-1) was 500 minutes and 180 minutes for both the CISD 1 gene product (mitoNEET) and the CISD3 gene product (Miner 2).

In addition to time monitoring, residual bound Fe—S cluster to NEET protein was measured at the final point of the spectrometry assay for each Test sample and compared to the Control sample data (in parenthesis table 2). This residual binding is measured by the differential percentage between the absorbance 458 nm at time zero and the absorbance 458 nm at the end of the experiment (i.e. respectively 500 or 180 minutes as described hereabove), showing the percentage of NEET protein still able to bind a Fe—S cluster.

TABLE 2

| | Time (in minutes) to achieve 50% loss of bound cluster (Absorbance 458 nm), (Vehicle Control sample data in parenthesis) | | | Residual cluster bound at end of experiment (Percentage Absorbance 458 nm at time zero) (Vehicle Control sample data in parenthesis) | | |
|---|---|---|---|---|---|---|
| Compound | CISD1 Gene Product (mitoNEET) | CISD2 Gene Product (NAF-1) | CISD3 Gene Product (Miner2) | CISD1 Gene Product (mitoNEET) | CISD2 Gene Product (NAF-1) | CISD3 Gene Product (DMSO 11%) |
| #71 | 100 (80) | 125 (310) | 70 (60) | 34% (16%) | 15% (3%) | 42% (11%) |
| #10 | 50% loss not achieved during 180 minutes (80) | 290 (310) | 50% loss not achieved during 180 minutes (60) | 62% (16%) | 42% (3%) | 56% (11%) |
| #52 | 100 (80) | 50% loss not achieved during 500 minutes | 50% loss not achieved during 180 minutes (60) | 47% (16%) | 50% (3%) | 54% (11%) |
| #54 | 105 (80) | 305 (210) | 85 (60) | 35% (16%) | 31% (3%) | 41% (11%) |
| #46 | 80 (80) | 90 (310) | 60 (60) | 18% (16%) | 14% (3%) | 13% (11%) |
| #74 | 90 (80) | 390 (310) | 65 (60) | 0% (16%) | 0% (3%) | 5% (11%) |
| #82 | 50% loss not achieved during 180 minutes (80) | 265 (310) | 50% loss not achieved during 180 minutes (60) | 60% (16%) | 27% (3%) | 64% (11%) |

TABLE 2-continued

| | Time (in minutes) to achieve 50% loss of bound cluster (Absorbance 458 nm), (Vehicle Control sample data in parenthesis) | | | Residual cluster bound at end of experiment (Percentage Absorbance 458 nm at time zero) (Vehicle Control sample data in parenthesis) | | |
|---|---|---|---|---|---|---|
| Compound | CISD1 Gene Product (mitoNEET) | CISD2 Gene Product (NAF-1) | CISD3 Gene Product (Miner2) | CISD1 Gene Product (mitoNEET) | CISD2 Gene Product (NAF-1) | CISD3 Gene Product (DMSO 11%) |
| #103 | 95 (80) | 415 (310) | 65 (60) | 4% (16%) | 4% (3%) | 20% (11%) |
| #107 | 105 (80) | 255 (310) | 75 (60) | 35% (16%) | 21% (3%) | 41% (11%) |
| #112 | 100 (80) | 425 (310) | 50% loss not achieved during 180 minutes (60) | 29% (16%) | 23% (3%) | 64% (11%) |
| #115 | 100 (80) | 240 (310) | 65 (60) | 34% (16%) | 15% (3%) | 28% (11%) |

Analysis of the absorbance enables the time for which 50% loss of bound Fe—S cluster is reached (i.e. a 50% absorbance decrease at 458 nm) for each Test sample and each Control sample (in parenthesis table 2) to be determined. The data are then compared to determine whether the compound of the invention stabilizes or destabilizes the NEET protein/Fe—S cluster binding.

Destabilisers enhance the release of bound Fe—S cluster (i.e. decrease the time needed to reach 50% Fe—S cluster bound loss by more than 25% for the Test sample compared to the Control sample). As illustrated by table 2, at the concentrations tested, destabilisers of CISD2 Gene Product (NAF-1) are compounds, #71 and #46.

Stabilisers of Fe—S cluster binding by the NEET proteins slow the release of bound Fe—S (i.e. increase the time needed to reach 50% Fe—S cluster bound loss by more than 25% for the Test sample compared to the Control sample). As illustrated by table 2, at the concentrations tested, stabilisers of CISD1 Gene Product (mitoNEET) are compounds #71, #10, #52, #54, #82, #107, #112, and #115. Stabilisers of CISD2 Gene Product (NAF-1) are the compounds #52, #74, #103, and #112. Stabilisers of CISD3 Gene Product (Miner2) are the compounds #10, #52 #54, #82, #107, and #112.

As reported by table 2 (second part: "Residual cluster bound at end of experiment"), stabilizers may prevent the Fe—S cluster release by the NEET protein, the residual cluster bound at the end of the spectrometry experiment being in a range of 30% to 78% meaning that 30% to 78% of the Fe—S cluster remains bound to the total protein in the assay at the end of the experiment.

Example B3—Compounds Inhibit NFκB Activation in Response to TNFa Stimulation

Compounds of the present invention have been tested for their capacity to inhibit NFκB. The results are shown in the following table.

TABLE 3

| Compounds | NFκB EC50 (μM) |
|---|---|
| #1 | 0.16 |
| #10 | 0.3 |
| #69 | 0.32 |

Materials and Methods

Construction of a NFκB Reporter Cell Line

The NFκB reporter construct was made by cloning 5 NFκB responsive elements upstream of a NanoLuciferase reporter gene flanked by AAVS1 genomic sequences.

NFκB Responsive element fused with NanoLuciferase and SV40 late Poly(A) signal was amplified from pNL3.2-NFκB-Nluc (Promega) using NFκB-NLUC-F and NFκB-NLUC-R primers and inserted by Infusion (TaKaRa) in AAVS1 SA-2A-puro-pA donor plasmid (Hockemeyer et al, Nat Biotechnol. 2009, 27, 851-7) digested by SalI. pCRISPR AAVS1-T2 expressing a guide RNA (gRNA) to target human AAVS1 (T2 target sequence) was constructed by inserting AAVS1-T2A hybridized primers in pLentiCRISPR v2-blast (Sanjana et al, Nat Methods. 2014, 11, 783-4) digested by Bsmb1.

Oligonucleotide Sequences

```
NFKB-NLUC-F:
                                    (SEQ ID NO: 1)
ggctctatggGTCGACGGCCTAACTGGCCGGTACC NFKB-NLUC-R:
                                    (SEQ ID NO: 2)
agcttagtactGTCGACGATCAGCGGAAGAGCGCCCA (SEQ ID NO: 3)
AAVS1-T2A-1 CACCGGGGGCCACTAGGGACAGGAT (SEQ ID NO: 4)
AAVS1-T2A-2 AAACATCCTGTCCCTAGTGGCCCCC
```

A549 cells were transfected by the plasmids and puromycine selected for 5 days (1 μg mL-1). Then clones were obtained by limiting dilution and selected to maximize TNF dependent NFkB-NanoLuciferase induction.

NFκB Reporter Assay

The reporter cells were seeded on a 96-well plate for overnight with DMEM including 10% FBS. Test compounds were added at varying concentrations. The cells then were treated with 4 ng/ml TNFα (Peprotech, ref E251) in DMEM+10% FBS. NanoGlo luciferase assay (Promega) was carried out 6 hours later. Luminescence was measured using a Spark 20M spectrofluorimeter (Tecan). Values were normalized to the luminescence measured in untreated cells.

The invention claimed is:

1. A compound selected from the group consisting of:
2-Benzamido-6-phenyl-5,7-dihydro-4H-thieno[2,3-c]pyridine-3-carboxylic acid (Compound #52);
2-Benzamido-6-(4-fluoro-2-methylphenyl)-5,7-dihydro-4H-thieno[2,3-c]pyridine-3-carboxylic acid (Compound #53);
2-[(3,4-Dimethoxybenzoyl)amino]-6-(4-fluoro-2-methylphenyl)-5,7-dihydro-4H-thieno[2,3-c]pyridine-3-carboxylic acid (Compound #54);
2-[(2-Fluoro-4-methoxybenzoyl)amino]-6-(4-fluoro-2-methyl-phenyl)-5,7-dihydro-4H-thieno[2,3-c]pyridine-3-carboxylic acid (Compound #55);
2-Benzamido-6-(2,4-difluorophenyl)-5,7-dihydro-4H-thieno[2,3-c]pyridine-3-carboxylic acid (Compound #56);
2-Benzamido-6-(o-tolyl)-5,7-dihydro-4H-thieno[2,3-c]pyridine-3-carboxylic acid (Compound #57);
2-Benzamido-6-[4-(trifluoromethyl)phenyl]-5,7-dihydro-4H-thieno[2,3-c]pyridine-3-carboxylic acid (Compound #92);
2-[(3,4-Dimethoxybenzoyl)amino]-6-(4-fluorophenyl)-5,7-dihydro-4H-thieno[2,3-c]pyridine-3-carboxylic acid (Compound #113);
6-tert-Butoxycarbonyl-2-[(2-methylbenzoyl)amino]-5,7-dihydro-4H-thieno[2,3-c]pyridine-3-carboxylic acid (Compound #126); and
6-iso-Butyl-2-[(2-methylbenzoyl)amino]-5,7-dihydro-4H-thieno[2,3-c]pyridine-3-carboxylic acid formate salt (Compound #129).

2. A pharmaceutical composition comprising a compound as defined in claim 1, and an acceptable pharmaceutical excipient.

* * * * *

UNITED STATES PATENT AND TRADEMARK OFFICE
CERTIFICATE OF CORRECTION

Page 1 of 2

PATENT NO. : 11,603,368 B2
APPLICATION NO. : 16/967751
DATED : March 14, 2023
INVENTOR(S) : Eric Meldrum et al.

It is certified that error appears in the above-identified patent and that said Letters Patent is hereby corrected as shown below:

In the Specification

Column 4,
Line 27, "$R_{1d'\ are\ a\ hydrogen}$." should read --$R_{1d'}$ are a hydrogen.--.
Line 56, "In a further preferred" should read --In a preferred--.
Line 57, "a unit;" should read --a -$CR_{1b}R_{1b'}$ unit;--.
Lines 59-62, "$R_{1a}$, $R_{1a'}$, $R_{1c'}$, and $R_{1d'}$ represent a hydrogen, and $R_{1b''}$ represents a phenyl optionally substituted by at least one ($C_1$-$C_6$)alkyl, preferably a methyl, and/or a halogen, preferably a fluorine; and" should read --$R_{1a}$, $R_{1a'}$, $R_{1c}$, $R_{1c'}$, $R_{1d}$, and $R_{1d'}$ represent a hydrogen, and one of $R_{1b}$ and $R_{1b'}$ represents a ($C_1$-$C_6$)alkyl, preferably a tert-butyl, or a phenyl and the other is a hydrogen; and--.

Column 5,
Line 5, "represents a a phenyl" should read --represents a phenyl--.

Column 85,

Lines 7-18, " 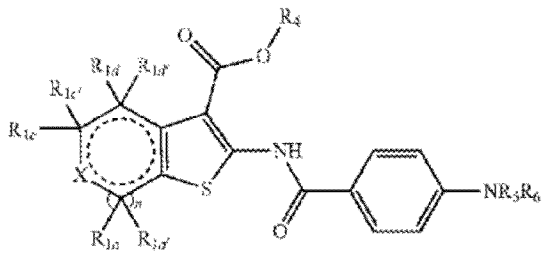 " should read

Signed and Sealed this
Fifth Day of September, 2023

Katherine Kelly Vidal
*Director of the United States Patent and Trademark Office*

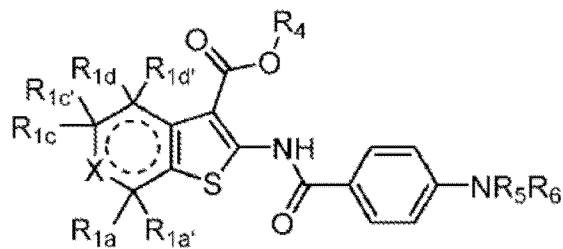
-- 13 --.
Column 88,
Line 62, "or asgenerated" should read --or as generated--.
Column 146,
Line 56, "maximize TNF" should read --maximize TNFα--.